(12) United States Patent
Hadari et al.

(10) Patent No.: US 10,793,639 B2
(45) Date of Patent: Oct. 6, 2020

(54) METHODS OF TREATING BY ADMINISTERING ANTI-KIT ANTIBODIES

(71) Applicant: Celldex Therapeutics, Inc., Hampton, NJ (US)

(72) Inventors: Yaron Hadari, Harrison, NY (US); Elizabeth M. Mandel-Bausch, Pleasant Prairie, WI (US); Susanne Radke, Hamden, CT (US); Joseph Schlessinger, Woodbridge, CT (US); Yoshihisa Suzuki, Hamden, CT (US)

(73) Assignee: Celldex Therapeutics, Inc., Hampton, NJ (US)

( * ) Notice: Subject to any disclaimer, the term of this patent is extended or adjusted under 35 U.S.C. 154(b) by 0 days.

(21) Appl. No.: 16/214,980

(22) Filed: Dec. 10, 2018

(65) Prior Publication Data

US 2019/0100598 A1 Apr. 4, 2019

Related U.S. Application Data

(62) Division of application No. 15/361,936, filed on Nov. 28, 2016, now Pat. No. 10,189,907, which is a division of application No. 13/981,852, filed as application No. PCT/US2012/022471 on Jan. 25, 2012, now Pat. No. 9,540,443.

(60) Provisional application No. 61/537,482, filed on Sep. 21, 2011, provisional application No. 61/507,430, filed on Jul. 13, 2011, provisional application No. 61/436,483, filed on Jan. 26, 2011.

(51) Int. Cl.
*A61K 39/395* (2006.01)
*C07K 16/28* (2006.01)
*A61K 47/68* (2017.01)
*C12N 9/24* (2006.01)
*G01N 33/68* (2006.01)
*A61K 45/06* (2006.01)
*G01N 33/573* (2006.01)
*A61K 39/00* (2006.01)

(52) U.S. Cl.
CPC ...... *C07K 16/2896* (2013.01); *A61K 39/3955* (2013.01); *A61K 39/39558* (2013.01); *A61K 45/06* (2013.01); *A61K 47/6817* (2017.08); *A61K 47/6849* (2017.08); *C07K 16/2803* (2013.01); *C12N 9/2497* (2013.01); *G01N 33/573* (2013.01); *G01N 33/6854* (2013.01); *A61K 2039/505* (2013.01); *C07K 2317/24* (2013.01); *C07K 2317/30* (2013.01); *C07K 2317/34* (2013.01); *C07K 2317/52* (2013.01); *C07K 2317/56* (2013.01); *C07K 2317/565* (2013.01); *C07K 2317/76* (2013.01); *C07K 2317/77* (2013.01); *C07K 2317/92* (2013.01); *G01N 2333/912* (2013.01)

(58) Field of Classification Search
None
See application file for complete search history.

(56) References Cited

U.S. PATENT DOCUMENTS

| | | |
|---|---|---|
| 5,268,358 A | 12/1993 | Fretto |
| 5,489,516 A | 2/1996 | Broudy et al. |
| 5,545,533 A | 8/1996 | Bartke et al. |
| 5,686,572 A | 11/1997 | Wolf et al. |
| 5,808,002 A | 9/1998 | Biihring |
| 5,817,310 A | 10/1998 | Ramakrishnan et al. |
| 5,882,644 A | 3/1999 | Chang et al. |
| 5,891,652 A | 4/1999 | Wolf et al. |
| 5,906,938 A | 5/1999 | Broudy et al. |
| 5,911,988 A | 6/1999 | Brownell et al. |
| 5,919,911 A | 7/1999 | Broudy et al. |
| 5,922,847 A | 7/1999 | Broudy et al. |
| 6,001,803 A | 12/1999 | Besmer et al. |
| 6,403,559 B1 | 6/2002 | Besmer et al. |
| 6,495,331 B1 | 12/2002 | Gelfand et al. |
| 6,555,367 B1 | 4/2003 | Spence et al. |
| 6,576,812 B1 | 6/2003 | Longley et al. |
| 6,977,159 B1 | 12/2005 | Longley et al. |
| 6,989,248 B2 | 1/2006 | Longley |
| 6,998,391 B2 | 2/2006 | Lyons et al. |
| 7,303,893 B1 | 12/2007 | Chien et al. |
| 7,419,777 B2 | 9/2008 | Bacus |

(Continued)

FOREIGN PATENT DOCUMENTS

| | | |
|---|---|---|
| EP | 0548867 A2 | 6/1993 |
| EP | 0787743 A2 | 8/1997 |

(Continued)

OTHER PUBLICATIONS

Staser et al., Jul. 2010, "Mast cells and the neurofibroma microenvironment," Blood 116(2):157-164.

Pummi et al., Jan. 2006, "Tight junction proteins and perineurial cells in neurofibromas," J Histochem Cytochem 54(1):53-61.

Adams et al., 2006, "Humanization of a recombinant monoclonal antibody to produce a therapeutic HER dimerization inhibitor, Pertuzumab", Cander Immunol Immunother, 55:717-727 (published online Sep. 3, 2005).

(Continued)

*Primary Examiner* — Phillip Gambel
(74) *Attorney, Agent, or Firm* — Jones Day

(57) ABSTRACT

Provided herein, in one aspect, are antibodies that immunospecifically bind to a human KIT antigen comprising the fourth and/or fifth extracellular Ig-like domains (that is, D4 and/or D5 domains), polynucleotides comprising nucleotide sequences encoding such antibodies, and expression vectors and host cells for producing such antibodies. The antibodies can inhibit KIT activity, such as ligand-induced receptor phosphorylation. Also provided herein are kits and pharmaceutical compositions comprising antibodies that specifically bind to a KIT antigen, as well as methods of treating or managing a KIT-mediated disorder or disease and methods of diagnosing a KIT-mediated disorder or disease using the antibodies described herein.

22 Claims, 27 Drawing Sheets

Specification includes a Sequence Listing.

(56) References Cited

U.S. PATENT DOCUMENTS

| | | | |
|---|---|---|---|
| 7,449,309 | B2 | 11/2008 | Longley |
| 7,906,302 | B2 | 3/2011 | Longley |
| 7,915,391 | B2 | 3/2011 | Ng et al. |
| 7,959,942 | B2 | 6/2011 | Cottone |
| 8,088,060 | B2 | 1/2012 | Cottone et al. |
| 8,133,485 | B2 | 3/2012 | Levi-Schaffer et al. |
| 8,133,733 | B2 | 3/2012 | Khan |
| 8,278,067 | B2 | 10/2012 | Longley |
| 8,436,150 | B2 | 5/2013 | Ng et al. |
| 8,552,157 | B2 | 10/2013 | Amatulli et al. |
| 8,791,249 | B2 | 7/2014 | Ng et al. |
| 9,067,986 | B2 | 6/2015 | Gurney et al. |
| 9,334,332 | B2 | 5/2016 | Hadari et al. |
| 9,540,443 | B2 | 1/2017 | Hadari et al. |
| 9,605,081 | B2 | 3/2017 | Hadari et al. |
| 10,184,007 | B2 | 1/2019 | Hadari et al. |
| 10,189,907 | B2 | 1/2019 | Hadari et al. |
| 10,239,943 | B2 | 3/2019 | LaVallee et al. |
| 2002/0118775 | A1 | 8/2002 | Persson et al. |
| 2004/0018593 | A1 | 1/2004 | Jill et al. |
| 2004/0110226 | A1 | 6/2004 | Lazar et al. |
| 2004/0248215 | A1 | 12/2004 | Keler et al. |
| 2005/0004066 | A1 | 1/2005 | Rockwell |
| 2005/0232917 | A1 | 10/2005 | Pullen et al. |
| 2005/0244409 | A1 | 11/2005 | Erickson-Miller et al. |
| 2005/0261175 | A1 | 11/2005 | Zsebo et al. |
| 2005/0276784 | A1 | 12/2005 | Besmer et al. |
| 2005/0281828 | A1 | 12/2005 | Bowdish et al. |
| 2006/0019280 | A1 | 1/2006 | Chen et al. |
| 2007/0004910 | A1 | 1/2007 | Sexton et al. |
| 2007/0225202 | A1 | 9/2007 | Andreev et al. |
| 2007/0253951 | A1 | 11/2007 | Ng et al. |
| 2008/0032989 | A1 | 2/2008 | Robinson et al. |
| 2008/0095775 | A1 | 4/2008 | Lewis et al. |
| 2008/0213774 | A1 | 9/2008 | Chen et al. |
| 2008/0260729 | A1 | 10/2008 | Nash et al. |
| 2008/0274469 | A1 | 11/2008 | Bastian et al. |
| 2008/0287309 | A1 | 11/2008 | Bowdish et al. |
| 2009/0022740 | A1 | 1/2009 | Bergstein |
| 2009/0022741 | A1 | 1/2009 | Bergstein |
| 2009/0028879 | A1 | 1/2009 | Bergstein |
| 2009/0075381 | A1 | 3/2009 | Clarke et al. |
| 2009/0136450 | A1 | 5/2009 | Chumakov et al. |
| 2009/0136497 | A1 | 5/2009 | Longley et al. |
| 2009/0136517 | A1 | 5/2009 | Garton et al. |
| 2009/0149389 | A1 | 6/2009 | Panitch et al. |
| 2009/0169547 | A1 | 7/2009 | Sahin et al. |
| 2009/0181017 | A1 | 7/2009 | Hass et al. |
| 2009/0181022 | A1 | 7/2009 | Nielson et al. |
| 2009/0186031 | A1 | 7/2009 | Woods et al. |
| 2009/0191201 | A1 | 7/2009 | Heiss et al. |
| 2009/0192133 | A1 | 7/2009 | Horton |
| 2009/0233905 | A1 | 9/2009 | Burke et al. |
| 2009/0246206 | A1 | 10/2009 | Nielson et al. |
| 2009/0304625 | A1 | 12/2009 | Husain et al. |
| 2010/0029674 | A1 | 2/2010 | Tiollier et al. |
| 2010/0124569 | A1 | 5/2010 | Abbot et al. |
| 2010/0129440 | A1 | 5/2010 | Zhao et al. |
| 2010/0143935 | A1 | 6/2010 | Davis |
| 2010/0173324 | A1 | 7/2010 | Mori et al. |
| 2010/0196923 | A1 | 8/2010 | Atala |
| 2010/0204058 | A1 | 8/2010 | Chang et al. |
| 2010/0226927 | A1 | 9/2010 | Weissman et al. |
| 2010/0298331 | A1 | 11/2010 | Lee et al. |
| 2010/0316640 | A1 | 12/2010 | Sundaram et al. |
| 2011/0059091 | A1 | 3/2011 | Chang et al. |
| 2011/0091428 | A1 | 4/2011 | Anversa |
| 2011/0123532 | A1 | 5/2011 | Gurney et al. |
| 2011/0182866 | A1 | 7/2011 | McNiece et al. |
| 2011/0223165 | A1 | 9/2011 | Ng et al. |
| 2011/0262465 | A1 | 10/2011 | Gao et al. |
| 2011/0268776 | A1 | 11/2011 | Schapira et al. |
| 2011/0281813 | A1 | 11/2011 | Advani et al. |
| 2011/0293574 | A1 | 12/2011 | Chute et al. |
| 2011/0311538 | A1 | 12/2011 | Schlessinger et al. |
| 2011/0318351 | A1 | 12/2011 | Bergstein |
| 2012/0065380 | A1 | 3/2012 | Yoo et al. |
| 2012/0189633 | A1 | 7/2012 | Hadari et al. |
| 2012/0328599 | A1 | 12/2012 | Bae et al. |
| 2013/0011406 | A1 | 1/2013 | Hadari et al. |
| 2013/0071397 | A1 | 3/2013 | Schlessinger et al. |
| 2013/0184221 | A9 | 7/2013 | Panitch et al. |
| 2013/0266595 | A1 | 10/2013 | Flygare et al. |
| 2014/0056905 | A1 | 2/2014 | Hadari et al. |
| 2014/0065168 | A1 | 3/2014 | Hadari et al. |
| 2017/0121408 | A1 | 5/2017 | LaVallee et al. |
| 2017/0158778 | A1 | 6/2017 | Hadari et al. |
| 2019/0106510 | A1 | 4/2019 | Hadari et al. |
| 2019/0153094 | A1 | 5/2019 | Lavallee et al. |

FOREIGN PATENT DOCUMENTS

| | | |
|---|---|---|
| EP | 1378752 A1 | 1/2004 |
| EP | 0586445 B1 | 9/2004 |
| EP | 0889125 B1 | 8/2008 |
| JP | 2009534052 A | 9/2009 |
| JP | 2013510166 A | 3/2013 |
| WO | WO 1992/17505 A1 | 10/1992 |
| WO | WO 1992/021766 A1 | 12/1992 |
| WO | WO 1993/010805 A1 | 6/1993 |
| WO | WO 1998/41090 A1 | 9/1998 |
| WO | WO 2000/067794 A1 | 11/2000 |
| WO | WO 2001/034201 A2 | 5/2001 |
| WO | WO 2003/065995 A2 | 8/2003 |
| WO | WO 2003/091437 A1 | 11/2003 |
| WO | WO 2004/002425 A2 | 1/2004 |
| WO | WO 2005/095640 A1 | 10/2005 |
| WO | WO 2006/017173 A1 | 2/2006 |
| WO | WO 2007/004060 A2 | 1/2007 |
| WO | WO 2007/127317 A2 | 11/2007 |
| WO | WO 2008/112290 A2 | 9/2008 |
| WO | WO 2008/153926 A2 | 12/2008 |
| WO | WO 2009/082624 A2 | 7/2009 |
| WO | WO 2009/135001 A2 | 11/2009 |
| WO | WO 2009/152288 A1 | 12/2009 |
| WO | WO 2010/136508 A2 | 12/2010 |
| WO | WO 2011/057022 A1 | 5/2011 |
| WO | WO 2011/119948 A1 | 9/2011 |
| WO | WO 2012/093172 A1 | 7/2012 |
| WO | WO 2012/103165 A2 | 8/2012 |
| WO | WO 2012/154480 A1 | 11/2012 |
| WO | WO 2013/177481 A1 | 11/2013 |
| WO | WO 2014/018625 A1 | 1/2014 |
| WO | WO 2015/050959 A1 | 4/2015 |
| WO | WO 2015/112822 A1 | 7/2015 |

OTHER PUBLICATIONS

Amir-Zaltsman et al., 2000, "Inhibitors of protein tyrosine phosphorylation: preliminary assessment of activity by time-resolved fluorescence", Luminescence, 15:377-380.

Ashman et al., 1994, "Epitope mapping and functional studies with three monoclonal antibodies to the C-kit receptor tyrosine kinase", J Cell Physiol, 158(3):545-554.

Atienza et al., 2006, "Label-free and real-time cell-based kinase assay for screening selective and potent receptor tyrosine kinase inhibitors using microelectronic sensor array", J Biomolec Screening, 11(6):634-643.

Bae et al., 2000, "Arginine-rich anti-vascular endothelial growth factor peptides inhibit tumor growth and metastasis by blocking angiogenesis", J Biol Chem, 275(18):13588-13596.

Bae et al., 2010, "Asymmetric recepor contact is required for tyrosine autophosphorylation of fibroblast growth factor receptor in living cells", Proc Natl Acad Sci USA, 107(7):2866-2867.

Baselga et al., 2005, "Critical update and emerging trends in epidermal growth factor receptor targeting in cancer", J Clin Oncol, 23(11):2445-2459.

Berezov et al., 2002, "Disabling receptor ensembles with rationally designed interface peptidomimetics", J Biol Chem, 277(31):28330-28339.

(56) References Cited

OTHER PUBLICATIONS

Besmer et al., 1986, "A new acute transforming feline retrovirus and relationship of its oncogene v-kit with the protein kinase gene family", Nature, 320:415-421.
Binetruy-Tournaire et al., 2000, "Identification of a peptide blocking vascular endothelial growth factor (VEGF)-mediated angiogenesis", EMBO J, 19(7):1525-1533.
Blechman et al., 1993a, "Soluble c-kit proteins and antireceptor monoclonal antibodies confine the binding site of stem cell factor", J Biol Chem, 268(6):4399-4406.
Blechman et al., 1993b, "Structure-function analyses of the kit receptor for the steel factor", Stem Cells, 11:12-21.
Blechman et al., 1995, "The fourth immunolglobulin domain of the stem cell factor receptor couples ligand binding to signal transduction", Cell, 80:103-113.
Blechman and Yarden, 1995, "Structural aspects of receptor dimerization. C-KIT as an example", Ann N Y Acad Sci 766:344-362.
Briddell et al., 1992, "Further phenotypic characterization and isolation of human hematopoietic progenitor cells using a monoclonal antibody to the c-kit receptor", Blood 79(12):3159-3167.
Broudy et al., 1992, "Isolation and characterization of a monoclonal antibody that recognizes the human *c-kit* receptor", Blood 79(2):338-346.
Broudy et al., 2001, "The fifth immunoglobulin-like domain of the Kit receptor is required for proteolytic cleavage from the cell surface", Cytokine 15(4):188-195.
Carlberg and Rohrschneider, 1994, "The effect of activating mutations on dimerization, tyrosine phosphorylation and internalization of the macrophage colony stimulating factor receptor", Molec Biol Cell, 5(1):81-95.
Chen et al., 2008, "A crystallographic snapshot of tyrosine transphosphorylation in action", Proc Natl Acad Sci USA, 105(50):19660-19665.
Edris et al., 2013, "Anti-KIT Monoclonal Antibody Inhibits Imatinib-resistant Gastrointestinal Stromal Tumor Growth", Proc. Natl. Acad. Sci. U S A., 110(9):3501-3506, (Epub Feb. 4, 2013).
Gedrich et al., "Regulation of Mast Cell Activity by KTN0158, a Humanized anti-KIT Monoclonal Antibody", Children's Tumor Foundation 2014 NF Conference, Jun. 7-10, 2014, Washington, D.C., Meeting Abstract.
Gedrich et al., "Regulation of Mast Cell Activity by KTN0158, a Humanized anti-Kit Monoclonal Antibody", Children's Tumor Foundation 2014 NF Conference, Jun. 7-10, 2014, Washington, D.C., Meeting Poster.
GenBan Accession No. AAC50968.1 (KIT_MOUSE), dated Feb. 6, 1997. Retrieved from the Internet: URL<http://www.ncbi.nlm.nih.gov/entrez/viewer.fcgi?db=protein&id=1817733>.
GenBan Accession No. P05532, dated May 1, 2007. Retrieved from the Internet: URL<http://www.ncbi.nlm.nih.gov/entrez/viewer.fcgi?1254373:PROT:4572902>.
Granier et al., 2007, "Structure and conformational changes in the c-terminal domain of the beta2-adrenoceptor", J Biol Chem, 282(18):13895-13905.
Hubbard et al., 2005, "EGF receptor inhibition: attacks on multiple fronts", Cancer Cell, 7(4):287-288.
Japanese Society for Bioinformatics (ed.), Encyclopedia of Bioinformatics, Jul. 1, 2006, pp. 462-463. (English abstract).
Jeffrey et al., 2013, "A potent anti-CD70 antibody-drug conjugate combining a dimeric pyrrolobenzodiazepine drug with site-specific conjugation technology", Bioconjugate Chem. 24:1256-1263.
Jiang et al., 2000, "Structure of the active core of human stem cell factor and analysis of binding to its receptor kit", EMBO J, 19(13):3192-3203.
Lebron et al., 2014, "A human monoclonal antibody targeting the stem cell factor receptor (c-Kit) blocks tumor cell signaling and inhibits tumor growth", Cancer Biol Ther 15(9):1208-1218.
Lemmon et al., 1997, "Kit receptor dimerization is driven by bivalent binding of stem cell factor", J Biol Chem, 272(10):6311-6317.
Lemmon et al., 2007, "A new twist in the transmembrane signaling tool-kit", Cell, 130(2):213-215.
Lennartsson et al., 2004, "Synergistic growth of stem cell factor and granulocyte macrophage colony-stimulating factor involves kinase-dependent and -independent contributions from c-kit", J.Biol Chem, 279(43):44544-44553.
Lev et al., 1992, "A recombinant ectodomain of the receptor for the stem cell factor (SCF) retains ligand-induced receptor dimerization and antagonizes SCF-stimulated cellular responses", J Biol Chem, 267(15):10866-10873.
Lev et al., 1993, "Interspecies molecular chimeras of Kit help define the binding site of the stem cell factor", Mol Cell Biol., 13(4):2224-2234.
Liang et al., 2013, "The c-kit receptor-mediated signal transduction and tumor-related diseases", Int. J. Biol. Sci., 9(5):435-443.
Liu et al., 2007, "Structural basis for stem cell factor: KIT signaling and activation of class III receptor tyrosine kinases", The EMBO Journal, 26(3):891-901.
Lokker et al., 1997, "Functional importance of platelet-derived growth factor (PDGF) receptor extracellular immunoglobulin-like domains", J Biol Chem, 272(52):33037-33044.
Lubeski et al., "KTN0182A, an anti-KIT, pyrrolobenzodiazepine (PBD)-containing antibody-drug conjugate (ADC) demonstrates potent antitumor activity in vitro and in vivo against a broad range of tumor types", 11th Annual PEGS, May 4-8, 2015, Boston, MA, Meeting Poster.
Lubeski et al., "KTN0182A, an anti-KIT, pyrrolobenzodiazepine (PBD)-containing antibody-drug conjugate (ADC) demonstrates potent antitumor activity in vitro and in vivo against a broad range of tumor types", 11th Annual PEGS, May 4-8, 2015, Boston, MA, Meeting Abstract.
Mandel et al., "KTN0158, a Humanized Anti-KIT Monoclonal Antibody, Reduces Airway Eosinophilia in a Feline Model of Allergic Asthma", American College of Allergy, Asthma & Immunology (ACAAI) 2014 Annual Scientific Meeting, Nov. 6-10, 2014, Atlanta, GA, Meeting Poster.
Mandel et al., "Regulation of Airway Eosinophilia in a Model of Feline Allergic Asthma by KTN0158, a Humanized anti-KIT Monoclonal Antibody", American College of Allergy, Asthma & Immunology (ACAAI) 2014 Annual Scientific Meeting, Nov. 6-10, 2014, Atlanta, GA, Meeting Abstract.
Matthews et al., 1991, "A receptor tyrosine kinase cDNA isolated from a population of enriched primitive hematopoietic cells and exhibiting close genetic linkage to c-kit", Proc Natl Acad Sci USA, 88:9026-9030.
Micke et al., 2003, "Characterization of c-kit expression in small cell lung cancer: prognostic therapeutic implications", Clin Cancer Res, 9:188-194.
Nakayama and Parandoosh, 1999, "An immunoassay for assessment of receptor tyrosine kinase autophosphorylation", J Immunol Methods, 225:67-74.
Omura et al., 1997, "Immunoglobulin-like domain 4-mediated receptor-receptor interactions contribute to platelet-derived growth factor-induced receptor dimerization.", J Biol Chem, 272(19):12676-12682.
Philo et al., 1996, "Human stem cell factor dimer forms a complex with two molecules of the extracellular domain of its receptor, kit", J Biol Chem, 271(12):6895-6902.
Protein Knowledgebase (UniProtKB), P10721 (KIT_HUMAN) [online] [retrieved on May 19, 2014]. Retrieved from the Internet http://www.uniport.org/uniprot/P10721#ref1, pp. 1-25.
Reshetnyak et al., 2013, "Structural basis for KIT receptor tyrosine kinase inhibition by antibodies targeting the D4 membrane-proximal region", Proc Natl Acad Sci USA, 110(44):17832-17837.
Roskoski et al., 2004, "The ErbB/HER receptor protein-tyrosine kinases and cancer", Biochem Biophys Res Com, 319(1):1-11.
Ruch et al., 2007, "Structure of a VEGF-VEGF receptor complex determined by electron microscopy", Nat Struct Mol Biol, 14(3):249-250.
Ryan et al., 1994, "Role for the stem cell factor/KIT complex in Schwann cell neoplasia and mast cell proliferation associated with neurofibromatosis", J Neurosci Res 37(3):415-432.

(56) References Cited

OTHER PUBLICATIONS

Sakai et al., 2007, "Pertuzumab, a novel HER dimerization inhibitor, inhibits the growth of human lung cancer cells mediated by the HER3 signaling pathway", Cancer Sci, 98(9):1498-1503.
Schittek et al., 1992, "Natural occurrence and origin of somatically mutated memory B cells in mice", J Exp Med, 176:427-428.
Sequence Alignment, GenBan Accession No. AAC50968.1 (KIT_MOUSE), dated May 1, 2007. [Retrieved from the Internet: URL<http://blast.ncbi.nlm.nih.gov/Blast.cgi>.
Shen et al., 2005, "Protein kinase inhibitors for treatment of cancer", Trends in Biopharmaceutical Industry, 1(3):15-19.
Shulman et al., 1997, "An antibody reactive with domain 4 of the platelet-derived growth beta receptor allows BB binding while inhibiting proliferation by impairing receptor dimerization", J Biol Chem, 272(28):17400-17404.
Sugimura et al., 2002, "Human-Antibody Engineering (Review)", Bioventure, 2(4): 30-33. (English abstract).
Tabone-Eglinger et al., 2008, "KIT mutations induce intracellular retention and activation of an immature form of the KIT protein in gastrointestinal stromal tumors", Clin Cancer Res 14(8):2285-2294.
Tamura et al., 2007, "Tyrosine kinases as targets for anti-inflammatory therapy", Anti-Inflammatory & Anti-Allergy Agents in Medicinal Chemistry, 6(1):47-60.
Tan et al., 2007, "Monitering interactions between receptor tyrosine kinases and their downstream effector proteins in living cells using bioluminescence resonance energy transfer", Molec Pharmacol, 72:1440-1446.
Tao et al., 2001, "Kinase insert domain receptor (KDR) extracellular immunoglobulin-like domains 4-contain structural features that block receptor dimerization and vascular endothelial g(rowth factor-induced signaling", J Biol Chem, 276(24):21916-21923.
Uniprot Submission D2VI02_NAEGR, dated Mar. 2, 2010. Retrieved from the internet: <URL: http://www.uniprot.org/uniprot?D2VI02.txt?version=1>]; aa 155-161.
Uniprot Submission Q0UL05_PHANO, dated Mar. 2, 2010. Retrieved from the Internet: <URL: http://www.uniprot.org/uniprot?Q0UL05.txt?version=1>]; aa 598-608.
Wiesmann et al., 2000, "Ligand-binding sites in lg-like domains of receptor tyrosine kinases", J Molec Med, 78(5):247-260.
Wikipedia, The Free Encyclopedia, "Humanized_antibody," [online], Retrieved from the Internet:< URL: http://en.wikipedia.org/wiki/Humanized_antibody>.
Yang et al., 2008, "Nf1-dependent tumors require a microenvironment containing Nf1+/-- and c-kit-dependent bone marrow", Cell, 135(3):437-448.
Yang et al., 2010, "Direct contacts between extracellular membrane-proximal domains are required for VEGF receptor activation and cell signaling", Proc Natl Acad Sci USA, 107(5):1906-1911.
Yarden et al., 1987, "Human proto-oncogene c-kit: a new cell surface receptor tyrosine kinase for an unidentified ligand", EMBO J, 6(11):3341-3351.
Yoo et al., 2005, "Arginine-rich anti-vascular endothelial growth factor (anti_VEGF) hexapeptide inhibits collagen-induced arthritis and VEGF-stimulated productions of TNF-alpha and IL-6 by human monocytes", J Immunol, 174(9):5846-5855.
Yuzawa et al., 2007, "Structural basis for activation of the receptor tyrosine KIT by stem cell factor", Cell, 13(2):323-334.
Zhang et al., 2000, "Crystal structure of human stem cell factot: implication for stem cell factor receptor dimerization and activation", Proc Natl Acad Sci USA, 97(14):7732-7737.
Zhang et al., 2006, "An allosteric mechanism for activation of kinase domain of epidermal growth factor receptor", Cell, 125:1137-1149.
Zhang et al., 2009, "Targeting cancer with small molecule kinase inhibitors", Nature Reviews Cancer, 9:28-39.
Lerner et al., 1991, "Monoclonal antibody YB5.B8 identifies the human c-kit protein product", Blood, 77:1876-1883.
London et al., "KTN0158, a humanized anti-KIT monoclonal antibody, demonstrates antitumor activity in dogs with mast cell tumors," AACR-NCI-EORTC International Conference on Molecular Targets and Cancer Therapeutics, Nov. 5-9, 2015, Boston, MA, Meeting Abstract published online Oct. 26, 2015.
Ashman and Griffith, Jan. 2013, "Therapeutic targeting of c-KIT in cancer," Expert Opin Investig Drugs, 22(1):103-115.
Ashman, Oct. 1999, "The biology of stem cell factor and its receptor C-kit," Int J Biochem Cell Biol, 31(10):1037-1051.
Balachandran et al., Mar. 2012, "Imatinib potentiates anti-tumor T cell responses in gastrointestinal stromal tumor through the inhibition of Ido," Nat Med, 17(9):1094-1100.
Bradding, Jun. 2008, "Asthma eosinophil disease, mast cell disease, or both?" Allergy Asthma Clin Immunol, 4(2):84-90.
Cheon et al., Mar. 2011, "Mast cell 5-lipoxygenase activity promotes intestinal polyposis in APCDelta468 mice," Cancer Res, 71(5):1627-1636.
Christiansson et al., May 2015, "The tyrosine kinase inhibitors imatinib and dasatinib reduce myeloid suppressor cells and release effector lymphocyte responses," Mol Cancer Ther, 14(5):1181-1191.
Coussens et al., Jun. 1999, "Inflammatory mast cells up-regulate angiogenesis during squamous epithelial carcinogenesis," Genes Dev, 13(11):1382-1397.
Finke et al., Jul. 2011, "MDSC as a mechanism of tumor escape from sunitinib mediated anti-angiogenic therapy," Int Immunopharmacol, 11(7):856-861.
Galli et al., 1999, "The regulation of mast cell and basophil development by the Kit ligand, SCF, and IL-3," in: Razin E, Rivera J ed. Signal Transduction in Mast Cells and Basophils, pp. 11-30.
Garton et al., "Inhibition of KIT in vivo modifies immune cell populations to improve the efficacy of checkpoint inhibitors in syngeneic mouse tumor models," American Association for Cancer Research (AACR) Annual Meeting, Apr. 16-20, 2016, New Orleans, LA, Meeting Abstract published online Mar. 16, 2016.
Garton et al., "Inhibition of KIT in vivo modifies immune cell populations to improve the efficacy of checkpoint inhibitors in syngeneic mouse tumor models," American Association for Cancer Research (AACR) Annual Meeting, Apr. 16-20, 2016, New Orleans, LA, poster presented on Apr. 19, 2016.
Gedrich et al., "Targeting KIT on innate immune cells enhances the antitumor activity of checkpoint inhibitors in vivo," Society for Immunotherapy of Cancer (SITC) 30th Annual Meeting, Nov. 6-8, 2015, National Harbor, MD, slide presentation on Nov. 7, 2015.
Gedrich et al., Nov. 4, 2015, "Targeting KIT on innate immune cells enhances the antitumor activity of checkpoint inhibitors in vivo," J Immunother Cancer 3(Suppl 2): O12, Meeting Abstract for Society for Immunotherapy of Cancer (SITC) 30th Annual Meeting, Nov. 6-8, 2015, National Harbor, MD.
Grimbaldeston et al., Sep. 2005, "Mast cell-deficient W-sash c-kit mutant Kit W-sh/W-sh mice as a model for investigating mast cell biology in vivo," Am J Pathol, 167(3):835-848.
Harding et al., May-Jun. 2010, "The immunogenicity of humanized and fully human antibodies: residual immunogenicity resides in the CDR regions," Mabs, 2(3):256-265.
Jacoby, et al., Dec. 1997, "Molecular analysis of the NF2 tumor-suppressor gene in schwannomatosis," Am J Hum Genet, 61(6):1293-1302.
Joensuu, 2006, "Gastrointestinal stromal tumor (GIST)," Ann Oncol, 17 Suppl 10:x280-6.
Kao et al., Jan. 2011, "Targeting immune suppressing myeloid-derived suppressor cells in oncology," Crit Rev Oncol Hematol, 77(1):12-19.
Lammie et al., Nov. 1994, "Expression of c-kit and kit ligand proteins in normal human tissues," J Histochem Cytochem, 42(11):1417-1425.
Larmonier et al., Nov. 2008, "Imatinib mesylate inhibits CD4+ CD25+ regulatory T cell activity and enhances active immunotherapy against BCR-ABL-tumors," J Immunol, 181(10):6955-6963.
London et al., "KTN0158, a humanized anti-KIT monoclonal antibody, demonstrates antitumor activity in dogs with mast cell tumors," AACR-NCI-EORTC International Conference on Molecular Targets and Cancer Therapeutics, Nov. 5-9, 2015, Boston, MA, poster presented Nov. 8, 2015.
London et al., "KTN0158, a humanized anti-KIT monoclonal antibody, demonstrates antitumor activity in dogs with mast cell

(56) References Cited

OTHER PUBLICATIONS tumors," The European Cancer Congress (ECC 2015), Sep. 25-29, 2015, Vienna, Austria, Meeting Abstract published online Sep. 11, 2015.
London et al., "KTN0158, a humanized anti-KIT monoclonal antibody, demonstrates antitumor activity in dogs with mast cell tumors," The European Cancer Congress (ECC 2015), Sep. 25-29, 2015, Vienna, Austria, poster presented Sep. 28, 2015.
Metcalfe et al., 1997, "Mast cells," Physiol Rev, 77:1033-1079.
Miettinen and Lasota, Sep. 2005, "KIT (CD117): a review on expression in normal and neoplastic tissues, and mutations and their clinicopathologic correlation," Appl Immunohistochem Mol Morphol, 13(3):205-220.
Mukherjee et al., Jun. 2009, "Human schwannomas express activated platelet-derived growth factor receptors and c-kit and are growth inhibited by Gleevec (Imatinib Mesylate)," Cancer Res, 69(12):5099-5107.
Ozao-Choy et al., Mar. 2009, "The novel role of tyrosine kinase inhibitor in the reversal of immune suppression and modulation of tumor microenvironment for immune-based cancer therapies," Cancer Res, 69(6):2514-2522.
Pan et al., Jan. 2008, "Reversion of immune tolerance in advanced malignancy: modulation of myeloid-derived suppressor cell development by blockade of stem-cell factor function," Blood, 111(1):219-228.
Plotkin, et al., Apr. 2012, "Quantitative assessment of whole-body tumor burden in adult patients with 13/1, 13/2 neurofibromatosis," PLoS One, 7(4):e35711.
Radinger et al., Aug. 2010, "Generation, isolation, and maintenance of human mast cells and mast cell lines," Curr Protoc Immunol, Chapter 7:Unit 7.37.
Reith et al., Mar. 1990, "W mutant mice with mild or severe developmental defects contain distinct point mutations in the kinase domain of the c-kit receptor," Genes Dev, 4(3):390-400.
Saleem et al., Jul. 15, 2012, "Cutting edge: mast cells critically augment myeloid-derived suppressor cell activity," J Immunol, 189(2):511-515.
Schlessinger, Oct. 2000, "Cell signaling by receptor tyrosine kinases," Cell, 103(2):211-225.
Soucek et al., Oct. 2007, "Mast cells are required for angiogenesis and macroscopic expansion of Myc-induced pancreatic islet tumors," Nat Med, 13(10):1211-1208.
Starkey et al., Jul. 1988, "Mast-cell-deficient W/Wv mice exhibit A decreased rate of tumor angiogenesis," Int J Cancer, 42(1):48-52.
Staser et al., Nov. 2012, "Pathogenesis of plexiform neurofibroma: tumor-stromal/hematopoietic interactions in tumor progression," Annu Rev Pathol, 7:469-495.
Theoharides and Conti, May 2004, "Mast cells: the Jekyll and Hyde of tumor growth," Trends Immunol, 25(5):235-241.
Ullrich and Schlessinger, Apr. 1990, "Signal transduction by receptors with tyrosine kinase activity," Cell, 61(2):203-212.
Yang et al., Jan. 2010, "Mast cells mobilize myeloid-derived suppressor cells and Treg cells in tumor microenvironment via IL-17 pathway in murine hepatocarcinoma model," PLoS One, 5(1):e8922.
Zoog et al., Mar. 2009, "Antagonists of CD117 (cKit) signaling inhibit mast cell accumulation in healing skin wounds," Cytometry A, 75(3):189-198.
Stahl et al., Jun. 2016, "Targeting KIT on innate immune cells to enhance the antitumor activity of checkpoint inhibitors," Immunotherapy, 8(7):767-774.
Rudikoff et al., Mar. 1982, "Single amino acid substitution altering antigen-binding specificity," Proc Natl Acad Sci U S A, 79(6):1979-1983.
Colman et al., Jan. 1994, "Effects of amino acid sequence changes on antibody-antigen interactions," Res Immunol, 145(1):33-36.
Kussie et al., Jan. 1994, "A single engineered amino acid substitution changes antibody fine specificity," J Immunol, 152(1):146-152.
Chen et al., Jun. 1995, "Enhancement and destruction of antibody function by somatic mutation: unequal occurrence is controlled by V gene combinatorial associations," EMBO J, 14(12):2784-2794.
Vajdos et al., Jul. 2002, "Comprehensive functional maps of the antigen-binding site of an anti-ErbB2 antibody obtained with shotgun scanning mutagenesis," J Mol Biol 320(2):415-428.
Kodukula et al., Mar. 1991, "Biosynthesis of phosphatidylinositol glycan-anchored membrane proteins. Design of a simple protein substrate to characterize the enzyme that cleaves the cooh-terminal signal peptide," J Biol Chem 266(7): 4464-4470.
Secor et al., Mar. 2000, "Mast cells are essential for early onset and severe disease in a murine model of multiple sclerosis," J Exp Med 191(5):813-822.
Shah et al., Sep. 2015, "c-Kit as a novel potential therapeutic target in colorectal cancer," Gastroenterology 149(3): 534-537 (published online in Jul. 2015).
Lebron et al., Sep. 2014, "A human monoclonal antibody targeting the stem cell factor receptor (c-Kit) blocks tumor cell signaling and inhibits tumor growth," Cancer Biology & Therapy 15(9): 1208-1218 (published online in Jun. 2014).
Dodd et al., Sep.-Oct. 2010, "Animal models of soft-tissue sarcoma," Disease Models & Mechanisms 3(9-10): 557-566 (published online in Aug. 2010).
Garton et al., Apr. 2017, "Anti-KIT monoclonal antibody treatment enhances the antitumor activity of immune checkpoint inhibitors by reversing tumor-induced immunosuppression," Mol Cancer Ther 16(4):671-680.
Imai and Takaoka, 2006, "Comparing antibody and small-molecule therapies for cancer", Nature Reviews Cancer 6(9): 714-727.
Brown et al., 2001, "Mechanisms underlying mast cell influence on EAE disease course," Molecular Immunology 38 (16-18): 1373-1378.
Notice of Allowance and Fee(s) Due dated May 20, 2020 in U.S. Appl. No. 16/270,116 (7 pages).

```
  1  MRGARGAWDF LCVLLLLLRV QTGSSQPSVS PGEPSPPSIH PGKSDLIVRV GDEIRLLCTD PGFVKWTFEI LDETNENKQN
                                         {D1
 81  EWITEKAEAT NTGKYTCTNK HGLSNSIYVF VRDPAKLFLV DRSLYGKEDN DTLVRCPLTD PEVTNYSLKG CQGKPLPKDL
                                      } {D2
161  RFIPDPKAGI MIKSVKRAYH RLCLHCSVDQ EGKSVLSEKF ILKVRPAFKA VPVVSVSKAS YLLREGEEFT VTCTIKDVSS
                                                            } {D3
241  SVYSTWKREN SQTKLQEKYN SWHHGDFNYE RQATLTISSA RVNDSGVFMC YANNTFGSAN VTTTLEVVDK GFINIFPMIN
                                                                                } {D4
321  TTVFVNDGEN VDLIVEYEAF PKPEHQQWIY MNRTFTDKWE DYPKSENESN IRYVSELHLT RLKGTEGGTY TFLVSNSDVN
              } {D5
401  AAIAFNVYVN TKPEILTYDR LVNGMLQCVA AGFPEPTIDW QIHPHTLFTP LLIGFVIVAG MMCIIVMILT KLVVQSSIDS
                                                }
481  SAFKHNGTVE CKAYNDVGKT SAYFNFAFKE PRNRLSFGKT LGAGAFGKVV EATAYGLIKS DAAMTVAVKM LKPSAHLTER EALMSELKVL
561  GNNYVYIDPT QLPYDHKWEF PRNRLSFGKT LGAGAFGKVV EATAYGLIKS DAAMTVAVKM LKPSAHLTER EALMSELKVL
641  SYLGNHMNIV NLLGACTIGG PTLVITEYCC YGDLLNFLRR KRDSFICSKQ EDHAEAALYK NLLHSKESSC SDSTNEYMDM
721  KPGVSYVVPT KADKRRSVRI GSYIERDVTP AIMEDDELAL DLEDLLSFSY QVAKGMAFLA SKNCIHRDLA ARNILLTHGR
801  ITKICDFGLA RDIKNDSNYV VKGNARLPVK WMAPESIFNC VYTFESDVWS YGIFLWELFS LGSSPYPGMP VDSKFYKMIK
881  EGFRMLSPEH APAEMYDIMK TCWDADPLKR PTFKQIVQLI EKQISESTNH IYSNLANCSP NRQKPVVDHS VRINSVGSTA
961  SSSQPLLVHD DV    (SEQ ID NO: 1)
```

Fig. 1

KIT Constructs

A. KIT D4/D5 Antigen (SEQ ID NO: 14): M1-E33 + V308-H515 (SEQ ID NO: 15) + 5 x His

```
  1  MRGARGAWDF LCVLLLLLRV QTGSSQPSVS PGEVDKGFIN IFPMINTTVF VNDGENVDLI
 61  VEYEAFPKPE HQQWIYMNRT FTDKWEDYPK SENESNIRYV SELHLTRLKG TEGGTYTFLV
121  SNSDVNAAIA FNVYVNTKPE ILTYDRLVNG MLQCVAAGFP EPTIDWYFCP GTEQRCSASV
181  LPVDVQTLNS SGPPFGKLVV QSSIDSSAFK HNGTVECKAY NDVGKTSAYF NFAFKEQIHP
241  HHHHHH
```

B. KIT D4 Antigen (SEQ ID NO: 16): M1-E33 + V308-K412 (SEQ ID NO: 17) + 6 x His

```
  1  MRGARGAWDF LCVLLLLLRV QTGSSQPSVS PGEVDKGFIN IFPMINTTVF VNDGENVDLI
 61  VEYEAFPKPE HQQWIYMNRT FTDKWEDYPK SENESNIRYV SELHLTRLKG TEGGTYTFLV
121  SNSDVNAAIA FNVYVNTKHH HHHH
```

C. KIT D5 Antigen (SEQ ID NO: 18): M1-E33 + N410-H515 (SEQ ID NO: 19) + 5 x His

```
  1  MRGARGAWDF LCVLLLLLRV QTGSSQPSVS PGENTKPEIL TYDRLVNGML QCVAAGFPEP
 61  TIDWYFCPGT EQRCSASVLP VDVQTLNSSG PPFGKLVVQS SIDSSAFKHN GTVECKAYND
121  VGKTSAYFNF AFKGNNKEQI HPHHHHHH
```

Fig. 2A-C

37M/C Variable Light Chain Region (SEQ ID NO:2)

```
VL FR1                          VL CDR1                VL FR2           VL CDR2
DIVMTQSQKFMSTSVGDRVSVTC KASQNVRTNVA WYQQKPGQSPKALIY SASYRYS ...

VL FR3                                VL CDR3       VL FR4
... GVPDRFTGSGSGTDFTLTISNVQSEDLADYFC QQYNSYPRT FGGGTKLEIKR
```

Fig. 3A

Variable Heavy Chain Region

```
                          VH
                          CDR1     VH FR2                    VH CDR2
             VH FR1
37M (SEQ ID NO:3)  QVQLKQSGAELVRPGASVKLSCKASGYTFT DYYIN WVKQRPGQGLEWIA RIYPGSGNTYYNEKFKG ...
37C (SEQ ID NO:5)  QVQLKQSGAELVRPGASVKLSCKASGYTFT DYYIN WVKQRPGQGLEWIA RIYPGSGNTYYNEKFKG ...

VH FR3                                VH CDR3   VH FR4
37M (SEQ ID NO:3) ... KATLTAEKSSSTAYMQLSSLTSEDSAVYFCAR GVYYFDY WGQGTTLTVSS
37C (SEQ ID NO:5) ... KATLTAEKSSSTAYMQLSSLTSEDSAVYFCAR GVYYFDY WGQGTTLTVSA
```

Fig. 3B

37M VL domain (SEQ ID NO: 2)

```
  1  DIVMTQSQKF MSTSVGDRVS VTCKASQNVR TNVAWYQQKP GQSPKALIYS ASYRYSGVPD
 61  RFTGSGSGTD FTLTISNVQS EDLADYFCQQ YNSYPRTFGG GTKLEIKR
```

DNA Sequence (324 bp) (SEQ ID NO: 8)

```
  1  gacattgtga tgacccagtc tcaaaaattc atgtccacat cagtaggaga caggtcagc
 61  gtcacctgca aggccagtca gaatgtgcgt actaatgtag cctggtatca acagaaacca
121  gggcaatctc ctaaagcact gatttactcg gcatcctacc gtacagtgg agtccctgat
181  cgcttcacag gcagtggatc tgggacagat ttcactctca ccatcagcaa tgtgcagtct
241  gaagacttgg cagactattt ctgtcagcaa tataacagct atccctcggac gttcggtgga
301  ggcaccaagc tggaaatcaa acgt
```

37M VH domain (SEQ ID NO: 3)

```
  1  QVQLKQSGAE LVRPGASVKL SCKASGYTFT DYYINWVKQR PGQGLEWIAR IYPGSGNTYY
 61  NEKFKGKATL TAEKSSSTAY MQLSSLTSED SAVYFCARGV YYFDYWGQGT TLTVSS
```

DNA Sequence (348 bp) (SEQ ID NO: 9)

```
  1  caggtccagc tgaagcagtc tggggctgag ctggtgaggc ctggggcctc agtgaagctg
 61  tcctgcaagg cttctggcta cactttcact gactactata taaactgggt gaagcagagg
121  cctggacagg gacttgagtg gattgcaagg atttaccctg gaagtggtaa tacttactac
181  aatgagaagt tcaagggcaa ggccacactg actgcagaaa aatcctccag cactgcctac
241  atgcagctca gcagcctgac atctgaggac tctgctgtct atttctgtgc aaggggggtg
301  tactactttg actactgggg ccaaggcacc actctcacag tctcctca
```

Fig. 4

Antibody 37C 37C light chain (SEQ ID NO: 6)

Protein Sequence

```
  1  MGWSCIILFL VATATGVHSD IVMTQSQKFM STSVGDRVSV TCKASQNVRT NVAWYQQKPG
 61  QSPKALIYSA SYRYSGVPDR FTGSGSGTDF TLTISNVQSE DLADYFCQQY NSYPRTFGGG
121  TKLEIKRTVA APSVFIFPPS DEQLKSGTAS VVCLLNNFYP REAKVQWKVD NALQSGNSQE
181  SVTEQDSKDS TYSLSSTLTL SKADYEKHKV YACEVTHQGL SSPVTKSFNR GEC
```

SEQ ID NO: 12 = light chain constant region 37C heavy chain (SEQ ID NO: 7)

```
  1  MGWSCIILFL VATATGVHSQ VQLKQSGAEL VRPGASVKLS CKASGYTFTD YYINWVKQRP
 61  GQGLEWIARI YPGSGNTYYN EKFKGKATLT AEKSSSTAYM QLSSLTSEDS AVYFCARGVY
121  YFDYWGQGTT LTVSAASTKG PSVFPLAPSS KSTSGGTAAL GCLVKDYFPE PVTVSWNSGA
181  LTSGVHTFPA VLQSSGLYSL SSVVTVPSSS LGTQTYICNV NHKPSNTKVD KKVEPKSCDK
241  THTCPPCPAP ELLGGPSVFL FPPKPKDTLM ISRTPEVTCV VVDVSHEDPE VKFNWYVDGV
301  EVHNAKTKPR EEQYNSTYRV VSVLTVLHQD WLNGKEYKCK VSNKALPAPI EKTISKAKGQ
361  PREPQVYTLP PSRDELTKNQ VSLTCLVKGF YPSDIAVEWE SNGQPENNYK TTPPVLDSDG
421  SFFLYSKLTV DKSRWQQGNV FSCSVMHEAL HNHYTQKSLS LSPGK
```

SEQ ID NO: 13 = heavy chain constant region

Fig. 5A

37C light chain DNA Sequence (SEQ ID NO: 10)

DNA Sequence

```
  1 atgggctgga gctgcatcat cctgttcctg gtggccaccg ccaccggtgt gcacagcgac
     M  G  W   S  C  I  I   L  F  L   V  A  T  A   T  G  V   H  S  D
 61 attgtgatga cccagtctca aaaattcatg tccacatcag taggagacag ggtcagcgtc
     I  V  M   T  Q  S  Q   K  F  M   S  T  S  V   G  D  R   V  S  V
121 acctgcaagg ccagtcagaa tgtgcgtact aatgtagcct ggtatcaaca gaaaccaggg
     T  C  K   A  S  Q  N   V  R  T   N  V  A  W   Y  Q  Q   K  P  G
181 caatctccta aagcactgat ttactcggca tcctaccggt acagtggagt ccctgatcgc
     Q  S  P   K  A  L  I   Y  S  A   S  Y  R  Y   S  G  V   P  D  R
241 ttcacaggca gtggatctgg gacagatttc actctcacca tcagcaatgt gcagtctgaa
     F  T  G   S  G  S  G   T  D  F   T  L  T  I   S  N  V   Q  S  E
301 gacttggcag actatttctg tcagcaatat cagcagtatc ctcggacgtt cggtggaggc
     D  L  A   D  Y  F  C   Q  Q  Y   N  S  Y  P   R  T  F   G  G  G
361 accaagctcg agatcaagag aaccgtggcc gcccccagcg tgttcatctt ccccccagc
     T  K  L   E  I  K  R   T  V  A   A  P  S  V   F  I  F   P  P  S
421 gacgagcagc tgaagagcgg caccgccagc gtggtgtgcc tgctgaacaa cttctacccc
     D  E  Q   L  K  S  G   T  A  S   V  V  C  L   L  N  N   F  Y  P
481 agagaggcca aggtgcagtg gaaggtggac aacgccctgc agagcggcaa cagccaggag
     R  E  A   K  V  Q  W   K  V  D   N  A  L  Q   S  G  N   S  Q  E
541 agcgtgaccg agcaggacag caaggacagc acctacagcc tgagcagcac cctgaccctg
     S  V  T   E  Q  D  S   K  D  S   T  Y  S  L   S  S  T   L  T  L
601 agcaaggccg actacgagaa gcacaaggtg tacgcctgcg aggtgaccca ccagggcctg
     S  K  A   D  Y  E  K   H  K  V   Y  A  C  E   V  T  H   Q  G  L
661 agcagccccg tgaccaagag cttcaacaga ggcgagtgct ga
     S  S  P   V  T  K  S   F  N  R   G  E  C
```

Fig. 5B

37C heavy chain DNA Sequence (SEQ ID NO: 11)

```
   1 atgggctgga gctgcatcat cctgttcctg gtggccaccg ccaccggcgt gcacagccag
     M   G   W   S   C   I   I   L   F   L   V   A   T   A   T   G   V   H   S   Q
  61 gtgcaattga agcagtctgg ggctgagctg gtgaggcctg gggcctcagt gaagctgtcc
     V   Q   L   K   Q   S   G   A   E   L   V   R   P   G   A   S   V   K   L   S
 121 tgcaaggctt ctggctacac tttcactgac tactatataa actgggtgaa gcagaggcct
     C   K   A   S   G   Y   T   F   T   D   Y   Y   I   N   W   V   K   Q   R   P
 181 ggacaggggac ttgagtggat tgcaaggatt taccctggaa gtggtaatac ttactacaat
     G   Q   G   L   E   W   I   A   R   I   Y   P   G   S   G   N   T   Y   Y   N
 241 gagaagttca agggcaaggc cacactgact gcagaaaaat cctccagcac tgcctacatg
     E   K   F   K   G   K   A   T   L   T   A   E   K   S   S   S   T   A   Y   M
 301 cagctcagca gcctgacatc tgaggactct gctgtctatt tctgtgcaag gggggtgtac
     Q   L   S   S   L   T   S   E   D   S   A   V   Y   F   C   A   R   G   V   Y
 361 tactttgact actggggcca aggcaccact ctcacagtct ccgcggccag cactaagggc
     Y   F   D   Y   W   G   Q   G   T   T   L   T   V   S   A   A   S   T   K   G
 421 cccagcgtgt tcccgctagc ccccagcagc aagagcacca gcggcggcac cgccgccctg
     P   S   V   F   P   L   A   P   S   S   K   S   T   S   G   G   T   A   A   L
 481 ggctgcctgg tgaaggacta cttccccgag cccgtgaccg tgagctggaa cagcggcgcc
     G   C   L   V   K   D   Y   F   P   E   P   V   T   V   S   W   N   S   G   A
 541 ctgaccagcg gcgtgcacac cttccccgcc gtgctgcaga gcagcggcct gtacagcctg
     L   T   S   G   V   H   T   F   P   A   V   L   Q   S   S   G   L   Y   S   L
 601 agcagcgtgg tgaccgtgcc cagcagcagc ctgggcaccc agacctacat ctgcaacgtg
     S   S   V   V   T   V   P   S   S   S   L   G   T   Q   T   Y   I   C   N   V
 661 aaccacaagc ccagcaacac caaggtggac aagaaggtgg agcccaagag ctgcgacaag
     N   H   K   P   S   N   T   K   V   D   K   K   V   E   P   K   S   C   D   K
 721 acccacacct gccccccctg ccccgccccc gagctgctgg gcggccccag cgtgttcctg
     T   H   T   C   P   P   C   P   A   P   E   L   L   G   P   S   V   F   L
 781 ttcccccca agcccaagga caccctgatg atcagcagaa ccccgaggt gacctgcgtg
     F   P   P   K   P   K   D   T   L   M   I   S   R   T   P   E   V   T   C   V
 841 gtggtggacg tgagccacga ggaccccgag gtgaagttca actggtacgt ggacggcgtg
     V   V   D   V   S   H   E   D   P   E   V   K   F   N   W   Y   V   D   G   V
 901 gaggtgcaca acgccaagac caagcccaga gaggagcagt acaacagcac ctacagagtg
     E   V   H   N   A   K   T   K   P   R   E   E   Q   Y   N   S   T   Y   R   V
 961 gtgagcgtgc tgaccgtgct gcaccaggac tggctgaacg gcaaggagta caagtgcaag
     V   S   V   L   T   V   L   H   Q   D   W   L   N   G   K   E   Y   K   C   K
1021 gtgagcaaca aggccctgcc cgcccccatc gagaagacca tcagcaaggc caagggccag
     V   S   N   K   A   L   P   A   P   I   E   K   T   I   S   K   A   K   G   Q
1081 cccagagagc cccaggtgta caccctgccc ccagcagag acgagctgac caagaaccag
     P   R   E   P   Q   V   Y   T   L   P   P   S   R   D   E   L   T   K   N   Q
1141 gtgagcctga cctgcctggt gaagggcttc taccccagcg acatcgccgt ggagtgggag
     V   S   L   T   C   L   V   K   G   F   Y   P   S   D   I   A   V   E   W   E
1201 agcaacggcc agcccgagaa caactacaag acccaccccc ccgtgctgga cagcgacggc
     S   N   G   Q   P   E   N   N   Y   K   T   T   P   P   V   L   D   S   D   G
1261 agcttcttcc tgtacagcaa gctgaccgtg gacaagagca gatggcagca gggcaacgtg
     S   F   F   L   Y   S   K   L   T   V   D   K   S   R   W   Q   Q   G   N   V
1321 ttcagctgca gcgtgatgca cgaggccctg cacaaccact acacccagaa gagcctgagc
     F   S   C   S   V   M   H   E   A   L   H   N   H   Y   T   Q   K   S   L   S
1381 ctgagccccg gcaagtag
     L   S   P   G   K
```

Fig. 5C

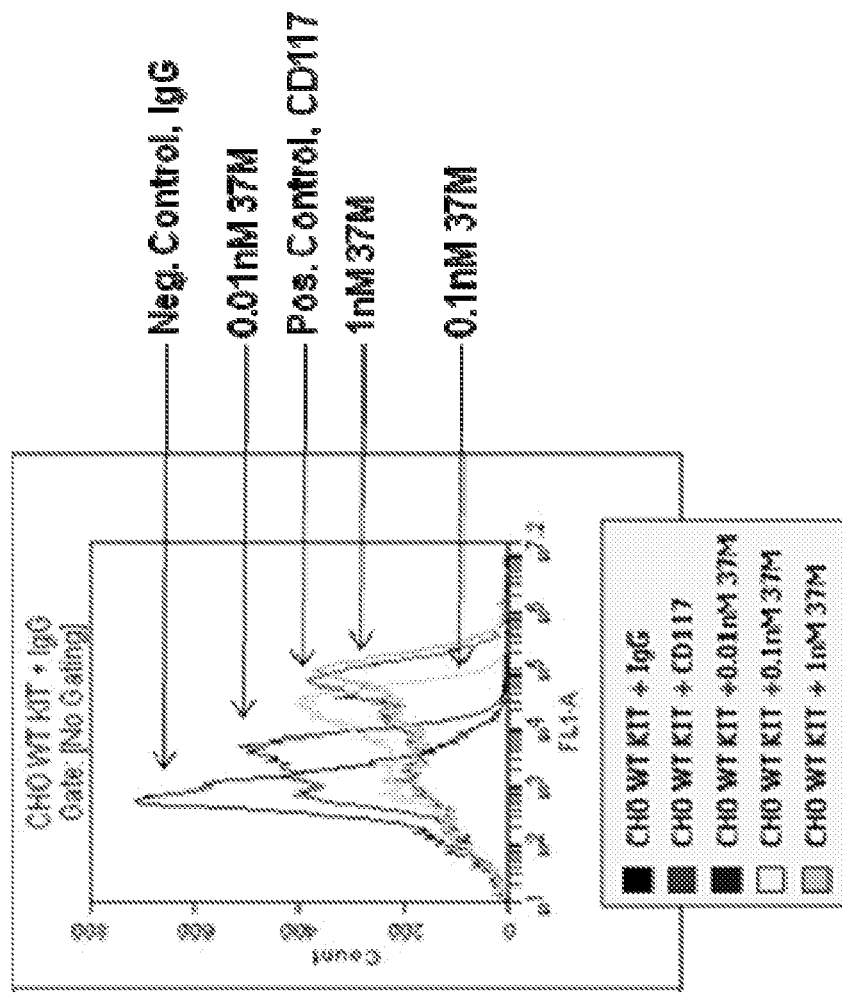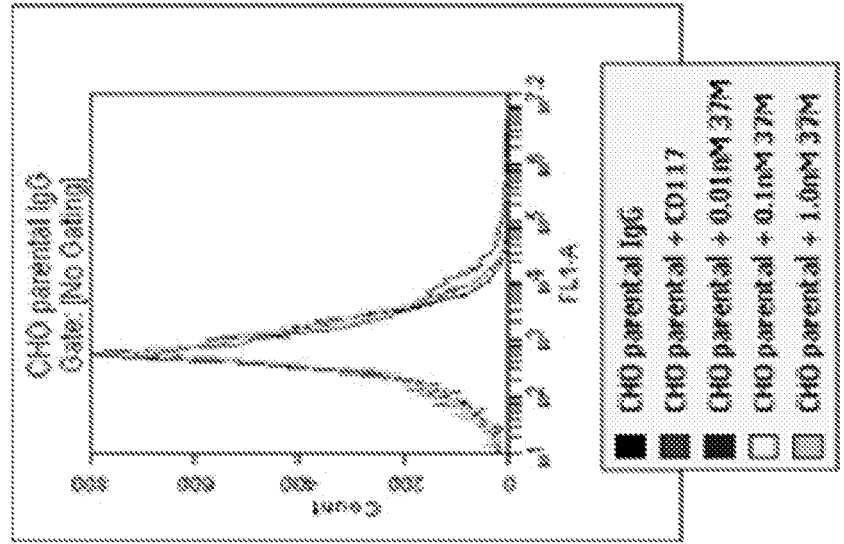
Fig. 10B-C

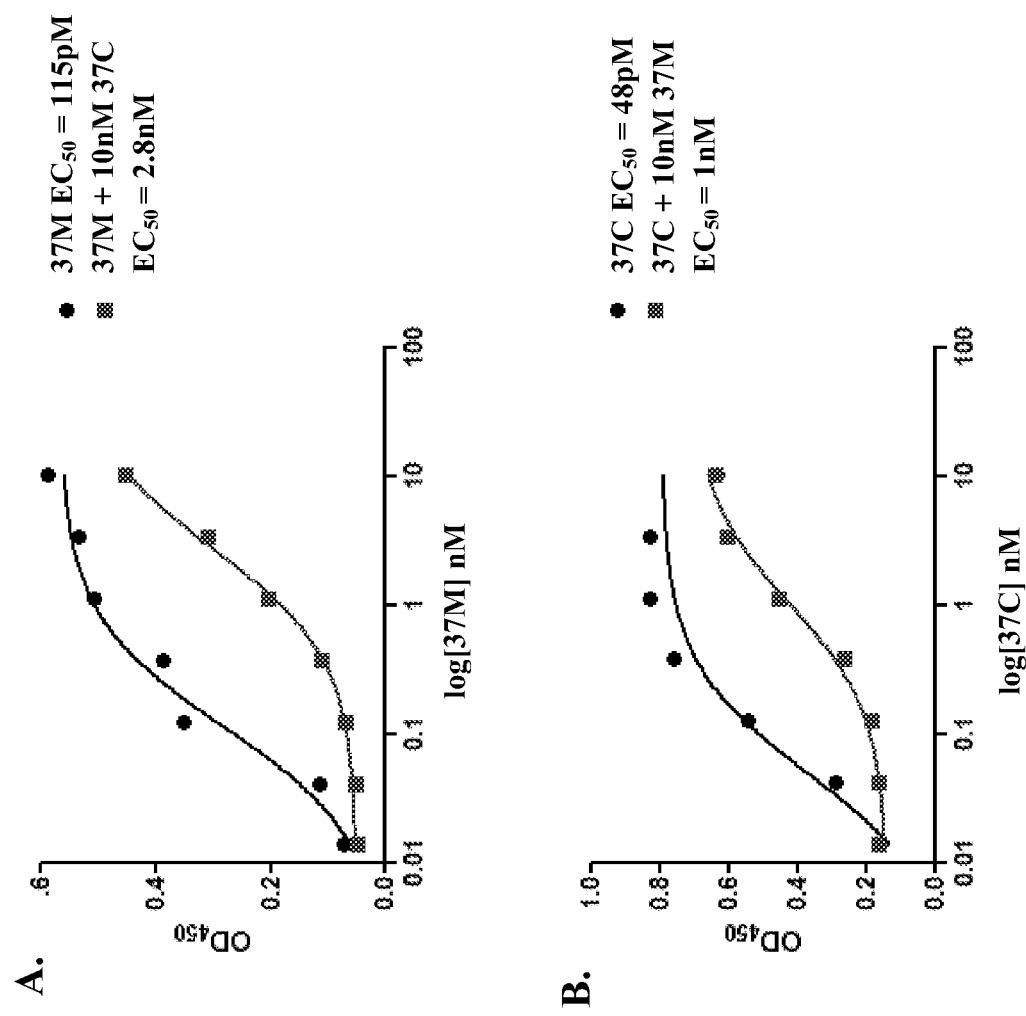
Fig. 14A-B

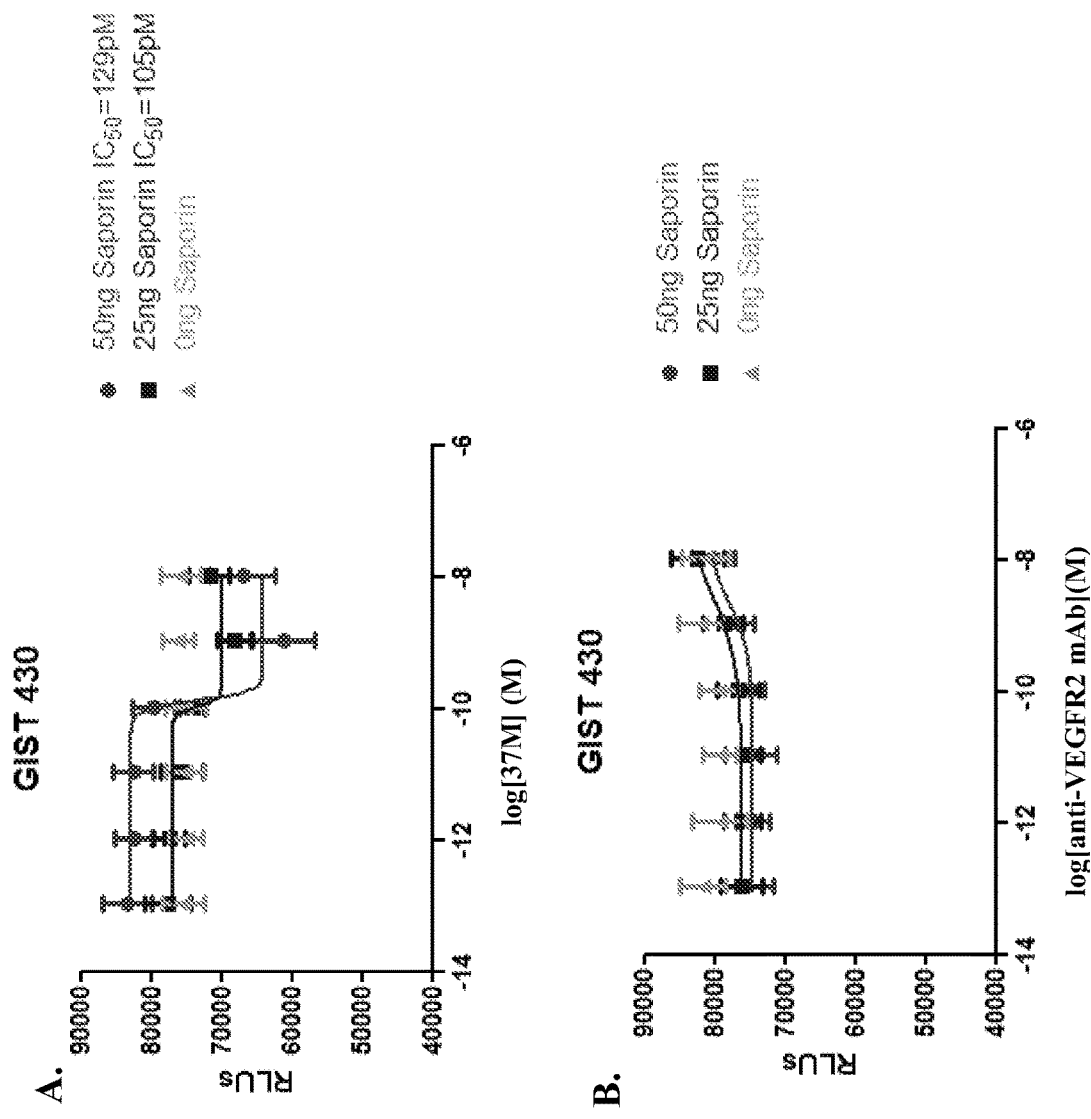
Fig. 15A-B

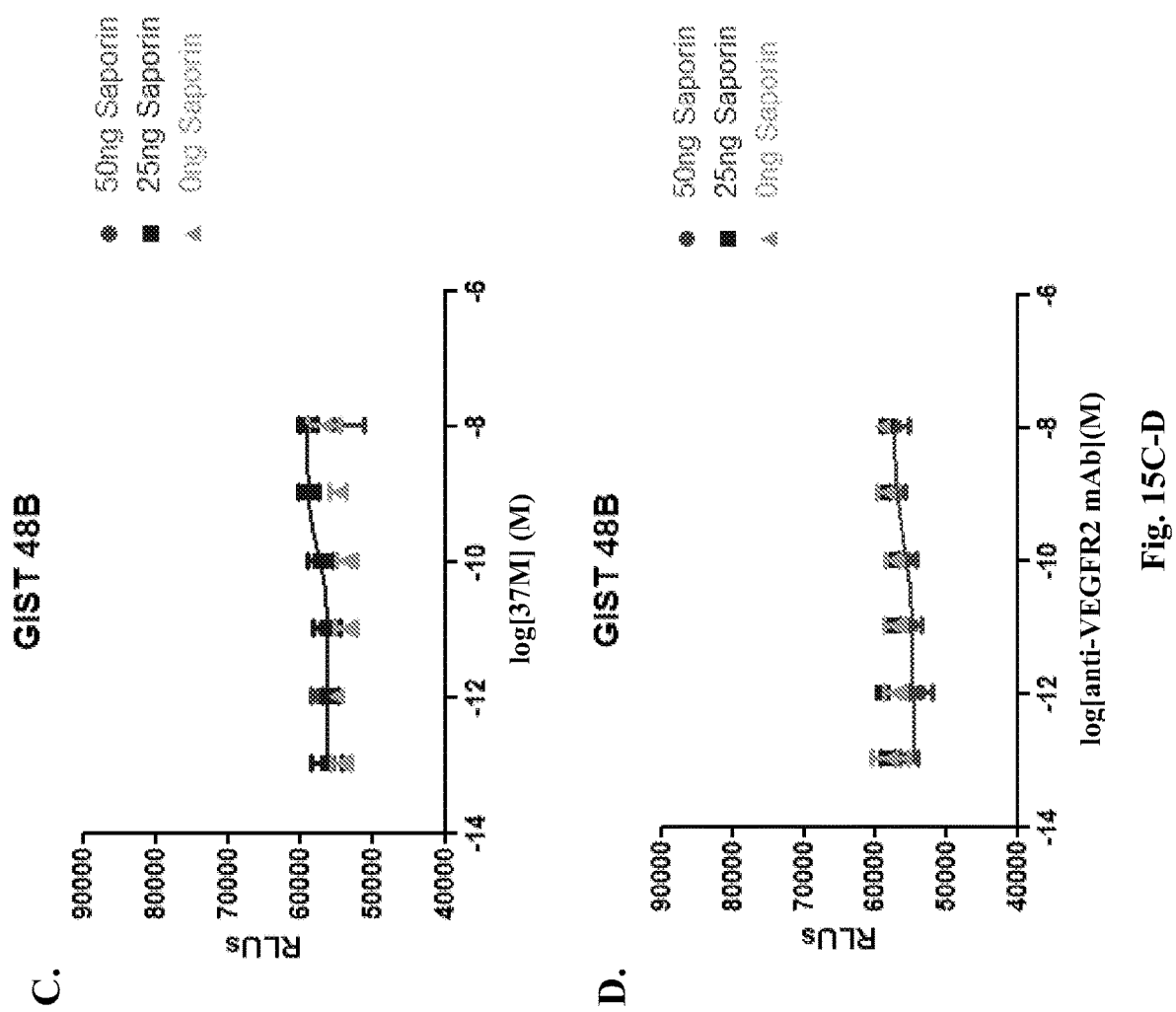
Fig. 15C-D

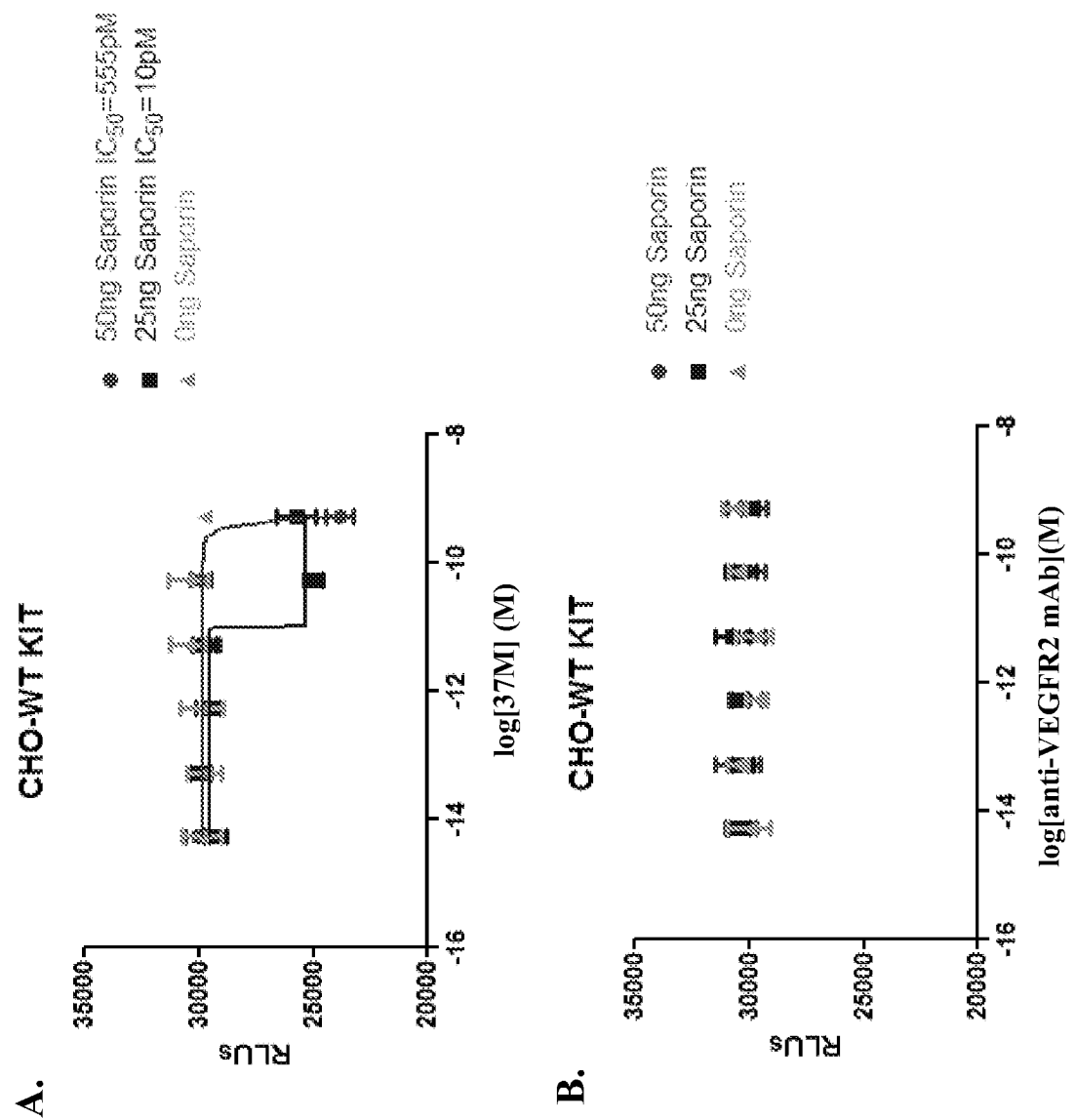
Fig. 16A-B

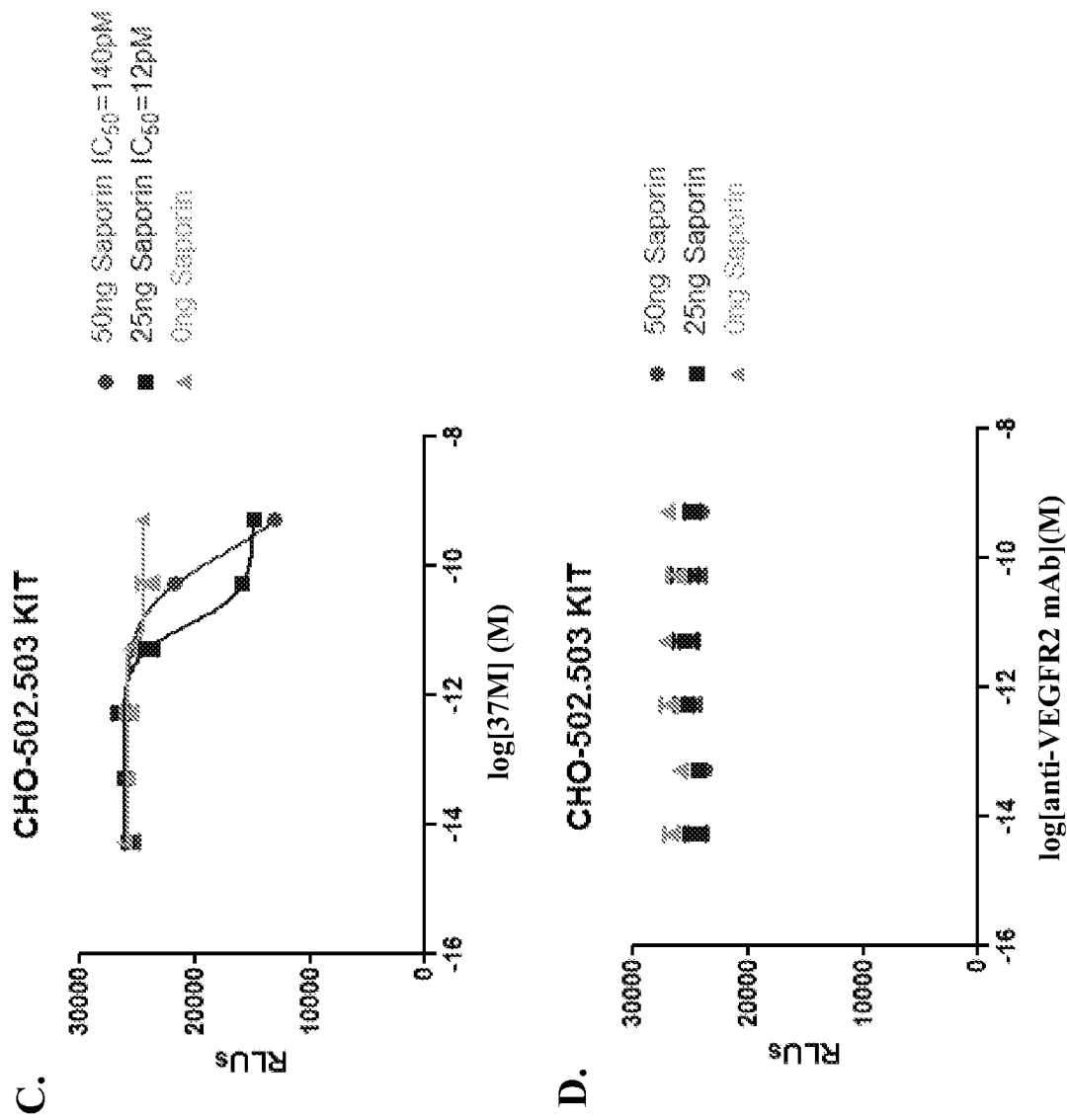
Fig. 16C-D

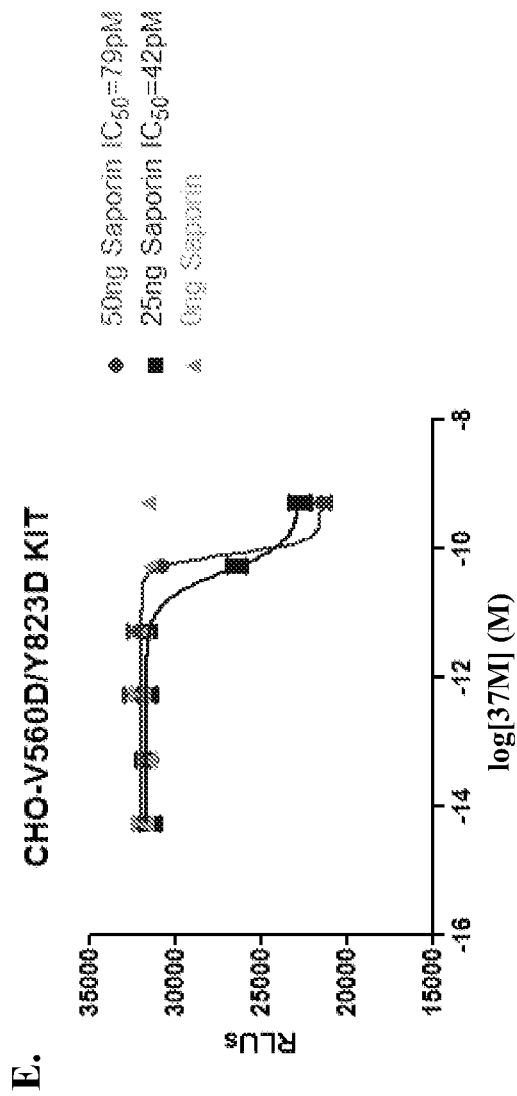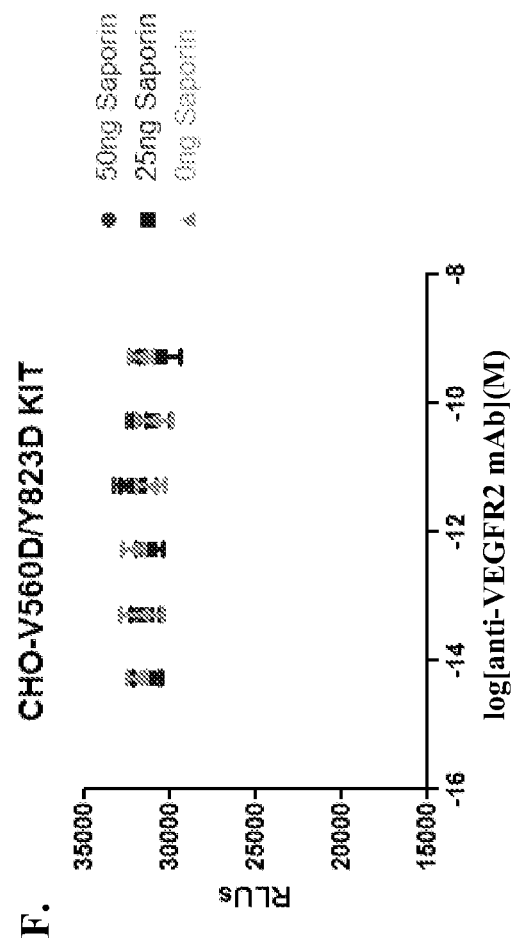
Fig. 16E-F

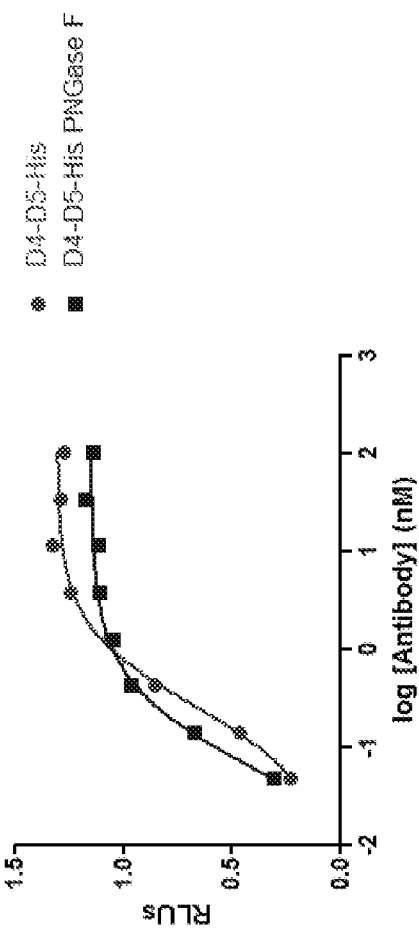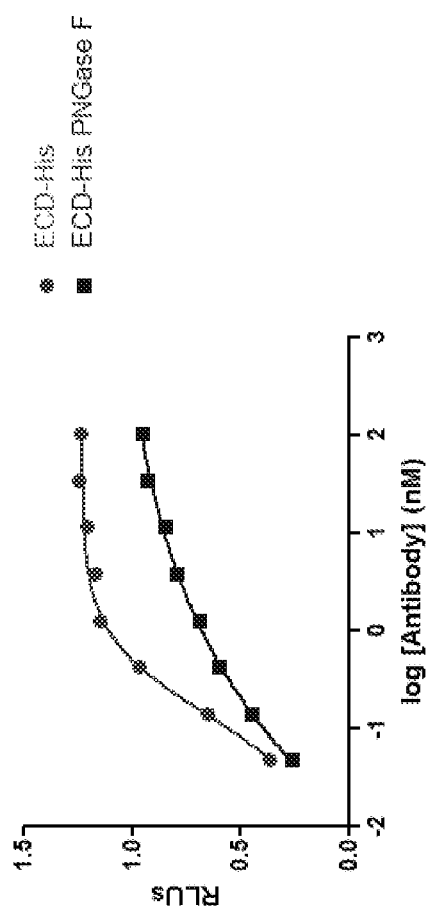
Fig. 17B-C

METHODS OF TREATING BY ADMINISTERING ANTI-KIT ANTIBODIES

This application is a divisional application of U.S. patent application Ser. No. 15/361,936, filed Nov. 28, 2016, which is a divisional application of U.S. patent application Ser. No. 13/981,852, which is a U.S. national stage of International Patent Application No. PCT/US2012/022471, filed Jan. 25, 2012, which claims the benefit of U.S. Provisional Application No. 61/436,483, filed Jan. 26, 2011, U.S. Provisional Application No. 61/507,430, filed Jul. 13, 2011, and U.S. Provisional Application No. 61/537,482, filed Sep. 21, 2011; the foregoing applications are hereby incorporated by reference in their entireties.

The instant application contains a Sequence Listing submitted as an ASCII text file named "12638-074-999 Sequence_Listing_CRF.TXT", created Nov. 23, 2016, and being 43,373 bytes in size. The Sequence Listing is hereby incorporated by reference in its entirety.

1. FIELD

Provided herein are antibodies that specifically bind to a KIT antigen, polynucleotides comprising nucleotide sequences encoding such antibodies, expression vectors and host cells for producing such antibodies, kits and pharmaceutical compositions comprising antibodies that immunospecifically bind to a KIT antigen, methods for treating or managing a KIT-mediated disorder, and diagnostic methods.

2. BACKGROUND

KIT (or c-Kit) is a type III receptor tyrosine kinase encoded by the c-kit gene. KIT comprises five extracellular immunoglobulin (Ig)-like domains, a single transmembrane region, an inhibitory cytoplasmic juxtamembrane domain, and a split cytoplasmic kinase domain separated by a kinase insert segment (see, e.g., Yarden et al., Nature, 1986, 323: 226-232; Ullrich and Schlessinger, Cell, 1990, 61:203-212; Clifford et al., J. Biol. Chem., 2003, 278:31461-31464). The human c-kit gene encoding the KIT receptor has been cloned as described by Yarden et al., EMBO J., 1987, 6:3341-3351. KIT is also known as CD117 or stem cell factor receptor ("SCFR"), because it is the receptor for the stem cell factor ("SCF") ligand (also known as Steel Factor or Kit Ligand). SCF ligand binding to the first three extracellular Ig-like domains of KIT induces receptor dimerization, and thereby activates intrinsic tyrosine kinase activity through the phosphorylation of specific tyrosine residues in the juxtamembrane and kinase domains (see, e.g., Weiss and Schlessinger, Cell, 1998, 94:277-280; Clifford et al., J. Biol. Chem., 2003, 278:31461-31464). Members of the Stat, Src, ERK, and AKT signaling pathways have been shown to be downstream signal transducers of KIT signaling.

The fourth (D4) and fifth (D5) extracellular Ig-like domains of KIT are believed to mediate receptor dimerization (see, e.g., International Patent Application Publication No. WO 2008/153926; Yuzawa et al., Cell, 2007, 130:323-334).

Expression of KIT has been detected in various cell types, such as mast cells, stem cells, brain cells, melanoblasts, ovary cells, and cancer cells (e.g., leukemia cells). Studies of loss-of-function KIT mutations indicate that KIT is important for the normal growth of hematopoietic progenitor cells, mast cells, melanocytes, primordial germ cells, and the interstitial cells of Cajal (see, e.g., Besmer, P., Curr. Opin. Cell Biol., 1991, 3:939-946; Lyman et al., Blood, 1998, 91:1101-1134; Ashman, L. K., Int. J. Biochem. Cell Biol., 1999, 31:1037-1051; Kitamura et al., Mutat. Res., 2001, 477:165-171; Mol et al., J. Biol. Chem., 2003, 278:31461-31464). Moreover, KIT plays an important role in hematopoiesis, melanogenesis, and gametogenesis (see Ueda et al., Blood, 2002, 99:3342-3349).

Abnormal KIT activity has been implicated in connection with a number of cancers. For example, gain-of-function KIT mutations resulting in SCF-independent, constitutive activation of KIT are found in certain cancer cells and are associated with certain cancers such as leukemia (e.g., chronic myelogenous leukemia) and gastrointestinal stromal tumors (see, e.g., Mol et al., J. Biol. Chem., 2003, 278: 31461-31464).

3. SUMMARY

Provided herein, in one aspect, are antibodies (and antigen-binding fragments thereof) that immunospecifically bind to a D4/D5 region in the extracellular domain of KIT (e.g., human KIT) and inhibit a KIT activity, as well as related compositions, reagents and methods.

In a specific embodiment, provided herein is antibody 37M (including antigen-binding fragments thereof) comprising a variable light ("VL") chain region comprising the amino acid sequence of SEQ ID NO: 2, and a variable heavy ("VH") chain region comprising the amino acid sequence of SEQ ID NO: 3. In a particular embodiment, provided herein is antibody 37C (including antigen-binding fragments thereof) comprising a VL chain region comprising the amino acid sequence of SEQ ID NO: 2 and a VH chain region comprising the amino acid sequence of SEQ ID NO: 5. In other particular embodiments, presented herein is an antibody (or an antigen-binding fragment thereof) comprising the CDRs of antibody 37M or 37C (e.g., VL CDRs of SEQ ID NO: 2 and/or VH CDRs of SEQ ID NO: 3 or 5; or SEQ ID NOs: 20, 21, 22, 23, 24, and/or 25). In certain embodiments, provided herein are antibodies (or antigen-binding fragments thereof) which compete with antibody 37M or 37C for binding to a D4/D5 region of KIT (e.g., human KIT), for example SEQ ID NO: 15. In certain embodiments, provided herein is an antibody (or an antigen-binding fragment thereof) that immunospecifically binds to a D4/D5 region of KIT (e.g., human KIT), for example SEQ ID NO: 15, wherein the antibody binds to the same epitope as an epitope of antibody 37M or 37C.

In one aspect, provided herein is an antibody (or an antigen-binding fragment thereof), which immunospecifically binds to a D4/D5 region of human KIT (e.g., SEQ ID NO: 15), comprising:

(A) a variable light ("VL") chain region comprising the amino acid sequence of SEQ ID NO: 2, and a variable heavy ("VH") chain region comprising the amino acid sequence of SEQ ID NO: 3; or (B) a VL chain region comprising the amino acid sequence of SEQ ID NO: 2 and a VH chain region comprising the amino acid sequence of SEQ ID NO: 5.

In a particular embodiment, an antibody (or an antigen-binding fragment thereof), which immunospecifically binds to a D4/D5 region of human KIT (e.g., SEQ ID NO: 15), comprises: a VL chain region comprising the amino acid sequence of SEQ ID NO: 2, and a VH chain region comprising the amino acid sequence of SEQ ID NO: 3 or SEQ ID NO: 3 with one amino acid substitution at the C-terminal amino acid (i.e., amino acid at position 116 of SEQ ID NO: 3). In a specific embodiment, the amino acid substitution at position 116 of SEQ ID NO: 3 is an S to A substitution.

In a second aspect, provided herein is an antibody (or an antigen-binding fragment thereof), which immunospecifically binds to a D4/D5 region of human KIT (e.g., SEQ ID NO: 15), comprising:

(i) a VL chain region comprising a VL CDR1, VL CDR2, and VL CDR3 having the amino acid sequences of SEQ ID NO: 20, SEQ ID NO: 21, and SEQ ID NO: 22, respectively; and (ii) a VH chain region comprising a VH CDR1, VH CDR2, and VH CDR3 having the amino acid sequences of SEQ ID NO: 23, SEQ ID NO: 24, and SEQ ID NO: 25, respectively.

In a third aspect, provided herein is an antibody (or an antigen-binding fragment thereof), which immunospecifically binds to a D4/D5 region of human KIT (e.g., SEQ ID NO: 15), comprising:

a VL chain region comprising a VL CDR1, VL CDR2, and VL CDR3 having the amino acid sequences of SEQ ID NO: 20, SEQ ID NO: 21, and SEQ ID NO: 22, respectively; and a VH chain region comprising the amino acid sequence of SEQ ID NO: 3 or 5.

In a fourth aspect, provided herein is an antibody (or an antigen-binding fragment thereof), which immunospecifically binds to a D4/D5 region of human KIT (e.g., SEQ ID NO: 15), comprising:

a VL chain region comprising the amino acid sequence of SEQ ID NO: 2; and a VH chain region comprising a VH CDR1, VH CDR2, and VH CDR3 having the amino acid sequences of SEQ ID NO:23, SEQ ID NO: 24, and SEQ ID NO: 25, respectively.

In certain embodiments, antibodies described herein comprise a human light chain constant region and a human heavy chain constant region. In further embodiments, the human light chain constant region is a human kappa light chain constant region. In another embodiment, the human heavy chain constant region is a human gamma heavy chain constant region. In certain embodiments, the antibody is an IgG1 isotype f antibody. In particular embodiments, the human light chain constant region comprises the amino acid sequence of SEQ ID NO: 12. In specific embodiments, the human heavy chain constant region comprises the amino acid sequence of SEQ ID NO: 13. In certain embodiments, an antibody described herein comprises (i) a human light chain constant region comprising the amino acid sequence of SEQ ID NO: 12, (ii) a variable light chain region comprising the amino acid sequence of SEQ ID NO: 2, (iii) a human heavy chain constant region comprising the amino acid sequence of SEQ ID NO: 13, and (iv) a variable heavy chain region comprising the amino acid sequence of SEQ ID NO: 3 or 5. In certain embodiments, an antibody described herein (or an antigen-binding fragment thereof) comprises a light chain comprising the amino acid sequence of SEQ ID NO: 6 (or the amino acid sequence of SEQ ID NO: 6 starting at position 20, lacking the signal peptide), and a heavy chain comprising the amino acid sequence of SEQ ID NO: 7 (or the amino acid sequence of SEQ ID NO: 7 starting at position 20, lacking the signal peptide).

In a particular embodiment, the antibody described herein (or an antigen-binding fragment thereof) is a monoclonal antibody, e.g., a murine, chimeric, or humanized monoclonal antibody. In a certain embodiment, the antibody described herein (or an antigen-binding fragment thereof) is an isolated antibody. In a particular embodiment, the antibody described herein (or an antigen-binding fragment thereof) is a chimeric antibody. In another embodiment, the antibody described herein (or an antigen-binding fragment thereof) is a humanized antibody comprising the CDRs of antibody 37M or 37C (e.g., VL CDRs of SEQ ID NO: 2 and/or VH CDRs of SEQ ID NO: 3 or 5; or SEQ ID NOs: 20, 21, 22, 23, 24, and/or 25). In another particular embodiment, the antibody described herein is an antigen-binding antibody fragment, e.g., a Fab antibody (e.g., a Fab antibody of antibody 37M or 37C). In yet another particular embodiment, the antibody described herein (or the antigen-binding fragment thereof) is a human IgG1 or IgG4 antibody. In yet another particular embodiment, the antibody described herein (or an antigen-binding fragment thereof) is an inhibitor of KIT activity. In a further embodiment, the antibody described herein (or an antigen-binding fragment thereof) which is an inhibitor of KIT activity, inhibits KIT receptor phosphorylation by at least 25% as determined by a solid phase ELISA assay. In one embodiment, the antibody described herein (or an antigen-binding fragment thereof) which is an inhibitor of KIT activity inhibits KIT receptor phosphorylation by 25% to 80% as determined by a solid phase ELISA assay. In another embodiment, the antibody described herein (or an antigen-binding fragment thereof) which is an inhibitor of KIT activity inhibits KIT receptor phosphorylation by at least 50% as determined by a solid phase ELISA assay. In yet another embodiment, an antibody described herein (or an antigen-binding fragment thereof) which is an inhibitor of KIT activity does not block KIT ligand binding to the KIT receptor. In a further embodiment, the antibody described herein (or an antigen-binding fragment thereof) which is an inhibitor of KIT activity does not inhibit KIT receptor dimerization. In yet a further embodiment, the antibody described herein (or an antigen-binding fragment thereof) which is an inhibitor of KIT activity enhances KIT receptor internalization or KIT receptor degradation. In another embodiment, an antibody described herein (or an antigen-binding fragment thereof) which is an inhibitor of KIT activity induces apoptosis when a cell expressing KIT is contacted with an effective amount of the antibody.

In a specific embodiment, an antibody provided herein (or an antigen-binding fragment thereof), which immunospecifically binds to a D4/D5 region of human KIT (e.g., SEQ ID NO: 15), immunospecifically binds to the same epitope as that of an antibody comprising a VL domain comprising the amino acid sequence of SEQ ID NO: 2, and a VH domain comprising the amino acid sequence of SEQ ID NO: 3 or 5. In a particular embodiment, an antibody provided herein (or an antigen-binding fragment thereof), which immunospecifically binds to a D4/D5 region of human KIT (e.g., SEQ ID NO: 15), immunospecifically binds to the same epitope as that of an antibody comprising (i) a VL chain region comprising VL CDR1, VL CDR2, and VL CDR3 having the amino acid sequences of SEQ ID NOs: 20, 21, and 22, respectively, and (ii) a VH chain region comprising VH CDR1, VH CDR2, and VH CDR3 having the amino acid sequences of SEQ ID NOs: 23, 24, and 25, respectively. In a certain embodiment, an antibody provided herein (or an antigen-binding fragment thereof), which immunospecifically binds to a D4/D5 region of human KIT (e.g., SEQ ID NO: 15), immunospecifically binds to the same epitope as that of antibody 37M or 37C.

In a specific embodiment, an antibody provided herein (or an antigen-binding fragment thereof), which immunospecifically binds to a D4/D5 region of human KIT (e.g., SEQ ID NO: 15), competes (e.g., in a dose-dependent manner) for binding to a D4/D5 region of human KIT with an antibody comprising a VL domain comprising the amino acid sequence of SEQ ID NO: 2, and a VH domain comprising the amino acid sequence of SEQ ID NO: 3 or 5. In a particular embodiment, an antibody provided herein (or an antigen-binding fragment thereof), which immunospecifically binds to a D4/D5 region of human KIT (e.g., SEQ ID NO: 15 competes (e.g., in a dose-dependent manner) for binding to a D4/D5 region of human KIT with an antibody comprising (i) a VL chain region comprising VL CDR1, VL CDR2, and VL CDR3 having the amino acid sequences of SEQ ID NOs: 20, 21, and 22, respectively, and (ii) a VH chain region comprising VH CDR1, VH CDR2, and VH CDR3 having the amino acid sequences of SEQ ID NOs: 23, 24, and 25, respectively. In a certain embodiment, an antibody provided herein (or an antigen-binding fragment thereof), which immunospecifically binds to a D4/D5 region of human KIT (e.g., SEQ ID NO: 15), competes (e.g., in a dose-dependent manner) for binding to a D4/D5 region of human KIT with antibody 37M or 37C. In a specific embodiment, an antibody provided herein (or an antigen-binding fragment thereof) which immunospecifically binds to a D4/D5 region of human KIT (e.g., SEQ ID NO: 15), and competes (e.g., in a dose-dependent manner) for binding to a D4/D5 region of human KIT with antibody 37M or 37C, comprises (i) VL CDR1, VL CDR2, and VL CDR3 having the amino acid sequences of SEQ ID NOs: 20, 21, and 22, respectively, and (ii) a VH chain region comprising VH CDR1, VH CDR2, and VH CDR3 having the amino acid sequences of SEQ ID NOs: 23, 24, and 25, respectively.

In certain embodiments, an antibody described herein or antigen-binding fragment thereof (e.g., antibody comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively) binds to an extracellular domain of human KIT comprising a mutation, for example a somatic mutation associated with cancer (e.g., GIST), such as a mutation in exon 9 of human KIT wherein the Ala and Tyr residues at positions 502 and 503 are duplicated. In certain embodiments, an antibody described herein or antigen-binding fragment thereof (e.g., antibody comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively) binds to an extracellular domain of wild-type human KIT and an extracellular domain of human KIT comprising a mutation, for example a somatic mutation associated with cancer (e.g., GIST), such as a mutation in exon 9 of human KIT wherein the Ala and Tyr residues at positions 502 and 503 are duplicated. In certain embodiments, an antibody described herein or antigen-binding fragment thereof (e.g., antibody comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively) binds to an extracellular domain of human KIT which is glycosylated. In certain embodiments, an antibody described herein or antigen-binding fragment thereof (e.g., antibody comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively) binds to an extracellular domain of human KIT which is not glycosylated.

In a eighth aspect, provided herein is a vector, e.g., a mammalian expression vector comprising one or more polynucleotides (or isolated polynucleotides) comprising nucleotide sequences encoding an antibody described herein (e.g., antibody 37M or 37C, or an antigen-binding fragment thereof, or an antibody comprising CDRs of antibody 37M or 37C). In a particular embodiment, provided herein is an expression vector (e.g., mammalian expression vector) comprising a polynucleotide (or isolated polynucleotide) comprising nucleotide sequences encoding a VL chain region and/or a VH chain region of an antibody described herein (e.g., antibody 37M or 37C, or an antigen-binding fragment thereof, or an antibody comprising CDRs of antibody 37M or 37C). In a particular embodiment, a polynucleotide comprises a nucleotide sequence of SEQ ID NO: 8 encoding a VL chain region. In a particular embodiment, a polynucleotide comprises the nucleotide sequence of SEQ ID NO: 9 encoding a VH chain region. In a particular embodiment, a polynucleotide comprises the nucleotide sequence of SEQ ID NO: 10 encoding a light chain. In a particular embodiment, a polynucleotide comprises the nucleotide sequence of SEQ ID NO: 11 encoding a heavy chain.

In a particular embodiment, a polynucleotide comprises a nucleotide sequence that has 85% sequence identity to SEQ ID NO: 8 and encodes a VL chain region of an antibody that immunospecifically binds to the D4/D5 region of KIT. In a particular embodiment, a polynucleotide comprises a nucleotide sequence that has 85% sequence identity to SEQ ID NO: 9 and encodes a VH chain region of an antibody that immunospecifically binds to the D4/D5 region of KIT. In a particular embodiment, a polynucleotide comprises a nucleotide sequence that has 85% sequence identity to SEQ ID NO: 10 and encodes a light chain of an antibody that immunospecifically binds to the D4/D5 region of KIT. In a particular embodiment, a polynucleotide comprises a nucleotide sequence that has 85% sequence identity to SEQ ID NO: 11 and encodes a heavy chain of an antibody that immunospecifically binds to the D4/D5 region of KIT.

In a ninth aspect, provided herein is a host cell comprising a vector described herein, e.g., a mammalian expression vector. In certain embodiments, a cell described herein comprises one or more polynucleotides comprising nucleotide sequences encoding an antibody provided herein which immunospecifically binds to a D4/D5 region of human KIT (e.g., antibody 37M or 37C, or an antigen-binding fragment thereof, or an antibody comprising the CDRs of antibody 37M or 37C). In a particular embodiment, a cell described herein comprises one or more polynucleotides comprising nucleotide sequences encoding a VL chain region and a VH chain region of an antibody provided herein which immunospecifically binds to a D4/D5 region of human KIT (e.g., antibody 37M or 37C, or an antigen-binding fragment thereof, or an antibody comprising the CDRs of antibody 37M or 37C).

In a tenth aspect, provided herein is a hybridoma cell producing an antibody described herein (e.g., antibody 37M, or an antigen-binding fragment thereof, or an antibody comprising CDRs of antibody 37M).

In a particular aspect, provided herein is a method of making an antibody which immunospecifically binds to a D4/D5 region of human KIT (SEQ ID NO: 15) comprising culturing the host cell or hybridoma cell described herein. In a specific embodiment, such method of making an antibody further comprises the step of purifying the antibody from said host cell or hybridoma cell.

In a specific aspect, provided herein is a method of making an antibody which immunospecifically binds to a D4/D5 region of human KIT (SEQ ID NO: 15) comprising administering to an animal (e.g., a non-human animal, such as a mouse or rat) a human KIT antigen having the amino acid sequence of: (i) SEQ ID NO: 14; (ii) SEQ ID NO: 14 without the first 25 amino acids (signal peptide); (iii) SEQ ID NO: 14 without the first 25-33 amino acids; or (iv) SEQ ID NO: 15, optionally with a 5×His tag at the C-terminus and/or 1-8 amino acids at the N-terminus, wherein the animal produces an antibody which immunospecifically binds to a D4/D5 region of human KIT (SEQ ID NO: 15). In a specific embodiment, such method further comprises the step of obtaining cells which produce an antibody which immunospecifically binds to a D4/D5 region of human KIT (SEQ ID NO: 15) from the animal. In a certain embodiment, such method further comprises the step of generating hybridoma cells from the cells obtained from the animal. In a particular embodiment, such method further comprises the step of obtaining one or more polynucleotides encoding the antibody or fragment thereof (e.g., VH domain and/or VL domain) from the animal or cells of the animal. In a particular embodiment, such method comprises the step of cloning one or more polynucleotides encoding the antibody or fragment thereof (e.g., VH domain and/or VL domain) from the animal or cells of the animal into a vector (e.g., an expression vector).

In a particular aspect, provided herein are isolated or purified KIT polypeptides having the amino acid sequence of: (i) SEQ ID NO: 14; (ii) SEQ ID NO: 14 without the first 25 amino acids (signal peptide); (iii) SEQ ID NO: 14 without the first 25-33 amino acids; or (iv) SEQ ID NO: 15, optionally with a 5×His tag at the C-terminus and/or 1-8 amino acids at the N-terminus, wherein the KIT polypeptides comprise less than the entire extracellular domain of KIT (e.g., human KIT). In a certain embodiment, provided herein is a composition comprising such isolated or purified KIT polypeptides.

In an eleventh aspect, provided herein is a pharmaceutical composition comprising an antibody described herein (e.g., antibody 37M or 37C, or an antigen-binding fragment thereof, or an antibody comprising CDRs of antibody 37M or 37C) and a pharmaceutically acceptable carrier.

In a twelfth aspect, provided herein is a kit comprising an antibody described herein (e.g., antibody 37M or 37C, or an antigen-binding fragment thereof, or an antibody comprising CDRs of antibody 37M or 37C).

In a thirteenth aspect, provided herein is a method for treating or managing a KIT-mediated disorder or disease in a subject in need thereof, comprising administering to the subject a therapeutically effective amount of an antibody described herein (e.g., antibody 37M or 37C, or an antigen-binding fragment thereof, or an antibody comprising CDRs of antibody 37M or 37C). In a particular embodiment, the KIT-mediated disorder or disease is cancer, an inflammatory condition, or fibrosis. In another particular embodiment, the cancer is leukemia, chronic myelogenous leukemia, lung cancer, small cell lung cancer, melanoma, sarcoma, or gastrointestinal stromal tumors. In yet another particular embodiment, the cancer is refractory to treatment by a tyrosine kinase inhibitor. In a further particular embodiment, the tyrosine kinase inhibitor is GLEEVEC® (imatinib mesylate) or SUTENT® (sunitinib).

In a particular embodiment, provided herein is a method for treating or managing a KIT-mediated disorder or disease in a subject in need thereof, comprising administering to the subject (i) an antibody described herein (e.g., antibody 37M or 37C, or an antigen-binding fragment thereof, or an antibody comprising CDRs of antibody 37M or 37C), and (ii) a second therapeutic agent. In a specific embodiment, the second therapeutic agent is a small molecule kinase inhibitor (e.g., imatinib mesylate or sunitinib). In a specific embodiment, the second therapeutic agent is a histone deacetylase inhibitor (e.g., vorinostat or suberoylanilide hydroxamic acid (SAHA)). In a particular embodiment, an antibody (or antigen-binding fragment) which immunospecifically binds to a D4/D5 region of human KIT for use in the methods provided herein is conjugated to an agent (e.g., a chemotherapeutic agent, a toxic agent, a detectable agent).

In an fourteenth aspect, provided herein is a method for diagnosing a subject with a KIT-mediated disorder or disease comprising contacting a sample obtained from the subject with an antibody described herein (e.g., antibody 37M or 37C, or an antigen-binding fragment thereof, or an antibody comprising CDRs of antibody 37M or 37C) and detecting the expression level of KIT in the sample. In a particular embodiment, the antibody is conjugated to a detectable molecule. In another particular embodiment, the detectable molecule is an enzyme, fluorescent molecule, luminescent molecule, or radioactive molecule.

In a fifteenth aspect, provided herein is a method for inhibiting KIT activity in a cell expressing KIT comprising contacting the cell with an effective amount of an antibody described herein (e.g., antibody 37M or 37C, or an antigen-binding fragment thereof, or an antibody comprising CDRs of antibody 37M or 37C).

In a sixteenth aspect, provided herein is a method for inducing or enhancing apoptosis in a cell expressing KIT comprising contacting the cell with an effective amount of an antibody described herein (e.g., antibody 37M or 37C, or an antigen-binding fragment thereof, or an antibody comprising CDRs of antibody 37M or 37C).

In a seventeenth aspect, provided herein is a method for inducing cell differentiation comprising contacting a cell expressing KIT with an effective amount of an antibody described herein (e.g., an antigen-binding fragment thereof, antibody 37M or 37C, or an antibody comprising CDRs of antibody 37M or 37C). In one embodiment, the cell is a stem cell.

In a particular aspect, provided herein is a conjugate comprising an agent linked (e.g., directly or via a linker) to an antibody described herein (or an antigen-binding fragment thereof), which antibody immunospecifically binds to a D4/D5 region of human KIT (e.g., SEQ ID NO: 15) and comprises:
(i) a VL chain region comprising a VL CDR1, VL CDR2, and VL CDR3 having the amino acid sequences of SEQ ID NO: 20, SEQ ID NO: 21, and SEQ ID NO: 22, respectively; and (ii) a VH chain region comprising a VH CDR1, VH CDR2, and VH CDR3 having the amino acid sequences of SEQ ID NO: 23, SEQ ID NO: 24, and SEQ ID NO: 25, respectively.

In certain embodiments, the agent conjugated to an anti-KIT antibody is a toxin (e.g., abrin, ricin A, pseudomonas exotoxin, cholera toxin, or diphtheria toxin). In particular embodiments, the conjugate is internalized by a cell (e.g., cell expressing KIT protein). In specific embodiments, the conjugate comprises an agent linked via a linker to an anti-KIT antibodies. In certain embodiments, the conjugate comprises an agent linked directly to an anti-KIT antibodies. In particular embodiments, the conjugate comprises an agent linked covalently to an anti-KIT antibody. In certain embodiments, the conjugate comprises an agent linked non-covalently to an anti-KIT antibody. In specific embodiments, the methods provided herein (e.g., method for treating cancer) comprise administering a conjugate described herein to an individual in need thereof.

3.1 Terminology

Unless defined otherwise, all technical and scientific terms used herein have the same meaning as is commonly understood by one of ordinary skill in the art.

As used herein and unless otherwise specified, the terms "about" or "approximately" mean within plus or minus 10% of a given value or range.

As used herein and unless otherwise specified, "administer" or "administration" refers to the act of injecting or otherwise physically delivering a substance (e.g., an anti-KIT antibody provided herein) to a subject or a patient, such as by mucosal, topical, intradermal, intravenous, intramuscular delivery and/or any other method of physical delivery described herein or known in the art.

As used herein and unless otherwise specified, the terms "antibody" and "immunoglobulin" and "Ig" are terms of art and can be used interchangeably herein and refer to a molecule with an antigen binding site that immunospecifically binds an antigen.

As used herein and unless otherwise specified, an "antigen" is a moiety or molecule that contains an epitope, and, as such, also is specifically bound by antibody. In a specific embodiment, the antigen, to which an antibody described herein binds, is KIT (e.g., human KIT), or a fragment thereof, for example, an extracellular domain of KIT (e.g., human KIT) or a D4/D5 region of KIT (e.g., human KIT).

As used herein and unless otherwise specified, an "epitope" is a term in the art and refers to a localized region of an antigen to which an antibody can specifically bind. A region or a polypeptide contributing to an epitope can be contiguous amino acids of the polypeptide or an epitope can come together from two or more non-contiguous regions of the polypeptide.

As used herein and unless otherwise specified, the terms "antigen binding domain," "antigen binding region," "antigen binding fragment," and similar terms refer to a portion of an antibody molecule which comprises the amino acid residues that interact with an antigen and confer on the antibody molecule its specificity for the antigen (e.g., the complementarity determining regions (CDR)). The antigen binding region can be derived from any animal species, such as rodents (e.g., mouse, rat or hamster) and humans. The CDRs of an antibody molecule can be determined by any method well known to one of skill in the art. In particular, the CDRs can be determined according to the Kabat numbering system (see Kabat et al. (1991) Sequences of proteins of immunological interest. (U.S. Department of Health and Human Services, Washington, D.C.) 5$^{th}$ ed.).

As used herein and unless otherwise specified, a "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein and unless otherwise specified, a "conformational epitope" or "nonlinear epitope" or "discontinuous epitope" refers to one comprised of at least two amino acids which are not consecutive amino acids in a single protein chain. For example, a conformational epitope can be comprised of two or more amino acids which are separated by a stretch of intervening amino acids but which are close enough to be recognized by an antibody (e.g., an anti-KIT antibody) described herein as a single epitope. As a further example, amino acids which are separated by intervening amino acids on a single protein chain, or amino acids which exist on separate protein chains, can be brought into proximity due to the conformational shape of a protein structure or complex to become a conformational epitope which can be bound by an anti-KIT antibody described herein. It will be appreciated by one of skill in the art that, in general, a linear epitope bound by an anti-KIT antibody described herein may or may not be dependent on the secondary, tertiary, or quaternary structure of the KIT receptor. For example, in some embodiments, an anti-KIT antibody described herein binds to a group of amino acids regardless of whether they are folded in a natural three dimensional protein structure. In other embodiments, an anti-KIT antibody described herein does not recognize the individual amino acid residues making up the epitope, and require a particular conformation (bend, twist, turn or fold) in order to recognize and bind the epitope.

As used herein and unless otherwise specified, the term "constant region" or "constant domain" refers to an antibody portion, e.g., a carboxyl terminal portion of a light and/or heavy chain which is not directly involved in binding of an antibody to antigen but which exhibits various effector functions, such as interaction with the Fc receptor. The terms refer to a portion of an immunoglobulin molecule having a generally more conserved amino acid sequence relative to an immunoglobulin variable domain.

As used herein and unless otherwise specified, the terms "D4/D5 region" or "D4/D5 domain" refer to a region within a KIT polypeptide spanning the fourth Ig-like extracellular ("D4") domain, the fifth Ig-like extracellular ("D5") domain, and the hinge region in between the D4 and D5 domains ("D4-D5 hinge region"), of KIT, in the following order from the amino terminus to the carboxyl terminus: D4, D4-D5 hinge region, and D5. As used herein, amino acids V308 to H515 of FIG. 1 and the polypeptide depicted at FIG. 2A herein are considered a D4/D5 region or domain.

As used herein and unless otherwise specified, the terms "KIT" or "KIT receptor" or "KIT polypeptide" refer to any form of full-length KIT including, but not limited to, native KIT, an isoform of KIT, an interspecies KIT homolog, or a KIT variant, e.g., naturally occurring (for example, allelic or splice variant, or mutant, e.g., somatic mutant) or artificially constructed variant (for example, a recombinant or chemically modified variant). KIT is a type III receptor tyrosine kinase encoded by the c-kit gene (see, e.g., Yarden et al., Nature, 1986, 323:226-232; Ullrich and Schlessinger, Cell, 1990, 61:203-212; Clifford et al., J. Biol. Chem., 2003, 278:31461-31464; Yarden et al., EMBO J., 1987, 6:3341-3351; Mol et al., J. Biol. Chem., 2003, 278:31461-31464). GenBank™ accession number NM_000222 provides an exemplary human KIT nucleic acid sequence. GenBank™ accession numbers NP_001087241, P10721, and AAC50969 provide exemplary human KIT amino acid sequences. GenBank™ accession number AAH75716 provides an exemplary murine KIT amino acid sequence. Native KIT comprises five extracellular immunoglobulin (Ig)-like domains (D1, D2, D3, D4, D5), a single transmembrane region, an inhibitory cytoplasmic juxtamembrane domain, and a split cytoplasmic kinase domain separated by a kinase insert segment (see, e.g., Yarden et al., Nature, 1986, 323:226-232; Ullrich and Schlessinger, Cell, 1990, 61:203-212; Clifford et al., J. Biol. Chem., 2003, 278:31461-31464). An exemplary amino acid sequence of the D4/D5 region of human KIT is provided in FIG. 1, at amino acid residues V308 to H515. In a specific embodiment, KIT is human KIT. In a particular embodiment, KIT can exist as a monomer, dimer, multimer, native form, or denatured form.

As used herein and unless otherwise specified, the terms "effective amount" or "therapeutically effective amount" refer to an amount of a therapy (e.g., an antibody or pharmaceutical composition provided herein) which is sufficient to reduce and/or ameliorate the severity and/or duration of a given disease and/or a symptom related thereto. These terms also encompass an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than an anti-KIT antibody provided herein). In some embodiments, "effective amount" as used herein also refers to the amount of an antibody described herein to achieve a specified result (e.g., inhibition (e.g., partial inhibition) of a KIT biological activity of a cell, such as inhibition of cell proliferation or cell survival, or enhancement or induction of apoptosis or cell differentiation).

In the context of a peptide or a polypeptide, the term "fragment" as used herein refers to a peptide or polypeptide that comprises less than full length amino acid sequence. Such a fragment can arise, for example, from a truncation at the amino terminus, a truncation at the carboxy terminus, and/or an internal deletion of a residue(s) from the amino acid sequence. Fragments can, for example, result from alternative RNA splicing or from in vivo protease activity. In certain embodiments, KIT fragments or antibody fragments (e.g., antibody fragments that immunospecifically bind to a KIT polypeptide) include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a KIT polypeptide or an antibody (e.g., antibody that immunospecifically bind to a KIT polypeptide), respectively. In a specific embodiment, a fragment of a KIT polypeptide or an antibody (e.g., antibody that immunospecifically bind to a KIT polypeptide) retains at least 1, at least 2, or at least 3 functions of the polypeptide or antibody.

As used herein and unless otherwise specified, the term "heavy chain" when used in reference to an antibody refers to any distinct types, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG$_1$, IgG$_2$, IgG$_3$ and IgG$_4$. In a specific embodiment, the heavy chain is a human heavy chain.

As used herein and unless otherwise specified, the term "host cell" refers to a particular cell that comprises an exogenous nucleic acid molecule, e.g., a cell that has been transfected or transformed with a nucleic acid molecule, and the progeny or potential progeny of such a parent cell. Progeny of such a cell may not be identical to the parent cell due to mutations or environmental influences that can occur in succeeding generations or integration of the nucleic acid molecule into the host cell genome.

As used herein and unless otherwise specified, the terms "immunospecifically binds," "immunospecifically recognizes," "specifically binds," and "specifically recognizes" are analogous terms in the context of antibodies and refer to molecules that specifically bind to an antigen (e.g., epitope or immune complex) as understood by one skilled in the art. For example, a molecule that specifically binds to an antigen can bind to other peptides or polypeptides, generally with lower affinity as determined by, e.g., immunoassays, Biacore™, KinExA 3000 instrument (Sapidyne Instruments, Boise, Id.), or other assays known in the art. In a specific embodiment, molecules that immunospecifically bind to an antigen bind to the antigen with a $K_a$ that is at least 2 logs, 2.5 logs, 3 logs, 4 logs or greater than the $K_a$ when the molecules bind to another antigen. In another specific embodiment, molecules that immunospecifically bind to an antigen do not cross react with other proteins. In another specific embodiment, molecules that immunospecifically bind to an antigen do not cross react with other non-KIT proteins.

As used herein and unless otherwise specified, the term "in combination" in the context of the administration of other therapies refers to the use of more than one therapy. The use of the term "in combination" does not restrict the order in which therapies are administered. The therapies may be administered, e.g., serially, sequentially, concurrently, or concomitantly.

As used herein and unless otherwise specified, an "isolated" or "purified" antibody is substantially free of cellular material or other contaminating proteins from the cell or tissue source from which the antibody is derived, or substantially free of chemical precursors or other chemicals when chemically synthesized.

As used herein and unless otherwise specified, an "isolated" polynucleotide or nucleic acid molecule is one which is separated from other nucleic acid molecules which are present in the natural source (e.g., in a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

The terms "Kabat numbering," and like terms are recognized in the art and refer to a system of numbering amino acid residues in the heavy and light chain variable regions of an antibody, or an antigen binding portion thereof (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242). Using the Kabat numbering system, CDRs within an antibody heavy chain molecule are typically present at amino acid positions 31 to 35 ("CDR1"), amino acid positions 50 to 65 ("CDR2"), and amino acid positions 95 to 102 ("CDR3"). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3).

As used herein and unless otherwise specified, the term "light chain" when used in reference to an antibody refers to any distinct types, e.g., kappa (κ) of lambda (λ) based on the amino acid sequence of the constant domains. Light chain amino acid sequences are well known in the art. In specific embodiments, the light chain is a human light chain.

As used herein and unless otherwise specified, the terms "manage," "managing," and "management" refer to the beneficial effects that a subject derives from a therapy (e.g., a prophylactic or therapeutic agent), which does not result in a cure of a KIT-mediated disease or disorder. In certain embodiments, a subject is administered one or more therapies (e.g., prophylactic or therapeutic agents, such as an antibody described herein) to "manage" a KIT-mediated disease (e.g., cancer, inflammatory condition, or fibrosis), one or more symptoms thereof, so as to prevent the progression or worsening of the disease.

As used herein and unless otherwise specified, the term "monoclonal antibody" refers to an antibody obtained from a population of homogenous or substantially homogeneous antibodies, and each monoclonal antibody will typically recognize a single epitope on the antigen. In specific embodiments, a "monoclonal antibody," as used herein, is an antibody produced by a single hybridoma or other cell (e.g., host cell producing a recombinant antibody), wherein the antibody immunospecifically binds to a KIT epitope (e.g., an epitope of a D4/D5 region of human KIT) as determined, e.g., by ELISA or other antigen-binding or competitive binding assay known in the art or in the Examples provided herein. Generally, a population of monoclonal antibodies can be generated by cells, a population of cells, or a cell line. The term "monoclonal" is not limited to any particular method for making the antibody. For example, monoclonal antibodies described herein can be made by the hybridoma method as described in Kohler et al.; Nature, 256:495 (1975) or can be isolated from phage libraries using the techniques as described herein, for example. Other methods for the preparation of clonal cell lines and of monoclonal antibodies expressed thereby are well known in the art (see, for example, Chapter 11 in: *Short Protocols in Molecular Biology*, (2002) 5th Ed., Ausubel et al., eds., John Wiley and Sons, New York).

As used herein and unless otherwise specified, the term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

As used herein and unless otherwise specified, the term "polyclonal antibodies" refers to an antibody population that includes a variety of different antibodies directed to the same and to different epitopes within an antigen or antigens. Methods for producing polyclonal antibodies are known in the art (See, e.g., see, for example, Chapter 11 in: *Short Protocols in Molecular Biology*, (2002) 5th Ed., Ausubel et al., eds., John Wiley and Sons, New York).

As used herein and unless otherwise specified, the terms "impede" or "impeding" in the context of a KIT-mediated disorder or disease refer to the total or partial inhibition (e.g., less than 100%, 95%, 90%, 80%, 70%, 60%, 50%, 40%, 30%, 20%, 10%, or 5%) or blockage of the development, recurrence, onset or spread of a KIT-mediated disease and/or symptom related thereto, resulting from the administration of a therapy or combination of therapies provided herein (e.g., a combination of prophylactic or therapeutic agents, such as an antibody described herein).

As used herein and unless otherwise specified, the term "prophylactic agent" refers to any agent that can totally or partially inhibit the development, recurrence, onset or spread of a KIT-mediated disease and/or symptom related thereto in a subject. In certain embodiments, the term "prophylactic agent" refers to an antibody described herein. In certain other embodiments, the term "prophylactic agent" refers to an agent other than an antibody described herein. Generally, a prophylactic agent is an agent which is known to be useful to or has been or is currently being used to prevent a KIT-mediated disease and/or a symptom related thereto or impede the onset, development, progression and/or severity of a KIT-mediated disease and/or a symptom related thereto. In specific embodiments, the prophylactic agent is a human anti-KIT antibody, such as a humanized or a fully human anti-KIT monoclonal antibody.

As used herein and unless otherwise specified, the term "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse, rabbit, goat, or cow) that is transgenic and/or transchromosomal for human immunoglobulin genes (see e.g., Taylor, L. D. et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences. In certain embodiments, the amino acid sequences of such recombinant human antibodies have been modified such thus the amino acid sequences of the VH and/or VL regions of the recombinant antibodies are sequences that, while derived from and related to human germline VH and VL sequences, do not naturally exist within the human antibody germline repertoire in vivo.

As used herein and unless otherwise specified, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) can be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* ($63^{rd}$ ed., 2009).

As used herein and unless otherwise specified, the terms "subject" and "patient" are used interchangeably. As used herein, a subject is preferably a mammal such as a non-primate (e.g., cows, pigs, horses, cats, dogs, goats, rabbits, rats, mice, etc.) or a primate (e.g., monkey and human), most preferably a human. In one embodiment, the subject is a mammal, preferably a human, having a KIT-mediated disorder or disease. In another embodiment, the subject is a mammal, preferably a human, at risk of developing a KIT-mediated disorder or disease. In another embodiment, the subject is a non-human primate.

As used herein and unless otherwise specified, the terms "therapies" and "therapy" can refer to any protocol(s), method(s), compositions, formulations, and/or agent(s) that can be used in the prevention, treatment, management, or amelioration of a condition or disorder or symptom thereof (e.g., cancer or one or more symptoms or condition associated therewith; inflammatory condition or one or more symptoms or condition associated therewith; fibrosis or one or more symptoms or condition associated therewith). In certain embodiments, the terms "therapies" and "therapy" refer to drug therapy, adjuvant therapy, radiation, surgery, biological therapy, supportive therapy, and/or other therapies useful in treatment, management, prevention, or amelioration of a condition or disorder or one or more symptoms thereof (e.g., cancer or one or more symptoms or condition associated therewith; inflammatory condition or one or more symptoms or condition associated therewith; fibrosis or one or more symptoms or condition associated therewith). In certain embodiments, the term "therapy" refers to a therapy other than an anti-KIT antibody described herein or pharmaceutical composition thereof. In specific embodiments, an "additional therapy" and "additional therapies" refer to a therapy other than a treatment using an anti-KIT antibody described herein or pharmaceutical composition. In a specific embodiment, a therapy includes the use of an anti-KIT antibody described herein as an adjuvant therapy. For example, using an anti-KIT antibody described herein in conjunction with a drug therapy, biological therapy, surgery, and/or supportive therapy.

As used herein and unless otherwise specified, the term "therapeutic agent" refers to any agent that can be used in the treatment, management or amelioration of a KIT-mediated disease and/or a symptom related thereto. In certain embodiments, the term "therapeutic agent" refers to an antibody described herein. In certain other embodiments, the term "therapeutic agent" refers to an agent other than an antibody described herein. Preferably, a therapeutic agent is an agent which is known to be useful for, or has been or is currently being used for the treatment, management or amelioration of a KIT-mediated disease or one or more symptoms related thereto. In specific embodiments, the therapeutic agent is a human anti-KIT antibody, such as a fully human anti-KIT monoclonal antibody.

As used herein and unless otherwise specified, the terms "treat," "treatment" and "treating" refer to the reduction or amelioration of the progression, severity, and/or duration of a KIT-mediated disease (e.g., cancer, inflammatory disorder, or fibrosis) resulting from the administration of one or more therapies (including, but not limited to, the administration of one or more prophylactic or therapeutic agents, such as an antibody provided herein).

As used herein and unless otherwise specified, the terms "variable region" or "variable domain" refer to a portion of an antibody, generally, a portion of a light or heavy chain, typically about the amino-terminal 110 to 120 amino acids in the mature heavy chain and about 90 to 100 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction of the antibody with antigen. In a specific embodiment, numbering of amino acid positions of antibodies described herein is according to the EU Index, as in Kabat et al. (1991) *Sequences of Proteins of Immunological Interest*, Fifth Edition, U.S. Department of Health and Human Services, NIH Publication No. 91-3242 ("Kabat et al."). In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

4. BRIEF DESCRIPTION OF THE FIGURES

FIG. 1 depicts the amino acid sequence of full length human KIT (SEQ ID NO: 1), GenBank™ accession number AAC50969. The first through fifth extracellular Ig-like domains (i.e., D1, D2, D3, D4, and D5) are indicated; "{" depicts the amino-terminal residue of each domain and "}" depicts the carboxyl-terminal residue of each domain. The D1 domain is depicted at P34 to R112, the D2 domain is depicted at D113 to P206, the D3 domain is depicted at A207 to D309, the D4 domain is depicted at K310 to N410, the hinge region between D4 and D5 is located at V409 to N410, and the D5 domain is depicted at T411 to K509. Also, the D1/D2 hinge region is located at D113 to L117; the D2/D3 hinge region is located at P206 to A210; and the D3/D4 hinge region is located at D309 to G311. The D4/D5 region comprises K310 to K509. The transmembrane domain comprises residues F525 to Q545, and the kinase domain comprises residues K589 to S933.

FIG. 2A depicts the amino acid sequence of the recombinant KIT D4/D5 polypeptide used to generate antibodies. Human KIT amino acids V308 to H515 (SEQ ID NO: 15) are depicted in bold. The recombinant KIT D4/D5 polypeptide depicted (SEQ ID NO: 14) contains (i) the first 33 amino acids (i.e., M1 to E33) of the amino terminus of human KIT (including the signal peptide (underlined, not bold) which is cleaved during processing and, as such, was not utilized as part of the antigen used to generate antibodies), (ii) the D4/D5 region of human KIT (bold), and (iii) a 5×His tag (italics) at the carboxyl terminus.

FIG. 2B depicts the amino acid sequence of the recombinant D4 domain polypeptide used in binding assays (see, e.g., section 6). In particular, the recombinant D4 domain polypeptide comprising residues V308 to K412 (SEQ ID NO: 17), depicted as bold, of human KIT includes the D4 domain (residues K310 to N410). The recombinant D4 domain polypeptide amino acid sequence depicted (SEQ ID NO: 16) contains (i) the first 33 amino acids of the amino terminus of human KIT (including the signal peptide (underlined, not bold) which is cleaved during processing and, as such, was not utilized as part of the polypeptide used in binding assays), (ii) the D4 domain (bold, single-underlined) of human KIT, and (iii) a 6×His tag (italics) at the carboxyl terminus.

FIG. 2C depicts the amino acid sequence of the recombinant D5 domain polypeptide used in binding assays (see, e.g., section 6). In particular, the recombinant D5 domain polypeptide comprising residues N410 to H515 (SEQ ID NO: 19), depicted as bold, of human KIT includes the D5 region (residues T411 to K509) of human KIT. The recombinant D5 domain polypeptide amino acid sequence depicted (SEQ ID NO: 18) contains (i) the first 33 amino acids of the amino terminus of human KIT (including the signal peptide (underlined, not bold) which is cleaved during processing and, as such, was not utilized as part of the polypeptide used in binding assays), (ii) the D5 domain (bold, double-underlined) of human KIT, and (iii) a 5×His tag (italics) at the carboxyl terminus.

FIG. 3A depicts the variable light chain region amino acid sequence of anti-KIT antibodies 37M and 37C (SEQ ID NO: 2). The framework regions (FR1, FR2, FR3, and FR4), and CDRs (CDR1, CDR2, and CDR3) are indicated.

FIG. 3B depicts the variable heavy chain region amino acid sequence of anti-KIT antibodies 37M (SEQ ID NO: 3), and 37C (SEQ ID NO: 5). The framework regions (FR1, FR2, FR3, and FR4), and CDRs (CDR1, CDR2, and CDR3) are indicated.

FIG. 4 depicts the amino acid sequences of the VL domain (SEQ ID NO: 2) and VH domain (SEQ ID NO: 3) of anti-KIT antibody 37M as well as the DNA sequences encoding the VL domain (SEQ ID NO: 8) and the VH domain (SEQ ID NO:9). The CDRs (CDR1, CDR2, and CDR3) are bold and underlined.

FIG. 5A depicts the amino acid sequences of the light chain (SEQ ID NO: 6) and the heavy chain (SEQ ID NO: 7) of antibody 37C. The VL domain (SEQ ID NO: 2) comprises amino acid residues D20-E124 of the light chain, and the VH domain (SEQ ID NO: 5) comprises amino acid residues Q20-A135 of the heavy chain. The CDRs (CDR1, CDR2, and CDR3) are underlined. The amino acid sequences of the light chain constant domain (SEQ ID NO: 12) and of the heavy chain constant domain (SEQ ID NO: 13) are depicted in bold. The light chain constant domain (SEQ ID NO: 12) corresponds to amino acid residues T128 to C233 of SEQ ID NO: 6. The heavy chain constant domain (SEQ ID NO: 13) corresponds to amino acid residues A136 to K465 of SEQ ID NO: 7. The signal peptides are double underlined. The signal peptide of the light chain comprises the amino acid sequence MGWSCIILFL VATATGVHS (SEQ ID NO: 43). The signal peptide of the heavy chain comprises the amino acid sequence MGWSCIILFL VATATGVHS (SEQ ID NO: 44). These signal peptides are removed during post-translational processing to yield the mature forms of the light chain and heavy chain.

FIG. 5B depicts the DNA sequence encoding the light chain of antibody 37C (SEQ ID NO: 10), and its corresponding amino acid sequence (SEQ ID NO: 6).

FIG. 5C depicts the DNA sequence encoding the heavy chain of antibody 37C (SEQ ID NO: 11), and its corresponding amino acid sequence (SEQ ID NO: 7).

Figure 6A:
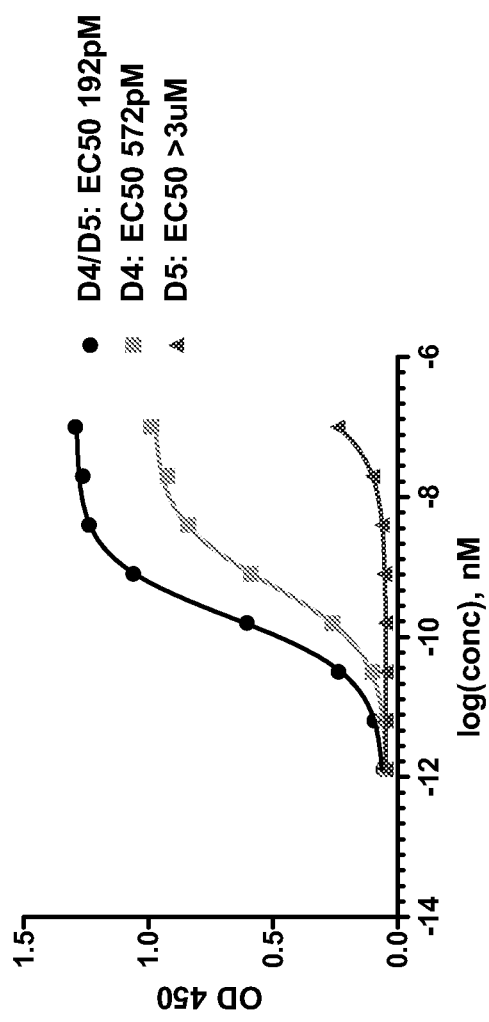

FIG. 6A depicts the binding activity of antibody 37M to the D4/D5 region of human KIT, as well as to either the D4 domain or D5 domain of human KIT by solid phase ELISA.

Figure 6B:
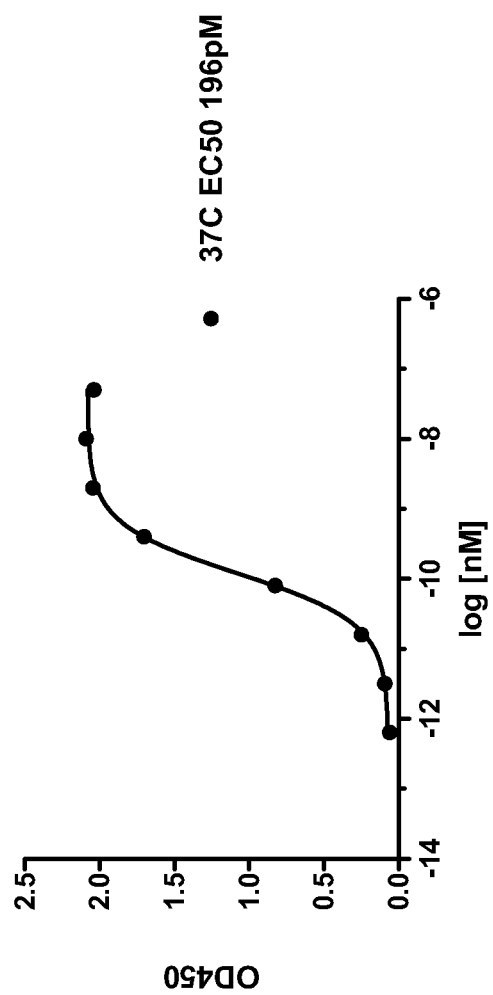

FIG. 6B depicts the binding activity of antibody 37C to the D4/D5 region of human KIT by solid phase ELISA.

Figure 7:
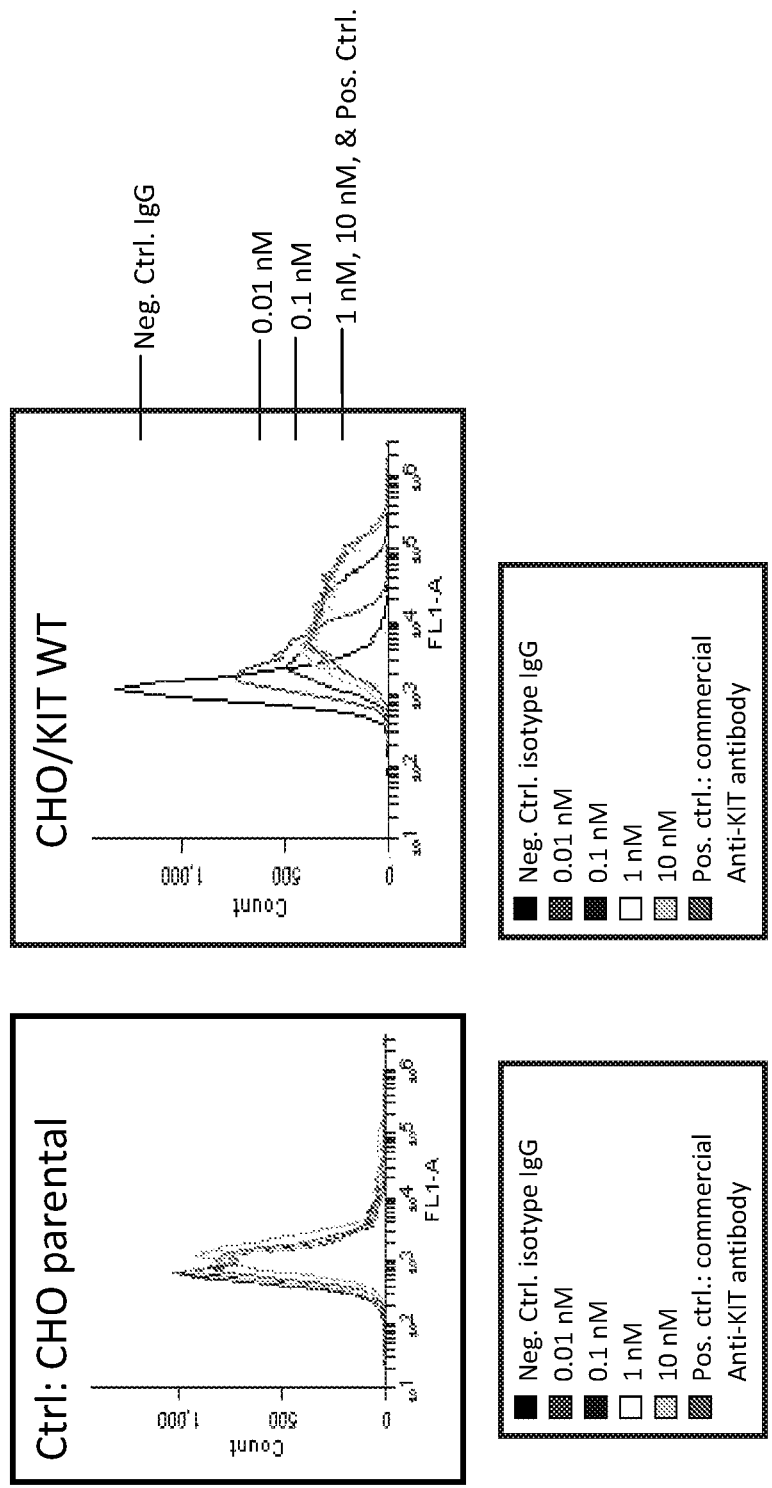

FIG. 7 depicts the activity of antibody 37M on CHO cells exogenously expressing wild-type human KIT (CHO/KIT-WT; right panel). Parental CHO cells not exogenously expressing wild-type human KIT (CHO parental; left panel) were used as controls.

Figure 8:
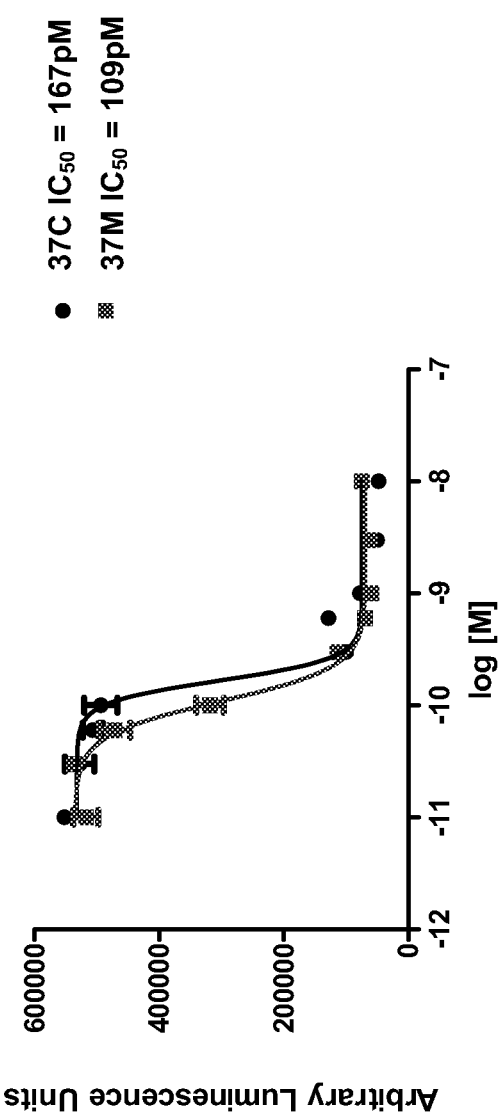

FIG. 8 depicts the inhibition of phosphorylation of the cytoplasmic domain of human KIT by antibodies 37M and 37C by cell-based phosphorylation assays. The 50% inhibition concentration of phosphorylation for 37M and 37C in these assays are calculated to be 109 pM and 167 pM, respectively.

Figure 9:
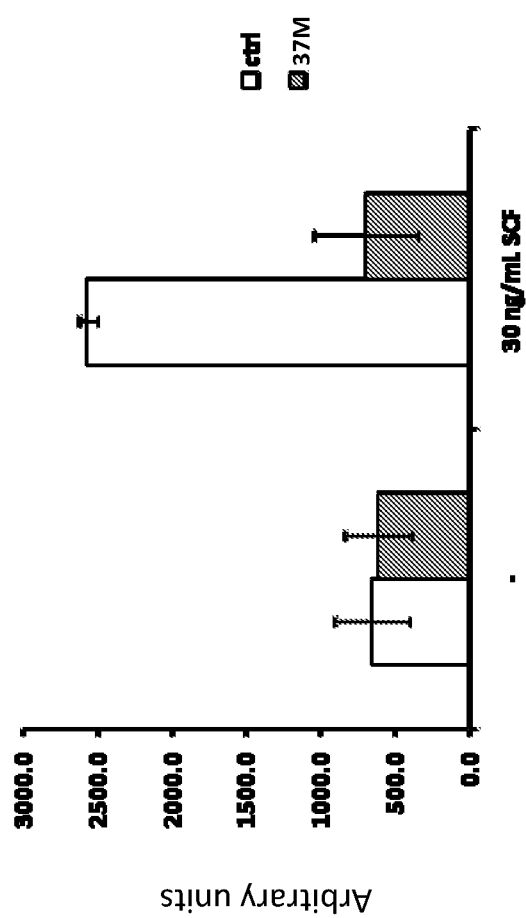

FIG. 9 depicts a bar graph showing that antibody 37M can inhibit colony formation by CHO/KIT-WT cells in soft agar assays. The control sample ("ctrl") included CHO/KIT-WT cells not exposed to any antibody.

Figure 10A:
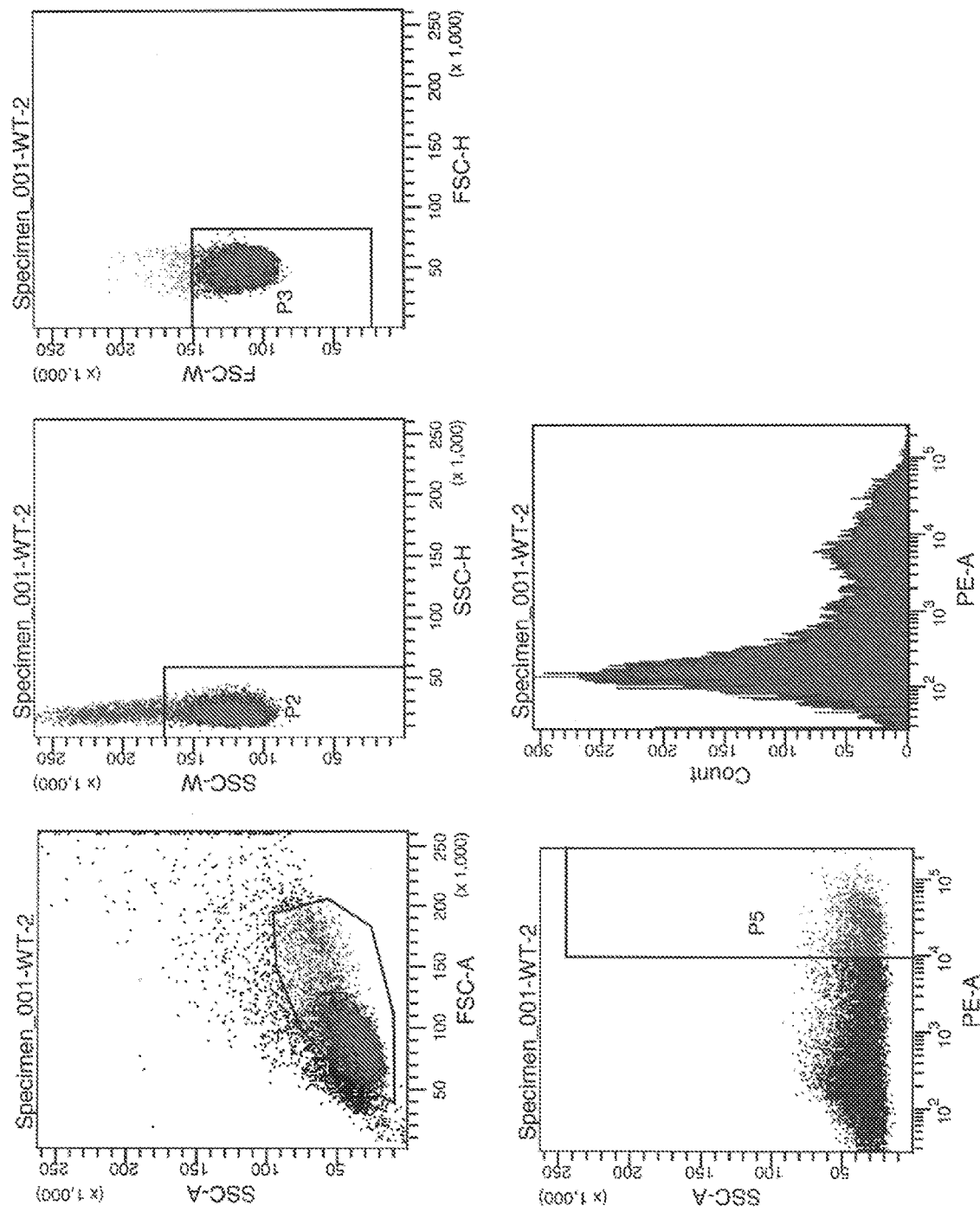

FIG. 10A shows the sort scheme for CHO/KIT-WT cells. P5 indicates the gated population of sorted cells that stained positive for KIT expression with a fluorescent signal intensity of $\geq 10^4$. Gating based on forward scatter (FSC) and side scatter (SSC) is also depicted.

FIG. 10B depicts a graph showing flow cytometry data for CHO parental cells, which are untransfected CHO cells, incubated with various concentrations of antibody 37M, an anti-KIT antibody (CD117), or an anti-IgG antibody (negative control) prior to processing for flow cytometry analysis.

FIG. 10C depicts a graph showing flow cytometry data for CHO cells recombinantly expressing wild-type KIT (CHO/KIT-WT) which were incubated with various concentrations of antibody 37M, an anti-KIT antibody (CD117), or an anti-IgG antibody (negative control) prior to processing for flow cytometry analysis.

Figure 11A:
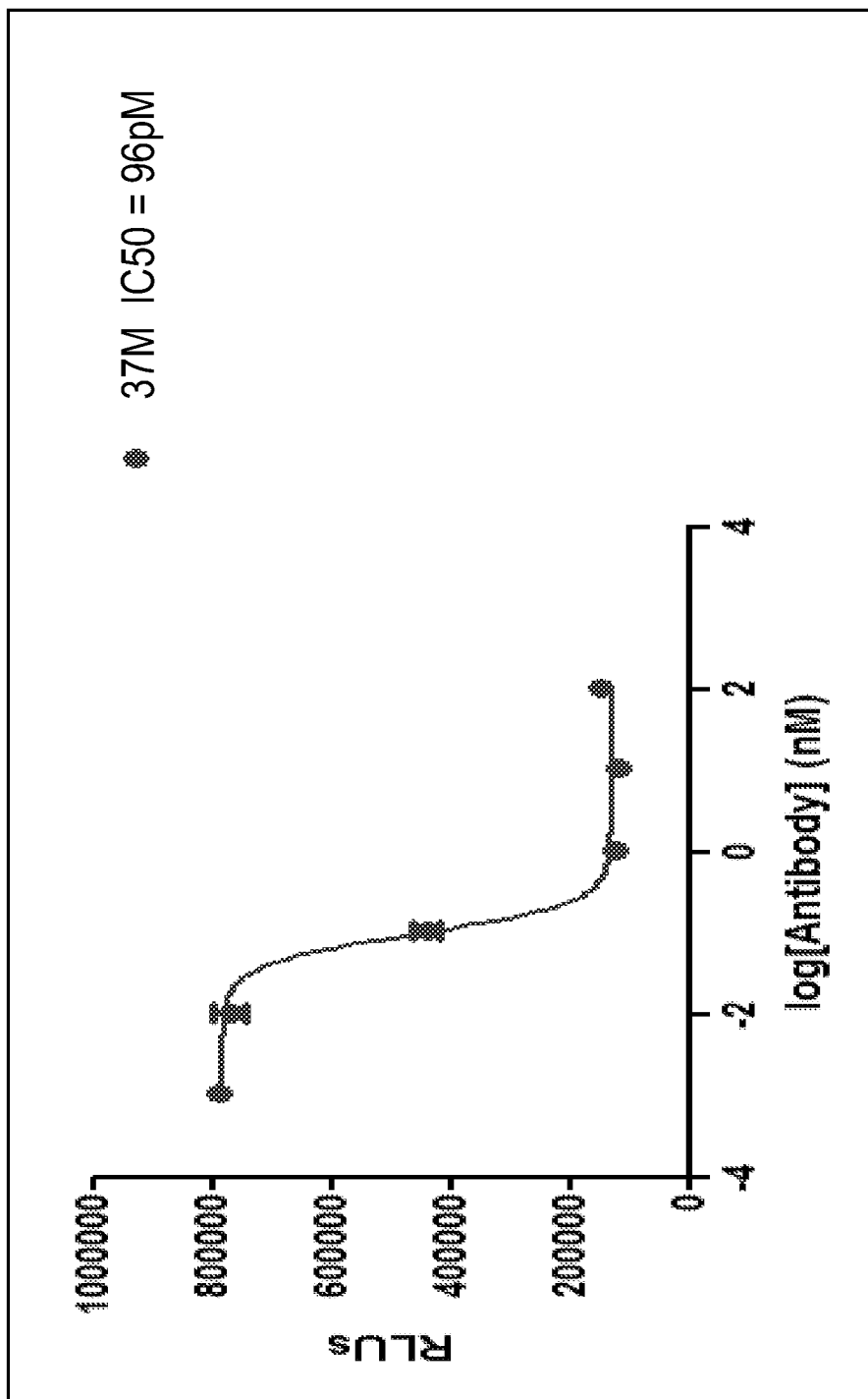

FIG. 11A depicts results from cell-based phosphorylation assays using CHO/KIT-WT cells demonstrating the ability of antibody 37M to inhibit KIT phosphorylation. The graph plots relative luminescence units (RLUs) against log concentration (M) of antibody 37M. The 50% inhibition concentration of phosphorylation for 37M in these assays was calculated to be approximately 96 pM.

Figure 11B:
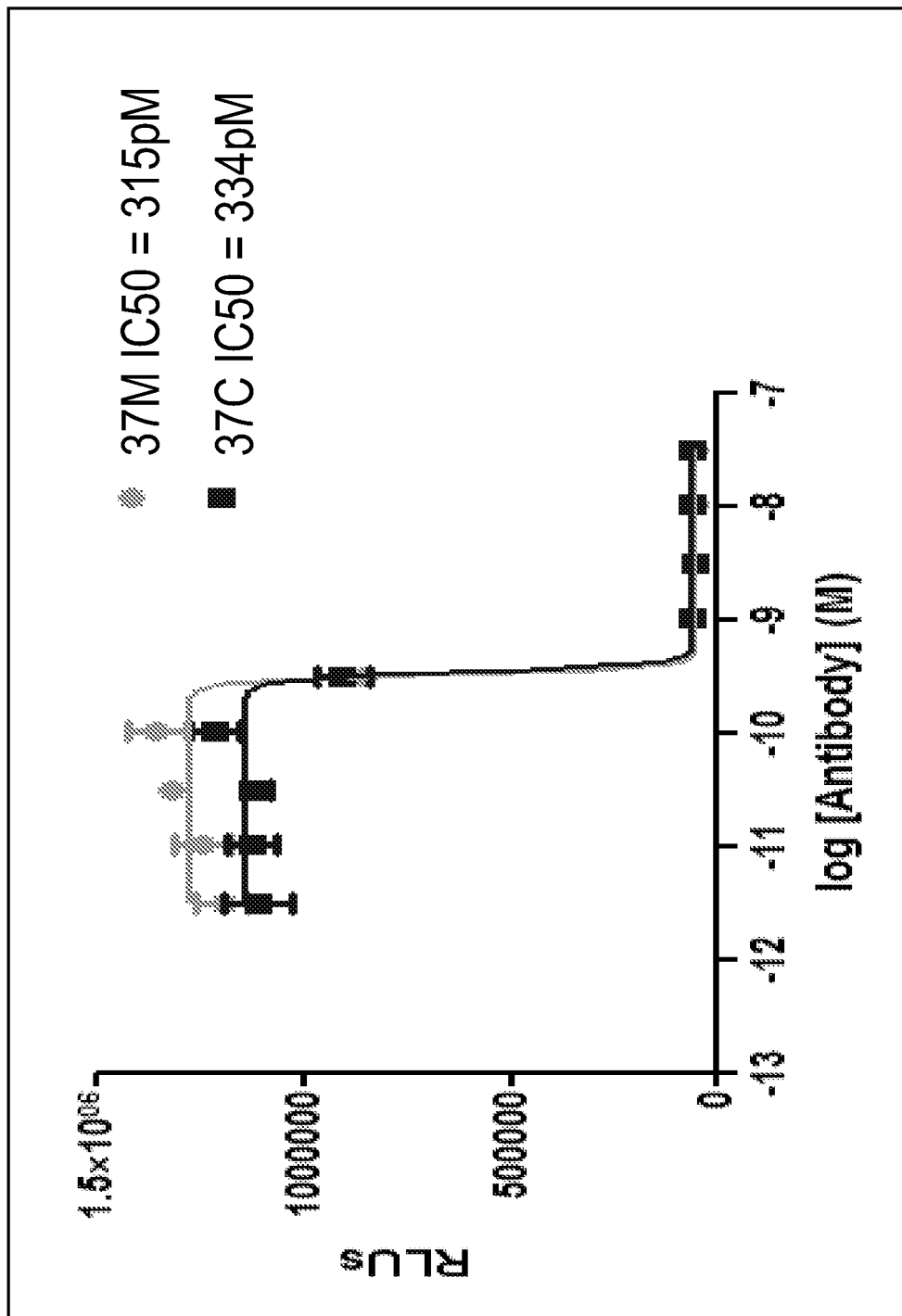

FIG. 11B depicts results from cell-based phosphorylation assays using sorted (high KIT expression) CHO/KIT-WT cells demonstrating the ability of antibody 37M or 37C to inhibit KIT phosphorylation. The depicted graph plots relative luminescence units (RLUs) versus log concentration (M) of either antibody 37M or antibody 37C. The $IC_{50}$ values of antibody 37M and antibody 37C were calculated to be approximately 315 pM and 334 pM, respectively.

Figure 12:
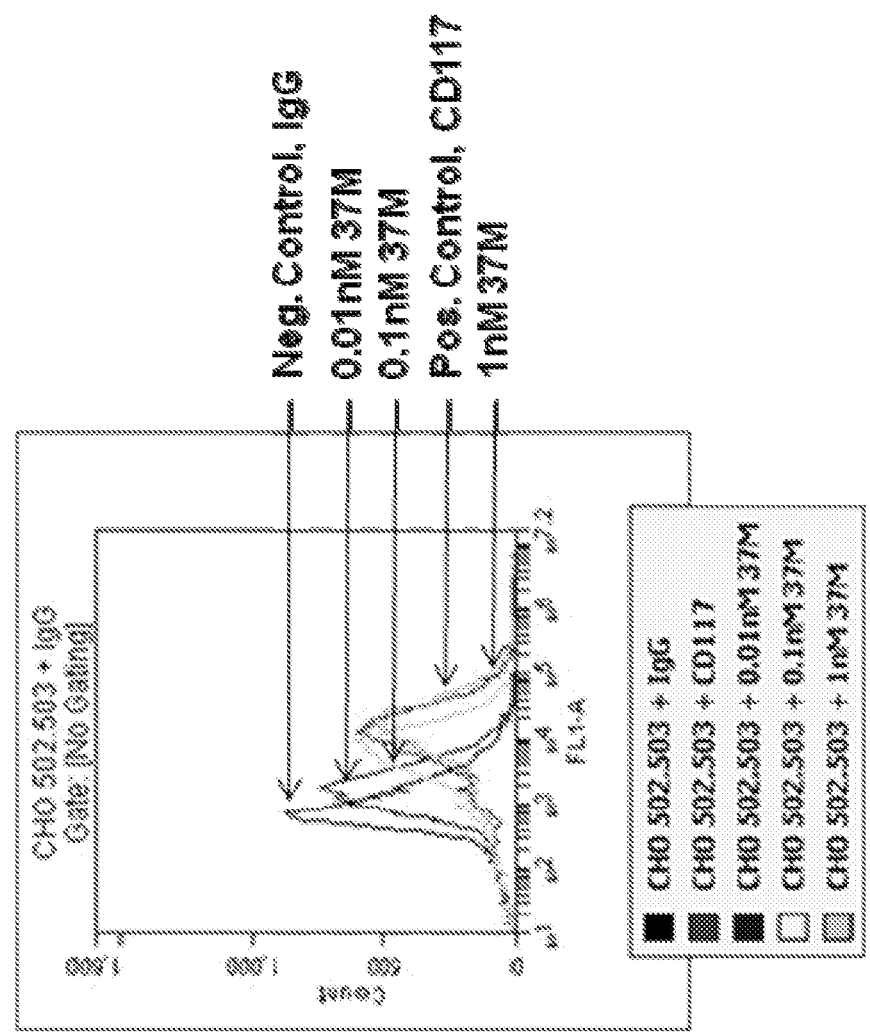

FIG. 12 depicts a graph showing flow cytometry data for CHO cells expressing a mutated form of KIT wherein the Ala and Tyr residues at positions 502 and 503, respectively, are duplicated (CHO 502.503). The CHO cells expressing the KIT duplication mutation were incubated with various concentrations of antibody 37M, an anti-KIT antibody (CD117), or an isotype control antibody (negative control) prior to processing for flow cytometry analysis.

Figure 13:
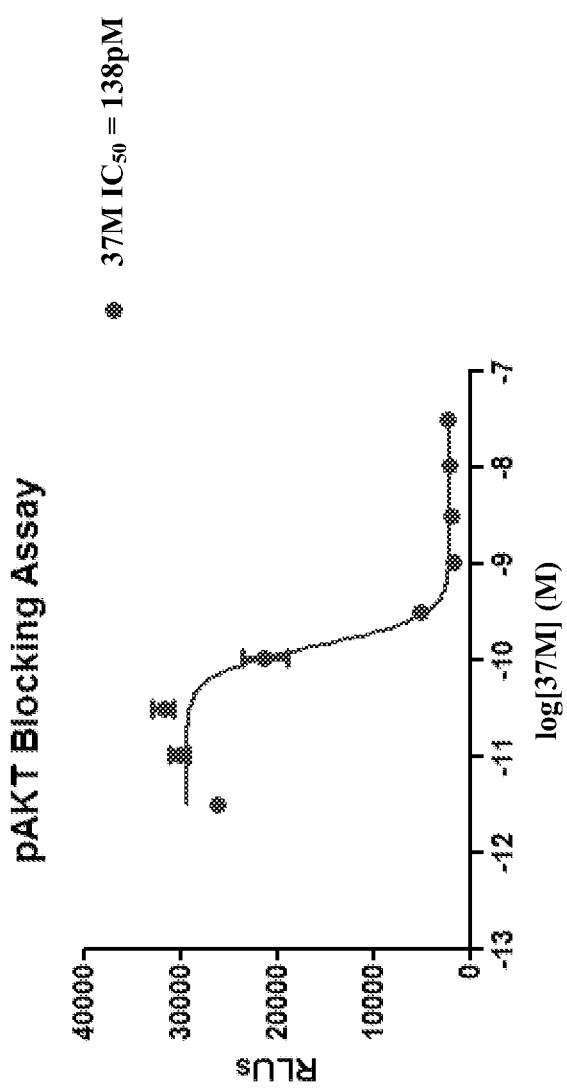

FIG. 13 depicts results from cell-based phosphorylation assays using sorted (high KIT expression) CHO/KIT-WT cells demonstrating the ability of antibody 37M to inhibit AKT phosphorylation. The depicted graph plots relative luminescence units (RLUs) versus log concentration (M) of antibody 37M. The $IC_{50}$ value of antibody 37M was calculated to be approximately 138 pM.

FIG. 14A depicts the results from competition binding assays (solid phase ELISA) where antibody 37M served as the reference antibody and antibody 37C served as the competitor antibody (10 nM), and the antigen is the KIT D4/D5 antigen depicted in FIG. 2A. The symbol "●" represents data points for antibody 37M binding affinity to the KIT D4/D5 antigen, at various concentrations and without competitor antibody 37C, and the symbol "■" represents data points for antibody 37M binding affinity to the KIT D4/D5 antigen, at various concentrations and with competitor antibody 37C (10 nM). The $EC_{50}$ value for reference antibody 37M, which was calculated to be 115 pM, increased to 2.8 nM in the presence of the competitor antibody 37C (10 nM).

FIG. 14B depicts the results from competition binding assays where antibody 37C served as the reference antibody and antibody 37M served as the competitor antibody (10 nM), and the antigen is the KIT D4/D5 antigen depicted in FIG. 2A. The symbol "●" represents data points for antibody 37C binding affinity to the KIT D4/D5 antigen, at various concentrations and without competitor antibody 37M, and the symbol "■" represents data points for antibody 37C binding affinity to the KIT D4/D5 antigen, at various concentrations and with competitor antibody 37M (10 nM). As shown in FIG. 14B, the $EC_{50}$ value for reference antibody 37C, which was calculated to be 48 pM, increased to 1 nM in the presence of competitor antibody 37M (10 nM).

FIGS. 15A-D depict data from experiments evaluating the effects of an antibody drug conjugate (ADC) targeting KIT protein on cell proliferation. In FIGS. 15A (GIST430 cells) and 15C (GIST 48B cells), the symbols "▲," "■," and "●" represent data points for cells exposed to antibody 37M and 0 ng, 25 ng, and 50 ng of saporin-conjugated secondary antibody ("saporin"), respectively. In FIGS. 15B (GIST430 cells) and D (GIST 48B cells), the symbols "▲," "■," and "●" represent data points for cells exposed to an anti-VEGFR-2 monoclonal antibody (anti-VEGFR-2 mAb) and 0 ng, 25 ng, and 50 ng of saporin-conjugated secondary antibody ("saporin"), respectively.

FIGS. 16A-F depict data from experiments evaluating the effects of an antibody drug conjugate (ADC) targeting KIT protein on proliferation of cells expressing wild-type KIT or mutant KIT. FIGS. 16A-B depict results from experiments with CHO cells engineered to express wild-type KIT (CHO/WT-KIT). FIGS. 16C-D depict results from experiments with CHO cells engineered to express mutant KIT containing a duplication of the Ala and Tyr residues at positions 502 and 503 (CHO/KIT-502.503)/FIGS. 16E-F depict results from experiments with CHO cells engineered to express mutant KIT containing V560D and Y823D amino acid substitutions. In FIGS. 16A, C and E, the symbols "▲," "■," and "●" represent data points for cells exposed to antibody 37M and 0 ng, 25 ng, and 50 ng of saporin-conjugated secondary antibody ("saporin"), respectively. In FIGS. 16B, D, and F, the symbols "▲," "■," and "●" represent data points for cells exposed to antibody 37M and 0 ng, 25 ng, and 50 ng of saporin-conjugated secondary antibody ("saporin"), respectively.

Figure 17A:
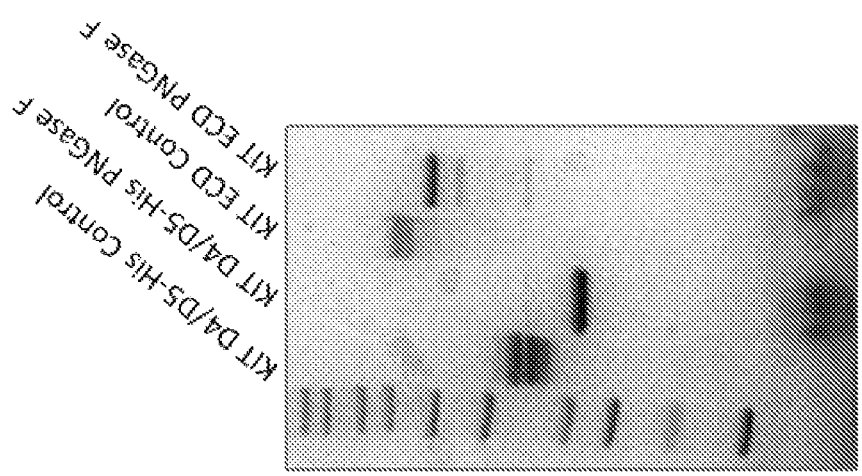

FIG. 17A depicts a gel showing KIT antigen, containing the entire extracellular domain (KIT ECD) or domains D4 and D5 (KIT D4/D5), in its glycosylated form ("Control") and de-glycosylated form due to exposure to the endoglycosidase N-Glycosidase F (PNGase F).

FIG. 17B depicts the binding activity of antibody 37M to glycosylated KIT D4/D5 antigen ("●"; "D4-D5-His") and de-glycosylated KIT D4/D5 antigen ("■"; "D4-D5-His PNGase F") (see FIGS. 2A and 17A) by solid phase ELISA.

FIG. 17C depicts the binding activity of antibody 37M to glycosylated ("●"; "ECD-His") and de-glycosylated ("■"; "ECD-His PNGase F") KIT antigen containing the entire extracellular domain (see FIG. 17A) by solid phase ELISA.

Figure 17D:
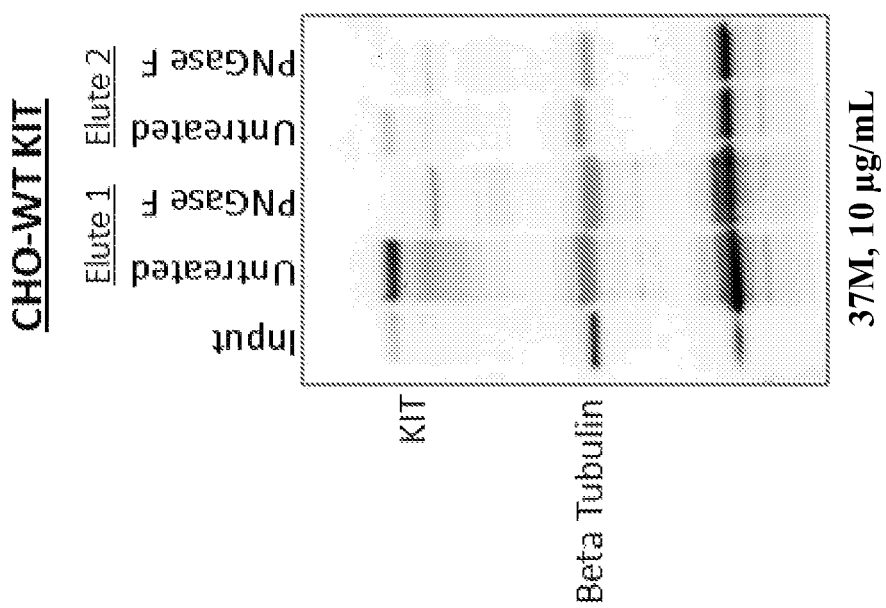

FIG. 17D depicts a Western blot of KIT protein immunoprecipitated by antibody 37M from lysate of CHO cells expressing wild-type KIT (CHO/WT-KIT). Immunoprecipitated KIT protein was untreated or treated with PNGase F prior to electrophoresis. A Western blot for beta-Tubulin protein was performed as a control.

5. DETAILED DESCRIPTION

Provided herein are antibodies (e.g., murine, chimeric or humanized antibodies), including antigen-binding fragments thereof, that immunospecifically bind to a KIT polypeptide (e.g., a KIT polypeptide containing the D4/D5 region of human KIT). Also provided are isolated nucleic acids (polynucleotides) encoding such antibodies (e.g., murine, chimeric, or humanized antibodies), and antigen-binding fragments thereof. Further provided are vectors and cells (e.g., host cells) comprising nucleic acids encoding such antibodies or antigen-binding fragments thereof. Also provided are methods of making such antibodies, cells, e.g., hybridoma cells, and antibodies produced by such cells, e.g., hybridoma cells. Also provided herein is a method of treating or managing a KIT-mediated disorder or disease (e.g., cancer, inflammatory condition, or fibrosis) or one or more effects of such KIT-mediated disorder or disease comprising administering one or more antibodies described herein, or an antigen-binding fragment thereof. Also provided herein is a method of diagnosing a KIT-mediated disorder or disease (e.g., cancer, inflammatory condition, or fibrosis) comprising contacting a sample with one or more antibodies (or antigen-binding fragment thereof) described herein and determining the expression level of KIT in the sample relative to a reference sample (e.g., a control sample). Further provided herein is a method for inhibiting KIT activity in a cell expressing KIT comprising contacting the cell with an effective amount of an antibody or antibodies described herein or an antigen-binding fragment thereof. Also further provided herein is a method for inducing or enhancing cell differentiation or apoptosis in a cell expressing KIT comprising contacting the cell with an effective amount of an antibody or antibodies described herein.

5.1 Antibodies

In specific aspects, provided herein are isolated antibodies (including antigen-binding fragments thereof) that immunospecifically bind to the D4/D5 region of KIT, e.g., human KIT. Amino acid residues V308 to H515 (SEQ ID NO: 15) of FIGS. 1 and 2 represent an exemplary D4/D5 region of human KIT. In a specific embodiment, an antibody described herein (or an antigen-binding fragment thereof) immunospecifically binds to a D4 domain of KIT, e.g., human KIT, for example, amino acid residues K310 to N410 of human KIT (see FIGS. 1, 2A and 2B). In another specific embodiment, an antibody described herein (or an antigen-binding fragment thereof) immunospecifically binds to a D5 domain of KIT, e.g., human KIT, for example, amino acid residues V409 to N410 of human KIT (see FIGS. 1, 2A and 2C) with lower affinity than to a D4 domain of KIT, e.g., human KIT. In a particular embodiment, an antibody described herein (or an antigen-binding fragment thereof) immunospecifically binds to a D4 domain of KIT, e.g., human KIT, with higher affinity than to a D5 domain of KIT, e.g., human KIT, for example, the higher affinity is at least 10 fold, 20 fold, 50 fold, 100 fold, 500 fold, or 1000 fold as determined by methods known in the art, e.g., ELISA or Biacore assays.

In a specific embodiment, an antibody described herein (or an antigen-binding fragment thereof) immunospecifically binds to a D4/D5 region of KIT, e.g., human KIT, and has higher affinity for a KIT antigen containing the D4/D5 region than for a KIT antigen consisting essentially of a D4 domain only or a KIT antigen consisting essentially of a D5 domain only. In a particular embodiment, an antibody described herein (or an antigen-binding fragment thereof) immunospecifically binds to a D4/D5 region of KIT, e.g., human KIT, and has at least 2 fold, 3 fold, 4 fold, 5 fold, or 10 fold higher affinity for a KIT antigen containing the D4/D5 region than for a KIT antigen consisting essentially of a D4 domain only. In a particular embodiment, an antibody described herein (or an antigen-binding fragment thereof) immunospecifically binds to a D4/D5 region of KIT, e.g., human KIT, and has approximately a 2 fold to 3 fold higher affinity for a KIT antigen containing the D4/D5 region than for a KIT antigen consisting essentially of a D4 domain only. In a particular embodiment, an antibody described herein (or an antigen-binding fragment thereof) immunospecifically binds to a D4/D5 region of KIT, e.g., human KIT, and has at least 5 fold, 10 fold, 50 fold, 100 fold, or 1,000 fold higher affinity for a KIT antigen containing the D4/D5 region than for a KIT antigen consisting essentially of a D5 domain only.

In a particular embodiment, an antibody described herein (or an antigen-binding fragment thereof) immunospecifically binds to a KIT antigen comprising or consisting essentially of the amino acid sequence of SEQ ID NO: 14 or 15. In a specific embodiment, an antibody described herein (or an antigen-binding fragment thereof) immunospecifically binds to a D4 domain of KIT, e.g., human KIT. In a particular embodiment, an antibody described herein immunospecifically binds to a KIT antigen comprising or consisting essentially of the amino acid sequence of SEQ ID NO: 16 or 17. In another specific embodiment, an antibody described herein (or an antigen-binding fragment thereof) immunospecifically binds a D4/D5 region of KIT, e.g., human KIT, wherein the antibody has higher affinity to a D4 domain of KIT than to a D5 domain of KIT, e.g., human KIT, as determined by methods known in the art, e.g., ELISA or Biacore assay. In another specific embodiment, an antibody described herein (or an antigen-binding fragment thereof) immunospecifically binds a D4/D5 region of KIT, e.g., human KIT, wherein the antibody has higher affinity to a D4 domain of KIT than to a D5 domain of KIT, e.g., human KIT, as determined by methods known in the art, e.g., ELISA or Biacore assay, and wherein the higher affinity is at least 2 fold, 5 fold, 10 fold, 50 fold, 100 fold, or 500 fold. In another specific embodiment, an antibody described herein (or an antigen-binding fragment thereof) immunospecifically binds a D4/D5 region of KIT, e.g., human KIT, wherein the antibody has higher affinity to a KIT antigen consisting essentially of the amino acid sequence of SEQ ID NO: 16 or 17, than to a KIT antigen consisting essentially of the amino acid sequence of SEQ ID NO: 18 or 19, as determined by methods known in the art, e.g., ELISA or Biacore assay. In another specific embodiment, an antibody described herein (or an antigen-binding fragment thereof) immunospecifically binds a D4/D5 region of KIT, e.g., human KIT, wherein the antibody has higher affinity to a KIT antigen consisting essentially of the amino acid sequence of SEQ ID NO: 16 or 17, than to a KIT antigen consisting essentially of the amino acid sequence of SEQ ID NO: 18 or 19, as determined by methods known in the art, e.g., ELISA or Biacore assay, and wherein the higher affinity is at least 2 fold, 5 fold, 10 fold, 50 fold, 100 fold, or 500 fold.

In particular embodiments, an antibody described herein (or an antigen-binding fragment thereof) does not bind the extracellular ligand binding site of KIT, e.g., the SCF binding site of KIT.

In particular embodiments, an antibody described herein (or an antigen-binding fragment thereof) does not inhibit ligand binding to KIT, e.g., does not inhibit KIT ligand (e.g., SCF) binding to KIT. In certain embodiments, an antibody described herein does not block or inhibit KIT dimerization. In a particular embodiment, an antibody described herein does not disrupt a KIT dimer (for example, does not induce dissociation of a KIT dimer into KIT monomers). In particular embodiments, an antibody described herein does not inhibit KIT dimerization and/or does not inhibit or block KIT ligand (e.g., SCF) binding to KIT (e.g., human KIT).

In certain embodiments, an antibody described herein blocks or inhibits KIT dimerization or disrupts a KIT dimer (for example, induces dissociation of a KIT dimer into KIT monomers). In particular embodiments, an antibody described herein inhibits KIT dimerization or induces dissociation of a KIT dimer, and does not inhibit or block KIT ligand (e.g., SCF) binding to KIT (e.g., human KIT).

In specific aspects, antibodies described herein are inhibitory antibodies, that is, antibodies that inhibit (e.g., partially inhibit) KIT activity, i.e., one or more KIT activities. In a specific embodiment, partial inhibition of a KIT activity results in, for example, about 25% to about 65% or 75% inhibition. In a specific embodiment, partial inhibition of a KIT activity results in, for example, about 35% to about 85% or 95% inhibition. Non-limiting examples of KIT activities include KIT dimerization, KIT phosphorylation (e.g., tyrosine phosphorylation), signaling downstream of KIT (e.g., Stat, AKT, MAPK, or Ras signaling), induction or enhancement of gene transcription (e.g., c-Myc), induction or enhancement of cell proliferation or cell survival. In a particular embodiment, an antibody described herein inhibits KIT phosphorylation. In a specific embodiment, an antibody described herein inhibits KIT tyrosine phosphorylation in the KIT cytoplasmic domain. In another particular embodiment, an antibody described herein inhibits cell proliferation. In yet another particular embodiment, an antibody described herein inhibits cell survival. In a specific embodiment, an antibody described herein induces apoptosis. In another specific embodiment, an antibody described herein induces cell differentiation, e.g., cell differentiation in a cell expressing KIT, e.g., human KIT. In a particular embodiment, an antibody described herein inhibits KIT activity but does not inhibit KIT dimerization. In another particular embodiment, an antibody described herein inhibits KIT activity and does not inhibit ligand binding to KIT, e.g., does not inhibit KIT ligand (e.g., SCF) binding to KIT, but does inhibit KIT dimerization.

In a particular embodiment, an antibody described herein inhibits a KIT activity, such as ligand-induced tyrosine phosphorylation of a KIT cytoplasmic domain, by about 25% to about 65% or 75%, as determined by a cell-based phosphorylation assay well known in the art, for example, the cell-based phosphorylation assay described in Example 3 (Section 6.3) below. In a certain embodiment, an antibody described herein inhibits a KIT activity, such as ligand-induced tyrosine phosphorylation of a KIT cytoplasmic domain, by about 35% to about 85% or 95%, as determined by a cell-based phosphorylation assay well known in the art, for example, the cell-based phosphorylation assay described in Example 3 (Section 6.3) below. In a particular embodiment, an antibody described herein (e.g., antibody 37M or 37C, an antigen-binding fragment thereof, an antibody comprising CDRs of antibody 37M, or a conjugate comprising, for example, antibody 37M or 37C, a KIT-binding fragment thereof, or an antibody comprising CDRs of antibody 37M, linked, covalently or noncovalently, to a therapeutic agent) inhibits a KIT activity, such as ligand-induced tyrosine phosphorylation of a KIT cytoplasmic domain, with a 50% inhibition concentration ($IC_{50}$) of less than about 500 pM, or less than about 250 pM, as determined by a cell-based phosphorylation assay well known in the art, for example, the cell-based phosphorylation assay described in Example 3 (Section 6.3) below. In a specific embodiment, the $IC_{50}$ is less than about 200 pM. In a specific embodiment, the $IC_{50}$ is in the range of about 50 pM to about 225 pM, or in the range of 100 pM to about 180 pM. In a specific embodiment, the $IC_{50}$ is in the range of about 50 pM to about 150 pM, or about 50 pM to about 125 pM, or about 50 pM to about 110 pM.

In a specific embodiment, an antibody described herein (i) immunospecifically binds to a KIT polypeptide comprising the D4/D5 region of human KIT, (ii) inhibits KIT phosphorylation (e.g., tyrosine phosphorylation), and (iii) does not affect KIT ligand (e.g., SCF) binding to KIT. In yet another specific embodiment, such an antibody does not inhibit KIT dimerization.

The antibodies provided herein generally do not immunospecifically bind to the D1, D2, or D3 domain of the extracellular domain of KIT, e.g., human KIT. That is, in some embodiments, an antibody described herein does not immunospecifically bind to a D1 domain of the extracellular domain of KIT (e.g., human KIT); in some embodiments, an antibody described herein does not immunospecifically bind to a D2 domain of the extracellular domain of KIT (e.g., human KIT); and in some embodiments, an antibody described herein does not immunospecifically bind to a D3 domain of the extracellular domain of KIT (e.g., human KIT). In some embodiments, an anti-KIT antibody described herein does not immunospecifically binds to a D5 domain of the extracellular domain of KIT (e.g., human KIT). In some embodiments, an antibody described herein does not specifically bind to a D4-D5 hinge region of KIT (e.g., human KIT). In certain embodiments, an antibody described herein does not immunospecifically bind to domain D1, D2, and/or D3 of KIT (e.g., human KIT).

In other specific embodiments, an antibody described herein immunospecifically binds to a monomeric form of KIT (e.g., human KIT). In particular embodiments, an antibody described herein does not immunospecifically bind to a monomeric form of KIT (e.g., human KIT). In specific embodiments, an antibody described herein immunospecifically binds to a dimeric form of KIT (e.g., human KIT). In specific embodiments, an antibody described herein does not bind to a monomeric form of KIT and specifically binds to a dimeric form of KIT or multimeric form of KIT. In certain embodiments, an antibody has higher affinity for a KIT monomer than a KIT dimer. In certain embodiments, an antibody has higher affinity for a KIT monomer than a KIT multimer.

In specific embodiments, an anti-KIT antibody described herein (or an antigen-binding fragment thereof) specifically binds to a native isoform or native variant of KIT (that is a naturally occurring isoform or variant of KIT in an animal (e.g., monkey, mouse, goat, donkey, dog, cat, rabbit, pig, rat, human, frog, or bird) that can be isolated from an animal, preferably a human). In particular embodiments, an antibody described herein immunospecifically binds to human KIT or a fragment thereof. In specific embodiments, an anti-KIT antibody described herein specifically binds to human KIT or a fragment thereof and does not specifically bind to a non-human KIT (e.g., monkey, mouse, goat, donkey, dog, cat, rabbit, pig, rat, or bird) or a fragment thereof. In specific embodiments, an anti-KIT antibody described herein specifically binds to human KIT or a fragment thereof and does not specifically bind to murine KIT. In certain embodiments, an anti-KIT antibody described herein specifically binds to human KIT or a fragment thereof and does not specifically bind to dog (canine) KIT. In certain embodiments, an antibody described herein specifically binds to v-Kit or a fragment thereof (see, e.g., Besmer et al., Nature, 1986, 320:415-21).

In some embodiments, an antibody described herein (or an antigen-binding fragment thereof) immunospecifically binds to a KIT antigen comprising one or more (e.g., 1, 2, 3, 4, 5, 6, 7, 8, 9, 10, 15 or 20) amino acid substitutions (e.g., conservative amino acid substitutions), deletions, or additions of the amino acid sequence depicted by SEQ ID NO: 14 or 15. In some embodiments, an antibody described herein immunospecifically binds to a KIT antigen that has at least about 70%, 75%, 80%, 85%, 90%, 95%, or 98% amino acid sequence identity to the amino acid sequence depicted by SEQ ID NO: 14 or 15, for example, at least about 70%, 75%, 80%, 85%, 90%, 95%, or 98% amino acid sequence identity to the amino acid sequence depicted by SEQ ID NO: 14 or 15 over the entire length. In some embodiments, an antibody described herein immunospecifically binds to a KIT antigen comprising at most 10 amino acid substitutions, deletions, or additions; at most 8 amino acid substitutions, deletions, or additions; at most 7 amino acid substitutions, deletions, or additions; at most 6 conservative amino acid substitutions, deletions, or additions; at most 5 amino acid substitutions, deletions, or additions, at most 4 amino acid substitutions, deletions, or additions, at most 3 amino acid substitutions, deletions, or additions or at most 2 amino acid substitutions, deletions, or additions of the amino acid sequence depicted by SEQ ID NO: 14 or 15.

In some embodiments, an antibody described herein (or an antigen-binding fragment thereof) immunospecifically binds to a KIT antigen comprising one or more (e.g., 1, 2, 3, 4, 5, 6, 7, 8, 9, or 10) conservative amino acid substitutions of the amino acid sequence depicted by SEQ ID NO: 14 or 15. In some embodiments, an antibody described herein immunospecifically binds to a KIT antigen comprising at most 10 conservative amino acid substitutions, at most 8 conservative amino acid substitutions, at most 7 conservative amino acid substitutions, at most 6 conservative amino acid substitutions, or at most 5 conservative amino acid substitutions of the amino acid sequence depicted by SEQ ID NO: 14 or 15.

In certain embodiments, an antibody described herein does not immunospecifically bind to a transmembrane region of KIT (e.g., human KIT). In some embodiments, an antibody described herein does not immunospecifically bind to a cytoplasmic juxtamembrane domain of KIT (e.g., human KIT). In some embodiments, an antibody described herein does not immunospecifically bind to a cytoplasmic domain of KIT (e.g., human KIT). In certain embodiments, an antibody described herein does not immunospecifically bind to a split cytoplasmic kinase domain of KIT (e.g., human KIT). In certain embodiments, an antibody described herein does not immunospecifically bind to a tyrosine phosphorylated epitope of KIT (e.g., human KIT).

In certain embodiments, an antibody described herein or antigen-binding fragment thereof (e.g., antibody comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively) binds to an extracellular domain of human KIT comprising a mutation, for example a somatic mutation associated with cancer (e.g., GIST), such as a mutation in exon 9 of human KIT wherein the Ala and Tyr residues at positions 502 and 503 are duplicated. In certain embodiments, an antibody described herein or antigen-binding fragment thereof (e.g., antibody comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively) binds to an extracellular domain of wild-type human KIT and an extracellular domain of human KIT comprising a mutation, for example a somatic mutation associated with cancer (e.g., GIST), such as a mutation in exon 9 of human KIT wherein the Ala and Tyr residues at positions 502 and 503 are duplicated (see, e.g., Marcia et al., (2000) Am. J. Pathol. 156(3):791-795; and Debiec-Rychter et al., (2004) European Journal of Cancer. 40:689-695, which are both incorporated herein by reference in their entireties, describing KIT mutations).

In certain embodiments, an antibody described herein or antigen-binding fragment thereof (e.g., antibody comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively) binds to an extracellular domain of human KIT which is glycosylated. In certain embodiments, an antibody described herein or antigen-binding fragment thereof (e.g., antibody comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively) binds to two different glycosylated forms of an extracellular domain of human KIT. For example, two forms of human KIT with different molecular weights, indicating different glycosylation patterns, have been observed by immunoblotting. In certain embodiments, an antibody described herein may specifically bind to both of these forms of human KIT which have different glycosylation patterns, e.g., one form is more glycosylated than the other. In certain embodiments, an antibody described herein or antigen-binding fragment thereof (e.g., antibody comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively) binds to an extracellular domain of human KIT which is not glycosylated.

In a particular embodiment, an antibody described herein is not an antibody described by International Patent Application No. WO 2008/153926, the contents of which are incorporated herein by reference in its entirety. In another particular embodiment, an antibody described herein does not immunospecifically bind to a KIT epitope described by International Patent Application No. WO 2008/153926, for example an epitope consisting essentially of the amino acid sequence SELHLTRLKGTEGGTYT (SEQ ID NO: 38) or LTRLKGTEGG (SEQ ID NO: 39).

In certain embodiments, an anti-KIT antibody described herein is not an antibody selected from the group consisting of: SR-1 antibody (see U.S. Patent Application Publication No. US 2007/0253951 A1; International Patent Application Publication No. WO 2007/127317); anti-KIT antibody obtained from hybridoma cell lines DSM ACC 2007, DSM ACC 2008, or DSM ACC 2009, which have been deposited at the Deutsche Sammlung von Mikroorganismen und Zellkulturen GmbH, DSM, Mascheroder Weg 1 b, D-38124 Braumschweig, Germany (see U.S. Pat. No. 5,545,533; International Patent Application Publication No. WO 92/021766); antibody produced by hybridoma cell line DSM ACC 2247 (or A3C6E2; Deposit No. DSM ACC 2247, at the Deutsche Sammlung von Mikroorganismen und Zellkulturen GmbH, DSM, Mascheroder Weg 1 b, D-38124 Braumschweig, Germany) (see U.S. Pat. No. 5,808,002); and anti-KIT antibodies designated K27, K44, K45, K49, K57, K69, and K94 (see, e.g., Blechman et al., Stem Cells, 1993, 11:12-21; Blechman et al., Cell, 1995, 80:103-113; Lev et al., Mol. Cell. Biol., 1993, 13:2224-2234; and European Patent Application Publication No. EP0548867 A2). In certain embodiments, an anti-KIT antibody described herein does not comprise a CDR of an antibody selected from such group. In particular embodiments, an anti-KIT antibody described herein does not comprise one or more (e.g., two, three, four, five, or six) CDRs (e.g., 3 VL CDRs and/or 3 VH CDRs) of an antibody selected from such group. In another embodiment, an antibody described herein is not competitively blocked (e.g., competitively blocked in a dose-dependent manner) by one of those antibodies, for example, as determined by competition binding assays (e.g., ELISAs). In certain embodiments, an anti-KIT antibody described herein is not antibody Ab1 or Ab21, which is described in U.S. Provisional Application No. 61/426,387, filed Dec. 22, 2010. In certain embodiments, an anti-KIT antibody described herein is not an antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21, as described in U.S. Provisional Application No. 61/426,387, filed Dec. 22, 2010 and Ab24-Ab192 as described in PCT International Patent Application No. PCT/US2011/29980 filed Mar. 25, 2011. In certain embodiments, an anti-KIT antibody described herein does not comprise a CDR, or one or more CDRs (e.g., 3 VL CDRs and/or 3VH CDRs), of an antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21, as described in U.S. Provisional Application No. 61/426,387, filed Dec. 22, 2010, and Ab24-Ab192 as described in PCT International Patent Application No. PCT/US2011/29980 filed Mar. 25, 2011. In particular embodiments, an anti-KIT antibody described herein does not comprise a CDR, or one or more CDRs (e.g., 3 VL CDRs and/or 3VH CDRs), VL chain region, or VH chain region of an antibody selected from the antibodies (e.g., antibodies Ab1-Ab21 and Ab24-Ab192) described in U.S. Provisional Application No. 61/426,387 filed Dec. 22, 2010 or PCT International Patent Application No. PCT/US2011/29980 filed Mar. 25, 2011. In certain embodiments, an anti-KIT antibody described herein is not antibody Ab1 or Ab21, or an antibody comprising CDRs (e.g., one, two, three, four, five, or six CDRs) of antibody Ab1 or Ab21, as described in U.S. Provisional Application No. 61/426,387, filed Dec. 22, 2010.

In a particular embodiment, an antibody described herein or antigen-binding fragment thereof, which immunospecifically bind to a KIT polypeptide (e.g., the D4/D5 region of KIT, for example, human KIT), does not comprise one or more (e.g., two, three, four, five, or six) CDRs (e.g., VL CDR1, VL CDR2, VL CDR3, VH CDR1, VH CDR2, and VH CDR3) of an antibody described in US Patent Application Publication NO. US 2008/0287309, for example antibody 36C1, 84H7, 63C10, or 65A12.

In a specific embodiment, an antibody described herein is not an antibody produced by the hybridoma (BA7.3C.9) having the American Type Culture Collection (ATCC) Accession number HB10716, as described for example in U.S. Pat. No. 5,919,911 or 5,489,516. In another specific embodiment, an antibody described herein does not comprise the CDRs (e.g., VL CDR1, VL CDR2, VL CDR3, VH CDR1, VH CDR2, and/or VH CDR3) of the antibody produced by the hybridoma (BA7.3C.9) having the American Type Culture Collection (ATCC) Accession number HB10716, as described for example in U.S. Pat. No. 5,919, 911 or 5,489,516. In another specific embodiment, an antibody described herein does not comprise the CDRs of the SR-1 antibody described for example in U.S. Pat. No. 5,919,911 or 5,489,516 or U.S. Patent Application Publication No. US 2007/0253951 A1 (see, e.g., [0032] or [0023]). In a further embodiment, an antibody described herein is not a humanized antibody of the antibody produced by the hybridoma (BA7.3C.9) having the American Type Culture Collection (ATCC) Accession number HB10716, as described for example in U.S. Pat. No. 5,919,911 or 5,489, 516.

In a specific embodiment, an antibody described herein is not the humanized antibodies of the SR-1 antibody as described in U.S. Patent Application Publication No. US 2007/0253951 A1. In a specific embodiment, an antibody described herein does not comprise one or more amino acid sequences selected from the group consisting of: SEQ ID NO: 2, SEQ ID NO: 4, SEQ ID NO: 6, SEQ ID NO: 8, and SEQ ID NO: 10 referenced in U.S. Patent Application Publication No. US 2007/0253951 A1. In a particular embodiment, an antibody described herein does not comprise the amino acid sequences of SEQ ID NOs: 2 and 4 or of SEQ ID NOs: 2 and 6 referenced in U.S. Patent Application Publication No. US 2007/0253951 A1. In a specific embodiment, an antibody described herein does not comprise one or more amino acid sequence that is at least 90% identical to the amino acid sequence selected from the group consisting of: SEQ ID NO: 2, SEQ ID NO: 4, SEQ ID NO: 6, SEQ ID NO: 8, and SEQ ID NO: 10 referenced in U.S. Patent Application Publication No. US 2007/0253951 A1. In a particular embodiment, an antibody described herein does not comprise one or more CDRs described in U.S. Patent Application Publication No. US 2007/0253951 A1, for example, amino acids 44 to 58 of SEQ ID NO: 8 (VL CDR1 of antibody SR-1; RASESVDIYGNSFMH), amino acids 74 to 80 of SEQ ID NO: 8 (VL CDR2 of antibody SR-1; LASNLES), amino acids 111 to 121 of SEQ ID NO: 8 (VL CDR3 of antibody SR-1; QQNNEDPYT), amino acids 50 to 54 of SEQ ID NO: 10 (VH CDR1 of antibody SR-1; SYNMH), amino acids 69 to 85 of SEQ ID NO: 10 (VH CDR2 of antibody SR-1; VIYSGNGDTSYNQKFKG), and/or amino acids 118 to 125 of SEQ ID NO: 10 (VH CDR3 of antibody SR-1; RDTRFGN), where SEQ ID NOs: 8 and 10 are those referenced in U.S. Patent Application Publication No. US 2007/0253951 A1 (see, e.g., [0032] or [0023]). In a particular embodiment, an antibody described herein does not comprise one or more CDRs described in U.S. Patent Application Publication No. US 2007/0253951 A1, for example, amino acids 43 to 58 of SEQ ID NO: 2 (VL CDR1), amino acids 74 to 80 of SEQ ID NO: 2 (VL CDR2), amino acids 113 to 121 of SEQ ID NO: 2 (VL CDR3), amino acids 50 to 54 of SEQ ID NO: 4 (VH CDR1), amino acids 69 to 85 of SEQ ID NO: 4 (VH CDR2), and/or amino acids 118 to 125 of SEQ ID NO: 4 (VH CDR3), where SEQ ID NOs: 2 and 4 are those referenced in U.S. Patent Application Publication No. US 2007/0253951 A1. In a particular embodiment, an antibody described herein is not a humanized antibody of antibody SR-1 as described in U.S. Patent Application Publication No. US 2007/0253951 A1.

In a specific embodiment, an antibody described herein is not an antibody selected from the group consisting of: antibody Anti-S100, ACK2, and ACK4 as described in U.S. Pat. No. 6,989,248 or 7,449,309. In a specific embodiment, an antibody described herein does not comprise one or more CDRs (e.g., 3 VL CDRs and/or 3 VH CDRs) of an antibody selected from the group consisting of: antibody Anti-S100, ACK2, and ACK4 as described in U.S. Pat. No. 6,989,248 or 7,449,309.

In particular aspects, provided herein are antibodies (e.g., a murine, chimeric or humanized antibody) or an antigen-binding fragment thereof, which immunospecifically bind to a KIT polypeptide (e.g., the D4/D5 region of KIT, for example, human KIT) and comprise an amino acid sequence as described herein, as well as antibodies which compete (e.g., compete in a dose-dependent manner) with such antibodies for binding to a KIT polypeptide.

In a particular embodiment, an antibody described herein, or an antigen-binding fragment thereof, comprises a VL chain region having the amino acid sequence of SEQ ID NO: 2, and/or comprises a VH chain region having the amino acid sequence of SEQ ID NO: 3 or 5. In a particular embodiment, an antibody described herein comprises a VL chain region having the amino acid sequence of SEQ ID NO: 2, and comprises a VH chain region having the amino acid sequence of SEQ ID NO: 3. In a particular embodiment, an antibody described herein comprises a VL chain region having the amino acid sequence of SEQ ID NO: 2, and comprises a VH chain region having the amino acid sequence of SEQ ID NO: 5. In certain embodiments, any of these antibodies can comprise a variable heavy chain and a variable light chain, for example, a separate variable heavy chain and a separate variable light chain. In a specific embodiment, the position (i.e., boundary) of a VL chain region described herein relative to the constant region may change by one, two, three, or four amino acid positions so long as immunospecific binding to KIT (e.g., the D4/D5 region of human KIT) is maintained (e.g., substantially maintained, for example, at least 50%, at least 60%, at least 70%, at least 80%, at least 90%, at least 95%). In a specific embodiment, the position (i.e., boundary) of a VH chain region described herein relative to the constant region may change by one, two, three, or four amino acid positions so long as immunospecific binding to KIT (e.g., the D4/D5 region of human KIT) is maintained (e.g., substantially maintained, for example, at least 50%, at least 60%, at least 70%, at least 80%, at least 90%, at least 95%).

In certain embodiments, an antibody described herein, or an antigen-binding fragment thereof, comprises a variable light (VL) chain region comprising an amino acid sequence described herein (e.g., see FIG. 3A). In certain embodiments, an antibody described herein comprises a VL chain region having the amino acid sequence of SEQ ID NO: 2, wherein the antibody immunospecifically binds to a KIT polypeptide, e.g., a human KIT polypeptide, for example, a D4/D5 region of KIT (e.g., human KIT), for example SEQ ID NO: 15. In certain embodiments, any of these antibodies can comprise a variable variable light chain, for example, a separate variable light chain. In certain embodiments, an antibody described herein comprises a VL chain region having the amino acid sequence of SEQ ID NO: 2.

In certain embodiments, an antibody described herein, or an antigen-binding fragment thereof, comprises a variable heavy (VH) chain region comprising an amino acid sequence described herein (e.g., see FIG. 3B). In certain embodiments, an antibody described herein comprises a VH chain region having the amino acid sequence of SEQ ID NO: 3 or 5, wherein the antibody immunospecifically binds to a KIT polypeptide, e.g., a human KIT polypeptide, for example, a D4/D5 region of KIT (e.g., human KIT), for example SEQ ID NO: 15. In certain embodiments, an antibody described herein comprises a VH chain region having the amino acid sequence of SEQ ID NO: 3. In certain embodiments, an antibody described herein comprises a VH chain region having the amino acid sequence of SEQ ID NO: 5. In certain embodiments, any of these antibodies can comprise a variable heavy chain, for example, a separate variable heavy chain.

In certain embodiments, an antibody described herein, or an antigen-binding fragment thereof, comprises one or more VL CDRs having the amino acid sequence described herein (e.g., see Tables 1), wherein the antibody immunospecifically binds to a KIT polypeptide, e.g., a human KIT polypeptide, for example, a D4/D5 region of KIT (e.g., human KIT), for example SEQ ID NO: 15. In certain embodiments, an antibody described herein comprises at least two VL CDRs from the same antibody sequence depicted at Tables 1, e.g., comprises VL CDR1 and VL CDR2 of antibody 37C. In certain embodiments, an antibody described herein comprises a VL CDR1, VL CDR2, and VL CDR3 from the same antibody sequence depicted at Tables 1, e.g., comprises VL CDR1, VL CDR2, and VL CDR3 of antibody 37C.

In particular embodiments, the VL CDR1 has the amino acid sequence of SEQ ID NO: 20. In certain embodiments, the VL CDR2 has the amino acid sequence of SEQ ID NO: 21. In specific embodiments, the VL CDR3 has the amino acid sequence of SEQ ID NO: 22. In a specific embodiment, an antibody described herein comprises a VL chain region comprising (i) a VL CDR1 having the amino acid sequence of SEQ ID NO: 20; (ii) a VL CDR2 having the amino acid sequence of SEQ ID NO: 21; and (iii) a VL CDR3 having the amino acid sequence of SEQ ID NO: 22, wherein the antibody immunospecifically binds to a KIT polypeptide, e.g., a human KIT polypeptide, for example, a D4/D5 region of KIT (e.g., human KIT), for example SEQ ID NO: 15. In a specific embodiment, a VL CDR1 has the sequence of SEQ ID NO: 20 that does not have an amino acid substitution at position 7 of SEQ ID NO: 20 (for example, the R amino acid at position 7 of SEQ ID NO: 20 is not substituted with G). In a specific embodiment, a VL CDR3 has the sequence of SEQ ID NO: 22 that does not have an amino acid substitution at position 8 of SEQ ID NO: 22 (for example, the R amino acid at position 8 of SEQ ID NO: 22 is not substituted with L).

In certain embodiments, an antibody described herein, or an antigen-binding fragment thereof, comprises one or more VH CDRs having the amino acid sequence described herein (e.g., see Table 3), wherein the antibody immunospecifically binds to a KIT polypeptide, e.g., a human KIT polypeptide, for example, a D4/D5 region of KIT (e.g., human KIT), for example SEQ ID NO: 15. In particular embodiments, the VH CDR1 has the amino acid sequence of SEQ ID NO: 23. In certain embodiments, the VH CDR2 has the amino acid sequence of SEQ ID NO: 24. In specific embodiments, the VH CDR3 has the amino acid sequence of SEQ ID NO: 25. In certain embodiments, an antibody described herein comprises at least two VH CDRs from the same antibody sequence depicted at Table 3, e.g., comprises VH CDR1 and VH CDR2 of antibody 37 M or 37C. In certain embodiments, an antibody described herein comprises a VH CDR1, VH CDR2, and VH CDR3 from the same antibody sequence depicted at Table 3, e.g., comprises VH CDR1, VH CDR2, and VH CDR3 of antibody 37M or 37C.

In a specific embodiment, an antibody described herein, or an antigen-binding fragment thereof, comprises a VH chain region comprising (i) a VH CDR1 having the amino acid sequence of SEQ ID NO: 23; (ii) a VH CDR2 having the amino acid sequence of SEQ ID NO: 24; and (iii) a VH CDR3 having the amino acid sequence of SEQ ID NO: 25, wherein the antibody immunospecifically binds to a KIT polypeptide, e.g., a human KIT polypeptide, for example, a D4/D5 region of KIT (e.g., human KIT), for example SEQ ID NO: 15.

In another specific embodiment, an antibody (e.g., murine, chimeric or humanized antibody) described herein, or an antigen-binding fragment thereof, comprises (i) a VL chain region comprising a VL CDR1, VL CDR2, and VL CDR3 having the amino acid sequences of SEQ ID NO: 20, 21, and 22, respectively; and (ii) a VH chain region comprising a VH CDR1, VH CDR2, and VH CDR3 having the amino acid sequences of SEQ ID NO: 23, 24, and 25, respectively, wherein the antibody immunospecifically binds to a KIT polypeptide, e.g., a human KIT polypeptide, for example, a D4/D5 region of KIT (e.g., human KIT), for example SEQ ID NO: 15.

In another specific embodiment, an antibody (e.g., murine, chimeric or humanized antibody) described herein, or an antigen-binding fragment thereof, comprises (i) a VL chain region comprising a VL CDR1, VL CDR2, and VL CDR3 having the amino acid sequences of SEQ ID NO: 20, 21, and 22, respectively; and (ii) a VH chain region having the amino acid sequence of SEQ ID NO: 3 or 5, wherein the antibody immunospecifically binds to a KIT polypeptide, e.g., a human KIT polypeptide, for example, a D4/D5 region of KIT (e.g., human KIT), for example SEQ ID NO: 15.

In another specific embodiment, an antibody (e.g., murine, chimeric or humanized antibody) described herein, or an antigen-binding fragment thereof, comprises (i) a VL chain region having the amino acid sequence of SEQ ID NO: 2; and (ii) a VH chain region comprising a VH CDR1, VH CDR2, and VH CDR3 having the amino acid sequences of SEQ ID NO: 23, 24, or 25, respectively, wherein the antibody immunospecifically binds to a KIT polypeptide, e.g., a human KIT polypeptide, for example, a D4/D5 region of KIT (e.g., human KIT), for example SEQ ID NO: 15.

Also provided herein are antibodies that bind the same or an overlapping epitope as an antibody described herein (e.g., antibody 37M or 37C), i.e., antibodies that compete for binding to KIT, or bind epitopes which overlap with epitopes bound by the antibodies described herein, e.g., an epitope located on a D4/D5 region of human KIT. Antibodies that recognize such epitopes can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as KIT. Numerous types of competitive binding assays are known, for example: solid phase direct or indirect radioimmunoassay (RIA), solid phase direct or indirect enzyme immunoassay (EIA), sandwich competition assay (see Stahli et al., (1983) Methods in Enzymology 9:242); solid phase direct biotin-avidin EIA (see Kirkland et al., (1986) J. Immunol. 137:3614); solid phase direct labeled assay, solid phase direct labeled sandwich assay (see Harlow and Lane, (1988) Antibodies: A Laboratory Manual, Cold Spring Harbor Press); solid phase direct label RIA using I-125 label (see Morel et al., (1988) Mol. Immunol. 25(1):7); solid phase direct biotin-avidin EIA (Cheung et al., (1990) Virology 176:546); and direct labeled RIA. (Moldenhauer et al., (1990) Scand J. Immunol. 32:77). Typically, such an assay involves the use of purified antigen (e.g., KIT, such as extracellular domain of KIT or a D4/D5 region of KIT) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener et al., J. Immunol., 1983, 130:2308-2315; Wagener et al., J. Immunol. Methods, 1984, 68:269-274; Kuroki et al., Cancer Res., 1990, 50:4872-4879; Kuroki et al., Immunol. Invest., 1992, 21:523-538; Kuroki et al., Hybridoma, 1992, 11:391-407, and *Using Antibodies: A Laboratory Manual*, Ed Harlow and David Lane editors (Cold Springs Harbor Laboratory Press, Cold Springs Harbor, N.Y., 1999), pp. 386-389.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an antibody described herein, e.g., antibody 37M or 37C, an antibody comprising VH CDRs and VL CDRs of 37M or 37C, or a humanized monoclonal antibody comprising VH CDRs and VL CDRs of antibody 37M or 37C. In a specific embodiment, a competition binding assay is carried out, for example, as described in section 6.6 below.

In specific aspects, provided herein is an antibody which competitively blocks (e.g., in a dose dependent manner), antibodies comprising the amino acid sequences described herein for specific binding to a KIT polypeptide (e.g., a D4/D5 region of KIT, for example human KIT), as determined using assays known to one of skill in the art or described herein (e.g., ELISA competitive assays). In particular embodiments, such competitively blocking antibody inhibits one or more KIT activities. In specific aspects, provided herein is an antibody which competes (e.g., in a dose dependent manner) for specific binding to a KIT polypeptide (e.g., a D4/D5 region of KIT, for example human KIT), with an antibody comprising the amino acid sequences described herein, as determined using assays known to one of skill in the art or described herein (e.g., ELISA competitive assays). In a certain embodiment, antibody 37M is an example of an antibody which competes, competitively inhibits (e.g., in a dose-dependent manner) or competitively blocks, antibody 37C from binding to a KIT polypeptide (e.g., a D4/D5 region of KIT, for example human KIT). In a particular embodiment, antibody 37C is an example of an antibody which competes, competitively inhibits, or competitively blocks (e.g., in a dose-dependent manner) antibody 37M from binding to a KIT polypeptide (e.g., a D4/D5 region of KIT, for example human KIT).

In specific aspects, provided herein is an antibody which competes (e.g., in a dose dependent manner) for specific binding to a KIT polypeptide (e.g., a D4/D5 region of KIT, for example human KIT), with an antibody comprising a VL chain region having the amino acid sequence of SEQ ID NO: 2 and a VH chain region having the amino acid sequence of SEQ ID NO: 3 or 5.

In specific aspects, provided herein is an antibody which competes (e.g., in a dose dependent manner) for specific binding to a KIT polypeptide (e.g., a D4/D5 region of KIT, for example human KIT), with an antibody comprising a light chain comprising the amino acid sequence of SEQ ID NO: 6 (or the amino acid sequence of SEQ ID NO: 6 starting at position 20, lacking the signal peptide) and a heavy chain comprising the amino acid sequence of SEQ ID NO: 7 (or the amino acid sequence of SEQ ID NO: 7 starting at position 20, lacking the signal peptide), for specific binding to a KIT polypeptide (e.g., a D4/D5 region of KIT, for example human KIT).

In specific aspects, provided herein is an antibody which competes (e.g., in a dose dependent manner) for specific binding to a KIT polypeptide (e.g., a D4/D5 region of KIT, for example human KIT), with an antibody comprising i) a VL chain region comprising a VL CDR1, VL CDR2, and VL CDR3 having the amino acid sequences of SEQ ID NO: 20, 21, and 22, respectively; and (ii) a VH chain region comprising a VH CDR1, VH CDR2, and VH CDR3 having the amino acid sequences of SEQ ID NO: 23, 24, and 25, respectively.

In a specific embodiment, an antibody described herein is one that is competitively blocked (e.g., in a dose dependent manner) by an antibody comprising a VL chain region having the amino acid sequence of SEQ ID NO: 2 and a VH chain region having the amino acid sequence of SEQ ID NO: 3 or 5, for specific binding to a KIT polypeptide (e.g., a D4/D5 region of KIT, for example human KIT).

In a specific embodiment, an antibody described herein is one that is competitively blocked (e.g., in a dose dependent manner) by an antibody comprising a light chain comprising the amino acid sequence of SEQ ID NO: 6 (or the amino acid sequence of SEQ ID NO: 6 starting at position 20, lacking the signal peptide) and a heavy chain comprising the amino acid sequence of SEQ ID NO: 7 (or the amino acid sequence of SEQ ID NO: 7 starting at position 20, lacking the signal peptide), for specific binding to a KIT polypeptide (e.g., a D4/D5 region of KIT, for example human KIT).

In another specific embodiment, an antibody described herein is one that is competitively blocked (e.g., in a dose dependent manner) by an antibody comprising (i) a VL chain region comprising a VL CDR1, VL CDR2, and VL CDR3 having the amino acid sequences of SEQ ID NO: 20, 21, and 22, respectively; and (ii) a VH chain region comprising a VH CDR1, VH CDR2, and VH CDR3 having the amino acid sequences of SEQ ID NO: 23, 24, and 25, respectively.

In another specific embodiment, such antibody is one that is not competitively blocked (e.g., in a dose dependent manner) by an antibody provided herein.

In another specific embodiment, an antibody described herein is one that is not competitively blocked (e.g., in a dose dependent manner) by antibody Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, or Ab21 as described in U.S. Provisional Application No. 61/426,387, filed Dec. 22, 2010, or by an antibody comprising the CDRs of such antibodies. In another specific embodiment, an antibody described herein is one that is not competitively blocked (e.g., in a dose dependent manner) by an antibody comprising (i) a VL chain region having the amino acid sequence:

```
DIQMTQSPTSLSAFVGDRVTITCQASQDIGNYLNWYQQKSGEPPKLLVY

DASFLKKGVPSRFSGSGSGTQYFLTIYSLQPEDFATYFCQHSDNLSVTF

GGGTKVEVK (SEQ ID NO: 45; VL chain region of Ab1)
or

DIQMTQSPTSLSAFVGDRVTITCQASQDIGNYLNWYQQKSGEPPKLLVY

DASFLKKGVPSRFSGSGSGTQYFLTIYSLQPEDFATYFCQHSDSLSVTF

GGGTKVEVK (SEQ ID NO: 47; VL chain region of Ab21);
and (ii) a VH chain region having the amino acid se-
quence
EVQLLESGGGLVQPGGSLRLSCAASGFTFSNYLMSWVRQAPGKGLEWVS

SIVPSGGFTHYADSVKGRFTISRDNSKNTLYLQMNSLRAEDTAVYYCAR

LQTGSWRVHAFDIWGQGTMVTVSS (SEQ ID NO: 46; VH chain region of Ab1 or Ab21).
```

In another specific embodiment, an antibody described herein, which competitively blocks (e.g., in a dose dependent manner) antibody 37M or 37C (e.g., an antibody comprising (i) a VL chain region having the amino acid sequence of SEQ ID NO: 2 and (ii) a VH chain region having the amino acid sequence of SEQ ID NO: 3 or 5), for specific binding to a KIT polypeptide (e.g., a D4/D5 region of KIT, for example human KIT), or binds to the same epitope as antibody 37M or 37C, is not one of the antibodies selected from the group consisting of antibodies Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21 as described in U.S. Provisional Application No. 61/426,387, filed Dec. 22, 2010, and an antibody comprising CDRs of antibody Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, or Ab21. In another specific embodiment, an antibody described herein, which competitively blocks (e.g., in a dose dependent manner) antibody 37M or 37C (e.g., an antibody comprising (i) a VL chain region having the amino acid sequence of SEQ ID NO: 2 and (ii) a VH chain region having the amino acid sequence of SEQ ID NO: 3 or 5), for specific binding to a KIT polypeptide (e.g., a D4/D5 region of KIT, for example human KIT), or binds to the same epitope as antibody 37M or 37C, is not one of the antibodies selected from the group consisting of antibodies Ab1-Ab21 as described in U.S. Provisional Application No. 61/426,387, filed Dec. 22, 2010, Antibodies Ab1-Ab21 and Ab24-Ab192 as described in PCT International Patent Application No. PCT/US2011/29980 filed Mar. 25, 2011, and an antibody comprising CDRs of any one of antibodies Ab1-Ab21 and Ab24-Ab192.

In another specific embodiment, an antibody described herein, which competitively blocks (e.g., in a dose dependent manner) antibody 37M or 37C (e.g., an antibody comprising (i) a VL chain region having the amino acid sequence of SEQ ID NO: 2 and (ii) a VH chain region having the amino acid sequence of SEQ ID NO: 3 or 5), for specific binding to a KIT polypeptide (e.g., a D4/D5 region of KIT, for example human KIT), or binds to the same epitope as antibody 37M or 37C, is not an antibody described in PCT International Patent Application Publication No. WO 2008/153926.

In another specific embodiment, an antibody described herein, which competitively blocks (e.g., in a dose dependent manner) antibody 37M or 37C (e.g., an antibody comprising (i) a VL chain region having the amino acid sequence of SEQ ID NO: 2 and (ii) a VH chain region having the amino acid sequence of SEQ ID NO: 3 or 5), for specific binding to a KIT polypeptide (e.g., a D4/D5 region of KIT, for example human KIT), or binds to the same epitope as antibody 37M or 37C, is not an antibody selected from the group consisting of: (i) SR-1 antibody described in U.S. Patent Application Publication No. US 2007/0253951 A1 and/or PCT International Patent Application Publication No. WO 2007/127317); (ii) an antibody obtained from hybridoma cell line DSM ACC 2007, DSM ACC 2008, or DSM ACC 2009, which have been deposited at the Deutsche Sammlung von Mikroorganismen und Zellkulturen GmbH, DSM, Mascheroder Weg 1 b, D-38124 Braumschweig, Germany (as described, e.g., in U.S. Pat. No. 5,545,533; PCT International Patent Application Publication No. WO 92/021766); (iii) an antibody produced by hybridoma cell line DSM ACC 2247 (or A3C6E2; Deposit No. DSM ACC 2247, at the Deutsche Sammlung von Mikroorganismen und Zellkulturen GmbH, DSM, Mascheroder Weg 1 b, D-38124 Braumschweig, Germany) as described, e.g., in U.S. Pat. No. 5,808,002; (iv) antibody designated K27, K44, K45, K49, K57, K69, or K94 as described, e.g., in Blechman et al., Stem Cells, 1993, 11:12-21; Blechman et al., Cell, 1995, 80:103-113; Lev et al., Mol. Cell. Biol., 1993, 13:2224-2234; and European Patent Application Publication No. EP0548867 A2; and (v) an antibody comprising CDRs of any one of the antibodies described in (i)-(iv).

In specific aspects, provided herein is an antibody, or an antigen-binding fragment thereof, which immunospecifically binds to the same epitope as that of an antibody comprising the amino acid sequences described herein for specific binding to a KIT polypeptide (e.g., a D4/D5 region of KIT, for example human KIT). Assays known to one of skill in the art or described herein (e.g., ELISA assays) can be used to determine if two antibodies bind to the same epitope.

In a specific embodiment, an antibody described herein, or an antigen-binding fragment thereof, immunospecifically binds to the same epitope as that of an antibody comprising a VL chain region having the amino acid sequence of SEQ ID NO: 2 and a VH chain region having the amino acid sequence of SEQ ID NO: 3 or 5. In a specific embodiment, an antibody described herein, or an antigen-binding fragment thereof, immunospecifically binds to the same epitope as that of an antibody comprising a light chain comprising the amino acid sequence of SEQ ID NO: 6 (or the amino acid sequence of SEQ ID NO: 6 starting at position 20, lacking the signal peptide) and a heavy chain comprising the amino acid sequence of SEQ ID NO: 7 (or the amino acid sequence of SEQ ID NO: 7 starting at position 20, lacking the signal peptide).

In another specific embodiment, an antibody described herein, or an antigen-binding fragment thereof, immunospecifically binds to the same epitope as that of an antibody comprising (i) a VL chain region comprising a VL CDR1, VL CDR2, and VL CDR3 having the amino acid sequences of SEQ ID NO: 20, 21, and 22, respectively; and (ii) a VH chain region comprising a VH CDR1, VH CDR2, and VH CDR3 having the amino acid sequences of SEQ ID NO: 23, 24, and 25, respectively.

Table 1, below, presents the VL CDR (in particular, VL CDR1, VL CDR2, and VL CDR3) amino acid sequences of antibodies 37M and 37C. Table 2, below, presents the VL framework (FR) amino acid sequences (in particular, VL FR1, VL FR2, VL FR3, and VL FR4 sequences) of antibodies 37M and 37C. Table 3, below, presents the VH CDR (in particular, VH CDR1, VH CDR2, and VH CDR3) amino acid sequences of antibodies 37M and 37C. Table 4, below, presents the VH FR amino acid sequences (in particular, VH FR1, VH FR2, VH FR3, and VH FR4 sequences) of antibodies 37M and 37C.

In certain aspects, an antibody described herein which immunospecifically binds to a D4/D5 region of a KIT polypeptide (e.g., human KIT polypeptide) may be described by its VL chain region or VH chain region, or by its 3 VL CDRs or its 3 VH CDRs. See, for example, Rader et al., 1998, Proc. Natl. Acad. Sci. USA, 95: 8910-8915, which is incorporated herein by reference in its entirety, which describes the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also, Clackson et al., 1991, Nature, 352:624-628, which is incorporated herein by reference in its entirety, describing methods of producing antibodies that bind a specific antigen by using a specific VL (or VH) and screening a library for the complimentary variable domains. The screen produced 14 new partners for a specific VH and 13 new partners for a specific VL, which were strong binders as determined by ELISA.

Thus, in certain aspects, provided herein is an antibody, which immunospecifically binds to a D4/D5 region of a KIT polypeptide (e.g., human KIT polypeptide), comprising a VL CDR1, VL CDR2, and VL CDR3 having the amino acid sequences of SEQ ID NOs: 20, 21, and 22, respectively. In certain embodiments, provided herein is an antibody, which immunospecifically binds to a D4/D5 region of a KIT polypeptide (e.g., human KIT polypeptide), comprising a VH CDR1, VH CDR2, and VH CDR3 having the amino acid sequences of SEQ ID NOs: 23, 24, and 25, respectively. In particular embodiments, provided herein is an antibody, which immunospecifically binds to a D4/D5 region of a KIT polypeptide (e.g., human KIT polypeptide), comprising a VL domain having the amino acid sequence of SEQ ID NO: 2, respectively. In some embodiments, provided herein is an antibody, which immunospecifically binds to a D4/D5 region of a KIT polypeptide (e.g., human KIT polypeptide), comprising a VH domain having the amino acid sequence of SEQ ID NO: 3 or 5.

In certain aspects, the CDRs of an antibody described herein is determined according to the method of Chothia and Lesk, 1987, J. Mol. Biol., 196:901-917, which will be referred to herein as the "Chothia CDRs" (see also, e.g., U.S. Pat. No. 7,709,226). Using the Kabat numbering system of numbering amino acid residues in the VH chain region and VL chain region, Chothia CDRs within an antibody heavy chain molecule are typically present at amino acid positions 26 to 32 ("CDR1"), amino acid positions 53 to 55 ("CDR2"), and amino acid positions 96 to 101 ("CDR3"). Using the Kabat numbering system of numbering amino acid residues in the VH chain region and VL chain region, Chothia CDRs within an antibody light chain molecule are typically present at amino acid positions 26 to 33 (CDR1), amino acid positions 50 to 52 (CDR2), and amino acid positions 91 to 96 (CDR3).

In a specific embodiment, the position of a CDR along the VH and/or VL region of an antibody described herein may vary by one, two, three or four amino acid positions so long as immunospecific binding to KIT (e.g., the D4/D5 region of human KIT) is maintained (e.g., substantially maintained, for example, at least 50%, at least 60%, at least 70%, at least 80%, at least 90%, at least 95%). For example, in one embodiment, the position defining a CDR of antibody 37M or 37C may vary by shifting the N-terminal and/or C-terminal boundary of the CDR by one, two, three, or four, amino acids, relative to the CDR position depicted in FIGS. 3A-5C, so long as immunospecific binding to KIT (e.g., the D4/D5 region) is maintained (e.g., substantially maintained, for example, at least 50%, at least 60%, at least 70%, at least 80%, at least 90%, at least 95%).

TABLE 1

VL CDR Amino Acid Sequences

| Ab 37M/C | VL CDR amino acid sequence | SEQ ID NO: |
|---|---|---|
| VL CDR1 | KASQNVRTNVA | 20 |
| VL CDR2 | SASYRYS | 21 |
| VL CDR3 | QQYNSYPRT | 22 |

TABLE 2

VL FR Amino Acid Sequences

| Ab 37M/C | VL Framework Region amino acid sequence | SEQ ID NO: |
|---|---|---|
| VL FR1 | DIVMTQSQKFMSTSVGDRVSVTC | 26 |
| VL FR2 | WYQQKPGQSPKALIY | 27 |
| VL FR3 | GVPDRFTGSGSGTDFTLTISNVQSEDLADYFC | 28 |
| VL FR4 | FGGGTKLEIKR | 29 |

TABLE 3

VH CDR Amino Acid Sequences

| Ab 37M/C | VH CDR amino acid sequence | SEQ ID NO: |
|---|---|---|
| VH CDR1 | DYYIN | 23 |
| VH CDR2 | RIYPGSGNTYYNEKFKG | 24 |
| VH CDR3 | GVYYFDY | 25 |

TABLE 4

VH FR Amino Acid Sequences

| Ab | | VH amino acid sequence | SEQ ID NO: |
|---|---|---|---|
| 37M | VH FR1 | QVQLKQSGAELVRPGASVKLSCKASGYTFT | 30 |
| | VH FR2 | WVKQRPGQGLEWIA | 31 |
| | VH FR3 | KATLTAEKSSSTAYMQLSSLTSEDSAVYFCAR | 32 |
| | VH FR4 | WGQGTTLTVSS | 33 |

TABLE 4-continued

VH FR Amino Acid Sequences

| Ab | | VH amino acid sequence | SEQ ID NO: |
|---|---|---|---|
| 37C | VH FR1 | QVQLKQSGAELVRPGASVKLSCKASGYTFT | 38 |
| | VH FR2 | WVKQRPGQGLEWIA | 39 |
| | VH FR3 | KATLTAEKSSSTAYMQLSSLTSEDSAVYFCAR | 40 |
| | VH FR4 | WGQGTTLTVSA | 41 |

In certain aspects, an antibody described herein comprises one or more VL framework regions (FRs) having the amino acid sequence described herein (e.g., see Table 2), wherein the antibody immunospecifically binds to a KIT polypeptide, e.g., a human KIT polypeptide, for example, a D4/D5 region of KIT (e.g., human KIT), for example SEQ ID NO: 15. In specific embodiments, an antibody (e.g., murine, chimeric or humanized antibody) described herein comprises a VL chain region comprising FR1, CDR1, FR2, CDR2, FR3, CDR3, and FR4. In certain embodiments, the VL FR1 has the amino acid sequence of SEQ ID NO: 26. In some embodiments, the VL FR2 has the amino acid sequence of SEQ ID NO: 27. In some embodiments, the VL FR3 has the amino acid sequence of SEQ ID NO: 28. In some embodiments, the VL FR4 has the amino acid sequence of SEQ ID NO: 29.

In certain embodiments, an anti-KIT antibody described herein comprises one or more VH FRs having the amino acid sequence described herein (e.g., see Table 4). In specific embodiments, an antibody (e.g., murine, chimeric or humanized antibody) comprises a VH chain region comprising FR1, CDR1, FR2, CDR2, FR3, CDR3, and FR4, respectively. In some embodiments, the VH FR1 has the amino acid sequence of SEQ ID NO: 30 or 38. In some embodiments, the VH FR2 has the amino acid sequence of SEQ ID NO: 31 or 39. In some embodiments, the VH FR3 has the amino acid sequence of SEQ ID NO: 32 or 40. In some embodiments, the VH FR4 has the amino acid sequence of SEQ ID NO: 33 or 41.

In a particular embodiment, an antibody described herein, comprises a VH FR1 having the amino acid sequence of SEQ ID NO: 38. In a particular embodiment, an antibody described herein, comprises a VH FR2 having the amino acid sequence of SEQ ID NO: 39. In a particular embodiment, an antibody described herein, comprises a VH FR3 having the amino acid sequence of SEQ ID NO: 40. In a particular embodiment, an antibody described herein, comprises a VH FR4 having the amino acid sequence of SEQ ID NO: 41.

In another specific embodiment, an antibody described herein comprises (i) a VL chain region comprising VL FR1, VL FR2, VL FR3, and VL FR4 having the amino acid sequences of SEQ ID NO: 26, 27, 28, and 29, respectively; and (ii) a VH chain region comprising VH FR1, VH FR2, VH FR3, and VH FR4 having the amino acid sequences of SEQ ID NO: 30, 31, 32, and 33, respectively. In a specific embodiment, an antibody described herein comprises a VL chain region comprising VL FR1, VL FR2, VL FR3, and VL FR4 having the amino acid sequences of SEQ ID NO: 26, 27, 28, and 29, respectively. In another specific embodiment, an antibody described herein comprises a VH chain region comprising VH FR1, VH FR2, VH FR3, and VH FR4 having the amino acid sequences of SEQ ID NO: 38, 39, 40, and 41, respectively.

In specific embodiments, an antibody described herein, which immunospecifically bind to a KIT polypeptide, e.g., a human KIT polypeptide, for example, a D4/D5 region of KIT (e.g., human KIT, for example SEQ ID NO: 15), comprises framework regions (e.g., framework regions of the VL domain and/or VH domain) that are human framework regions or derived from human framework regions. Non-limiting examples of human framework regions are described in the art, e.g., see Kabat et al. (1991) *Sequences of Proteins of Immunological Interest*, Fifth Edition, U.S. Department of Health and Human Services, NIH Publication No. 91-3242). In certain embodiment, an antibody described herein comprises framework regions (e.g., framework regions of the VL domain and/or VH domain) that are primate (e.g., non-human primate) framework regions or derived from primate (e.g., non-human primate) framework regions.

In specific aspects, provided herein is an antibody comprising an antibody light chain and heavy chain, e.g., a separate light chain and heavy chain. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which immunospecifically binds to a KIT polypeptide (e.g., a KIT polypeptide comprising a D4/D5 region of KIT, for example human KIT (e.g., SEQ ID NO: 15)) comprises a light chain wherein the amino acid sequence of the VL chain region comprises any amino acid sequence described herein (e.g., SEQ ID NO: 2), and wherein the constant region of the light chain comprises the amino acid sequence of a human kappa light chain constant region. In another particular embodiment, an antibody described herein, which immunospecifically binds to a KIT polypeptide (e.g., a KIT polypeptide comprising a KIT polypeptide comprising a D4/D5 region of KIT, for example human KIT (e.g., SEQ ID NO: 15)) comprises a light chain wherein the amino acid sequence of the VL chain region can comprise any amino acid sequence described herein (e.g., SEQ ID NO: 2), and wherein the constant region of the light chain comprises the amino acid sequence of a human lambda light chain constant region. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242. In a specific embodiment, an antibody described herein comprises a light chain comprising the amino acid sequence of SEQ ID NO: 6 (or the amino acid sequence of SEQ ID NO: 6 starting at position 20, lacking the signal peptide).

In a particular embodiment, an antibody described herein, which immunospecifically binds to a KIT polypeptide (e.g., a KIT polypeptide comprising a KIT polypeptide comprising a D4/D5 region of KIT, for example human KIT (e.g., SEQ ID NO: 15)), comprises a light chain comprising a constant region having the amino acid sequence of SEQ ID NO: 12

(TVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC).

With respect to the heavy chain, in a specific embodiment, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In a particular embodiment, an antibody described herein, which immunospecifically binds to a KIT polypeptide (e.g., a KIT polypeptide comprising a KIT polypeptide comprising a D4/D5 region of KIT, for example human KIT (e.g., SEQ ID NO: 15)), comprises a heavy chain wherein the amino acid sequence of the VH chain region can comprise any amino acid sequence described herein (e.g., any of SEQ ID NOs: 3 and 5), and wherein the constant region of the heavy chain comprises the amino acid sequence of a human gamma (γ) heavy chain constant region. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242. In a specific embodiment, an antibody described herein comprises a heavy chain comprising the amino acid sequence of SEQ ID NO: 7.

In a particular embodiment, an antibody described herein, which immunospecifically binds to a KIT polypeptide (e.g., a KIT polypeptide comprising a KIT polypeptide comprising a D4/D5 region of KIT, for example human KIT (e.g., SEQ ID NO: 15)), comprises a heavy chain comprising a constant region having the amino acid sequence of SEQ ID NO: 13

(ASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK).

In a specific embodiment, an antibody described herein, which immunospecifically binds to a KIT polypeptide (e.g., a D4/D5 region of KIT, for example human KIT) comprises a VL chain region and a VH chain region comprising any amino acid sequences described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which immunospecifically binds to a KIT polypeptide (e.g., a D4/D5 region of KIT, for example human KIT) comprises a VL chain region and a VH chain region comprising any amino acid sequences described herein, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. In a particular embodiment, the constant regions comprise the amino acid sequences of the constant regions of a human IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule.

In yet another specific embodiment, an antibody described herein, which immunospecifically binds to a KIT polypeptide (e.g., a D4/D5 region of KIT, for example human KIT), comprises a VL chain region and a VH chain region comprising any amino acid sequences described herein, and wherein the constant regions comprise the amino acid sequences of the constant regions of a human IgG1 (e.g., isotype a, z, or f) or human IgG4. In a particular embodiment, an antibody described herein, which immunospecifically binds to a KIT polypeptide (e.g., a D4/D5 region of KIT, for example human KIT) comprises a VL chain region and a VH chain region comprising any amino acid sequences described herein, and wherein the constant regions comprise the amino acid sequences of the constant region of a human IgG1 (isotype f). Non-limiting examples of human constant regions are described in the art, e.g., see Kabat et al. (1991) *Sequences of Proteins of Immunological Interest*, Fifth Edition, U.S. Department of Health and Human Services, NIH Publication No. 91-3242. In another specific embodiment, an antibody described herein, which immunospecifically binds to a KIT polypeptide (e.g., a D4/D5 region of KIT, for example human KIT), comprises a VL chain region and a VH chain region comprising any amino acid sequences described herein, and wherein the antibody further comprises (i) a light chain constant region comprising the amino acid sequence of SEQ ID NO: 12, and (ii) a heavy chain constant region comprising the amino acid sequence of SEQ ID NO: 13.

In another particular embodiment, an antibody described herein, which immunospecifically binds to a KIT polypeptide (e.g., a D4/D5 region of KIT, for example human KIT), comprises a light chain and a heavy chain, wherein (i) the light chain comprises a VL chain region comprising a VL CDR1, VL CDR2, and VL CDR3 having the amino acid sequences of SEQ ID NO: 20, 21, and 22, respectively; (ii) the heavy chain comprises a VH chain region comprising a VH CDR1, VH CDR2, and VH CDR3 having the amino acid sequences of SEQ ID NO: 23, 24, and 25, respectively; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 (optionally IgG1 (isotype f)) heavy chain. In particular embodiments, the light chain constant region comprises the amino acid sequence of SEQ ID NO: 12; and the heavy chain constant region comprises the amino acid sequence of SEQ ID NO: 13.

In another particular embodiment, an antibody described herein, which immunospecifically binds to a KIT polypeptide (e.g., a D4/D5 region of KIT, for example human KIT), comprises a light chain and a heavy chain, wherein (i) the light chain comprises a VL chain region comprising a VL CDR1, VL CDR2, and VL CDR3 having the amino acid sequences of SEQ ID NO: 20, 21, and 22, respectively; (ii) the heavy chain comprises a VH chain region comprising a VH CDR1, VH CDR2, and VH CDR3 having the amino acid sequences of SEQ ID NO: 23, 24, and 25, respectively; (iii) the light chain further comprises a light chain constant domain comprising the amino acid sequence of SEQ ID NO: 12; and (iv) the heavy chain further comprises a heavy chain constant domain comprising the amino acid sequence of SEQ ID NO: 13.

In another particular embodiment, an antibody described herein, which immunospecifically binds to a KIT polypeptide (e.g., a D4/D5 region of KIT, for example human KIT), comprises a light chain and a heavy chain, wherein (i) the light chain comprises a VL chain region comprising the amino acid sequence of SEQ ID NO: 2; (ii) the heavy chain comprises a VH chain region comprising the amino acid sequence of SEQ ID NO: 3; (iii) the light chain further comprises a constant domain comprising the amino acid sequence of the constant domain of a human kappa light chain; and (iv) the heavy chain further comprises a constant domain comprising the amino acid sequence of the constant domain of a human IgG1 (optionally IgG1 (isotype f)) heavy chain. In particular embodiments, the light chain constant domain comprises the amino acid sequence of SEQ ID NO: 12; and the heavy chain constant domain comprises the amino acid sequence of SEQ ID NO: 13.

In another particular embodiment, an antibody described herein, which immunospecifically binds to a KIT polypeptide (e.g., a D4/D5 region of KIT, for example human KIT), comprises a light chain and a heavy chain, wherein (i) the light chain comprises a VL chain region comprising the amino acid sequence of SEQ ID NO: 2; (ii) the heavy chain comprises a VH chain region comprising the amino acid sequence of SEQ ID NO: 5; (iii) the light chain further comprises a constant domain comprising the amino acid sequence of the constant domain of a human kappa light chain; and (iv) the heavy chain further comprises a constant domain comprising the amino acid sequence of the constant domain of a human IgG1 (optionally IgG1 (isotype f)) heavy chain. In another particular embodiment, an antibody described herein, which immunospecifically binds to a KIT polypeptide (e.g., a D4/D5 region of KIT, for example human KIT), comprises a light chain and a heavy chain, wherein (i) the light chain comprises a VL chain region comprising the amino acid sequence of SEQ ID NO: 2; (ii) the heavy chain comprises a VH chain region comprising the amino acid sequence of SEQ ID NO: 5; (iii) the light chain further comprises a constant domain comprising the amino acid sequence of SEQ ID NO: 12; and (iv) the heavy chain further comprises a constant domain comprising the amino acid sequence of SEQ ID NO: 13.

In certain embodiments, with respect to any of these antibodies described herein, the VL chain region comprises human framework regions or is derived from human framework regions. In certain other embodiments, the VH chain region comprises human framework regions or is derived from human framework regions. In still other embodiments, the VL chain region and VH chain region comprise human framework regions.

In certain embodiments, with respect to any of these antibodies described herein, the VL chain region comprises primate (e.g., non-human primate) framework regions or is derived from primate (e.g., non-human primate) framework regions. In certain other embodiments, the VH chain region comprises primate (e.g., non-human primate) framework regions or is derived from primate (e.g., non-human primate) framework regions. In still other embodiments, the VL chain region and VH chain region comprise primate (e.g., non-human primate) framework regions.

For example, CDRs from antigen-specific non-human antibodies, typically of rodent origin, are grafted onto homologous human or non-human primate acceptor frameworks. In one embodiment, the non-human primate acceptor frameworks are from Old World apes. In a specific embodiment, the Old World ape acceptor framework is from Pan troglodytes, Pan paniscus or Gorilla gorilla. In a particular embodiment, the non-human primate acceptor frameworks are from the chimpanzee Pan troglodytes. In a particular embodiment, the non-human primate acceptor frameworks are Old World monkey acceptor frameworks. In a specific embodiment, the Old World monkey acceptor frameworks are from the genus *Macaca*. In a certain embodiment, the non-human primate acceptor frameworks are is derived from the cynomolgus monkey *Macaca* cynomolgus. Non-human primate framework sequences are described in U.S. Patent Application Publication No. US 2005/0208625.

In certain embodiments, an antibody described herein, which immunospecifically binds to a KIT polypeptide (e.g., a D4/D5 region of KIT, for example human KIT), comprises a light chain and a heavy chain, wherein (i) the light chain comprises a VL chain region comprising human framework regions; (ii) the heavy chain comprises a VH chain region comprising human framework regions; (iii) the light chain further comprises a light chain constant domain comprising the amino acid sequence of SEQ ID NO: 12; and (iv) the heavy chain further comprises a heavy chain constant domain comprising the amino acid sequence of SEQ ID NO: 13.

In certain embodiments, an antibody described herein, which immunospecifically binds to a KIT polypeptide (e.g., a D4/D5 region of KIT, for example human KIT), comprises a light chain and a heavy chain, wherein (i) the light chain comprises a VL chain region comprising VL FR1, VL FR2, VL FR3, and VL FR4 having the amino acid sequence of SEQ ID NO: 26, 27, 28, and 29, respectively; (ii) the heavy chain comprises a VH chain region comprising VH FR1, VH FR2, VH FR3, and VH FR4 having the amino acid sequence of SEQ ID NO: 30, 31, 32, and 33, respectively; (iii) the light chain further comprises a light chain constant domain comprising the amino acid sequence of SEQ ID NO: 12; and (iv) the heavy chain further comprises a heavy chain constant domain comprising the amino acid sequence of SEQ ID NO: 13.

In certain embodiments, an antibody described herein, which immunospecifically binds to a KIT polypeptide (e.g., a D4/D5 region of KIT, for example human KIT), comprises a light chain and a heavy chain, wherein (i) the light chain comprises a VL chain region comprising VL FR1, VL FR2, VL FR3, and VL FR4 having the amino acid sequence of SEQ ID NO: 30, 31, 32, and 33, respectively; (ii) the heavy chain comprises a VH chain region comprising VH FR1, VH FR2, VH FR3, and VH FR4 having the amino acid sequence of SEQ ID NO: 38, 39, 40, and 41, respectively; (iii) the light chain further comprises a light chain constant domain comprising the amino acid sequence of SEQ ID NO: 12; and (iv) the heavy chain further comprises a heavy chain constant domain comprising the amino acid sequence of SEQ ID NO: 13.

In particular embodiments, an antibody described herein, which immunospecifically binds to a KIT polypeptide (e.g., a D4/D5 region of KIT, for example human KIT), comprises a light chain and a heavy chain, wherein the light chain comprises the amino acid sequence of SEQ ID NO: 6 (or the amino acid sequence of SEQ ID NO: 6 starting at position 20, lacking the signal peptide), and the heavy chain comprises the amino acid sequence of SEQ ID NO: 7 (or the amino acid sequence of SEQ ID NO: 7 starting at position 20, lacking the signal peptide). In a particular embodiment, the light chain comprises a signal peptide having the amino acid sequence MGWSCIILFLVATATGVHS (SEQ ID NO: 43). In a specific embodiment, the heavy chain comprises a signal peptide having the amino acid sequence MGWSCI-ILFLVATATGVHS (SEQ ID NO: 44).

In particular embodiments, an antibody described herein, which immunospecifically binds to a KIT polypeptide (e.g., a D4/D5 region of KIT, for example human KIT), comprises a light chain and a heavy chain, wherein the light chain comprises the amino acid sequence of SEQ ID NO: 6 starting at amino acid residue 20 of SEQ ID NO: 6, and the heavy chain comprises the amino acid sequence of SEQ ID NO: 7 starting at amino acid residue 20 of SEQ ID NO: 7. In particular embodiments, an antibody described herein, which immunospecifically binds to a KIT polypeptide (e.g., a D4/D5 region of KIT, for example human KIT), comprises a light chain and a heavy chain, wherein the light chain comprises the amino acid sequence of SEQ ID NO: 6, and the heavy chain comprises the amino acid sequence of SEQ ID NO: 7, wherein the signal peptides of the heavy chain and of the light chain have been removed (i.e., the signal peptide has been cleaved or processed).

In certain aspects, also provided herein are antibodies, which immunospecifically binds to a KIT polypeptide (e.g., a D4/D5 region of KIT, for example human KIT), comprising one or more amino acid residue substitutions, e.g., in the VL chain region or VH chain region, for example, the CDRs or FRs. In specific embodiments, none of the amino acid residue substitutions are located within the CDRs. In specific embodiments, all of the amino acid substitutions are in the FRs.

In certain embodiments, an antibody described herein comprises a VL chain region having at least 80%, at least 85%, at least 90%, at least 95%, or at least 98% sequence identity to the amino acid sequence of SEQ ID NO: 2, wherein the antibody immunospecifically binds to a KIT polypeptide, e.g., a human KIT polypeptide, for example, a D4/D5 region of KIT (e.g., human KIT, for example SEQ ID NO: 15). In certain embodiments, an antibody described herein comprises a VL chain region having at least 80%, at least 85%, at least 90%, at least 95%, or at least 98% sequence identity to the amino acid sequence of SEQ ID NO: 2, wherein the antibody immunospecifically binds to a KIT polypeptide, e.g., a human KIT polypeptide, for example, a D4/D5 region of KIT (e.g., human KIT, for example SEQ ID NO: 15), and wherein the antibody comprises CDRs (e.g., VL CDRs) that are identical to the CDRs (e.g., VL CDRs) of antibody 37M or 37C (e.g., SEQ ID NO: 20, 21, and 22). In a specific embodiment, such antibody comprises a VL CDR1 having the sequence of SEQ ID NO: 20 that does not have an amino acid substitution at position 7 of SEQ ID NO: 20 (for example, the R amino acid at position 7 of SEQ ID NO: 20 is not substituted with G). In a specific embodiment, such antibody comprises a VL CDR3 having the sequence of SEQ ID NO: 22 that does not have an amino acid substitution at position 8 of SEQ ID NO: 22 (for example, the R amino acid at position 8 of SEQ ID NO: 22 is not substituted with L). In certain embodiments, an antibody described herein comprises a light having at least 80%, at least 85%, at least 90%, at least 95%, or at least 98% sequence identity to the amino acid sequence of SEQ ID NO: 6 (or the amino acid sequence of SEQ ID NO: 6 starting at position 20, lacking the signal peptide), wherein the antibody immunospecifically binds to a KIT polypeptide, e.g., a human KIT polypeptide, for example, a D4/D5 region of KIT (e.g., human KIT, for example SEQ ID NO: 15).

In certain embodiments, an antibody described herein comprises a VL chain region comprising VL framework regions having at least 80%, at least 85%, at least 90%, at least 95%, or at least 98% sequence identity to the amino acid sequence of the framework regions of SEQ ID NO: 2, wherein the antibody immunospecifically binds to a KIT polypeptide, e.g., a human KIT polypeptide, for example, a D4/D5 region of KIT (e.g., human KIT, for example SEQ ID NO: 15). In a particular embodiment, the antibody comprises VL CDRs that are identical to the VL CDRs of antibody 37M or 37C (e.g., SEQ ID NO: 20, 21, and 22). In a specific embodiment, such antibody comprises a VL CDR1 having the sequence of SEQ ID NO: 20 that does not have an amino acid substitution at position 7 of SEQ ID NO: 20 (for example, the R amino acid at position 7 of SEQ ID NO: 20 is not substituted with G). In a specific embodiment, such antibody comprises a VL CDR3 having the sequence of SEQ ID NO: 22 that does not have an amino acid substitution at position 8 of SEQ ID NO: 22 (for example, the R amino acid at position 8 of SEQ ID NO: 22 is not substituted with L).

In certain embodiments, an antibody described herein comprises a VH chain region having at least 80%, at least 85%, at least 90%, at least 95%, or at least 98% sequence identity to the amino acid sequence of SEQ ID NO: 3 or 5, wherein the antibody immunospecifically binds to a KIT polypeptide, e.g., a human KIT polypeptide, for example, a D4/D5 region of KIT (e.g., human KIT, for example SEQ ID NO: 15). In certain embodiments, an antibody described herein comprises a VH chain region having at least 80%, at least 85%, at least 90%, at least 95%, or at least 98% sequence identity to the amino acid sequence of SEQ ID NO: 3, wherein the antibody immunospecifically binds to a KIT polypeptide, e.g., a human KIT polypeptide, for example, a D4/D5 region of KIT (e.g., human KIT, for example SEQ ID NO: 15). In certain embodiments, an antibody described herein comprises a VH chain region having at least 80%, at least 85%, at least 90%, at least 95%, or at least 98% sequence identity to the amino acid sequence of SEQ ID NO: 5, wherein the antibody immunospecifically binds to a KIT polypeptide, e.g., a human KIT polypeptide, for example, a D4/D5 region of KIT (e.g., human KIT, for example SEQ ID NO: 15). In certain embodiments, an antibody described herein comprises a heavy chain having at least 80%, at least 85%, at least 90%, at least 95%, or at least 98% sequence identity to the amino acid sequence of SEQ ID NO: 7, wherein the antibody immunospecifically binds to a KIT polypeptide, e.g., a human KIT polypeptide, for example, a D4/D5 region of KIT (e.g., human KIT, for example SEQ ID NO: 15). In specific embodiments, such antibody comprises CDRs (e.g., VH CDRs) identical to the CDRs (e.g., VH CDRs) of antibody 37M or 37C (e.g., SEQ ID NOs: 20-25).

In certain embodiments, an antibody described herein comprises a VH chain region comprising VH framework regions having at least 80%, at least 85%, at least 90%, at least 95%, or at least 98% sequence identity to the amino acid sequence of the framework regions of SEQ ID NO: 3, wherein the antibody immunospecifically binds to a KIT polypeptide, e.g., a human KIT polypeptide, for example, a D4/D5 region of KIT (e.g., human KIT, for example SEQ ID NO: 15). In specific embodiments, such antibody comprises CDRs (e.g., VH CDRs) identical to the CDRs (e.g., VH CDRs) of antibody 37M or 37C (e.g., SEQ ID NOs: 20-25).

In certain embodiments, an antibody described herein comprises (i) a VL chain region having at least 80%, at least 85%, at least 90%, at least 95%, or at least 98% sequence identity to the amino acid sequence of SEQ ID NO: 2, and (ii) a VH chain region having at least 80%, at least 85%, at least 90%, at least 95%, or at least 98% sequence identity to the amino acid sequence of SEQ ID NO: 3, wherein the antibody immunospecifically binds to a KIT polypeptide, e.g., a human KIT polypeptide, for example, a D4/D5 region of KIT (e.g., human KIT, for example SEQ ID NO: 15). In specific embodiments, such antibody comprises CDRs (e.g., VL CDRs and/or VH CDRs) identical to the CDRs (e.g., VL CDRs and/or VH CDRs) of antibody 37M or 37C (e.g., SEQ ID NOs: 20-25). In a specific embodiment, such antibody comprises a VL CDR1 having the sequence of SEQ ID NO: 20 that does not have an amino acid substitution at position 7 of SEQ ID NO: 20 (for example, the R amino acid at position 7 of SEQ ID NO: 20 is not substituted with G). In a specific embodiment, such antibody comprises a VL CDR3 having the sequence of SEQ ID NO: 22 that does not have an amino acid substitution at position 8 of SEQ ID NO: 22 (for example, the R amino acid at position 8 of SEQ ID NO: 22 is not substituted with L).

In certain embodiments, an antibody described herein comprises (i) a VL chain region having at least 80%, at least 85%, at least 90%, at least 95%, or at least 98% sequence identity to the amino acid sequence of SEQ ID NO: 2, and (ii) a VH chain region having at least 80%, at least 85%, at least 90%, at least 95%, or at least 98% sequence identity to the amino acid sequence of SEQ ID NO: 5, wherein the antibody immunospecifically binds to a KIT polypeptide, e.g., a human KIT polypeptide, for example, a D4/D5 region of KIT (e.g., human KIT, for example SEQ ID NO: 15). In specific embodiments, such antibody comprises CDRs identical to the CDRs of antibody 37M or 37C (e.g., SEQ ID NOs: 20-25). In a specific embodiment, such antibody comprises a VL CDR1 having the sequence of SEQ ID NO: 20 that does not have an amino acid substitution at position 7 of SEQ ID NO: 20 (for example, the R amino acid at position 7 of SEQ ID NO: 20 is not substituted with G). In a specific embodiment, such antibody comprises a VL CDR3 having the sequence of SEQ ID NO: 22 that does not have an amino acid substitution at position 8 of SEQ ID NO: 22 (for example, the R amino acid at position 8 of SEQ ID NO: 22 is not substituted with L).

In certain embodiments, an antibody described herein comprises (i) a light chain comprising a constant region having at least 80%, at least 85%, at least 90%, at least 95%, or at least 98% sequence identity to the amino acid sequence of SEQ ID NO: 12, and (ii) a heavy chain comprising a constant region having at least 80%, at least 85%, at least 90%, at least 95%, or at least 98% sequence identity to the amino acid sequence of SEQ ID NO: 13, wherein the antibody immunospecifically binds to a KIT polypeptide, e.g., a human KIT polypeptide, for example, a D4/D5 region of KIT (e.g., human KIT, for example SEQ ID NO: 15). In certain embodiments, an antibody described herein comprises a light chain comprising a constant region having at least 80%, at least 85%, at least 90%, at least 95%, or at least 98% sequence identity to the amino acid sequence of SEQ ID NO: 12. In certain embodiments, an antibody described herein comprises a heavy chain comprising a constant region having at least 80%, at least 85%, at least 90%, at least 95%, or at least 98% sequence identity to the amino acid sequence of SEQ ID NO: 13. In specific embodiments, such antibody comprises CDRs identical to the CDRs of antibody 37M or 37C (e.g., SEQ ID NOs: 20-25).

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions X 100%). In one embodiment, the two sequences are the same length. In a certain embodiment, the percent identity is determined over the entire length of an amino acid sequence or nucleotide sequence.

The determination of percent identity between two sequences (e.g., amino acid sequences or nucleic acid sequences) can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In particular embodiments, the glycosylation of antibodies described herein is modified. For example, an aglycosylated antibody can be made (i.e., the antibody lacks glycosylation) or an antibody comprising a mutation or substitution at one or more glycosylation sites to eliminate glycosylation at the one or more glycosylation sites can be made. Glycosylation can be altered to, for example, increase the affinity of the antibody for a target antigen (e.g., human KIT, for example, a D4/D5 region of human KIT). Such carbohydrate modifications can be accomplished by, for example, altering one or more sites of glycosylation within the antibody sequence. For example, one or more amino acid substitutions can be made that result in elimination of one or more variable region (e.g., VL and/or VH CDRs or VL and/or VH FRs) glycosylation sites to thereby eliminate glycosylation at that site. Such aglycosylation can increase the affinity of the antibody for antigen (e.g., human KIT, for example, a D4/D5 region of human KIT). Such an approach is described in further detail in U.S. Pat. Nos. 5,714,350 and 6,350,861.

Glycosylation can occur via N-linked (or asparagine-linked) glycosylation or O-linked glycosylation. N-linked glycosylation involves carbohydrate modification at the side-chain $NH_2$ group of an asparagine amino acid in a polypeptide. O-linked glycosylation involves carbohydrate modification at the hydroxyl group on the side chain of a serine, threonine, or hydroxylysine amino acid.

In specific embodiments, an asparagine (N) residue within a VH (e.g., SEQ ID NO: 3 or 5) or VL region (e.g., SEQ ID NO: 2) of an antibody described herein is substituted with a serine (S) or another amino acid (e.g., alanine, glycine, glutamine, serine, threonine, tyrosine, cysteine). In other specific embodiments, an asparagine (N) residue within a VH CDR (e.g., VH CDR1, VH CDR2, and/or VH CDR3) and/or a VL CDR (e.g., VL CDR1, VL CDR2, and/or VL CDR3) of an antibody described herein is substituted with a serine (S) or another amino acid (e.g., alanine, glycine, glutamine, serine, threonine, tyrosine, cysteine). In other specific embodiments, an asparagine (N) residue within a VH FR (e.g., VH FR1, VH FR2, VH FR3 and/or VH FR4) and/or a VL FR (e.g., VL FR1, VL FR2, VL FR3, and/or VL FR4) of an antibody described herein is substituted with a serine (S) or another amino acid (e.g., alanine, glycine, glutamine, serine, threonine, tyrosine, cysteine).

In certain embodiments, aglycosylated antibodies can be produced in bacterial cells which lack the necessary glycosylation machinery. Cells with altered glycosylation machinery have been described in the art and can be used as host cells in which to express recombinant antibodies described herein to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342.

In certain embodiments, one or more modifications can be made to the Fc region of an antibody described here, generally, to alter one or more functional properties of the antibody, such as serum half-life, complement fixation, Fc receptor binding, and/or antigen-dependent cellular cytotoxicity. These modifications are known in the art, and are described in for example, International Patent Application Publication No. WO 2008/153926 A2.

In specific embodiments, an asparagine (N) residue within the constant region of a heavy chain (e.g., SEQ ID NO: 13) and/or the constant region of a light region (e.g., SEQ ID NO: 12) of an antibody described herein is substituted with a serine (S) or another amino acid (e.g., alanine, glycine, glutamine, serine, threonine, tyrosine, cysteine).

In specific embodiments, an asparagine (N) residue within a heavy chain (e.g., SEQ ID NO: 7) and/or a light region (e.g., SEQ ID NO: 6) of an antibody described herein is substituted with a serine (S) or another amino acid (e.g., alanine, glycine, glutamine, serine, threonine, tyrosine, cysteine).

Provided herein are antibodies that immunospecifically bind to KIT antigen and that can modulate KIT activity. In certain embodiments, an antibody provided herein immunospecifically binds to a KIT polypeptide, e.g., a human KIT polypeptide, and inhibits a KIT activity. KIT activity can relate to any activity of KIT known or described in the art, e.g., KIT receptor dimerization, KIT receptor phosphorylation (tyrosine phosphorylation), signaling downstream of the KIT receptor (e.g., AKT, MAPK/ERK, Ras, Stat1, Stat3, or Stat5 signaling), KIT ligand (e.g., SCF) induced transcriptional regulation (e.g., SCF-induced transcriptional activation of c-Myc), induction or enhancement of cell proliferation, or cell survival. KIT activity or KIT function are used interchangeably herein. In certain aspects, KIT activity is induced by KIT ligand (e.g., SCF) binding to KIT receptor. In particular aspects, KIT activity can be induced or enhanced by gain-of-function mutations which can result, for example, in dimerization and constitutively active KIT signaling (see, e.g., Mol et al., J. Biol. Chem., 2003, 278: 31461-31464; Hirota et al., J. Pathology, 2001, 193:505-510). Such gain-of-function can allow for KIT receptor dimerization and KIT signaling to occur in the absence of KIT ligand (e.g., SCF) binding to KIT receptor. In certain embodiments, an increase in KIT activity or signaling can occur, in the absence of KIT ligand (e.g., SCF) binding KIT receptor, due to high (or overexpression) expression of KIT receptors. High or overexpression of KIT in a cell refers to an expression level which is at least about 10%, 20%, 30%, 40%, 50%, 60%, 70%, 80%, 90%, or 100% more than the expression level of a reference cell known to have normal KIT expression or KIT activity or more than the average expression level of KIT in a population of cells or samples known to have normal KIT expression or KIT activity. Expression levels of KIT can be assessed by methods described herein or known to one of skill in the art (e.g., Western blotting or immunohistochemistry). In particular embodiments, KIT activity that is higher than normal KIT activity can lead to cellular transformation, neoplasia, and tumorogenesis. In particular embodiments, KIT activity that is higher than normal KIT activity can lead to other KIT-mediated disorders or diseases.

In certain embodiments, an anti-KIT antibody described herein does not block or inhibit binding of KIT ligand (e.g., SCF) to KIT receptor. In certain embodiments, an anti-KIT antibody described herein only negligibly (e.g., less than about 2% or 3%) inhibits or reduces binding of KIT ligand (e.g., SCF) to KIT receptor. In certain embodiments, an anti-KIT antibody described herein does not induce or enhance dissociation of KIT ligand (e.g., SCF) from the KIT receptor. In certain embodiments, an anti-KIT antibody described herein only negligibly (e.g., less than about 2% or 3%) induces or enhances dissociation of KIT ligand (e.g., SCF) from the KIT receptor.

In specific embodiments, antibodies described herein specifically bind to an extracellular domain of KIT (e.g., D4/D5 region of KIT, for example human KIT) and block or inhibit (e.g., partially inhibit) binding of KIT ligand (e.g., SCF) to KIT by at least about 5%, 10%, 15%, 20%, 25%, 30%, 35%, 40%, 45%, 50%, 55%, 60%, 65%, 70%, 75%, 80%, 85%, 90%, 95%, or 98%, as assessed by methods described herein or known to one of skill in the art, e.g., ELISA assay, flow cytometry, or competition assay.

In certain aspects, inhibition by anti-KIT antibodies described herein (e.g., monoclonal antibody) of KIT ligand (e.g., SCF) binding to KIT can be characterized by $IC_{50}$ values, which reflects the concentration of anti-KIT antibodies achieving 50% inhibition of binding of KIT ligand to KIT. Thus, in specific embodiments, an anti-KIT antibody described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) inhibits binding of KIT ligand to KIT with an IC$_{50}$ of at most about 10,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, or 0.001 nM, as assessed by methods described herein and/or known to one of skill in the art, (e.g., ELISA assay or flow cytometry). In specific embodiments, an anti-KIT antibody described herein inhibits binding of KIT ligand to KIT with an IC$_{50}$ of at least about 10,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, or 0.001 nM, as assessed by methods described herein and/or known to one of skill in the art, (e.g., ELISA assay or flow cytometry). In particular embodiments, an anti-KIT antibody described herein inhibits binding of KIT ligand to KIT with an IC$_{50}$ in the range of about 0.01 nM to 10,000 nM, 0.01 nM to 1,000 nM, 0.1 nM to 500 nM, 0.1 nM to 100 nM, or 0.1 nM to 50 nM, as assessed by methods described herein and/or known to one of skill in the art, (e.g., ELISA assay or flow cytometry).

In certain embodiments, an anti-KIT antibody described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) does not block or inhibit KIT receptor dimerization. In certain embodiments, an anti-KIT antibody described herein only negligibly (e.g., less than about 2% or 3% or within a standard of error or deviation) inhibits or reduces KIT receptor dimerization. In certain embodiments, an anti-KIT antibody described herein does not induce or enhance KIT receptor dimer dissociation. In certain embodiments, an anti-KIT antibody described herein only negligibly (e.g., less than about 2% or 3% or within a standard of error or deviation) induces or enhances KIT receptor dimer dissociation. In a particular embodiment, an anti-KIT antibody described herein can specifically bind to a KIT receptor dimer and do not block or inhibit KIT receptor dimerization. In a particular embodiment, an anti-KIT antibody described herein can specifically bind to a KIT receptor monomer and do not block or inhibit KIT receptor dimerization.

In certain aspects, as an inhibitor of KIT activity, an antibody described herein can block or inhibit (e.g., partially inhibit) dimerization of KIT. Generally, KIT receptor dimerization is induced when KIT ligand binds to KIT. Thus, in specific embodiments, antibodies described herein specifically bind to KIT and block or inhibit (e.g., partially inhibit) dimerization of KIT receptors by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., immunoprecipitation assay, relative to dimerization of KIT receptors in the presence of KIT ligand stimulation without any antibody or with an unrelated antibody (e.g., an antibody that does not immunospecifically bind to KIT). In a specific embodiment, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and partially inhibit dimerization of KIT receptors by about 25% to 75%. Blocking or inhibition (e.g., partial inhibition) of dimerization of KIT receptors by antibodies described herein can be assessed in the presences of KIT ligand stimulation. For example, cells expressing KIT are contacted with KIT ligand in the presence or absence of anti-KIT antibodies described herein, and the level of KIT receptor dimerization is determined. In certain embodiments, KIT ligand induced KIT receptor dimerization in the absence of anti-KIT antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than KIT receptor dimerization in the presence of anti-KIT antibody as assessed by methods described herein or known to one of skill in the art (e.g., immunoprecipitation assays). Tyrosine phosphorylation of one or more residues in the cytoplasmic domain of KIT can be an indicator of KIT receptor dimerization.

In certain embodiments, an antibody described herein can inhibit (e.g., partially inhibit) KIT activity by at least about 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to KIT activity in the presence of KIT ligand stimulation without any antibody or with an unrelated antibody (e.g., an antibody that does not immunospecifically bind to KIT). In certain embodiments, an antibody described herein can inhibit (e.g., partially inhibit) KIT activity by at least about 25% to about 65% as assessed by methods described herein and/or known to one of skill in the art, relative to KIT activity in the presence of KIT ligand stimulation without any antibody or with an unrelated antibody (e.g., an antibody that does not immunospecifically bind to KIT). Non-limiting examples of KIT activity can include KIT receptor phosphorylation, KIT receptor signaling, KIT ligand (e.g., SCF) mediated cell proliferation, KIT ligand (e.g., SCF) mediated cell survival, and transcriptional activation of a KIT target gene (e.g., c-Myc).

As an inhibitor of KIT activity, an antibody described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) can block (e.g., partially block) or inhibit (e.g., partially inhibit) phosphorylation of KIT, specifically tyrosine phosphorylation of one or more residues in the cytoplasmic domain of KIT. Generally, KIT receptor dimerization and phosphorylation is induced when KIT ligand binds to KIT. However, in certain aspects, KIT receptor dimerization and/or phosphorylation can occur independently of KIT ligand binding to KIT receptor. For example KIT receptor dimerization and/or phosphorylation can occur due to gain-of-function mutations or overexpression of KIT.

Non-limiting examples of tyrosine residues in the cytoplasmic domain of murine KIT that can be phosphorylated, e.g., upon ligand stimulation, include 544, 546, 552, 567, 569, 577, 608, 645, 671, 674, 702, 719, 728, 745, 772, 821, 844, 853, 868, 878, 898, and 934 (see Ueda et al., Blood, 2002, 99:3342-3349). The corresponding tyrosine residues in the cytoplasmic domain of human KIT can be readily determined. Non-limiting examples of tyrosine residues in the cytoplasmic domain of human KIT (e.g., GenBank Accession No. P10721) that can be phosphorylated, e.g., upon ligand stimulation, include residues 568, 570, 703, 721, 730, 747, 823, 900, and 936. In a specific embodiment, an anti-KIT antibody described herein can inhibit receptor phosphorylation at tyrosine residue 719 of murine KIT. In another specific embodiment, an anti-KIT antibody described herein can inhibit receptor phosphorylation at tyrosine residue 703 or 721 of human KIT.

Thus, in specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and block or inhibit tyrosine phosphorylation in the cytoplasmic domain of KIT by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., ELISA assay as described in section 6 or immunoblotting assay, relative to phosphorylation in the presence of KIT ligand stimulation without any antibody or with an unrelated antibody (e.g., an antibody that does not immunospecifically bind to KIT). In particular embodiments, antibodies described herein specifically bind to KIT and block or inhibit tyrosine phosphorylation in the cytoplasmic domain of KIT by at least about 25%, optionally to about 65% or 75%, as assessed by methods described herein or known to one of skill in the art, e.g., ELISA assay as described in section 6 or immunoblotting assay. In certain embodiments, antibodies described herein specifically bind to KIT and block or inhibit tyrosine phosphorylation of the cytoplasmic domain of KIT by at least about 25% to about 80% as assessed by methods described herein or known to one of skill in the art, e.g., ELISA assay as described in section 6 or immunoblotting assay. In specific embodiments, antibodies described herein specifically bind to KIT and block or inhibit tyrosine phosphorylation of the cytoplasmic domain of KIT with an $IC_{50}$ of less than about 400 pM or less than about 500 pM as assessed by methods described herein (e.g., phosphorylation inhibition assay with CHO cells expressing wild-type KIT as described in Section 6 below) or known to one of skill in the art. In specific embodiments, antibodies described herein specifically bind to KIT and block or inhibit tyrosine phosphorylation of the cytoplasmic domain of KIT with an $IC_{50}$ of less than about 200 pM. In specific embodiments, antibodies described herein specifically bind to KIT and block or inhibit tyrosine phosphorylation of the cytoplasmic domain of KIT with an $IC_{50}$ of less than about 150 pM. In specific embodiments, antibodies described herein specifically bind to KIT and block or inhibit tyrosine phosphorylation of the cytoplasmic domain of KIT with an $IC_{50}$ in the range of about 100 pM to about 500 pM, about 25 pM to about 200 pM, or about 40 pM to about 160 pM, or about 50 pM to about 125 pM. For example, an $IC_{50}$ for inhibition of tyrosine phosphorylation can be determined by assaying lysates from cells, e.g., CHO cells, recombinantly expressing KIT, in ELISA which detects tyrosine phosphorylation, for example, as described in Section 6 below. In certain embodiments, cells, e.g., CHO cells, recombinantly expressing KIT, are sorted, e.g., sorted to select for cells highly expressing KIT, prior to use in the phosphorylation inhibition assays. In some embodiments, the cells are not sorted prior to use in the phosphorylation inhibition assays.

In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and reduce tyrosine phosphorylation of the cytoplasmic domain of KIT by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., ELISA assay as described in section 6 or immunoblotting assay, relative to phosphorylation in the presence of KIT ligand stimulation without any antibody or with an unrelated antibody (e.g., an antibody that does not immunospecifically bind to KIT). In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and reduce tyrosine phosphorylation of the cytoplasmic domain of KIT by at least about 25% or 35%, optionally to about 75% as assessed by methods described herein or known to one of skill in the art, e.g., ELISA assay as described in section 6 or immunoblotting assay, relative to phosphorylation in the presence of KIT ligand stimulation without any antibody or with an unrelated antibody (e.g., an antibody that does not immunospecifically bind to KIT).

In specific embodiments, antibodies described herein specifically bind to KIT and block or inhibit phosphorylation of one or more tyrosine residues in the cytoplasmic domain of KIT by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., immunoblotting assay, relative to phosphorylation in the presence of KIT ligand stimulation without any antibody or with an unrelated antibody (e.g., an antibody that does not immunospecifically bind to KIT). In specific embodiments, blocking or inhibition (e.g., partial inhibition) of phosphorylation of one or more tyrosine residues of the cytoplasmic domain of KIT by antibodies described herein can be assessed upon KIT ligand stimulation. For example, cells expressing KIT are contacted with KIT ligand in the presence or absence of anti-KIT antibodies described herein, and the level of phosphorylation of one or more tyrosine residues in the cytoplasmic domain of KIT can be determined. In certain embodiments, KIT ligand induced phosphorylation of one or more tyrosine residues of the cytoplasmic domain of KIT the absence of anti-KIT antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than KIT ligand induced phosphorylation of one or more tyrosine residues of the cytoplasmic domain of KIT in the presence of anti-KIT antibody, as assessed by methods described herein or known to one of skill in the art (e.g., immunoblotting assays), relative to phosphorylation in the presence of KIT ligand stimulation without any antibody or with an unrelated antibody (e.g., an antibody that does not immunospecifically bind to KIT).

In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and induce or enhance KIT receptor internalization by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, relative to internalization in the presence of an unrelated antibody (e.g., an antibody that does not immunospecifically bind to KIT). In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and induce or enhance KIT receptor internalization by at least about 25% or 35%, optionally to about 75%, as assessed by methods described herein or known to one of skill in the art, relative to internalization in the presence of an unrelated antibody (e.g., an antibody that does not immunospecifically bind to KIT). In specific embodiments, antibodies described herein specifically bind to KIT and induce or enhance KIT receptor internalization by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, relative to internalization in the presence of an unrelated antibody (e.g., an antibody that does not immunospecifically bind to KIT). Techniques for the quantitation or visualization of cell surface receptors are well known in the art and include a variety of fluorescent and radioactive techniques. For example, one method involves incubating the cells with a radiolabeled anti-receptor antibody. Alternatively, the natural ligand of the receptor can be conjugated to a fluorescent molecule or radioactive-label and incubated with the cells. Additional receptor internalization assays are well known in the art and are described in, for example, Jimenez et al., Biochemical Pharmacology, 1999, 57:1125-1131; Bernhagen et al., Nature Medicine, 2007, 13:587-596; and Conway et al., J. Cell Physiol., 2001, 189:341-55.

In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and inhibit or reduce KIT receptor internalization by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, relative to internalization in the presence of an unrelated antibody (e.g., an antibody that does not immunospecifically bind to KIT). In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and inhibit or reduce KIT receptor internalization by at least about 25% or 35%, optionally to about 75%, as assessed by methods described herein or known to one of skill in the art, relative to internalization in the presence of an unrelated antibody (e.g., an antibody that does not immunospecifically bind to KIT). In specific embodiments, antibodies described herein specifically bind to KIT and inhibit or reduce KIT receptor internalization by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, relative to internalization in the presence of an unrelated antibody (e.g., an antibody that does not immunospecifically bind to KIT).

In specific embodiments, antibodies described herein specifically bind to KIT and induce or enhance KIT receptor turnover by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assay), relative to turnover in the presence of an unrelated antibody (e.g., an antibody that does not immunospecifically bind to KIT). In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and induce or enhance KIT receptor turnover by at least about 25% or 35%, optionally to about 75%, as assessed by methods described herein or known to one of skill in the art (e.g., pulse-chase assay), relative to turnover in the presence of an unrelated antibody (e.g., an antibody that does not immunospecifically bind to KIT). In specific embodiments, antibodies described herein specifically bind to KIT and induce or enhance KIT receptor turnover by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assay), relative to turnover in the presence of an unrelated antibody (e.g., an antibody that does not immunospecifically bind to KIT). Methods for the determining receptor turnover are well known in the art. For example, cells expressing KIT can be pulse-labeled using $^{35}$S-EXPRESS Protein Labeling mix (NEG772, NEN Life Science Products), washed and chased with unlabeled medium for a period of time before protein lysates from the labeled cells are immunoprecipitated using an anti-KIT antibody and resolved by SDS-PAGE and visualized (e.g., exposed to a PhosphoImager screen (Molecular Dynamics), scanned using the Typhoon8600 scanner (Amersham), and analyzed using ImageQuant software (Molecular Dynamics)) (see, e.g., Chan et al., Development, 2004, 131:5551-5560).

In specific embodiments, antibodies described herein specifically bind to KIT and induce or enhance KIT receptor degradation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assays), relative to degradation in the presence of an unrelated antibody (e.g., an antibody that does not immunospecifically bind to KIT). In specific embodiments, antibodies described herein specifically bind to KIT and induce or enhance KIT receptor degradation by at least about 25% or 35%, optionally to about 75%, as assessed by methods described herein or known to one of skill in the art (e.g., pulse-chase assays), relative to degradation in the presence of an unrelated antibody (e.g., an antibody that does not immunospecifically bind to KIT). In specific embodiments, antibodies described herein specifically bind to KIT and induce or enhance KIT receptor degradation by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to degradation in the presence of an unrelated antibody (e.g., an antibody that does not immunospecifically bind to KIT). Techniques for quantitating or monitoring ubiquitination and/or degradation (e.g., kinetics or rate of degradation) of cell surface receptors are well known in the art and involve a variety of fluorescent and radioactive techniques (see, e.g., International Patent Application Publication No. WO 2008/153926 A2). For example, pulse chase experiments or experiments using radiolabeled ligands such as $^{125}$I-SCF can be carried out to quantitatively measure degradation of KIT.

Moreover, signaling events downstream of KIT receptor phosphorylation can serve as indicators of KIT activity. For example, KIT ligand (e.g., SCF) binding to its receptor KIT stimulates several distinct signaling pathways, including for example members of Src family kinases, phosphatidylinositol (PI) 3-kinases, and Ras mitogen-activated protein kinase (MAPK) (see Munugalavadla et al., Mol. Cell. Biol., 2005, 25:6747-6759). Phosphorylated tyrosines in the cytoplasmic domain of KIT can provide for binding sites for SH2 domain-containing proteins, which include, but are not limited to, proteins of the p21Ras-mitogen activated protein kinase (MAPK) pathway, the p85 subunit of PI 3-kinase, phospholipase C-gamma$_1$, the Grb2 adaptor protein, the Src family kinases (SFKs), Cbl, CRKL, p62Dok-1, SHP1, and SHP2 (see Ueda et al., Blood, 2002, 99:3342-3349).

Thus, in certain aspects, anti-KIT antibodies described herein which act as inhibitors of KIT activity can inhibit signaling of a member of the Src family kinases, PI 3-kinases, or Ras-MAPK. In particular embodiments, anti-KIT antibodies described herein which act as inhibitors of KIT activity can inhibit binding (or inhibit interaction), to the cytoplasmic domain of KIT, of one or more SH2 domain-containing proteins, such as proteins of the p21Ras-MAPK pathway, the p85 subunit of PI 3-kinase, phospholipase C-gamma1, the Grb2 adaptor protein, a member of the SFK, Cbl, CRKL, p62Dok-1, SHP1, and SHP2. In certain embodiments, anti-KIT antibodies described herein which act as inhibitors of KIT activity can inhibit activation by KIT of one or more SH2 domain-containing proteins, such as proteins of the p21Ras-MAPK pathway, the p85 subunit of PI 3-kinase, phospholipase C-gamma1, the Grb2 adaptor protein, a member of the SFK, Cbl, CRKL, p62Dok-1, SHP1, and SHP2.

In particular embodiments, anti-KIT antibodies described herein which act as inhibitors of KIT activity can inhibit downstream signaling such as phosphorylation of MAPK, phosphorylation of AKT, or phosphorylation of Stat1, Stat3, or Stat5. Thus, in certain embodiments, an anti-KIT antibody described herein can inhibit or reduce phosphorylation of MAPK (e.g., KIT ligand (e.g., SCF) induced phosphorylation of MAPK) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay, relative to phosphorylation in the presence of KIT ligand stimulation without any antibody or with an unrelated antibody (e.g., an antibody that does not immunospecifically bind to KIT). In certain embodiments, an anti-KIT antibody described herein can inhibit or reduce phosphorylation of AKT (e.g., KIT ligand (e.g., SCF) induced phosphorylation of AKT) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay, relative to phosphorylation in the presence of KIT ligand stimulation without any antibody or with an unrelated antibody (e.g., an antibody that does not immunospecifically bind to KIT). In particular embodiments, an anti-KIT antibody described herein can inhibit or reduce phosphorylation of Stat3 (e.g., KIT ligand (e.g., SCF) induced phosphorylation of Stat3) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay, relative to phosphorylation in the presence of KIT ligand stimulation without any antibody or with an unrelated antibody (e.g., an antibody that does not immunospecifically bind to KIT). In particular embodiments, an anti-KIT antibody described herein can inhibit or reduce phosphorylation of Stat1 or Stat5 (e.g., KIT ligand (e.g., SCF) induced phosphorylation) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay, relative to phosphorylation in the presence of KIT ligand stimulation without any antibody or with an unrelated antibody (e.g., an antibody that does not immunospecifically bind to KIT).

In certain aspects, an anti-KIT antibody described herein which can act as an inhibitor of KIT activity or activity can inhibit cellular proliferation of cells (e.g., TF-1 cells) that express KIT and that respond to KIT signaling (e.g., cells that proliferate in response to KIT ligand stimulation and KIT signaling). Cell proliferation assays are described in the art and can be readily carried out by one of skill in the art. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H) thymidine incorporation (see, e.g., Blechman et al., Cell, 1995, 80:103-113; Chen, J., 1996, Oncogene 13:1395-403; Jeoung, J., 1995, J. Biol. Chem. 270:18367 73), by direct cell count at various time intervals (e.g., 12-hour or 24-hour intervals), or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription.

In specific embodiments, antibodies described herein specifically bind to KIT and inhibit cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., BrdU incorporation assay). In specific embodiments, antibodies described herein specifically bind to KIT and inhibit cell proliferation by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., BrdU incorporation assay).

In certain aspects, an anti-KIT antibody described herein which can act as an inhibitor of KIT activity can reduce or inhibit survival of cells that express KIT and that respond to KIT signaling (e.g., cells that proliferate in response to KIT ligand stimulation and KIT signaling). Cell survival assays are described in the art and can be readily carried out by one of skill in the art. For example, cell viability can be assessed by using trypan-blue staining or other cell death or viability markers known in the art. In a specific embodiment, the level of cellular ATP is measured to determined cell viability. In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes can include enlargement, granularity, cells with ragged edges, a filmy appearance, rounding, detachment from the surface of the well, or other changes. These changes are given a designation of T (100% toxic), PVH (partially toxic-very heavy—80%), PH (partially toxic-heavy—60%), P (partially toxic—40%), Ps (partially toxic-slight—20%), or 0 (no toxicity—0%), conforming to the degree of cytotoxicity seen. A 50% cell inhibitory (cytotoxic) concentration ($IC_{50}$) is determined by regression analysis of these data.

In specific embodiments, antibodies described herein specifically bind to KIT and inhibit (e.g, partially inhibit) cell survival by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., trypan blue exclusion assay). In specific embodiments, antibodies described herein specifically bind to KIT and inhibit cell survival by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., trypan blue assay).

In certain aspects, an anti-KIT antibody described herein, which can act as an inhibitor of KIT activity, is capable of inducing apoptosis (i.e., programmed cell death) of cells (e.g., MO7E cells) that express KIT and that respond to KIT signaling (e.g., cells that proliferate in response to KIT ligand stimulation and KIT signaling). Apoptosis are described in the art and can be readily carried out by one of skill in the art. For example, flow cytometry can be used to detect activated caspase 3, an apoptosis-mediating enzyme, in cells undergoing apoptosis, or Western blotting can be used to detect cleavage of poly(ADP-ribose) polymerase (PARP) (see, e.g., Smolich et al., Blood, 2001, 97:1413-1421). Cleavage of PARP is an indicator of apoptosis. In specific embodiments, antibodies described herein specifically bind to KIT and induce or enhance apoptosis by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., flow cytometry to detect activated caspase 3). In specific embodiments, antibodies described herein specifically bind to KIT and induce or enhance apoptosis by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., flow cytometry to detect activated caspase 3).

In certain aspects, an anti-KIT antibody described herein, which can act as an inhibitor of KIT activity, is capable of inhibiting or decreasing anchorage independent cell growth (e.g., colony formation) by cells (e.g., H526 cells or CHO cells expressing exogenous KIT) that express KIT and that respond to KIT signaling (e.g., cells that proliferate in response to KIT ligand stimulation and KIT signaling), as measured by methods commonly known in the art, e.g., soft agar assay. In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and inhibit or decrease anchorage independent cell growth by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., soft agar assay). In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and inhibit or decrease anchorage independent cell growth by at least about 25% or 35%, optionally to about 75%, as assessed by methods described herein or known to one of skill in the art (e.g., soft agar assay). In specific embodiments, antibodies described herein specifically bind to KIT and inhibit or decrease anchorage independent cell growth by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., soft agar assay).

Cells and cell lines which are appropriate for use in the assays described herein relating to KIT activity are readily available (e.g., ATCC) or can be readily identified using methods known in the art. For example, cells and/or cell lines that express KIT endogenously or that possess KIT signaling or activity are known to one of skill in the art. In certain embodiments, cells or cell lines that are appropriate for use in the assays described herein can express KIT, either endogenously or recombinantly. In particular embodiments, cells or cell lines for use in cell proliferation assays can express KIT, endogenously or recombinantly, and proliferate or increase proliferation in response to KIT ligand (e.g., SCF) stimulation. Cells or cell lines for use in cell viability assays can express KIT, endogenously or recombinantly, and exert changes in cell viability in response to KIT ligand (e.g., SCF) stimulation. Cells or cell lines for use in apoptosis assays can express KIT, endogenously or recombinantly, and exert changes in apoptosis in response to KIT ligand (e.g., SCF) stimulation.

Non-limiting examples of cells that can be used in the methods and assays described herein include primary cells, transformed cells, stem cells, mast cells, primordial germ cells, oocytes, spermatocytes, embryonic stem cells, hematopoietic cells, erythroleukemia cells (e.g., F36P and TF-1 cell lines), human myeloid leukemia cell lines, such as MO7E cells; gastrointestinal stromal tumor cell lines such as ST-882, GIST430, and GIST882; neuroblastoma cell lines such as SK-N-SH, SK-SY5Y, H-EP1, SK-N-BE(2), SK-N-BE(ZkM17), SK-N-BE(2)C, LA-N-1, or LA-N-1-5s; and small cell lung carcinoma cell lines such as H526, ECC12, TMK1, MKN7, GCIY, and HGC27.

Alternatively, cells and cell lines that express KIT, e.g., human KIT, can routinely be generated recombinantly. Non-limiting examples of cells that can be engineered to express KIT recombinantly include COS cells, HEK 293 cells, CHO cells, fibroblasts (e.g., human fibroblasts) such as NIH3T3 cells, and MEFS. In a specific embodiment, cells for use in the methods described herein are CHO cells exogenously expressing full-length human KIT (e.g., SEQ ID NO: 1).

In certain aspects, an anti-KIT antibody described herein, which can act as an inhibitor of KIT activity, is capable of inhibiting tumor growth or inducing tumor regression in mouse model studies. For example, tumor cell lines can be introduced into nude mice, and the mice can be administered with anti-KIT antibodies described herein one or more times, and tumor progression of the injected tumor cells can be monitored over a period of weeks and/or months. In some cases, administration of anti-KIT antibodies to the nude mice can occur prior to introduction of the tumor cell lines. Any appropriate tumor cell line (e.g., tumor cell line expressing KIT) can be used in the mouse xenograft models described herein. Non-limiting examples of tumor cell lines for use in these xenograft mouse models include megakaryoblastic leukemia cell lines such as MO7e; gastrointestinal stromal tumor cell lines such as ST-882, GIST430, GIST48, GIST48B and GIST882; human erythroleukemic cell lines such as HEL and TF-1; human promyelocytic leukemia cell line, HL60; neuroblastoma cell lines such as SK-N-SH, SK-SY5Y, H-EP1, SK-N-BE(2), SK-N-BE(ZkM17), SK-N-BE(2)C, LA-N-1, or LA-N-1-5s; and small cell lung carcinoma cell lines such as H526, DMS153, DMS79, ECC12, TMK1, MKN7, GCIY, and HGC27. In a specific embodiments, a tumor cell line for use in a xenograft mouse model is the GIST882, GIST430, GIST48, GIST48B, HEL, HL60, H526, DMS153, or DMS79 cell line. In certain embodiments, suitable cell lines for use in xenograft tumor models can be generated by recombinantly expressing KIT in cell. In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and inhibit tumor grow or induce tumor regression in a mouse model by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art. In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and inhibit tumor grow or induce tumor regression in a mouse model by at least about 25% or 35%, optionally to about 75%, as assessed by methods described herein or known to one of skill in the art. In specific embodiments, antibodies described herein specifically bind to KIT and inhibit tumor grow or induce tumor regression in a mouse model by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art. Determining tumor growth inhibition or tumor regression can be assessed by monitoring tumor size over a period of time, such as by physical measurement of palpable tumors, or other visual detection methods. For example, tumor cell lines can be generated to recombinantly express a visualization agent, such as green fluorescent protein (GFP) or luciferase, then in vivo visualization of GFP can be carried out by microscopy, and in vivo visualization of luciferase can be carried out by administering luciferase substrate to the xenograft mice and detecting luminescent due to the luciferase enzyme processing the luciferase substrate. The degree or level of detection of GFP or luciferase correlates to the size of the tumor in the xenograft mice.

In certain aspects, anti-KIT antibodies described herein bind specifically to KIT antigen and can increase survival of animals in tumor xenograft models. In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and increase survival of mice in tumor xenograft models by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art. In specific embodiments, antibodies described herein (e.g., antibody 37M or 37C or an antigen-binding fragment thereof, or an antibody comprising CDRs of antibody 37M, or a conjugate comprising, for example, antibody 37M or 37C or a KIT-binding fragment thereof linked, covalently or noncovalently, to a therapeutic agent) specifically bind to KIT and increase survival of mice in tumor xenograft models by at least about 25% or 35%, optionally to about 75%, as assessed by methods described herein or known to one of skill in the art. In specific embodiments, antibodies described herein specifically bind to KIT and increase survival of mice in tumor xenograft models by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art. Survival can be determined by plotting a survival curve of number of surviving mice against time (e.g., days or weeks) after tumor cell line injection.

Provided herein are antibodies that immunospecifically bind a KIT polypeptide, e.g., a human KIT polypeptide, e.g., a D4/D5 region of KIT, for example, human KIT, with a particular affinity.

"Affinity" of an antibody described herein for an epitope (e.g., KIT epitope) is a term well understood in the art and refers to the extent, or strength, of binding of an antibody to an epitope. Affinity can be measured and/or expressed in a number of ways known in the art, including, but not limited to, equilibrium dissociation constant ($K_D$ or $K_d$), apparent equilibrium dissociation constant ($K_D'$ or $K_d'$), and $IC_{50}$ (amount needed to effect 50% inhibition in a competition assay). It is understood that, for purposes described herein, an affinity is an average affinity for a given population of antibodies which bind to an epitope. Values of $K_D$' described herein in terms of milligram (mg) Ig per mL or mg/mL indicate mg Ig per mL of serum, although plasma can be used. When antibody affinity is used as a basis for administration of the treatment methods described herein, or selection for the treatment methods described herein, antibody affinity can be measured before and/or during treatment, and the values obtained can be used by a clinician in assessing whether a human patient is an appropriate candidate for treatment.

In specific aspects, provided herein are antibodies (e.g., antibodies comprising the CDRs of antibody 37M or 37C or an antibody which binds to the same epitope as that of antibody 37M or 37C) that have a high binding affinity (e.g., antibodies having a $K_D$ of less than 100 nM, 50 nM, 10 nM, 1 nM, 500 pM, 200 pM, 100 pM, or 50 pM) for a KIT antigen, preferably a human KIT antigen, in particular the D4/D5 region of a human KIT. In a specific embodiment, an antibody described herein has an association rate constant or $k_{on}$ rate (antibody (Ab)+antigen (Ag)$^{k_{on}}$→Ab-Ag) of at least $2 \times 10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, or at least $10^8$ M$^{-1}$ s$^{-1}$. In a certain embodiment, an antibody described herein has a $k_{on}$ of at least $2 \times 10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, or at least $10^8$ M$^{-1}$ s$^{-1}$.

In another embodiment, an antibody described herein has a $k_{off}$ rate ((Ab-Ag)$^{k_{off}}$→antibody (Ab)+antigen) of less than $10^{-1}$ s$^{-1}$, less than $5 \times 10^{-1}$ s$^{-1}$, less than $10^{-2}$ s$^{-1}$, less than $5 \times 10^{-2}$ s$^{-1}$, less than $10^{-3}$ s$^{-1}$, less than $5 \times 10^{-3}$ s$^{-1}$, less than $10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-10}$ s$^{-1}$. In a specific embodiment, an antibody described herein has a $k_{on}$ of less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-1}$.

In another embodiment, an antibody described herein has an affinity constant or $K_a$($k_{on}/k_{off}$) of at least $10^2$ M$^{-1}$, at least $5 \times 10^2$ M$^{-1}$, at least $10^3$ M$^{-1}$, at least $5 \times 10^3$ M$^{-1}$, at least $10^4$ M$^{-1}$, at least $5 \times 10^4$ M$^{-1}$, at least $10^5$ M$^{-1}$, at least $5 \times 10^5$ M$^{-1}$, at least $10^6$ M$^{-1}$, at least $5 \times 10^6$ M$^{-1}$, at least $10^7$ M$^{-1}$, at least $5 \times 10^7$ M$^{-1}$, at least $10^8$ M$^{-1}$, at least $5 \times 10^8$ M$^{-1}$, at least $10^9$ M$^{-1}$ at least $5 \times 10^9$ M$^{-1}$, at least $10^{10}$ M$^{-1}$, at least $5 \times 10^{10}$ M$^{-1}$, at least $10^{11}$ M$^{-1}$, at least $5 \times 10^{11}$ M$^{-1}$, at least $10^{12}$ M$^{-1}$, at least $5 \times 10^{12}$ M$^{-1}$, at least $10^{13}$ M$^{-1}$, at least $5 \times 10^{13}$ M$^{-1}$, at least $10^{14}$ M$^{-1}$, at least $5 \times 10^{14}$ M$^{-1}$, at least $10^{15}$ M$^{-1}$, or at least $5 \times 10^{15}$ M$^{-1}$.

In a particular embodiment, an antibody described herein has a dissociation constant or $K_D$ ($k_{off}/k_{on}$) of less than $10^{-2}$ M, less than $5 \times 10^{-2}$ M, less than $10^{-3}$ M, less than $5 \times 10^{-3}$ M, less than $10^{-4}$ M, less than $5 \times 10^{-4}$ M, less than $10^{-5}$ M, less than $5 \times 10^{-5}$ M, less than $10^{-6}$ M, less than $5 \times 10^{-6}$ M, less than $10^{-7}$ M, less than $5 \times 10^{-7}$ M, less than $10^{-8}$ M, less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-11}$ M, less than $10^{-12}$ M, less than $5 \times 10^{-12}$ M, less than $10^{-13}$ M, less than $5 \times 10^{-13}$ M, less than $10^{-14}$ M, less than $5 \times 10^{-14}$ M, less than $10^{-15}$ M, or less than $5 \times 10^{-15}$ M.

In specific embodiments, an antibody (e.g., antibody comprising the CDRs of antibody 37M or 37C or an antibody which binds to the same epitope as that of antibody 37M or 37C) immunospecifically binds to a KIT antigen (e.g., a D4/D5 region of KIT, for example human KIT), and has a dissociation constant ($K_D$) of less than 500,000 pM (500 nM), less than 100,000 pM (100 nM), less than 50,000 pM (50 nM), less than 10,000 pM (10 nM), less than 3,000 pM (3 nM), less than 2,500 pM (2.5 nM), less than 2,000 pM, less than 1,500 pM, less than 1,000 pM, less than 750 pM, less than 500 pM, less than 250 pM, less than 200 pM, less than 150 pM, less than 100 pM, less than 75 pM as assessed using an assay described herein or known to one of skill in the art (e.g., a Biacore™ assay) (Biacore™ International AB, Uppsala, Sweden). In a specific embodiment, an antibody described herein (e.g., antibody comprising the CDRs of antibody 37M or 37C or an antibody which binds to the same epitope as that of antibody 37M or 37C) immunospecifically binds to a KIT antigen (e.g., a D4/D5 region of KIT, for example human KIT), and has a $K_D$ in the range of from 25 to 100,000 pM, 25 to 75,000 pM, 25 to 50,000 pM, 25 to 40,000 pM, 25 to 30,000 pM, 25 to 20,000 pM, 25 to 10,000 pM, 25 to 1,000 pM, 25 to 500 pM, 25 to 250 pM, 25 to 100 pM, or 25 to 50 pM as assessed using methods described herein or known to one of skill in the art (e.g., a Biacore™ assay, assay using KinExA 3000 instrument). In a particular embodiment, an antibody described herein (e.g., antibody comprising the CDRs of antibody 37M or 37C or an antibody which binds to the same epitope as that of antibody 37M or 37C) immunospecifically bind to a KIT antigen (e.g., a D4/D5 region of KIT, for example human KIT), and has a $K_D$ of about 1 nM to about 25 nM, or any value in between, as assessed using methods described herein or known to one of skill in the art (e.g., a Biacore™ assay, assay using KinExA 3000 instrument). In a particular embodiment, antibodies described herein (e.g., antibody comprising the CDRs of antibody 37M or 37C or an antibody which binds to the same epitope as that of antibody 37M or 37C) immunospecifically bind to a KIT antigen (e.g., a D4/D5 region of KIT, for example human KIT), and have a $K_D$ of about 100 pM to about 25 nM, or any value in between, as assessed using methods described herein or known to one of skill in the art (e.g., a Biacore™ assay, assay using KinExA 3000 instrument). In a particular embodiment, an antibody described herein (e.g., antibody comprising the CDRs of antibody 37M or 37C or an antibody which binds to the same epitope as that of antibody 37M or 37C) immunospecifically binds to a KIT antigen (e.g., a D4/D5 region of KIT, for example human KIT), and has a $K_D$ of about 1 pM to about 250 nM, or any value in between, as assessed using methods described herein or known to one of skill in the art (e.g., a Biacore™ assay, assay using KinExA 3000 instrument). In a particular embodiment, an antibody described herein (e.g., antibody comprising the CDRs of antibody 37M or 37C or an antibody which binds to the same epitope as that of antibody 37M or 37C) immunospecifically binds to KIT antigen, (e.g., a D4/D5 region of KIT, for example human KIT), and has a $K_D$ of about 1 nM, 1.5 nM, 2 nM, 2.5 nM, 3 nM, 3.5 nM, 4 nM, 4.5 nM, 5 nM, 5.5 nM, 6 nM, 6.5 nM, 7 nM, 8 nM, 9 nM, 10 nM, 11 nM, 12 nM, 13 nM, 14 nM, 15 nM, 16 nM, 17 nM, 18 nM, 19 nM, 20 nM, or 21 nM, as assessed using methods described herein or known to one of skill in the art (e.g., a Biacore™ assay, assay using KinExA 3000 instrument). In a particular embodiment, an antibody described herein (e.g., antibody comprising the CDRs of antibody 37M or 37C or an antibody which binds to the same epitope as that of antibody 37M or 37C) immunospecifically binds to KIT antigen (e.g., a D4/D5 region of KIT, for example human KIT), and has a $K_D$ from about 100 pM to about 10 nM, as assessed using methods described herein or known to one of skill in the art (e.g., ELISA, assay using KinExA 3000 instrument, or Biacore™ assay). In a particular embodiment, an antibody described herein (e.g., antibody comprising the CDRs of antibody 37M or 37C or an antibody which binds to the same epitope as that of antibody 37M or 37C) immunospecifically binds to KIT antigen (e.g., a D4/D5 region of KIT, for example human KIT), and has a $K_D$ from about 50 pM to about 1 nM, as assessed using methods described herein or known to one of skill in the art (e.g., ELISA, assay using KinExA 3000 instrument, or Biacore™ assay).

In specific embodiments, an anti-KIT antibody (e.g., antibody comprising the CDRs of antibody 37M or 37C or an antibody which binds to the same epitope as that of antibody 37M or 37C) immunospecifically binds to a KIT antigen (e.g., a D4/D5 region of KIT, for example human KIT), and has a concentration at 50% binding to antigen of less than 3000 pM (3 nM), less than 2500 pM (2.5 nM), less than 2000 pM, less than 1500 pM, less than 1000 pM, less than 750 pM, less than 500 pM, less than 250 pM, less than 200 pM, less than 150 pM, less than 100 pM, less than 75 pM as assessed using an assay described herein or known to one of skill in the art (e.g., solid phase ELISA as described in section 6). In a specific embodiment, an antibody described herein (e.g., antibody comprising the CDRs of antibody 37M or 37C or an antibody which binds to the same epitope as that of antibody 37M or 37C) immunospecifically binds to a KIT antigen (e.g., a D4/D5 region of KIT, for example human KIT), and has a concentration at 50% binding to antigen in the range of from 25 to 500,000 pM (500 nM), 25 to 250,000 pM (250 nM), 25 to 100,000 pM (100 nM), 25 to 75,000 pM (75 nM), 25 to 50,000 pM (50 nM), 25 to 40,000 pM (40 nM), 25 to 30,000 pM (30 nM), 25 to 20,000 pM (20 nM), 25 to 10,000 pM (10 nM), 25 to 1,000 pM (1 nM), 25 to 500 pM, 25 to 250 pM, 25 to 100 pM, or 25 to 50 pM as assessed using methods described herein or known to one of skill in the art (e.g., solid phase ELISA as described in section 6). In a particular embodiment, an antibody described herein (e.g., antibody comprising the CDRs of antibody 37M or 37C or an antibody which binds to the same epitope as that of antibody 37M or 37C) immunospecifically binds to a KIT antigen (e.g., a D4/D5 region of KIT, for example human KIT), and has a concentration at 50% binding to antigen of about 1 nM to about 25 nM, or any value in between, as assessed using methods described herein or known to one of skill in the art (e.g., solid phase ELISA as described in section 6). In a particular embodiment, an antibody described herein (e.g., antibody comprising the CDRs of antibody 37M or 37C or an antibody which binds to the same epitope as that of antibody 37M or 37C) immunospecifically binds to a KIT antigen (e.g., a D4/D5 region of KIT, for example human KIT), and has a concentration at 50% binding to antigen of about 50 pM to about 500 pM, or any value in between, as assessed using methods described herein or known to one of skill in the art (e.g., solid phase ELISA as described in section 6). In a particular embodiment, an antibody described herein (e.g., antibody comprising the CDRs of antibody 37M or 37C or an antibody which binds to the same epitope as that of antibody 37M or 37C) immunospecifically binds to KIT antigen (e.g., a D4/D5 region of KIT, for example human KIT), and has a concentration at 50% binding of about 0.5 nM, 0.25 nM, 0.1 nM, 1 nM, 1.5 nM, 2 nM, 2.5 nM, 3 nM, 3.5 nM, 4 nM, 4.5 nM, 5 nM, 5.5 nM, 6 nM, 6.5 nM, 7 nM, 8 nM, 9 nM, 10 nM, 11 nM, 12 nM, 13 nM, 14 nM, 15 nM, 16 nM, 17 nM, 18 nM, 19 nM, 20 nM, 30 nM, 40 nM, 50 nM, 60 nM, 70 nM, 80 nM, 90 nM, 100 nM, 150 nM, 200 nM, 250 nM, 300 nM, 350 nM, 400 nM, or 500 nM, or less, as assessed using methods described herein or known to one of skill in the art (e.g., solid phase ELISA as described in section 6). In a particular embodiment, antibodies described herein (e.g., antibody comprising the CDRs of antibody 37M or 37C or an antibody which binds to the same epitope as that of antibody 37M or 37C) immunospecifically bind to KIT antigen (e.g., a D4/D5 region of KIT, for example human KIT), and have a concentration at 50% binding from about 100 pM to about 10 nM, as assessed using methods described herein or known to one of skill in the art (e.g., ELISA, assay using KinExA 3000 instrument, or Biacore™ assay).

In specific embodiments, an anti-KIT antibody which is an antigen-binding fragment of a whole or entire antibody, e.g., Fab fragment, has comparable affinity to KIT relative to the affinity of the whole or entire anti-KIT antibody. In certain embodiments, an anti-KIT antibody which is an antigen-binding fragment of a whole or entire antibody, e.g., Fab fragment, specifically binds to KIT and has a $K_D$ that is comparable to the $K_D$ of the whole or entire anti-KIT antibody as assessed using methods described herein or known to one of skill in the art (e.g., a Biacore™ assay, assay using KinExA 3000 instrument). In certain embodiments, an anti-KIT antibody which is an antigen-binding fragment of a whole or entire antibody, e.g., Fab fragment, specifically binds to KIT and has a $K_D$ that is less than the $K_D$ of the whole or entire anti-KIT antibody as assessed using methods described herein or known to one of skill in the art (e.g., a Biacore™ assay, assay using KinExA 3000 instrument). In particular embodiments, an anti-KIT antibody which is an antigen-binding fragment of a whole or entire antibody, e.g., Fab fragment, specifically binds to KIT and has a $K_D$ that is about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 75%, or 85%, less than the $K_D$ of the whole or entire anti-KIT antibody as assessed using methods described herein or known to one of skill in the art (e.g., a Biacore™ assay, assay using KinExA 3000 instrument). In particular embodiments, an anti-KIT antibody which is an antigen-binding fragment of a whole or entire antibody, e.g., Fab fragment, specifically binds to KIT and has a $K_D$ that is at most about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 65% or 75% less than the $K_D$ of the whole or entire anti-KIT antibody as assessed using methods described herein or known to one of skill in the art (e.g., a Biacore™ assay, assay using KinExA 3000 instrument).

In certain embodiments, an anti-KIT antibody which is an antigen-binding fragment of the native (or entire) antibody, e.g., Fab fragment, specifically binds to KIT and has a $K_D$ that is more than the $K_D$ of the native (or entire) anti-KIT antibody as assessed using methods described herein or known to one of skill in the art (e.g., a Biacore™ assay, assay using KinExA 3000 instrument). In particular embodiments, an anti-KIT antibody which is an antigen-binding fragment of a whole or entire antibody, e.g., Fab fragment, specifically binds to KIT and has a $K_D$ that is about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, or 95% higher than the $K_D$ of the whole or entire anti-KIT antibody as assessed using methods described herein or known to one of skill in the art (e.g., a Biacore™ assay, assay using KinExA 3000 instrument). In particular embodiments, an anti-KIT antibody which is an antigen-binding fragment of a whole or entire antibody, e.g., Fab fragment, specifically binds to KIT and has a $K_D$ that is at most about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, or 95% higher than the $K_D$ of the whole or entire anti-KIT antibody as assessed using methods described herein or known to one of skill in the art (e.g., a Biacore™ assay, assay using KinExA 3000 instrument). In particular embodiments, an anti-KIT antibody which is an antigen-binding fragment of a whole or entire antibody, e.g., Fab fragment, specifically binds to KIT and has a $K_D$ that is at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, or 95% higher than the $K_D$ of the whole or entire anti-KIT antibody as assessed using methods described herein or known to one of skill in the art (e.g., a Biacore™ assay, assay using KinExA 3000 instrument). In particular embodiments, an anti-KIT antibody which is an antigen-binding fragment of a whole or entire antibody, e.g., Fab fragment, specifically binds to KIT and has a $K_D$ that is about 1 fold, 1.1 fold, 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold or 5 fold higher than the $K_D$ of the whole or entire anti-KIT antibody as assessed using methods described herein or known to one of skill in the art (e.g., a Biacore™ assay, assay using KinExA 3000 instrument).

Methods for determining affinity of an antibody to its target antigen are readily available and described in the art. For example, the affinities and binding properties of an antibody for its target antigen, can be determined by a variety of in vitro assay methods (biochemical or immunological based assays) known in the art such as equilibrium methods (e.g., enzyme-linked immunoabsorbent assay (ELISA), or radioimmunoassay (RIA)), or kinetics (e.g., Biacore™ analysis), and other methods such as indirect binding assays, competitive inhibition assays, fluorescence resonance energy transfer (FRET), immunoprecipitation, gel electrophoresis and chromatography (e.g., gel filtration). These and other methods can utilize a label on one or more of the components being examined and/or employ a variety of detection methods including but not limited to chromogenic, fluorescent, luminescent, or isotopic labels. In certain embodiments, use of labels is not necessary, e.g., Biacore™ systems utilize the natural phenomenon of surface plasmon resonance (SPR) to deliver data in real time, without the use of labels. A detailed description of binding affinities and kinetics can be found in Paul, W. E., ed., *Fundamental Immunology*, 4th Ed. (Lippincott-Raven, Philadelphia 1999), which focuses on antibody-immunogen interactions.

In certain aspects, the affinity of an antibody described herein for a KIT antigen, e.g., human KIT, for example a D4/D5 region of KIT (e.g., human KIT), can be characterized indirectly using cell-based assays. For example, cells expressing KIT on their cell membrane surface can be contacted with anti-KIT antibodies, and cellular activities downstream of KIT can be determined using assays known in the art. For examples, phosphorylation of the cytoplasmic domain of KIT can be determined by immunoblotting (or Western blotting) following contacting the cells with an anti-KIT antibody; cellular extracts are obtained and processed for immunoblotting (e.g., subjecting the cellular extracts to sodium dodecyl sulfate polyacrylamide gel electrophoresis (SDS-PAGE) and transferring the proteins separated on the gel to a membrane (e.g., nitrocellulose or polyvinylidene fluoride (PVDF)) with an antibody that specifically binds to a phosphorylated tyrosine in the cytoplasmic domain of KIT, but does not bind an unphosphorylated tyrosine.

In certain embodiments, an anti-KIT antibody described herein specifically binds to a KIT antigen, e.g., human KIT, for example a D4/D5 region of KIT (e.g., human KIT), and induces or enhances dimerization and phosphorylation of KIT, in the presence or absence of the KIT ligand SCF. In some embodiments, an anti-KIT antibody described herein can inhibit or decrease KIT ligand, e.g., SCF, binding to KIT (i.e., an anti-KIT antibody can compete with a KIT ligand, e.g., SCF, for binding to KIT). In such case, cells can be contacted with an anti-KIT antibody and a KIT ligand, and the degree of inhibition of KIT phosphorylation can be determined as an indication of the degree of the anti-KIT antibody competing with the KIT ligand for binding to KIT.

Antibodies include, but are not limited to, monoclonal antibodies, recombinantly produced antibodies, multispecific antibodies (including bi-specific antibodies), murine antibodies, human antibodies, humanized antibodies, chimeric antibodies, synthetic antibodies, tetrameric antibodies comprising two heavy chain and two light chain molecule, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single-chain Fvs (scFv) (e.g., including monospecific, bispecific, etc.), camelized antibodies, affybodies, Fab fragments, F(ab') fragments, disulfide-linked Fvs (sdFv), anti-idiotypic (anti-Id) antibodies (including, e.g., anti-anti-Id antibodies), and epitope-binding fragments of any of the above. In certain embodiments, antibodies described herein refer to polyclonal antibody populations. Antibodies can be of any type (e.g., IgG, IgE, IgM, IgD, IgA or IgY), any class, (e.g., $IgG_1$, $IgG_2$, $IgG_3$, $IgG_4$, $IgA_1$ or $IgA_2$), or any subclass (e.g., IgG2a or IgG2b) of immunoglobulin molecule. In certain embodiments, antibodies described herein are IgG antibodies, or a class (e.g., human IgG1 or $IgG_4$) or subclass thereof. In specific embodiments, a monoclonal antibody is an antibody produced by a single hybridoma or other cell, wherein the antibody immunospecifically binds to a D4/D5 region of human KIT epitope as determined, e.g., by ELISA or other antigen-binding or competitive binding assay known in the art or in the Examples provided herein. The term "monoclonal" is not limited to any particular method for making the antibody.

In a particular embodiment, an antibody provided herein is a Fab fragment that immunospecifically binds to a KIT polypeptide, such as the D4/D5 region of KIT. In a specific embodiment, antibodies described herein are monoclonal antibodies or isolated monoclonal antibodies. In another specific embodiment, an antibody described herein is a humanized monoclonal antibody. In yet another specific embodiment, an antibody described herein is a murine monoclonal antibody, e.g., a murine monoclonal antibody obtained from a hybridoma. In a particular embodiment, an antibody described herein is a recombinant antibody, for example, a recombinant human antibody or a recombinant monoclonal antibody. In certain embodiments, an antibody described herein contains non-human amino acid sequences, e.g., non-human CDRs or non-human (e.g., non-human primate) framework residues.

Antibodies provided herein include immunoglobulin molecules of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody (e.g., human IgG antibody), or a class (e.g., human IgG1 or IgG4) or subclass thereof. In another specific embodiment, an antibody described herein is an IgG1 (e.g., human IgG1 (isotype a, z, or f)) or IgG4 antibody. In certain embodiments, an antibody described herein is a whole or entire antibody, e.g., a whole or entire humanized antibody.

Antibodies provided herein can include antibody fragments that retain the ability to specifically bind to an epitope, i.e., KIT epitope (e.g., a KIT epitope within a KIT polypeptide containing the D4/D5 region of human KIT). In a specific embodiment, fragments include Fab fragments (an antibody fragment that contains the antigen-binding domain and comprises a light chain and part of a heavy chain (i.e., the VH and CH1 domains of a heavy chain) bridged by a disulfide bond); Fab' (an antibody fragment containing a single antigen-binding domain comprising an Fab and an additional portion of the heavy chain through the hinge region); F(ab')$_2$ (two Fab' molecules joined by interchain disulfide bonds in the hinge regions of the heavy chains; the Fab' molecules can be directed toward the same or different epitopes); a bispecific Fab (a Fab molecule having two antigen binding domains, each of which can be directed to a different epitope); a single chain Fab chain comprising a variable region, also known as a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which can be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody can be directed towards the same or different epitopes); and a triabody (a trimerized sFv, formed in a manner similar to a diabody, but in which three antigen-binding domains are created in a single complex; the three antigen binding domains can be directed towards the same or different epitopes). Antibodies provided herein can also include one or more CDR sequences of an antibody. The CDR sequences can be linked together on a scaffold when two or more CDR sequences are present. In certain embodiments, an antibody comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs, see Pluckthun in *The Pharmacology of Monoclonal Antibodies*, vol. 113, Rosenburg and Moore eds. Springer-Verlag, New York, pp. 269-315 (1994). Without being bound by any particular theories, Fv molecules can be able to penetrate tissues because of their small size. A whole antibody can be enzymatically cleaved by pepsin to produce a F(ab')$_2$ fragment, or can be enzymatically cleaved by papain to produce two Fab fragments.

In certain embodiments, the antibodies described herein can be from any animal origin including birds (e.g., chicken or rooster) and mammals (e.g., human, mouse, donkey, sheep, rabbit, goat, guinea pig, camel, dog, cat, pig, rat, monkey, cow, hamster, or horse). In certain embodiments, the antibodies described herein are human or humanized monoclonal antibodies. In a certain embodiment, an antibody described herein is a murine antibody. In a particular embodiment, an antibody described herein is an antibody obtained from, or produced by, a hybridoma cell. In a particular embodiment, an antibody described herein is an engineered antibody, for example, antibody produced by recombinant methods. In a specific embodiment, an antibody described herein is a humanized antibody comprising one or more non-human (e.g., rodent or murine) CDRs and one or more human framework regions (FR), and optionally human heavy chain constant region and/or light chain constant region. In a specific embodiment, an antibody described herein comprises one or more primate (or non-human primate) framework regions.

Antibodies provided herein can include antibodies comprising chemical modifications, for example, antibodies which have been chemically modified, e.g., by covalent attachment of any type of molecule to the antibody. For example, but not by way of limitation, an anti-KIT antibody can be glycosylated, acetylated, pegylated, phosphorylated, or amidated, can be derivitized via protective/blocking groups, or can further comprise a cellular ligand and or other protein or peptide, etc. For example, an antibody provided herein can be chemically modified, e.g., by glycosylation, acetylation, pegylation, phosphorylation, amidation, derivatization by known protecting/blocking groups, proteolytic cleavage, linkage to a cellular ligand or other protein, etc. Further, an anti-KIT antibody described herein can contain one or more non-classical amino acids.

In a particular embodiment, provided herein is an anti-KIT antibody which has been modified in a manner suitable for large scale manufacturing, e.g., the manufacturing platform of Lonza (Basel, Switzerland). For example, the BI-HEX® technology platform (Boehringer Ingleheim, Germany) can be used to adapt the anti-KIT antibodies described herein for suitable large scale manufacturing in recombinant mammalian cell expression systems. Such adaptation can involve cloning polynucleotide sequences encoding the necessary domains of an anti-KIT antibody, such as one or more CDRs or FRs, into a suitable expression vector which also contains polynucleotide sequences encoding suitable constant regions, so that an entire antibody is produced. The polynucleotide sequences provided by the expression vectors are nucleotide sequences which can be optimized to maximize antibody yield and stability for cell culture manufacturing conditions and purification processes.

5.1.1. Conjugates

In some embodiments, provided herein are antibodies, or antigen-binding fragments thereof, conjugated or recombinantly fused to a diagnostic, detectable or therapeutic agent or any other molecule. The conjugated or recombinantly fused antibodies can be useful, e.g., for monitoring or prognosing the onset, development, progression and/or severity of a KIT-mediated disorder or disease, for example, as part of a clinical testing procedure, such as determining the efficacy of a particular therapy. The conjugated or recombinantly fused antibodies can be useful, e.g., for treating or managing a KIT-mediated disorder (e.g., cancer), or for treating or managing effects of a KIT-mediated disorder (e.g., cancer). Antibodies described herein can also be conjugated to a molecule (e.g., polyethylene glycol)

which can affect one or more biological and/or molecular properties of the antibodies, for example, stability (e.g., in serum), half-life, solubility, and antigenicity.

In a particular aspect, provided herein is a conjugate comprising an agent (e.g., therapeutic agent) linked to an antibody described herein (or an antigen-binding fragment thereof), which antibody immunospecifically binds to a D4/D5 region of human KIT (e.g., SEQ ID NO: 15). In a specific embodiment, the conjugated antibody specifically binds a D4/D5 region of KIT (e.g., human KIT), and comprises antibody 37M or 37C, a KIT-binding portion thereof, e.g., any such portion described herein, or an antibody comprising the CDRs (e.g., 3 VL CDRs and/or 3 VH CDRS) of antibody 37M or 37C. In a specific embodiment, a conjugated antibody specifically binds a D4/D5 region of KIT (e.g., human KIT) and comprises a VL chain region comprising VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively. In one embodiment, an antibody that is conjugated is one that binds a D4/D5 region of human KIT with an affinity of less than about 200 pM. In another embodiment, an antibody that is conjugated is one that inhibits a biological activity of KIT. In specific embodiments, a conjugate comprises an antibody described herein and a molecule (e.g., therapeutic or drug moiety), wherein the antibody is linked directly to the molecule, or by way of one or more linkers. In certain embodiments, an antibody is covalently conjugated to a molecule. In a particular embodiment, an antibody is non-covalently conjugated to a molecule. In specific embodiments, an antibody described herein, e.g., an antibody conjugated to an agent, binds to wild-type human KIT. In certain embodiments, an antibody described herein, e.g., antibody conjugated to an agent, binds to an extracellular domain of human KIT comprising a mutation, for example a somatic mutation associated with cancer (e.g., GIST), such as a mutation in exon 9 of human KIT wherein the Ala and Tyr residues at positions 502 and 503 are duplicated.

Such diagnosis and detection can be accomplished, for example, by coupling the antibody to detectable molecules or substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I,), carbon ($^{14}$C), Sulfur ($^{35}$S), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

Provided are antibodies described herein, or antigen-binding fragments thereof, conjugated or recombinantly fused to a therapeutic moiety (or one or more therapeutic moieties) and uses of such antibodies. The antibody can be conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, auristatin or a derivative thereof, e.g., monomethyl auristatin E (MMAE), monomethyl auristatin F (MMAF), auristatin PYE, and auristatin E (AE) (see, e.g., U.S. Pat. No. 7,662,387 and U.S. Pat. Application Publication Nos. 2008/0300192 and 2008/0025989); a microtubule-disrupting agent, e.g., maytansine or a derivative thereof, e.g., maytansinoid DM1 (see, e.g., U.S. Pat. Nos. 7,851,432, 7,575,748, and 5,416,064); a prodrug, e.g., a prodrug of a CC-1065 (rachelmycin) analogue; antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); minor-groove-binding alkylating agent; anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399, 633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451, 812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein); DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof. In one embodiment, an antibody that is conjugated to such therapeutic/drug moiety is one that binds a D4/D5 region of human KIT with an affinity of less than about 200 pM. In another embodiment, an antibody that is conjugated to such therapeutic/drug moiety is one that inhibits a biological activity of KIT. In a specific embodiment, an antibody that is conjugated to such therapeutic/drug moiety is one that comprises CDRs of antibody 37M or 37C (e.g., VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively).

In particular embodiments, a therapeutic moiety or drug moiety is an antitubulin drug, such as an auristatin or a derivative thereof. Non-limiting examples of auristatins include monomethyl auristatin E (MMAE), monomethyl auristatin F (MMAF), auristatin PYE, and auristatin E (AE) (see, e.g., U.S. Pat. No. 7,662,387 and U.S. Pat. Application Publication Nos. 2008/0300192 and 2008/0025989). In certain embodiments, a therapeutic moiety or drug moiety is a microtubule-disrupting agent such as maytansine or a derivative thereof, e.g., maytansinoid DM1 or DM4 (see, e.g., U.S. Pat. Nos. 7,851,432, 7,575,748, and 5,416,064). In certain embodiments, a therapeutic moiety or drug moiety is a prodrug, e.g., a prodrug of a CC-1065 (rachelmycin) analogue (see, e.g., U.S. Patent Application Publication No. 2008/0279868, and PCT International Patent Application Publication Nos. WO 2009/017394, WO 2010/062171, and WO 2007/089149). In one embodiment, an antibody that is conjugated to such therapeutic/drug moiety is one that binds a D4/D5 region of human KIT with an affinity of less than about 200 pM. In another embodiment, an antibody that is conjugated to such therapeutic/drug moiety is one that inhibits a biological activity of KIT. In a specific embodiment, an antibody that is conjugated to such therapeutic/drug moiety is one that comprises CDRs of antibody 37M or 37C (e.g., VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively).

In a specific embodiment, the antibody and therapeutic/drug agent are conjugated by way of one or more linkers. In another specific embodiment, the antibody and therapeutic/drug agent are conjugated directly.

In specific embodiments, non-limiting examples of therapeutic moieties or drug moieties for conjugation to an antibody described herein include calicheamicins (e.g., LL-E33288 complex, for example, gamma-calicheamicin, see, e.g., U.S. Pat. No. 4,970,198) and derivatives thereof (e.g., gamma calicheamicin hydrazide derivatives), duocarmycins and derivatives thereof (e.g., CC-1065 (NSC 298223), or an achiral analogue of duocarmycin (for example AS-1-145 or centanamycin)), taxanes and derivatives thereof, and enediynes and derivatives thereof (See, e.g., PCT International Patent Application Publication Nos. WO 2009/017394, WO 2010/062171, WO 2007/089149, WO 2011/021146, WO 2008/150261, WO 2006/031653, WO 2005/089809, WO 2005/089807, and WO 2005/089808, each of which is incorporated by reference herein in its entirety). In a specific embodiment, an antibody that is conjugated to such therapeutic/drug moiety is one that comprises CDRs of antibody 37M or 37C (e.g., VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively). In a specific embodiment, the antibody and therapeutic agent are conjugated by way of one or more linkers. In another specific embodiment, the antibody and therapeutic agent are conjugated directly.

Non-limiting examples of calicheamicins suitable for conjugation to an antibody described herein are disclosed, for example, in U.S. Pat. Nos. 4,671,958; 5,053,394; 5,037,651; 5,079,233; and 5,108,912; and PCT International Patent Application Publication Nos. WO 2011/021146, WO 2008/150261, WO 2006/031653, WO 2005/089809, WO 2005/089807, and WO 2005/089808; which are incorporated by reference herein in their entirety. In particular embodiments, these compounds may contain a methyltrisulfide that reacts with appropriate thiols to form disulfides, and at the same time introduces a functional group such as a hydrazide or other functional group that may be useful for conjugating calicheamicin to an antibody described herein. In certain embodiments, stabilizing the disulfide bond that is present in calicheamicin conjugates by adding dimethyl substituents may yield an improved antibody/drug conjugate. In specific embodiments, the calicheamicin derivative is N-acetyl gamma calicheamicin dimethyl hydrazide, or NAc-gamma DMH (CL-184,538), as one of the optimized derivatives for conjugation. Disulfide analogs of calicheamicin which can be conjugated to the antibody described herein are described, for example, in U.S. Pat. Nos. 5,606,040 and 5,770,710, which are incorporated by reference herein in their entirety. In a certain embodiment, a moiety (e.g., calicheamicin or a derivative thereof) is conjugated to an antibody by a linker. In a particular embodiment, a moiety (e.g., calicheamicin or a derivative thereof) is hydrolyzed from the antibody-drug conjugate at the linker. In one embodiment, a moiety (e.g., calicheamicin or a derivative thereof) is hydrolyzed from an antibody conjugate at the linker between about a pH of 3.0 and pH 4.0 for 1-24 hours at a temperature from 20 to 50° C., preferably 37° C.

In specific embodiments, non-limiting examples of therapeutic moieties or drug moieties for conjugation to an antibody described herein include pyrrolobenzodiazepines (PBDs) and derivatives thereof, for example, PBD dimers (e.g., SJG-136 or SG2000), C2-unsaturated PBD dimers, pyrrolobenzodiazepine dimers bearing C2 aryl substitutions (e.g., SG2285), PBD dimer pro-drug that is activated by hydrolysis (e.g., SG2285), and polypyrrole-PBD (e.g., SG2274) (see, e.g., PCT International Patent Application Publication Nos. WO 2000/012507, WO 2007/039752, WO 2005/110423, WO 2005/085251, and WO 2005/040170, and U.S. Pat. No. 7,612,062, each of which is incorporated by reference herein in its entirety). In a specific embodiment, an antibody that is conjugated to such therapeutic/drug moiety is one that comprises CDRs of antibody 37M or 37C (e.g., VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively). In a specific embodiment, the antibody and therapeutic agent is conjugated by way of one or more linkers.

Further, an antibody described herein can be conjugated or recombinantly fused to a therapeutic moiety or drug moiety that modifies a given biological response. Therapeutic moieties or drug moieties are not to be construed as limited to classical chemical therapeutic agents. For example, the drug moiety can be a protein, peptide, or polypeptide possessing a desired biological activity. Such proteins can include, for example, a toxin such as abrin, ricin A, pseudomonas exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

Provided herein are antibodies recombinantly fused or chemically conjugated (covalent or non-covalent conjugations) to a heterologous protein or polypeptide (or fragment thereof, preferably to a polypeptide of about 10, about 20, about 30, about 40, about 50, about 60, about 70, about 80, about 90 or about 100 amino acids) to generate fusion proteins. In particular, provided herein are fusion proteins comprising an antigen-binding fragment of an antibody described herein (e.g., a Fab fragment, Fd fragment, Fv fragment, F(ab)$_2$ fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses KIT. For example, an antibody that immunospecifically binds to a cell surface receptor expressed by a particular cell type (e.g., an immune cell) can be fused or conjugated to a modified antibody described herein. In specific embodiments, the heterologous protein or polypeptide (or fragment thereof) binds to a second target (e.g., a target other than KIT) (see, e.g., PCT International Patent Application Publication No. WO 2009/088805 and U.S. Patent Application Publication No. US 2009/0148905).

Provided herein is a conjugated or fusion protein comprising any antibody described herein, or an antigen-binding fragment thereof, and a heterologous polypeptide (e.g., a polypeptide other than KIT). In one embodiment, a conjugated or fusion protein described herein comprises an anti-KIT antibody described herein, and a heterologous polypeptide. In another embodiment, a conjugated or fusion protein described herein comprises an antigen-binding fragment of an anti-KIT antibody described herein, and a heterologous polypeptide. In another embodiment, a conjugated or fusion protein described herein comprises a VH domain having the amino acid sequence of any one of the VH domains of an anti-KIT antibody described herein, and/or a VL domain having the amino acid sequence of any one of the VL domains of an anti-KIT antibody described herein, and a heterologous polypeptide. In another embodiment, a conjugated or fusion protein described herein comprises one or more VH CDRs having the amino acid sequence of any one of SEQ ID NO: 23, 24, and 25, and a heterologous polypeptide. In another embodiment, a conjugated or fusion protein comprises one or more VL CDRs having the amino acid sequence of any one of the VL CDRs of an anti-KIT antibody described herein (e.g., VL CDRs in Table, SEQ ID NOs: 21, 22, and 23), and a heterologous polypeptide. In another embodiment, a conjugated or fusion protein described herein comprises at least one VH domain and at least one VL domain of an anti-KIT antibody described herein, and a heterologous polypeptide. In yet another embodiment, a conjugated or fusion protein described herein comprises at least one VH CDR and at least one VL CDR of an anti-KIT antibody described herein (e.g., VL CDRs in Table 1 and VH CDRs in Table 3), and a heterologous polypeptide.

In addition, an antibody described herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

In certain embodiments, an antibody described herein, or an antigen-binding fragment thereof, is conjugated to one or more molecules (e.g., therapeutic or drug moiety) directly or indirectly via one or more linker molecules. In particular embodiments, a linker is an enzyme-cleavable linker or a disulfide linker. In a specific embodiment, the cleavable linker is cleavable via an enzyme such an aminopeptidase, an aminoesterase, a dipeptidyl carboxy peptidase, or a protease of the blood clotting cascade. In particular embodiments, a linker comprises 1, 2, 3, 4, 5, 6, 7, 8, 9, 10, 11, 12, 13, 14, 15, or 20 amino acid residues. In certain embodiments, a linker consists of 1 to 10 amino acid residues, 1 to 15 amino acid residues, 5 to 20 amino acid residues, 10 to 25 amino acid residues, 10 to 30 amino acid residues, or 10 to 50 amino acid residues.

In certain embodiments, a moiety is conjugated to an antibody by one or more linkers. In a particular embodiment, a moiety is hydrolyzed from the antibody-drug conjugate at the linker. In one embodiment, a moiety is hydrolyzed from the antibody conjugate at the linker between about a pH of 3.0 and pH 4.0 for about 1-24 hours, and at a temperature from about 20 to 50° C., preferably 37° C. In a specific embodiment, a linker is stable in the blood stream but releases the conjugated moiety once it is inside the targeted cells. In certain embodiments, a moiety is conjugated to an antibody described herein via one or more triazole-containing linkers (see, e.g., International Patent Application Publication No. WO 2007/018431, which is incorporated by reference herein in its entirety). Non-limiting examples of linkers and spacers for incorporation into antibody-drug conjugates described herein are disclosed in PCT International Patent Application Publication Nos. WO 2007/018431, WO 2004/043493, and WO 2002/083180.

Moreover, antibodies described herein can be fused to marker sequences, such as a peptide to facilitate purification. In preferred embodiments, the marker amino acid sequence is a hexa-histidine peptide, such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating therapeutic moieties (including polypeptides) to antibodies are well known, see, e.g., Amrnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992, which are incorporated herein by reference in their entireties.

Fusion proteins can be generated, for example, through the techniques of gene-shuffling, motif-shuffling, exon-shuffling, and/or codon-shuffling (collectively referred to as "DNA shuffling"). DNA shuffling can be employed to alter the activities of antibodies described herein (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, can be altered by being subjected to random mutagenesis by error-prone PCR, random nucleotide insertion or other methods prior to recombination. A polynucleotide encoding an antibody described herein can be recombined with one or more components, motifs, sections, parts, domains, fragments, etc. of one or more heterologous molecules.

An antibody described herein can also be conjugated to a second antibody to form an antibody heteroconjugate as described in U.S. Pat. No. 4,676,980, which is incorporated herein by reference in its entirety.

The therapeutic moiety or drug conjugated or recombinantly fused to an antibody described herein that immunospecifically binds to a KIT antigen can be chosen to achieve the desired prophylactic or therapeutic effect(s), e.g., reducing tumor size or burden, reducing cancer cell growth or proliferation, or inducing death of cancer cells. In certain embodiments, the antibody is a modified antibody. A clinician or other medical personnel should consider the following when deciding on which therapeutic moiety or drug to conjugate or recombinantly fuse to an antibody described herein: the nature of the disease, the severity of the disease, and the condition of the subject.

Antibodies described herein can also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.2 Polynucleotides

In certain aspects, provided herein are polynucleotides comprising a nucleotide sequence encoding an antibody described herein or a fragment thereof (e.g., a variable light chain region and/or variable heavy chain region) that immunospecifically binds to a KIT antigen, and vectors, e.g., vectors comprising such polynucleotides for recombinant expression in host cells (e.g., E. coli and mammalian cells). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells. Also provided herein are polynucleotides encoding KIT antigens (e.g., SEQ ID NO: 14 or 15) for generating anti-KIT antibodies described herein.

In particular aspects, provided herein are polynucleotides comprising nucleotide sequences encoding antibodies (e.g., a murine, chimeric, or humanized antibody) or antigen-binding fragments thereof, which immunospecifically bind to a KIT polypeptide (e.g., the D4/D5 region of KIT, for example, human KIT) and comprises an amino acid sequence as described herein, as well as antibodies which compete with such antibodies for binding to a KIT polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Tables 1 and 2). The polynucleotides can comprise nucleotide sequences encoding a heavy chain comprising the VH FRs and CDRs of antibodies described herein (see, e.g., Tables 3 and 4). In specific embodiments, a polynucleotide described herein encodes a VL chain region having the amino acid sequence of SEQ ID NO: 2. In specific embodiments, a polynucleotide described herein encodes a VH chain region having the amino acid sequence of any one of SEQ ID NOs: 3 and 5. In particular embodiments, a polynucleotide described herein encodes a VL chain region having the amino acid sequence of SEQ ID NO: 2. In particular embodiments, a polynucleotide described herein encodes a VH chain region having the amino acid sequence of SEQ ID NO: 3. In particular embodiments, a polynucleotide described herein encodes a VH chain region having the amino acid sequence of SEQ ID NO: 5.

In particular embodiments, a polynucleotide described herein encodes a VL chain region, wherein the polynucleotide comprises the nucleic acid sequence of SEQ ID NO: 8. In particular embodiments, a polynucleotide described herein encodes a VH chain region, wherein the polynucleotide comprises the nucleic acid sequence of SEQ ID NO: 9. In particular embodiments, a polynucleotide encodes an antibody described herein, wherein the polynucleotide comprises the nucleic acid sequence of SEQ ID NO: 8 encoding a VL chain region and the nucleic acid sequence of SEQ ID NO: 9 encoding a VH chain region. In particular embodiments, one or more polynucleotides comprise the nucleic acid sequence of SEQ ID NO: 8 encoding a VL chain region and the nucleic acid sequence of SEQ ID NO: 9 encoding a VH chain region. In particular embodiments, a polynucleotide described herein encodes a VL chain region, wherein the polynucleotide comprises a nucleic acid sequence that is at least 80%, at least 85%, at least 90%, at least 95%, or at least 98% identical to the nucleic acid sequence of SEQ ID NO: 8. In particular embodiments, a polynucleotide described herein encodes a VH chain region, wherein the polynucleotide comprises a nucleic acid sequence that is at least 80%, at least 85%, at least 90%, at least 95%, or at least 98% identical to the nucleic acid sequence of SEQ ID NO: 9.

In particular embodiments, a polynucleotide described herein encodes a light chain, wherein the polynucleotide comprises the nucleic acid sequence of SEQ ID NO: 10. In a particular embodiment, a polynucleotide described herein encodes a heavy chain, wherein the polynucleotide comprises the nucleic acid sequence of SEQ ID NO: 11. In a certain embodiment, a polynucleotide comprises the nucleic acid sequence of SEQ ID NO: 10 encoding a light chain and the nucleic acid sequence of SEQ ID NO: 11 encoding a heavy chain. In a certain embodiment, one or more polynucleotides comprise the nucleic acid sequence of SEQ ID NO: 10 encoding a light chain and the nucleic acid sequence of SEQ ID NO: 11 encoding a heavy chain. In particular embodiments, a polynucleotide described herein encodes a light chain, wherein the polynucleotide comprises a nucleic acid sequence that is at least 80%, at least 85%, at least 90%, at least 95%, or at least 98% identical to the nucleic acid sequence of SEQ ID NO: 10. In particular embodiments, a polynucleotide described herein encodes a heavy chain, wherein the polynucleotide comprises a nucleic acid sequence that is at least 80%, at least 85%, at least 90%, at least 95%, or at least 98% identical to the nucleic acid sequence of SEQ ID NO: 11.

In particular embodiments, provided herein are polynucleotides comprising a nucleotide sequence encoding an anti-KIT antibody comprising a VL chain region (e.g., containing FR1-CDR1-FR2-CDR2-FR3-CDR3-FR4) having the amino acid sequences described herein (e.g., see Tables 1 and 2). In specific embodiments, provided herein are polynucleotides comprising a nucleotide sequence encoding an anti-KIT antibody comprising a VH chain region (e.g., containing FR1-CDR1-FR2-CDR2-FR3-CDR3-FR4) having the amino acid sequence described herein (e.g., see Tables 3 and 4).

In a particular embodiment, a polynucleotide described herein comprises a nucleotide sequence encoding an antibody provided herein comprising a VL chain region having the amino acid sequence of SEQ ID NO: 2, and a VH chain region having the amino acid sequence of SEQ ID NO: 3. In a particular embodiment, a polynucleotide described herein comprises a nucleotide sequence encoding an antibody provided herein comprising a VL chain region having the amino acid sequence of SEQ ID NO: 2, and a VH chain region having the amino acid sequence of SEQ ID NO: 5.

In a particular embodiment, a polynucleotide described herein comprises a nucleotide sequence encoding an antibody provided herein comprising a light chain comprising the amino acid sequence of SEQ ID NO: 6 (or the amino acid sequence of SEQ ID NO: 6 starting at position 20, lacking the signal peptide), and a heavy chain comprising the amino acid sequence of SEQ ID NO: 7 (or the amino acid sequence of SEQ ID NO: 7 starting at position 20, lacking the signal peptide).

In certain embodiments, a polynucleotide described herein comprises a nucleotide sequence encoding an antibody provided herein comprising a variable light (VL) chain region comprising an amino acid described herein (e.g., see FIG. 3A), wherein the antibody immunospecifically binds to a KIT polypeptide, e.g., a human KIT polypeptide, for example, a D4/D5 region of KIT (e.g., human KIT), for example SEQ ID NO: 15.

In certain embodiments, a polynucleotide described herein comprises a nucleotide sequence encoding an antibody provided herein comprising a variable heavy (VH) chain region comprising an amino acid sequence described herein (e.g., see FIG. 3B), wherein the antibody immunospecifically binds to a KIT polypeptide, e.g., a human KIT polypeptide, for example, a D4/D5 region of KIT (e.g., human KIT), for example SEQ ID NO: 15.

In certain embodiments, a polynucleotide described herein comprises a nucleotide sequence encoding an antibody provided herein comprises one or more VL CDRs having the amino acid sequence described herein (e.g., see Table 1), wherein the antibody immunospecifically binds to a KIT polypeptide, e.g., a human KIT polypeptide, for example, a D4/D5 region of KIT (e.g., human KIT), for example SEQ ID NO: 15.

In certain embodiments, a polynucleotide described herein comprises a nucleotide sequence encoding an antibody provided herein comprising one or more VH CDRs having the amino acid sequence described herein (e.g., see Table 3), wherein the antibody immunospecifically binds to a KIT polypeptide, e.g., a human KIT polypeptide, for example, a D4/D5 region of KIT (e.g., human KIT), for example SEQ ID NO: 15.

In another specific embodiment, a polynucleotide described herein comprises a nucleotide sequence encoding an antibody provided herein (e.g., murine, chimeric, or humanized antibody) comprising: (i) a VL chain region comprising a VL chain region comprising a VL CDR1, VL CDR2, and VL CDR3 having the amino acid sequences of SEQ ID NOs: 20, 21, and 22, respectively; and (ii) a VH chain region comprising a VH CDR1, VH CDR2, and VH CDR3 having the amino acid sequences of SEQ ID NOs: 23, 24, and 25, respectively.

In specific aspects, provided herein is a polynucleotide described herein comprises a nucleotide sequence encoding an antibody provided herein (e.g., murine, chimeric, or humanized antibody) which competitively blocks (e.g., in a dose dependent manner), antibodies comprising the amino acid sequences described herein from specific binding to a KIT polypeptide (e.g., a D4/D5 region of KIT, for example human KIT), as determined using assays known to one of skill in the art or described herein (e.g., ELISA competitive assays).

In certain aspects, a polynucleotide comprises a nucleotide sequence encoding an antibody described herein comprising a VL chain region comprising one or more VL FRs having the amino acid sequence described herein (e.g., see Table 2), wherein the antibody immunospecifically binds to a KIT polypeptide, e.g., a human KIT polypeptide, for example, a D4/D5 region of KIT (e.g., human KIT), for example SEQ ID NO: 15. In certain aspects, a polynucleotide comprises a nucleotide sequence encoding an antibody described herein comprising a VH chain region comprising one or more VH FRs having the amino acid sequence described herein (e.g., see Table 4), wherein the antibody immunospecifically binds to a KIT polypeptide, e.g., a human KIT polypeptide, for example, a D4/D5 region of KIT (e.g., human KIT), for example SEQ ID NO: 15.

In specific embodiments, a polynucleotide provided herein comprises a nucleotide sequence encoding an antibody described herein comprising: framework regions (e.g., framework regions of the VL domain and VH domain) that are human framework regions, wherein the immunospecifically binds to a KIT polypeptide, e.g., a human KIT polypeptide, for example, a D4/D5 region of KIT (e.g., human KIT, for example SEQ ID NO: 15).

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody described herein, which immunospecifically binds to a KIT polypeptide (e.g., a KIT polypeptide comprising a D4/D5 region of KIT, for example human KIT (e.g., SEQ ID NO: 15)), wherein the antibody comprises a light chain, and wherein the amino acid sequence of the VL chain region can comprise any amino acid sequence described herein (e.g., SEQ ID NO: 2), and wherein the constant region of the light chain comprises the amino acid sequence of a human kappa light chain constant region. In a particular embodiment, the light chain comprises the amino acid sequence of SEQ ID NO: 12. In another particular embodiment, a polynucleotide provided herein comprises a nucleotide sequence encoding an antibody described herein, which immunospecifically binds to a KIT polypeptide (e.g., a KIT polypeptide comprising a KIT polypeptide comprising a D4/D5 region of KIT, for example human KIT (e.g., SEQ ID NO: 15)), and comprises a light chain, wherein the amino acid sequence of the VL chain region can comprises any amino acid sequence described herein (e.g., SEQ ID NO: 3 or 5), and wherein the constant region of the light chain comprises the amino acid sequence of a human lambda light chain constant region. For example, human constant region sequences can be those described in U.S. Pat. No. 5,693,780. In certain embodiments, the constant region of the light chain comprises the amino acid sequence of SEQ ID NO: 12.

In a particular embodiment, a polynucleotide provided herein comprises a nucleotide sequence encoding an antibody described herein, which immunospecifically binds to a KIT polypeptide (e.g., a KIT polypeptide comprising a KIT polypeptide comprising a D4/D5 region of KIT, for example human KIT (e.g., SEQ ID NO: 15)), wherein the antibody comprises a heavy chain, wherein the amino acid sequence of the VH chain region can comprise any amino acid sequence described herein (e.g., SEQ ID NO: 3 or 5), and wherein the constant region of the heavy chain comprises the amino acid sequence of a human gamma (γ) heavy chain constant region. For example, human constant region sequences can be any one of those described in U.S. Pat. No. 5,693,780 or Kabat et al. (1971) *Ann. NY Acad. Sci.* 190: 382-391 and, Kabat et al. (1991) *Sequences of Proteins of Immunological Interest*, Fifth Edition, U.S. Department of Health and Human Services, NIH Publication No. 91-3242. In particular embodiments, the constant region of the heavy chain comprises the amino acid sequence of SEQ ID NO: 13.

In yet another specific embodiment, a polynucleotide provided herein comprises a nucleotide sequence encoding an antibody described herein (or an antigen-binding fragment thereof), which immunospecifically binds to a KIT polypeptide (e.g., a D4/D5 region of KIT, for example human KIT), wherein the antibody comprises a VL chain region and a VH chain region comprising any amino acid sequences described herein, and wherein the constant regions comprise the amino acid sequences of the constant regions of a human IgG1 (e.g., isotype a, z, or f) or human IgG4. In a particular embodiment, a polynucleotide provided herein comprises a nucleotide sequence encoding an antibody described herein, which immunospecifically binds to a KIT polypeptide (e.g., a D4/D5 region of KIT, for example human KIT), wherein the antibody comprises a VL chain region and a VH chain region comprising any amino acid sequences described herein, and wherein the constant regions comprise the amino acid sequences of the constant region of a human IgG1 (isotype f). In certain embodiments, the constant region of the light chain comprises the amino acid sequence of SEQ ID NO: 12. In particular embodiments, the constant region of the heavy chain comprises the amino acid sequence of SEQ ID NO: 13.

In another particular embodiment, a polynucleotide provided herein comprises a nucleotide sequence encoding an antibody described herein (or an antigen-binding fragment thereof), which immunospecifically binds to a KIT polypeptide (e.g., a D4/D5 region of KIT, for example human KIT), wherein the antibody comprises a light chain and a heavy chain, and wherein (i) the light chain comprises a VL chain region comprising a VL CDR1, VL CDR2, and VL CDR3 having the amino acid sequences of SEQ ID NO: 20, 21, and 22, respectively; (ii) the heavy chain comprises a VH chain region comprising a VH CDR1, VH CDR2, and VH CDR3 having the amino acid sequences of SEQ ID NO: 23, 24, and 25, respectively; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 (optionally IgG1 (isotype f)) heavy chain. In certain embodiments, the constant region of the light chain comprises the amino acid sequence of SEQ ID NO: 12. In particular embodiments, the constant region of the heavy chain comprises the amino acid sequence of SEQ ID NO: 13.

In another particular embodiment, a polynucleotide provided herein comprises a nucleotide sequence encoding an antibody described herein (or an antigen-binding fragment thereof), which immunospecifically binds to a KIT polypeptide (e.g., a D4/D5 region of KIT, for example human KIT), wherein the antibody comprises a light chain and a heavy chain, and wherein (i) the light chain comprises a VL chain region comprising the amino acid sequence of SEQ ID NO: 2; (ii) the heavy chain comprises a VH chain region comprising the amino acid sequence of SEQ ID NO: 3; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 (optionally IgG1 (isotype f)) heavy chain. In certain embodiments, the constant region of the light chain comprises the amino acid sequence of SEQ ID NO: 12. In particular embodiments, the constant region of the heavy chain comprises the amino acid sequence of SEQ ID NO: 13.

In another particular embodiment, a polynucleotide provided herein comprises a nucleotide sequence encoding an antibody described herein, which immunospecifically binds to a KIT polypeptide (e.g., a D4/D5 region of KIT, for example human KIT), wherein the antibody comprises a light chain and a heavy chain, and wherein (i) the light chain comprises a VL chain region comprising the amino acid sequence of SEQ ID NO: 2; (ii) the heavy chain comprises a VH chain region comprising the amino acid sequence of SEQ ID NO: 5; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 (optionally IgG1 (isotype f)) heavy chain. In certain embodiments, the constant region of the light chain comprises the amino acid sequence of SEQ ID NO: 12. In particular embodiments, the constant region of the heavy chain comprises the amino acid sequence of SEQ ID NO: 13.

In certain embodiments, with respect to a polynucleotide provided herein comprising a nucleotide sequence encoding a VL chain region and VH chain region of any of these antibodies described herein, the polynucleotide of the VL chain region further comprises human framework regions; and the VH chain region further comprises human framework regions.

In certain embodiments, a polynucleotide provided herein comprises a nucleotide sequence encoding an antibody described herein, which immunospecifically binds to a KIT polypeptide (e.g., a D4/D5 region of KIT, for example human KIT), wherein the antibody comprises a light chain and a heavy chain, and wherein (i) the light chain comprises a VL chain region comprising human framework regions; (ii) the heavy chain comprises a VH chain region comprising human framework regions; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 (optionally IgG1 (isotype f)) heavy chain. In certain embodiments, the constant region of the light chain comprises the amino acid sequence of SEQ ID NO: 12. In particular embodiments, the constant region of the heavy chain comprises the amino acid sequence of SEQ ID NO: 13.

In a specific embodiment, provided herein are polynucleotides comprising a nucleotide sequence encoding an anti-KIT antibody, or a fragment or domain thereof, designated herein (see, e.g., Tables 1-4 and FIGS. 3A-5C) as antibody 37M or 37C. In a specific embodiment, provided herein are polynucleotides comprising a nucleotide sequence encoding an anti-KIT antibody, or a fragment or domain thereof, designated herein (see, e.g., Tables 1-4 and FIGS. 3A-5C) as antibody 37C. In a specific embodiment, provided herein are polynucleotides comprising a nucleotide sequence encoding an anti-KIT antibody, or a fragment or domain thereof, designated herein (see, e.g., Tables 1-4 and FIGS. 3A-5C) as antibody 37M.

In certain embodiments, polynucleotides described herein comprise a nucleotide sequence encoding a light chain or a VL chain region comprising the VL CDR1, VL CDR2, and VL CDR3 amino acid sequences of those of antibody 37M or 37C (e.g., as designated in Tables 1 and 2). In certain embodiments, polynucleotides described herein comprise a nucleotide sequence encoding a heavy chain or a VH chain region comprising the VH CDR1, VH CDR2, and VH CDR3 amino acid sequences of those of antibody 37M or 37C (e.g., as designated in Tables 3 and 4). In a specific embodiment, polynucleotides described herein comprise nucleotide sequences encoding (i) a VL chain region comprising the VL CDR1, VL CDR2, and VL CDR3 amino acid sequences of those of antibody 37M or 37C (e.g., as designated in Tables 1 and 2); and (ii) a VH chain region comprising the VH CDR1, VH CDR2, and VH CDR3 amino acid sequences of those of antibody 37M or 37C (e.g., as designated in Tables 3 and 4).

In certain embodiments, polynucleotides described herein comprise a nucleotide sequence encoding a light chain or a VL chain region comprising the VL FR1, VL FR2, VL FR3, and VL FR4 amino acid sequences of those of antibody 37M or 37C (e.g., as designated in Tables 1 and 2). In certain embodiments, polynucleotides described herein comprise a nucleotide sequence encoding a heavy chain or a VH chain region comprising the VH FR1, VH FR2, VH FR3, and VH FR4 amino acid sequences of those of antibody 37M or 37C (e.g., as designated in Tables 3 and 4). In a particular embodiment, polynucleotides described herein comprise nucleotide sequences encoding (i) a light chain or a VL chain region comprising the VL FR1, VL FR2, VL FR3, and VL FR4 amino acid sequences of those of antibody 37M or 37C (e.g., as designated in Tables 1 and 2); and (ii) a heavy chain or a VH chain region comprising the VH FR1, VH FR2, VH FR3, and VH FR4 amino acid sequences of those of antibody 37M or 37C (e.g., as designated in Tables 3 and 4).

Also provided herein are polynucleotides encoding an anti-KIT antibody or a fragment thereof that are optimized, e.g., by codon/RNA optimization, replacement with heterologous signal sequences, and elimination of mRNA instability elements. Methods to generate optimized nucleic acids encoding an anti-KIT antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-KIT antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-KIT antibody encoded by polynucleotides that have not been optimized.

In certain embodiments, an optimized polynucleotide sequence encoding an anti-KIT antibody described herein or a fragment thereof (e.g., VL domain and/or VH domain) can hybridize to an antisense polynucleotide of an unoptimized polynucleotide sequence encoding an anti-KIT antibody described herein or a fragment thereof (e.g., VL domain and/or VH domain). In specific embodiments, an optimized nucleotide sequence encoding an anti-KIT antibody described herein or a fragment hybridizes under high stringency conditions to antisense polynucleotide of an unoptimized polynucleotide sequence encoding an anti-KIT antibody described herein or a fragment thereof. In a specific embodiment, an optimized nucleotide sequence encoding an anti-KIT antibody described herein or a fragment thereof hybridizes under high stringency, intermediate or lower stringency hybridization conditions to an antisense polynucleotide of an unoptimized nucleotide sequence encoding an anti-KIT antibody described herein or a fragment thereof. Information regarding hybridization conditions have been described, see, e.g., U.S. Patent Application Publication No. US 2005/0048549 (e.g., paragraphs 72-73), which is incorporated herein by reference in its entirety.

In certain embodiments, an optimized polynucleotide sequence encoding a VL region of an antibody described herein is at least 75%, at least 80%, at least 85%, at least 90%, at least 95%, at least 98% identical to the nucleotide sequence of SEQ ID NO: 8. In certain embodiments, an optimized polynucleotide sequence encoding a VH region of an antibody described herein is at least 75%, at least 80%, at least 85%, at least 90%, at least 95%, at least 98% identical to the nucleotide sequence of SEQ ID NO: 9.

The polynucleotides can be obtained, and the nucleotide sequence of the polynucleotides determined, by any method known in the art. Nucleotide sequences encoding antibodies described herein, e.g., antibodies described in Tables 1-4, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-KIT antibodies described herein can be readily isolated and sequenced using conventional procedures (e.g., by using oligonucleotide probes that are capable of binding specifically to genes encoding the heavy and light chains of the anti-KIT antibodies). Hybridoma cells can serve as a source of such DNA. Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of anti-KIT antibodies in the recombinant host cells.

In phage display methods, functional antibody domains are displayed on the surface of phage particles which carry the polynucleotide sequences encoding them. In particular, a library of DNA sequences encoding VH and VL domains are generated (e.g., amplified from animal cDNA libraries such as human cDNA libraries or random libraries are generated by chemical synthesis). The DNA encoding the VH and VL domains are recombined together with an scFv linker by PCR and cloned into a phagemid vector. The vector is electroporated in E. coli and the E. coli is infected with helper phage. Phage expressing an antigen-binding domain that binds to a particular antigen can be selected or identified with antigen, e.g., using labeled antigen or antigen bound or captured to a solid surface or bead. After phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produced Fab, Fab' and $F(ab')_2$ fragments can also be employed using methods known in the art such as those disclosed in PCT Publication No. WO 92/22324; Mullinax et al., 1992, BioTechniques, 12(6):864-869; Sawai et al., 1995, AJRI, 34:26-34; and Better et al., 1988, Science, 240:1041-1043.

Antibodies can be isolated from antibody phage libraries generated using the techniques described in McCafferty et al., Nature, 348:552-554 (1990). Clackson et al., Nature, 352:624-628 (1991). Marks et al., J. Mol. Biol., 222:581-597 (1991) describe the isolation of murine and human antibodies, respectively, using phage libraries. Chain shuffling can be used in the production of high affinity (nM range) human antibodies (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable domain, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

In a non-limiting example, the Dyax (Cambridge, Mass.) technology platform can be used to convert Fab-phage or Fabs to complete IgG antibodies, such as the Dyax pR rapid reformatting vectors (RR). Briefly, by PCR, a Fab-encoding DNA fragment is inserted into a Dyax pR-RRV between a eukaryotic leader sequence and an IgG heavy chain constant region cDNA. Antibody expression is driven by the human cytomegalovirus (hCMV). In a second cloning step, bacterial regulatory elements are replaced by the appropriate eukaryotic sequences (i.e., the IRES (internal ribosome entry site) motif). The expression vector can also include the SV40 origin of replication. The Dyax pRh1(a,z), pRh1(f), pRh4 and pRm2a are expression vectors allowing expression of reformatted FAbs as human IgG1 (isotype a,z), human IgG1 (isotype F), human IgG4, and mouse IgG2a, respectively. Expressing vectors can be introduced into a suitable host cell (e.g., HEK293T cells, CHO cells)) for expression and purification.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH chain region (e.g., SEQ ID NO: 3 or 5) and/or VL chain region (e.g., SEQ ID NO: 2) provided herein. In specific embodiments, polynucleotides described herein hybridize under high stringency or intermediate stringency hybridization conditions to polynucleotides which are complements to polynucleotides encoding a VH chain region (e.g., SEQ ID NO: 3 or 5) and/or VL chain region (e.g., a SEQ ID NO: 2) provided herein.

In specific embodiments, polynucleotides described herein hybridize under high stringency, intermediate or lower stringency hybridization conditions to polynucleotides which are complements to a polynucleotide comprising SEQ ID NO: 8 or SEQ ID NO: 9. In specific embodiments, polynucleotides described herein hybridize under high stringency or intermediate stringency hybridization conditions to polynucleotides which are complements to a polynucleotide comprising SEQ ID NO: 8 or SEQ ID NO: 9.

In specific embodiments, polynucleotides described herein hybridize under high stringency, intermediate or lower stringency hybridization conditions to polynucleotides which are complements to a polynucleotide comprising SEQ ID NO: 10 or SEQ ID NO: 11. In specific embodiments, polynucleotides described herein hybridize under high stringency or intermediate stringency hybridization conditions to polynucleotides which are complements to a polynucleotide comprising SEQ ID NO: 10 or SEQ ID NO: 11.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3.

In specific embodiments, polynucleotides described herein have at least 80%, 85%, 90%, 95%, or 98% sequence identity to a polynucleotide comprising SEQ ID NO: 8 encoding a VL chain region of an antibody described herein. In specific embodiments, polynucleotides described herein have at least 80%, 85%, 90%, 95%, or 98% sequence identity to a polynucleotide comprising SEQ ID NO: 9 encoding a VH chain region of an antibody described herein.

In specific embodiments, polynucleotides described herein have at least 80%, 85%, 90%, 95%, or 98% sequence identity to a polynucleotide comprising SEQ ID NO: 10 encoding a light chain of an antibody described herein. In specific embodiments, polynucleotides described herein have at least 80%, 85%, 90%, 95%, or 98% sequence identity to a polynucleotide comprising SEQ ID NO: 11 encoding a heavy chain of an antibody described herein.

5.3 Host Cells and Recombinant Expression of Antibodies

In certain aspects, provided herein are host cells recombinantly expressing the antibodies described herein (or an antigen-binding fragment thereof) and related expression vectors. Provided herein are vectors (e.g., expression vectors) comprising polynucleotides comprising nucleotide sequences encoding anti-KIT antibodies or a fragment for recombinant expression in host cells, preferably in mammalian cells. Also provided herein are host cells comprising such vectors for recombinantly expressing anti-KIT antibodies described herein (e.g., antibody 37M or 37C). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that immunospecifically binds to a KIT antigen involves construction of an expression vector containing a polynucleotide that encodes the antibody. Once a polynucleotide encoding an antibody molecule, heavy and/or light chain of an antibody, or fragment thereof (preferably, but not necessarily, containing the heavy and/or light chain variable domain) described herein has been obtained, the vector for the production of the antibody molecule can be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and the variable domain of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain of an antibody described herein, or a fragment thereof, and a second vector comprising a polynucleotide encoding a light chain of an antibody described herein, or a fragment thereof. In other embodiments, a first host cell comprises a first vector comprising a polynucleotide encoding a heavy chain of an antibody described herein, or a fragment thereof, and a second host cell comprises a second vector comprising a polynucleotide encoding a light chain of an antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, a mammalian expression vector is pOptiVEC™ or pcDNA3.3. Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies described herein which immunospecifically bind to a KIT antigen is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT2O and T47D, NS0 (a murine myeloma cell line that does not endogenously produce any immunoglobulin chains), CRL7O3O and HsS78Bst cells. In certain embodiments, humanized monoclonal anti-KIT antibodies described herein are produced in mammalian cells, such as CHO cells.

For long-term, high-yield production of recombinant proteins, stable expression is preferred. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the antibody molecule. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, NY (1990); and in Chapters 12 and 13, Dracopoli et al. (eds.), Current Protocols in Human Genetics, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, $_1$%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

5.4 Methods of Producing Antibodies

Antibodies described herein (or an antigen-binding fragment thereof) that immunospecifically bind to a KIT antigen can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

In some embodiments, human antibodies are produced. In particular embodiments, an antibody described herein, which binds to the same epitope of KIT (e.g., a D4/D5 region of human KIT) as antibody 37M or 37C, is a human antibody. In particular embodiments, an antibody described herein, which competitively blocks (e.g., in a dose-dependent manner) antibody 37M or 37C from binding to KIT (e.g., a D4/D5 region of human KIT), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., KIT). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., D4/D5 region of human KIT). Such methods are known and are described in the art, see, e.g., Shinmoto et al., Cytotechnology, 2004, 46:19-23; Naganawa et al., Human Antibodies, 2005, 14:27-31.

In some embodiments, human antibodies can be generated by inserting polynucleotides encoding human CDRs (e.g., VL CDRs and/or VH CDRs) of an antibody into an expression vector containing nucleotide sequences encoding human framework region sequences. In certain embodiments, such expression vectors further comprise nucleotide sequences encoding a constant region of a human light and/or heavy chain. In some embodiments, human antibodies can be generated by inserting human CDRs (e.g., VL CDRs and/or VH CDRs) of an antibody obtained from a phage library into such human expression vectors.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., D4/D5 region of human KIT) used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)). Additionally, a RIMMS (repetitive immunization multiple sites) technique can be used to immunize an animal (Kilptrack et al., 1997 Hybridoma 16:381-9, incorporated by reference in its entirety).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the human KIT antigen. The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In some embodiments, mice (or other animals, such as rats, monkeys, donkeys, pigs, sheep, hamster, or dogs) can be immunized with an antigen (e.g., KIT, preferably the D4/D5 region of KIT) and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma clones are then assayed by methods known in the art for cells that secrete antibodies capable of binding a polypeptide of the antigen (e.g., human KIT, for example, the D4/D5 region of human KIT). Ascites fluid, which generally contains high levels of antibodies, can be generated by immunizing mice with positive hybridoma clones.

Accordingly, described herein are methods of generating antibodies by culturing a hybridoma cell secreting an anti-KIT antibody wherein. In specific embodiments, the hybridoma is generated by fusing splenocytes isolated from a mouse (or other animal, such as rat, monkey, donkey, pig, sheep, or dog) immunized with a KIT antigen with myeloma cells and then screening the hybridomas resulting from the fusion for hybridoma clones that secrete an antibody able to bind to the KIT antigen. In certain embodiments, the hybridoma is generated by fusing lymph nodes isolated from a mouse (or other animal, such as rat, monkey, donkey, pig, sheep, or dog) immunized with a KIT antigen with myeloma cells, and then screening the hybridomas resulting from the fusion for hybridoma clones that secrete an antibody able to bind to the KIT antigen.

Antibodies described herein include antibody fragments which recognize specific KIT antigens and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it can be preferable to use human, humanized or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741.

A chimeric antibody is a molecule in which different portions of the antibody are derived from different immunoglobulin molecules. For example, a chimeric antibody can contain a variable region of a mouse monoclonal antibody fused to a constant region of a human antibody. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. The humanized antibody can be selected from any class of immunoglobulins, including IgM, IgG, IgD, IgA and IgE, and any isotype, including IgG$_1$, IgG$_2$, IgG$_3$ and IgG$_4$. Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

Further, antibodies that immunospecifically bind to a KIT antigen can, in turn, be utilized to generate anti-idiotype antibodies that "mimic" an antigen using techniques well known to those skilled in the art. (See, e.g., Greenspan &

Bona, 1989, FASEB J. 7(5):437-444; and Nissinoff, 1991, J. Immunol. 147(8):2429-2438).

5.5 Pharmaceutical Compositions and Kits

Provided herein are compositions, pharmaceutical compositions, and kits comprising one or more antibodies described herein (or antigen-binding fragments thereof). In particular aspects, compositions described herein can be for in vitro, in vivo, or ex vivo uses. In specific embodiments, provided herein is a pharmaceutical composition comprising an antibody described herein (or an antigen-binding fragment thereof) and a pharmaceutically acceptable carrier or excipient.

Therapeutic formulations containing one or more antibodies provided herein can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.; *Remington: The Science and Practice of Pharmacy,* 21st ed. (2006) Lippincott Williams & Wilkins, Baltimore, Md.), in the form of lyophilized formulations or aqueous solutions. Acceptable carriers, excipients, or stabilizers are nontoxic to recipients at the dosages and concentrations employed, and include buffers such as phosphate, citrate, and other organic acids; and/or non-ionic surfactants such as TWEEN™, PLURONICS™ or polyethylene glycol (PEG).

Formulations, such as those described herein, can also contain more than one active compounds (for example, molecules, e.g., antibody or antibodies described herein) as necessary for the particular indication being treated. In certain embodiments, formulations comprise an antibody provided herein and one or more active compounds with complementary activities that do not adversely affect each other. Such molecules are suitably present in combination in amounts that are effective for the purpose intended. For example, an antibody described herein can be combined with one or more other therapeutic agents (e.g., a tyrosine kinase inhibitor such as imatinib mesylated or sunitinib, or a histone deacetylase inhibitor such as vorinostat). Such combination therapy can be administered to the patient serially or simultaneously or in sequence.

The formulations to be used for in vivo administration can be sterile. This is readily accomplished by filtration through, e.g., sterile filtration membranes.

In specific aspects, the pharmaceutical compositions provided herein contain therapeutically effective amounts of one or more of the antibodies provided herein, and optionally one or more additional prophylactic of therapeutic agents, in a pharmaceutically acceptable carrier. Such pharmaceutical compositions are useful in the prevention, treatment, management or amelioration of a KIT-mediated disorder or disease, such as cancer (e.g., GIST) or an inflammatory bowel disease, or one or more of the symptoms thereof.

Pharmaceutical carriers suitable for administration of the antibodies provided herein include any such carriers known to those skilled in the art to be suitable for the particular mode of administration.

In addition, the antibodies described herein can be formulated as the sole pharmaceutically active ingredient in the composition or can be combined with other active ingredients (such as one or more other prophylactic or therapeutic agents).

The compositions can contain one or more antibodies provided herein. In one embodiment, the antibodies are formulated into suitable pharmaceutical preparations, such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers.

In the compositions, one or more antibodies provided herein (or conjugates thereof) is (are) mixed with a suitable pharmaceutical carrier. The concentrations of the antibody or antibodies in the compositions can, for example, be effective for delivery of an amount, upon administration, that treats, prevents, or ameliorates a KIT-mediated disorder or disease or a symptom thereof. In particular embodiments, concentrations of an antibody-drug conjugate or antibody-drug conjugates in the compositions can, for example, be effective for delivery of an amount of a drug(s), upon administration, that treats, prevents, or ameliorates a KIT-mediated disorder or disease or a symptom thereof.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

In certain aspects, an antibody provided herein (or an antibody-drug conjugate thereof) is included in the pharmaceutically acceptable carrier in an effective amount sufficient to exert a therapeutically useful effect in the absence of, or with minimal or negligible, undesirable side effects on the patient treated. A therapeutically effective concentration can be determined empirically by testing the compounds in in vitro and in vivo systems using routine methods and then extrapolated therefrom for dosages for humans.

The concentration of antibody in the pharmaceutical composition will depend on, e.g., the physicochemical characteristics of the antibody, the dosage schedule, and amount administered as well as other factors known to those of skill in the art. In certain aspects, the concentration of antibody-drug conjugate in the pharmaceutical composition will depend on, e.g., the physicochemical characteristics of the antibody and/or the drug, the dosage schedule, and amount administered as well as other factors known to those of skill in the art.

In one embodiment, a therapeutically effective dosage produces a serum concentration of antibody of from about 0.1 ng/ml to about 50-100 µg/ml. The pharmaceutical compositions, in another embodiment, provide a dosage of from about 0.001 mg to about 2000 mg of antibody per kilogram of body weight for administration over a period of time, e.g., every day, every week, every 2 weeks, or every 3 weeks. Pharmaceutical dosage unit forms can be prepared to provide from about 0.01 mg to about 2000 mg, and in one embodiment from about 10 mg to about 500 mg of the antibody and/or a combination of other optional essential ingredients per dosage unit form.

In a particular embodiment, an antibody-drug conjugate described herein is administered at an effective dosage of about 1 to 100 mg of antibody-drug conjugate per kilogram of body weight for administration over a period of time, e.g., every day, every week, every 2 weeks, or every 3 weeks.

The antibody can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody, the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as sterile parenteral solutions or suspensions, tablets, capsules, pills, powders, granules, and oral solutions or suspensions, and oil-water emulsions containing suitable quantities of the compounds or pharmaceutically acceptable derivatives thereof. The antibody is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

In certain embodiments, one or more anti-KIT antibodies described herein are in a liquid pharmaceutical formulation. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, and pH buffering agents and the like.

Actual methods of preparing such dosage forms are known, or will be apparent, to those skilled in this art; for example, see, e.g., *Remington's Pharmaceutical Sciences* (1990) Mack Publishing Co., Easton, Pa.; *Remington: The Science and Practice of Pharmacy*, 21st ed. (2006) Lippincott Williams & Wilkins, Baltimore, Md.

Dosage forms or compositions containing antibody in the range of 0.005% to 100% with the balance made up from non-toxic carrier can be prepared. Methods for preparation of these compositions are known to those skilled in the art.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents. Other routes of administration may include, enteric administration, intracerebral administration, nasal administration, intraarterial administration, intracardiac administration, intraosseous infusion, intrathecal administration, and intraperitoneal administration.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Pharmaceutical carriers also include ethyl alcohol, polyethylene glycol and propylene glycol for water miscible vehicles; and sodium hydroxide, hydrochloric acid, citric acid or lactic acid for pH adjustment.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

The antibody can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and can be empirically determined.

In other embodiments, the pharmaceutical formulations are lyophilized powders, which can be reconstituted for administration as solutions, emulsions and other mixtures. They can also be reconstituted and formulated as solids or gels.

The lyophilized powder is prepared by dissolving a antibody provided herein, in a suitable solvent. In some embodiments, the lyophilized powder is sterile. The solvent can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Antibodies provided herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

The antibodies and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, the anti-KIT antibodies described herein are targeted (or otherwise administered) to the bone marrow, such as in a patient having or at risk of having leukemia. In some embodiments, anti-KIT antibodies described herein are targeted (or otherwise administered) to the gastrointestinal tract, such as in a patient having or at risk of having gastrointestinal stromal tumors. In some embodiments, anti-KIT antibodies described herein are targeted (or otherwise administered) to the lungs, such as in a patient having or at risk of lung cancer (e.g., small cell lung cancer). In some embodiments, anti-KIT antibodies described herein are targeted (or otherwise administered) to the brain, such as in a patient having or at risk of having neuroblastoma. In specific embodiments, an anti-KIT antibody described herein is capable of crossing the blood-brain barrier.

Provided herein is a pharmaceutical pack or kit comprising one or more containers filled with one or more of the ingredients of the pharmaceutical compositions described herein, such as one or more antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises an antibody described herein, preferably a purified antibody, in one or more containers. In a specific embodiment, the kits described herein contain a substantially isolated KIT antigen as a control. In another specific embodiment, the kits described herein further comprise a control antibody which does not react with the KIT antigen. In another specific embodiment, the kits described herein contain one or more elements for detecting the binding of a modified antibody to a KIT antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, the kit can include a recombinantly produced or chemically synthesized KIT antigen. The KIT antigen provided in the kit can also be attached to a solid support. In a more specific embodiment the detecting means of the above described kit includes a solid support to which KIT antigen is attached. Such a kit can also include a non-attached reporter-labeled anti-human antibody. In this embodiment, binding of the antibody to the KIT antigen can be detected by binding of the said reporter-labeled antibody.

5.6 Therapeutic Methods

Provided herein are methods for impeding, preventing, treating and/or managing a KIT-mediated disorder or disease (e.g., cancer). Such methods comprise administering to a subject in need thereof a therapeutically effective amount of an anti-KIT antibody described herein (e.g., antibodies 37M and 37C and humanized versions thereof, and antigen-binding fragments thereof). In certain aspects, also provided herein are methods for preventing, treating or managing one or more symptoms of a KIT-mediated disorder or disease.

In specific embodiments, methods described herein for treating a KIT-mediated disorder or disease provide for the reduction or amelioration of the progression, severity, and/or duration of a KIT-mediated disorder or disease (e.g., cancer, inflammatory condition, or fibrosis) resulting from the administration of one or more therapies (including, but not limited to, the administration of one or more prophylactic or therapeutic agents, such as an anti-KIT antibody described herein). In further specific embodiments, methods described herein for treating a KIT-mediated disorder or disease relate to reducing one or more symptoms of a KIT-mediated disorder or disease. In specific embodiments, an antibody described herein, such as antibody 37M or 37C or a humanized version thereof, or an antigen-binding fragment thereof, or a conjugate thereof, is for use in treating or managing a KIT-mediated disorder (e.g., cancer). In a particular embodiment, provided herein is an antibody for use in treating or managing a KIT-mediated disorder (e.g., cancer), wherein the antibody comprises (i) a VL chain region having the amino acid sequence of SEQ ID NO: 2, and/or (ii) a VH chain region having the amino acid sequence of SEQ ID NO: 3 or 5. In another particular embodiment, provided herein is an antibody, or an antigen-binding fragment thereof, for use in treating or managing a KIT-mediated disorder (e.g., cancer), wherein the antibody comprises (i) a VL chain region comprising a VL CDR1, VL CDR2, and VL CDR3, wherein the VL CDR1 has the amino acid sequence of SEQ ID NO: 20, the VL CDR2 has the amino acid sequence of SEQ ID NO: 21, and the VL CDR3 has the amino acid sequence of SEQ ID NO: 22, respectively; and/or (ii) a VH chain region comprising a VH CDR1, VH CDR2, and VH CDR3 having the amino acid sequences of SEQ ID NO: 23, 24, and 25, respectively: In a specific embodiment, the antibody used in the methods described herein is internalized by the cell to which it binds. In a particular embodiment, a conjugate is used in the methods described herein, wherein the conjugate comprises an antibody described herein (e.g., antibody 37M or 37C), or a KIT-binding fragment thereof. In a specific embodiment, the conjugate comprises an antibody described herein (e.g., antibody 37M or 37C), or a KIT-binding fragment thereof, linked, covalently or non-covalently, to a therapeutic agent, such as a toxin. In a certain embodiment, the conjugate used in the methods described herein is internalized into a cell to which it binds.

As used herein and unless otherwise specified, the terms "KIT-mediated disorder" or "KIT-mediated disease" are used interchangeably and refer to any disease that is completely or partially caused by, or is the result of, KIT expression and/or activity or lack thereof. In one aspect, a KIT-mediated disorder or disease can be known to one of skill in the art or can be ascertained by one of skill in the art. In a certain embodiment, a KIT-mediated disease or disorder is associated with KIT expression and/or activity. For example, KIT expression and/or activity may contribute, in combination with one or more other factors (e.g., mutation or expression and/or activity of another gene), to development and/or progression of a KIT-mediated disease or disorder. In a certain embodiment, a KIT-mediated disease or disorder is associated with one or more mutations of KIT.

In certain embodiments, KIT is aberrantly (e.g., highly) expressed by cells (e.g., on the surface of cells). In particular embodiments, KIT expression is at least about 10%, 20%, 30%, 40%, 50%, 60%, 70%, 80%, 90%, or 100% higher than KIT expression on the surface of a control cell (e.g., a cell expressing normal levels of KIT, for example, a mast cell, stem cell, brain cell, melanoblast, or ovary cell). In particular embodiments, KIT expression is at least about 10%, 20%, 30%, 40%, 50%, 60%, 70%, 80%, 90%, or 100% higher than the average KIT expression on the surface of a control cell population (e.g., a cell population expressing normal levels of KIT, for example, a mast cell population, stem cell population, brain cell population, melanoblast population, or ovary cell population). In specific embodiments, such control cells can be obtained or derived from a healthy individual (e.g., healthy human). In some embodiments, KIT can be aberrantly upregulated in a particular cell type, whether or not KIT is aberrantly expressed on the cell surface. In particular embodiments, KIT signaling or activity can be aberrantly upregulated in a particular cell type, whether or not KIT is aberrantly expressed on the cell surface. In particular embodiments, KIT signaling is at least about 10%, 20%, 30%, 40%, 50%, 60%, 70%, 80%, 90%, or 100% higher than KIT signaling of a control cell (e.g., a cell containing normal KIT signaling, for example, a mast cell, stem cell, brain cell, melanoblast, or ovary cell). In particular embodiments, KIT signaling is at least about 10%, 20%, 30%, 40%, 50%, 60%, 70%, 80%, 90%, or 100% higher than average KIT signaling of a control cell population (e.g., a cell population containing normal KIT signaling, for example, a mast cell population, stem cell population, brain cell population, melanoblast population, or ovary cell population). In certain embodiments, normal, aberrant or excessive cell signaling is caused by binding of KIT to a KIT ligand. In other embodiments, aberrant or excessive cell signaling occurs independent of binding of KIT to a KIT ligand.

In certain embodiments, a KIT-mediated disease is fibrosis or an inflammatory disorder, e.g., inflammatory bowel disease (IBD), such as Crohn's disease (CD) or ulcerative colitis (UC). In other embodiments, a KIT-mediated disease is cancer, such as lung cancer (e.g., small cell lung cancer), leukemia, neuroblastoma, melanoma, sarcoma (e.g., Ewing's sarcoma) or gastrointestinal stromal tumor (GIST).

In certain aspects, a KIT-mediated disorder or disease can be characterized by gain-of-function KIT activity, increase in KIT activity, or overexpression of KIT. In one embodiment, a KIT-mediated disorder or disease is completely or partially caused by or is the result of gain-of-function KIT activity or expression, e.g., overexpression, of KIT. In certain embodiments, the gain-of-function KIT activity can occur independent of KIT ligand (e.g., SCF) binding KIT receptor. In particular aspects, high or overexpression of KIT in a cell refers to an expression level which is at least about 35%, 45%, 55%, or 65% more than the expression level of a reference cell known to have normal KIT expression or KIT activity or more than the average expression level of KIT in a population of cells or samples known to have normal KIT expression or KIT activity. Expression levels of KIT can be assessed by methods described herein or known to one of skill in the art (e.g., Western blotting or immunohistorychemistry). In particular embodiments, a KIT-mediated disorder or disease is characterized by KIT activity which is higher than normal KIT activity and contributes to cellular transformation, neoplasia, and tumorogenesis. In particular aspects, high or increase of KIT activity in a cell refers to a KIT activity level which is at least about 35%, 45%, 55%, or 65% more than the expression level of a reference cell known to have normal KIT activity or more than the average level of KIT activity in a population of cells or samples known to have normal KIT activity. Non-limiting examples of a KIT activity includes tyrosine phosphorylation of the cytoplasmic domain of KIT, and signaling downstream of KIT, such as Stat or Akt signaling.

Non-limiting examples of disorders or KIT-mediated disorders or diseases include cancers such as breast cancer, leukemia (e.g., chronic myelogenous leukemia, acute myeloid leukemia, mast cell leukemia), lung cancer (e.g., small cell lung cancer), neuroblastoma, gastrointestinal stromal tumors (GIST), melanoma, colorectal cancer, sarcoma (e.g., Ewing's sarcoma), and germ cell tumors (e.g., seminoma). In a particular embodiment, a cancer which is treated or managed by the methods provided herein is characterized by a gain-of-function KIT mutation or overexpression of KIT.

In a specific embodiment, a method described herein is for treating cancer (e.g., GIST, lung cancer, or sarcoma (e.g., Ewing's sarcoma)), wherein said method comprises administering to a subject in need thereof a therapeutically effective amount of an antibody described herein (e.g., antibody 37M or 37C, or an antigen binding fragment thereof (e.g., KIT-binding fragment thereof, for example 3 VL domain CDRs and/or 3 VH domain CDRs), or a humanized version of antibody 37M or 37C, or a conjugate comprising, for example an antibody comprising CDRs of antibody 37M or 37C (or a KIT-binding fragment thereof) linked, covalently or non-covalently, to a therapeutic agent). In certain aspects, also provided herein are methods for preventing, treating or managing one or more symptoms of cancer, wherein said methods comprise administering to a subject in need thereof a therapeutically effective amount of an antibody described herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C or a KIT-binding fragment thereof, linked, covalently or non-covalently, to a therapeutic agent). In a specific embodiment, an antibody for use in the methods of treating cancer described herein comprises a VL domain comprising the amino acid sequence of SEQ ID NO: 2 (or CDRs of SEQ ID NO: 2), and/or a VH domain comprising the amino acid sequence of SEQ ID NO: 3 or 5 (or CDRs of SEQ ID NO: 3 or 5). In a specific embodiment, an antibody for use in the methods of treating cancer described herein comprises CDRs of antibody 37M or 37C (e.g., VL CDR1, VL CDR2, and VL CDR3 having the amino acid sequences of SEQ ID NO: 20, SEQ ID NO: 21, and SEQ ID NO: 22, respectively; and/or VH CDR1, VH CDR2, and VH CDR3 having the amino acid sequences of SEQ ID NO: 23, SEQ ID NO: 24, and SEQ ID NO: 25, respectively).

In a specific embodiment, a method described herein is for treating GIST, wherein said method comprises administering to a subject in need thereof a therapeutically effective amount of an antibody described herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C or a KIT-binding fragment thereof, linked, covalently or non-covalently, to a therapeutic agent). In certain aspects, also provided herein are methods for preventing, treating or managing one or more symptoms of GIST, wherein said methods comprise administering to a subject in need thereof a therapeutically effective amount of an antibody described herein (e.g., antibody 37M or 37C, or an antigen binding fragment thereof (e.g., KIT-binding fragment thereof), or a humanized version of antibody 37M or 37C, or a conjugate comprising, for example an antibody comprising the CDRs of antibody 37M or 37C or a KIT-binding fragment thereof, linked, covalently or non-covalently, to a therapeutic agent). In a specific embodiment, an antibody for use in the methods of treating GIST described herein comprises a VL domain comprising the amino acid sequence of SEQ ID NO: 2 (or CDRs of SEQ ID NO: 2), and/or a VH domain comprising the amino acid sequence of SEQ ID NO: 3 or 5 (or CDRs of SEQ ID NO: 3 or 5). In a specific embodiment, an antibody for use in the methods of treating GIST described herein comprises CDRs of antibody 37M or 37C (e.g., VL CDR1, VL CDR2, and VL CDR3 having the amino acid sequences of SEQ ID NO: 20, SEQ ID NO: 21, and SEQ ID NO: 22, respectively; and/or VH CDR1, VH CDR2, and VH CDR3 having the amino acid sequences of SEQ ID NO: 23, SEQ ID NO: 24, and SEQ ID NO: 25, respectively).

In a specific embodiment, a method described herein is for treating lung cancer (e.g., small cell lung carcinoma), wherein said method comprises administering to a subject in need thereof a therapeutically effective amount of an antibody described herein (e.g., antibody 37M or 37C, or an antigen binding fragment thereof, or a conjugate comprising for example an antibody comprising CDRs of antibody 37M or 37C or a KIT-binding fragment thereof linked, covalently or non-covalently, to a therapeutic agent). In certain aspects, also provided herein are methods for preventing, treating or managing one or more symptoms of lung cancer (e.g., small cell lung carcinoma), wherein said methods comprise administering to a subject in need thereof a therapeutically effective amount of an antibody described herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C, linked, covalently or non-covalently, to a therapeutic agent). In a specific embodiment, an antibody for use in the methods of treating lung cancer (e.g., small cell lung cancer) comprises a VL domain comprising the amino acid sequence of SEQ ID NO: 2 (or CDRs of SEQ ID NO: 2), and/or a VH domain comprising the amino acid sequence of SEQ ID NO: 3 or 5 (or CDRs of SEQ ID NO: 3 or 5). In a specific embodiment, an antibody for use in the methods for treating lung cancer (e.g., small cell lung cancer) described herein comprises CDRs of antibody 37M or 37C (e.g., VL CDR1, VL CDR2, and VL CDR3 having the amino acid sequences of SEQ ID NO: 20, SEQ ID NO: 21, and SEQ ID NO: 22, respectively; and/or VH CDR1, VH CDR2, and VH CDR3 having the amino acid sequences of SEQ ID NO: 23, SEQ ID NO: 24, and SEQ ID NO: 25, respectively).

In a specific embodiment, a method described herein is for treating melanoma, wherein said method comprises administering to a subject in need thereof a therapeutically effective amount of an antibody described herein (e.g., antibody 37M or 37C, or an antigen binding fragment thereof, or a humanized antibody of antibody 37M or 37C, or a conjugate comprising for example an antibody comprising CDRs of antibody 37M or 37C, linked, covalently or non-covalently, to a therapeutic agent). In certain aspects, also provided herein are methods for preventing, treating or managing one or more symptoms of melanoma, wherein said methods comprise administering to a subject in need thereof a therapeutically effective amount of an antibody described herein (e.g., antibody 37M or 37C, or an antigen binding fragment thereof, or a humanized antibody of antibody 37M or 37C, or a conjugate comprising for example an antibody comprising CDRs of antibody 37M or 37C, linked, covalently or non-covalently, to a therapeutic agent). In a specific embodiment, an antibody for use in the methods of treating melanoma described herein comprises a VL domain comprising the amino acid sequence of SEQ ID NO: 2 (or CDRs of SEQ ID NO: 2), and/or a VH domain comprising the amino acid sequence of SEQ ID NO: 3 or 5 (or CDRs of SEQ ID NO: 3 or 5). In a specific embodiment, an antibody for use in the methods for treating melanoma described herein comprises CDRs of antibody 37M or 37C (e.g., VL CDR1, VL CDR2, and VL CDR3 having the amino acid sequences of SEQ ID NO: 20, SEQ ID NO: 21, and SEQ ID NO: 22, respectively; and/or VH CDR1, VH CDR2, and VH CDR3 having the amino acid sequences of SEQ ID NO: 23, SEQ ID NO: 24, and SEQ ID NO: 25, respectively).

In specific embodiments, a cancer treated in accordance with the methods described herein can be any type of cancer which comprises cancer or tumor cells expressing KIT or a mutated form thereof, which can be confirmed by any histologically or cytologically method known to one of skill in the art.

In certain embodiments, a cancer is metastatic. In certain embodiments, a cancer is an advanced cancer which has spread outside the site or organ of origin, either by local invasion or metastasis.

In particular embodiments, a cancer is a recurrent cancer which has regrown, either at the initial site or at a distant site, after a response to initial therapy (e.g., after surgery to remove the tumor and adjuvant therapy following surgery). In some embodiments, a cancer is a refractory cancer which progresses even though an anti-tumor agent, such as a chemotherapeutic agent, is being administered, or has been administered, to the cancer patient. A non-limiting example of a refractory cancer is one which is refractory to a tyrosine kinase inhibitor, such as GLEEVEC® (imatinib mesylate), SUTENT® (SU11248 or sunitinib), IRESSA™ (gefitinib), TARCEVA® (erlotinib), NEXAVAR® (sorafenib), or VOTRIENT™ (pazopanib). In some embodiments, a cancer is a refractory cancer which progresses even though radiation or chemotherapy is being administered, or has been administered, to the cancer patient.

In specific embodiments, provided herein are methods for treating a refractory cancer in a patient in need thereof comprising administering to the patient a therapeutically effective amount of an antibody described herein, wherein the refractory cancer is refractory or resistant to an anti-cancer agent such as a tyrosine kinase inhibitor (e.g., GLEEVEC® (imatinib mesylate) or SUTENT® (SU11248 or Sunitinib)). Other non-limiting examples of tyrosine kinse inhibitors include 706 and AMNI07 (nilotinib). RAD00I, PKC412, gefitinib (IRESSA™), erlotinib (TARCEVA®), sorafenib (NEXAVAR®), pazopanib (VOTRIENT™), axitinib, bosutinib, cediranib (RECENTIN®), SPRYCEL® (dasatinib), lapatinib (TYKERB®), lestaurtinib, neratinib, nilotinib (TASIGNA®), semaxanib, toceranib (PALLADIA™), vandetanib (ZACTIMA™), and vatalanib. In certain embodiments, the refractory cancer was initially responsive to an anti-cancer agent, such as a tyrosine kinase inhibitor (e.g., GLEEVEC® or SU11248 (i.e., sunitinib)), but has developed resistance the anti-cancer agent. In certain embodiments, a subject has one or more mutations in KIT that confers resistance to an anti-cancer agent such as a tyrosine kinase inhibitor.

In particular embodiments, an antibody described herein is administered to a patient who has previously received, or is currently receiving, one or more anti-cancer therapies, for example, a chemotherapeutic agent, or a tyrosine kinase inhibitor (e.g., GLEEVEC® (imatinib mesylate), SUTENT® (SU11248 or sunitinib), IRESSA™ (gefitinib), TARCEVA® (erlotinib), NEXAVAR® (sorafenib), or VOTRIENT™ (pazopanib)) or a histone deacetylase inhibitor (e.g., vorinostat or suberoylanilide hydroxamic acid (SAHA)). In other particular embodiments, an antibody described herein is administered to a patient who is, or is suspected of being, resistant or refractory to an anti-cancer therapy, for example, a tyrosine kinase inhibitor, e.g., GLEEVEC® (imatinib mesylate), SUTENT® (SU11248 or sunitinib), IRESSA™ (gefitinib), TARCEVA® (erlotinib), NEXAVAR® (sorafenib), or VOTRIENT™ (pazopanib).

In particular embodiments, an antibody described herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C, linked, covalently or non-covalently, to a therapeutic agent) is administered to a patient who has previously received, or is currently receiving, one or more anti-cancer therapies, for example, an anti-growth factor receptor antibody (e.g., anti-HER2 antibody, anti-EGFR antibody, anti-VEGFR antibody, or anti-KIT antibody), or anti-growth factor antibody (e.g., anti-EGF antibody, anti-VEGF antibody). In other particular embodiments, an antibody described herein is administered to a patient who is, or is suspected of being, resistant or refractory to an anti-cancer therapy, for example, an anti-growth factor receptor antibody (e.g., anti-HER2 antibody, anti-EGFR antibody, anti-VEGFR antibody, or anti-KIT antibody) or anti-growth factor antibody (e.g., anti-EGF antibody, anti-VEGF antibody).

In a particular embodiment, a method described herein for treating or managing cancer in a subject in need thereof, can achieve at least one, two, three, four or more of the following effects due to administration of a therapeutically effective amount of an anti-KIT antibody described herein: (i) the reduction or amelioration of the severity of cancer (e.g., leukemia, lung cancer, or gastrointestinal stromal cancer) and/or one or more symptoms associated therewith; (ii) the reduction in the duration of one or more symptoms associated with a cancer (e.g., leukemia, lung cancer, or gastrointestinal stromal cancer); (iii) the prevention in the recurrence of a tumor (e.g., lung tumor or gastrointestinal stromal tumor); (iv) the regression of a cancer (e.g., leukemia, lung cancer, or gastrointestinal stromal tumor) and/or one or more symptoms associated therewith; (v) the reduction in hospitalization of a subject; (vi) the reduction in hospitalization length; (vii) the increase in the survival of a subject; (viii) the inhibition of the progression of a cancer (e.g., leukemia, lung cancer, or gastrointestinal stromal tumor) and/or one or more symptoms associated therewith; (ix) the enhancement or improvement of the therapeutic effect of another therapy (e.g., surgery, radiation, chemotherapy, or another tyrosine kinase inhibitor); (x) a reduction or elimination in the cancer cell population (e.g., leukemia cell population, lung cancer cell population, gastrointestinal stromal tumor cell population); (xi) a reduction in the growth of a tumor or neoplasm; (xii) a decrease in tumor size (e.g., volume or diameter); (xiii) a reduction in the formation of a newly formed tumors; (xiv) eradication, removal, or control of primary, regional and/or metastatic cancer; (xv) ease in removal of a tumor by reducing tumor and/or edema-related vascularization prior to surgery; (xvi) a decrease in the number or size of metastases; (xvii) a reduction in mortality; (xviii) an increase in tumor-free survival rate of patients; (xvix) an increase in relapse-free survival; (xx) an increase in the number of patients in remission; (xxi) a decrease in hospitalization rate; (xxii) the size of the tumor is maintained and does not increase or increases by less than the increase of a tumor after administration of a standard therapy as measured by conventional methods available to one of skill in the art, such as computed tomography (CT) scan, magnetic resonance imaging (MRI), dynamic contrast-enhanced MRI (DCE-MRI), or a positron emission tomography (PET) scan; (xxiii) the prevention of the development or onset of one or more symptoms associated cancer; (xxiv) an increase in the length of remission in patients; (xxv) the reduction in the number of symptoms associated with cancer; (xxvi) an increase in symptom-free survival of cancer patients; (xxvii) a decrease in the concentration of one or more inflammatory mediators (e.g., cytokines or interleukins) in biological specimens (e.g., plasma, serum, cerebral spinal fluid, urine, or any other biofluids) of a subject with a cancer (e.g., leukemia, lung cancer, or gastrointestinal stromal cancer); (xxviii) a decrease in circulating tumor cells (CTCs) in the blood of a subject with cancer (e.g., leukemia, lung cancer, or gastrointestinal stromal cancer); (xxix) inhibition (e.g., partial inhibition) or decrease in tumor metabolism or perfusion; and (xxx) improvement in the quality of life as assessed by methods well known in the art, e.g., questionnaires.

In certain aspects, provided herein are methods for killing cancer cells in an individual in need thereof, wherein said method comprises administering to said individual an effective amount of an antibody described herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C, linked, covalently or non-covalently, to a therapeutic agent). In certain aspects, provided herein are methods for inhibiting growth or proliferation of cancer cells in an individual in need thereof, wherein said method comprises administering to said individual an effective amount of an antibody described herein (e.g., antibody 37M or 37C, or an antigen binding fragment thereof (e.g., KIT-binding fragment thereof), or a humanized version of antibody 37M or 37C, or a conjugate comprising, for example antibody 37M or 37C, a KIT-binding fragment thereof, or an antibody comprising CDRs of antibody 37M or 37C, linked, covalently or non-covalently, to a therapeutic agent). In certain embodiments, partial inhibition of growth or proliferation of cancer cells is achieved, for example, inhibition of at least about 20% to about 55% of growth or proliferation of cancer cells.

In certain aspects, provided herein are methods for reducing tumor size or load in an individual in need thereof, wherein said method comprises administering to said individual an effective amount of an antibody described herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C, linked, covalently or non-covalently, to a therapeutic agent).

Other non-limiting examples of KIT-mediated disorders or diseases include systemic mast cell disorders (e.g., mastocytosis), hematologic disorders, fibrosis (e.g., idiopathic pulmonary fibrosis (TPF), scleroderma, or myelofibrosis) and inflammatory conditions such as asthma, rheumatoid arthritis, inflammatory bowel disease, and allergic inflammation.

In a particular embodiment, a method described herein for treating or managing a KIT-mediated disorder, e.g., fibrosis or an inflammatory condition (e.g., asthma, rheumatoid arthritis, inflammatory bowel disease, and allergic inflammation), in a subject in need thereof, can achieve at least one, two, three, four or more of the following effects due to administration of a therapeutically effective amount of an anti-KIT antibody described herein: (i) the reduction or amelioration of the severity of fibrosis or an inflammatory condition (e.g., asthma, rheumatoid arthritis, inflammatory bowel disease, and allergic inflammation) and/or one or more symptoms associated therewith; (ii) the reduction in the duration of one or more symptoms associated with fibrosis or an inflammatory condition (e.g., asthma, rheumatoid arthritis, inflammatory bowel disease, and allergic inflammation); (iii) the prevention in the recurrence of fibrosis or an inflammatory condition (e.g., asthma, rheumatoid arthritis, inflammatory bowel disease, and allergic inflammation); (iv) the reduction in hospitalization of a subject; (v) the reduction in hospitalization length; (vi) the inhibition (e.g., partial inhibition) of the progression of fibrosis or an inflammatory condition (e.g., asthma, rheumatoid arthritis, inflammatory bowel disease, and allergic inflammation) and/or one or more symptoms associated therewith; (vii) the enhancement or improvement of the therapeutic effect of another therapy (e.g., anti-inflammatory therapy such as steriods); (viii) an increase in the number of patients in remission (i.e., a time period characterized by no or minimal symptoms associated with the inflammatory condition); (ix) an increase in the length of remission in patients; (x) a decrease in hospitalization rate; (xi) the reduction in the number of symptoms associated with fibrosis or an inflammatory condition (e.g., asthma, rheumatoid arthritis, inflammatory bowel disease, and allergic inflammation); (xii) a decrease in the concentration of one or more inflammatory mediators (e.g., cytokines or interleukins) in biological specimens (e.g., plasma, serum, cerebral spinal fluid, urine, or any other biofluids) of a subject with fibrosis or an inflammatory condition (e.g., asthma, rheumatoid arthritis, inflammatory bowel disease, and allergic inflammation); and (xiii) improvement in the quality of life as assessed by methods well known in the art, e.g., questionnaires.

In certain embodiments, an anti-KIT antibody described herein may be administered by any suitable method to a subject in need thereof. Non-limiting examples of administration methods include mucosal, intradermal, intravenous, intratumoral, subcutaneous, intramuscular delivery and/or any other method of physical delivery described herein or known in the art. In one embodiment, an anti-KIT antibody or a pharmaceutical composition thereof is administered systemically (e.g., parenterally) to a subject in need thereof. In another embodiment, an anti-KIT antibody or a pharmaceutical composition thereof is administered locally (e.g., intratumorally) to a subject in need thereof. Each dose may or may not be administered by an identical route of administration. In some embodiments, an anti-KIT antibody described herein can be administered via multiple routes of administration simultaneously or subsequently to other doses of the same or a different an anti-KIT antibody described herein.

When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof. In certain embodiments, an anti-KIT antibody described herein is administered prophylactically or therapeutically to a subject. An anti-KIT antibody described herein can be prophylactically or therapeutically administered to a subject so as to prevent, lessen or ameliorate a KIT-mediated disorder or disease (e.g., cancer, inflammatory condition, fibrosis) or symptom thereof.

The dosage and frequency of administration of an anti-KIT antibody described herein or a pharmaceutical composition thereof is administered to a subject in need thereof in accordance with the methods for treating a KIT-mediated disorder or disease provided herein will be efficacious while minimizing side effects. The exact dosage of an anti-KIT antibody described herein to be administered to a particular subject or a pharmaceutical composition thereof can be determined by a practitioner, in light of factors related to the subject that requires treatment. Factors which can be taken into account include the severity of the disease state, general health of the subject, age, and weight of the subject, diet, time and frequency of administration, combination(s) with other therapeutic agents or drugs, reaction sensitivities, and tolerance/response to therapy. The dosage and frequency of administration of an anti-KIT antibody described herein or a pharmaceutical composition thereof can be adjusted over time to provide sufficient levels of the anti-KIT antibody or to maintain the desired effect.

The precise dose to be employed in the formulation will also depend on the route of administration, and the seriousness of a KIT-mediated disorder or disease (e.g., cancer, inflammatory condition, fibrosis), and should be decided according to the judgment of the practitioner and each patient's circumstances.

Effective doses can be extrapolated from dose-response curves derived from in vitro or animal model test systems.

In one embodiment, for the anti-KIT antibodies described herein, the dosage administered to a patient, to manage a KIT-mediated disorder or disease (e.g., cancer, inflammatory condition, fibrosis) is typically 0.1 mg/kg to 100 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies described herein can be reduced by enhancing uptake and tissue penetration of the antibodies by modifications such as, for example, lipidation.

In one embodiment, approximately 0.001 mg/kg (mg of antibody per kg weight of a subject) to approximately 500 mg/kg of an anti-KIT antibody described herein is administered to manage a KIT-mediated disorder or disease (e.g., cancer, inflammatory condition, fibrosis).

In some embodiments, an effective amount of an antibody provided herein is from about 0.01 mg to about 1,000 mg. In specific embodiments, an "effective amount" of an anti-KIT antibody described herein refers to an amount of an anti-KIT antibody described herein which is sufficient to achieve at least one, two, three, four or more of the following effects: (i) the reduction or amelioration of the severity of a KIT-mediated disorder or disease (e.g., cancer, inflammatory condition, fibrosis) and/or one or more symptoms associated therewith; (ii) the reduction in the duration of one or more symptoms associated with a KIT-mediated disorder or disease (e.g., cancer, inflammatory condition, fibrosis); (iii) the prevention of the recurrence of a tumor (e.g., gastrointestinal stromal tumor); (iv) the regression of a KIT-mediated disorder or disease (e.g., cancer, inflammatory condition, fibrosis) and/or one or more symptoms associated therewith; (v) the reduction in hospitalization of a subject; (vi) the reduction in hospitalization length; (vii) the increase in the survival of a subject; (viii) the inhibition (e.g., partial inhibition) of the progression of a KIT-mediated disorder or disease (e.g., cancer, inflammatory condition, fibrosis) and/or one or more symptoms associated therewith; (ix) the enhancement or improvement of the therapeutic effect of another therapy; (x) a reduction or elimination in the cancer cell population (e.g., leukemia cell population, lung cancer cell population, gastrointestinal stromal cancer cell population); (xi) a reduction in the growth of a tumor or neoplasm; (xii) a decrease in tumor size (e.g., volume or diameter); (xiii) a reduction in the formation of a newly formed tumors; (xiv) eradication, removal, or control of primary, regional and/or metastatic cancer; (xv) ease in removal of a tumor by reducing tumor and/or edema-related vascularization prior to surgery; (xvi) a decrease in the number or size of metastases; (xvii) a reduction in mortality; (xviii) an increase in tumor-free survival rate of patients; (xvix) an increase in relapse-free survival; (xx) an increase in the number of patients in remission; (xxi) a decrease in hospitalization rate; (xxii) the size of the tumor is maintained and does not increase or increases by less than the increase of a tumor after administration of a standard therapy as measured by conventional methods available to one of skill in the art, such as computed tomography (CT) scan, magnetic resonance imaging (MRI), dynamic contrast-enhanced MRI (DCE-MRI), or a positron emission tomography (PET) scan; (xxiii) the prevention of the development or onset of one or more symptoms associated cancer; (xxiv) an increase in the length of remission in patients; (xxv) the reduction in the number of symptoms associated with cancer; (xxvi) an increase in symptom-free survival of cancer patients; (xxvii) a decrease in the concentration of one or more inflammatory mediators (e.g., cytokines or interleukins) in biological specimens (e.g., plasma, serum, cerebral spinal fluid, urine, or any other biofluids) of a subject with a KIT-mediated disorder or disease (e.g., cancer, inflammatory condition, fibrosis); (xxviii) a decrease in circulating tumor cells (CTCs) in the blood of a subject with cancer; (xxix) inhibition (e.g., partial inhibition) or decrease in tumor metabolism or perfusion; and (xxx) improvement in the quality of life as assessed by methods well known in the art, e.g., questionnaires. In some embodiments, "effective amount" as used herein also refers to the amount of an antibody described herein to achieve a specified result (e.g., inhibition of one or more KIT biological activities of a cell, such as inhibition of cell proliferation).

In some embodiments, an anti-KIT antibody described herein is administered as necessary, e.g., weekly, biweekly (i.e., once every two weeks), monthly, bimonthly, trimonthly, etc., as determined by a physician.

In some embodiments, a single dose of an anti-KIT antibody described herein is administered one or more times to a patient to impede, prevent, manage, treat and/or ameliorate a KIT-mediated disorder or disease (e.g., cancer, inflammatory condition, fibrosis).

In particular embodiments, an anti-KIT antibody or pharmaceutical composition thereof is administered to a subject in accordance with the methods for treating a KIT-mediated disorder or disease (e.g., cancer, inflammatory condition, fibrosis) presented herein in cycles, wherein the anti-KIT antibody or pharmaceutical composition is administered for a period of time, followed by a period of rest (i.e., the anti-KIT antibody or pharmaceutical composition is not administered for a period of time).

Also, presented herein are combination therapies for the treatment of a KIT-mediated disorder or disease (e.g., cancer, inflammatory condition, fibrosis) which involve the administration of an anti-KIT antibody described herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C, linked, covalently or non-covalently, to a therapeutic agent) in combination with one or more additional therapies (e.g., chemotherapeutic agent, tyrosine kinase inhibitor, or histone deacetylase inhibitor) to a subject in need thereof. In a specific embodiment, presented herein are combination therapies for the treatment of a KIT-mediated disorder or disease (e.g., cancer, inflammatory condition, fibrosis) which involve the administration of an amount (e.g., a therapeutically effective amount or a sub-optimal amount) of an anti-KIT antibody described herein in combination with an amount (e.g., a therapeutically effective amount or a sub-optimal amount) of another therapy (e.g., chemotherapeutic agent, tyrosine kinase inhibitor, or histone deacetylase inhibitor) to a subject in need thereof.

In combination therapies, one or more anti-KIT antibodies provided herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C, linked, covalently or non-covalently, to a therapeutic agent) can be administered prior to, concurrently with, or subsequent to the administration of one or more additional therapies (e.g., agents, surgery, or radiation) for use in treating, managing, and/or ameoliorating a KIT-mediated disorder or disease (e.g., cancer, inflammatory condition, fibrosis). The use of the term "in combination" does not restrict the order in which one or more anti-KIT antibodies and one or more additional therapies are administered to a subject. In specific embodiments, the therapies can be administered serially or sequentially.

In specific embodiments, one or more anti-KIT antibodies provided herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C, linked, covalently or non-covalently, to a therapeutic agent) can be administered prior to, concurrently with, or subsequent to the administration of one or more additional therapies such as anticancer agents, for example, tyrosine kinase inhibitors (e.g., imatinib myselyate (Gleevec®) or sunitinib (SUTENT), or histone deacetylase inhibitors (e.g., vorinostat or suberoylanilide hydroxamic acid (SAHA)), for treating, managing, and/or ameoliorating a KIT-mediated disorder or disease (e.g., cancer, for example, GIST, melanoma, or lung cancer).

In another specific embodiment, presented herein are combination therapies for the treatment of a KIT-mediated disorder or disease (e.g., cancer, inflammatory condition, fibrosis) which involve the administration of an amount of an anti-KIT antibody described herein (e.g., antibody 37M or 37C, or an antigen binding fragment thereof (e.g., KIT-binding fragment thereof), or a humanized version of antibody 37M or 37C, or a conjugate comprising, for example an antibody comprising CDRs of antibody 37M or 37C, linked, covalently or non-covalently, to a therapeutic agent) in combination with an amount of another therapy (e.g., chemotherapeutic agent, tyrosine kinase inhibitor, or histone deacetylase inhibitor) to a subject in need thereof. In a specific embodiment, the combination therapies result in a synergistic effect. In certain embodiments, the combination therapies result in an additive effect.

In a specific embodiment, presented herein are combination therapies for the treatment of cancer which involve the administration of an amount of an anti-KIT antibody described herein in combination with an amount of another therapy (e.g., surgery, radiation, stem cell transplantation, or chemotherapy) to a subject in need thereof. In a specific embodiment, the combination therapies result in a synergistic effect. In another specific embodiment, the combination therapies result in an additive effect.

In a specific embodiment, presented herein are combination therapies for the treatment of an inflammatory condition which involve the administration of an amount of an anti-KIT antibody described herein in combination with an amount of another therapy (e.g., anti-inflammatory therapy, for example, steroid therapy) to a subject in need thereof. In a specific embodiment, the combination therapies result in a synergistic effect. In another specific embodiment, the combination therapies result in an additive effect.

Non-limiting examples of another therapy for use in combination with antibodies described herein include, another anti-KIT antibody that immunospecifically bind to a different epitope of KIT, one or more other antibodies (e.g., anti-HER2 antibody, anti-EGFR antibody, anti-VEGF antibody), anti-inflammatory therapy, chemotherapy (e.g., microtubule disassembly blocker, antimetabolite, topisomerase inhibitor, and DNA crosslinker or damaging agent), radiation, surgery, and tyrosine kinase inhibitors (e.g., imatinib mesylate (GLEEVEC®), sunitinib (SUTENT® or SU11248), gefitinib (IRESSA™), erlotinib (TARCEVA®), sorafenib (NEXAVAR®), pazopanib (VOTRIENT™), axitinib, bosutinib, cediranib (RECENTIN®), SPRYCEL® (dasatinib), lapatinib (TYKERB®), lestaurtinib, neratinib, nilotinib (TASIGNA®), semaxanib, toceranib (PALLADIA™), vandetanib (ZACTIMA™), and vatalanib). In a specific embodiment, another therapy for use in combination with antibodies described herein is imatinib mesylate.

Other non-limiting examples of another therapy for use in combination with antibodies described herein (an antibody comprising CDRs of antibody 37M or 37C or a conjugate comprising an antibody comprising CDRs of antibody 37M and an agent) include a histone deacetylase inhibitor, such as vorinostat or suberoylanilide hydroxamic acid (SAHA) or a compound having the chemical formula (I), (II), or (III) as set forth below. In a specific embodiment, provided herein is a method for treating cancer (e.g., GIST or lung cancer) comprising (i) administering an antibody (or antigen-binding fragment thereof) comprising a VL chain region comprising a VL CDR1, VL CDR2, and VL CDR3 having the amino acid sequences of SEQ ID NO: 20, SEQ ID NO: 21, and SEQ ID NO: 22, respectively; and/or a VH chain region comprising a VH CDR1, VH CDR2, and VH CDR3 having the amino acid sequences of SEQ ID NO: 23, SEQ ID NO: 24, and SEQ ID NO: 25, respectively, or an antibody conjugate comprising such antibody and an agent, wherein said antibody, or antigen-binding fragment thereof, specifically binds to a KIT antigen; and (ii) a histone deacetylase inhibitor, for example, vorinostat or suberoylanilide hydroxamic acid (SAHA) or a compound having the chemical formula (I), (II), or (III) as set forth below. In a specific embodiment, provided herein is a method for treating cancer (e.g., GIST or lung cancer) comprising (i) administering an antibody (or an antigen-binding fragment thereof) comprising a VL chain region comprising VL CDR1, VL CDR2, and VL CDR3 of SEQ ID NO: 2; and/or a VH chain region comprising VH CDR1, VH CDR2, and VH CDR3 or SEQ ID NO: 3 or 5, or an antibody conjugate comprising such antibody and an agent, wherein said antibody, or antigen-binding fragment thereof, specifically binds to a KIT antigen; and (ii) a histone deacetylase inhibitor, for example, vorinostat or suberoylanilide hydroxamic acid (SAHA) or a compound having the chemical formula (I), (II), or (III) as set forth below.

In one embodiment, provided herein for use in the methods described herein in combination with anti-KIT antibodies are compounds of Formula (I)

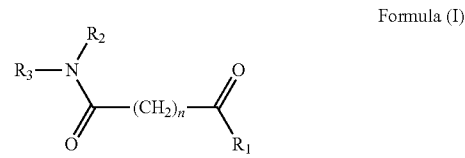

Formula (I)

or a pharmaceutically acceptable salt, hydrate, or solvate thereof, wherein $R_1$ is hydroxylamino;

each of $R_2$ and $R_3$ are independently the same as or different from each other, substituted or unsubstituted, branched or unbranched, and are hydrogen, hydroxyl, alkyl, alkenyl, cycloalkyl, aryl, alkyloxy, aryloxy, arylalkyloxy or pyridine; or $R_2$ and $R_3$ are bonded together to form a piperidine; and n is an integer from 5 to 7.

In one embodiment, $R_2$ is hydrogen atom and $R_3$ is substituted or unsubstituted phenyl. In a certain embodiment, $R_3$ is phenyl substituted with methyl, cyano, nitro, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methoxy, phenyloxy, benzyloxy, phenylaminooxy, phenylaminocarbonyl, methoxycarbonyl, methylaminocarbonyl, dimethylamino, dimethylaminocarbonyl, or hydroxylaminocarbonyl. In another embodiment, $R_3$ is unsubstituted phenyl. In a further embodiment, n is 6.

In one embodiment, provided herein for use in the methods described herein in combination with anti-KIT antibodies are compounds of Formula (II)

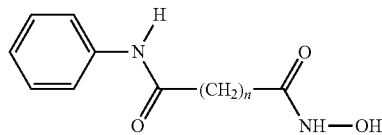

Formula (II)

or a pharmaceutically acceptable salt, or solvate thereof, wherein n is an integer from 5 to 8. In one embodiment n is 6.

In one embodiment, provided herein for use in the methods described herein in combination with anti-KIT antibodies is a compound of Formula (III) (SAHA)

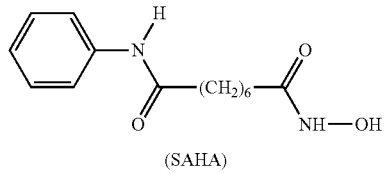

Formula (III)

(SAHA)

or a pharmaceutically acceptable salt, hydrate or solvate thereof.

Compounds of Formulae I-III can be synthesized according to the methods described in U.S. Reissued Pat. No. RE38,506 and U.S. Pat. No. 6,087,367, each of which is herewith incorporated by reference in its entirety.

In one embodiment, provided herein for use in the methods described herein in combination with anti-KIT antibodies is a Form I polymorph of SAHA characterized by an X-ray diffraction pattern substantially similar to that set forth in FIG. 13A of U.S. Pat. No. 7,456,219, which is herewith incorporated by reference in its entirety. In one embodiment the Form I polymorph of SAHA is characterized by an X-ray diffraction pattern including characteristic peaks at about 9.0, 9.4, 17.5, 19.4, 20.0, 24.0, 24.4, 24.8, 25.0, 28.0, and 43.3 degrees 2θ, as measured with a Siemens D500 Automated Powder Diffractometer (range: 4-40 degrees 2θ; source: Cu; λ=1.54 Angstrom, 50 kV, 40 mA).

In a certain embodiment, the Form I polymorph of SAHA is characterized by a Differential Scanning Calorimetry (DSC) thermogram having a single maximum value at about 164.4±2.0° C., as measured by a Perkins Elmer DSC 6 Instrument at a heating rate of 10° C./min from 50° C. to at least 30° C. above the observed melting temperature.

The Form I polymorph of SAHA can be synthesized according to the methods described in U.S. Pat. No. 7,456, 219.

In one embodiment, provided herein is a crystalline composition comprising Lysine and SAHA characterized by an X-ray diffraction pattern substantially similar to that set forth in FIG. 1 of International Patent Application Publication No. WO2008/042146, which is herewith incorporated by reference in its entirety. In another embodiment, the crystalline composition is characterized by an X-ray diffraction pattern including characteristic peaks at about 6.8, 20.1 and 23.2 degrees 2θ, as measured with a PANanalytical X'Pert Pro X-ray powder diffractometer (range: 2-40 degrees 2θ; source: Cu Kα1 and Kα2). In another embodiment, the crystalline composition is characterized by an X-ray diffraction pattern including characteristic peaks at about 6.8, 12.6, 18.7, 20.1 23.2, and 24.0 degrees 2θ, as measured with a PANanalytical X'Pert Pro X-ray powder diffractometer (range: 2-40 degrees 2θ; source: Cu Kα1 and Kα2). In another embodiment, the crystalline composition is characterized by an X-ray diffraction pattern including characteristic peaks at about 6.8, 12.0, 12.6, 16.4, 18.7, 20.1 23.2, 24.0, 29.3 degrees 2θ, as measured with a PANanalytical X'Pert Pro X-ray powder diffractometer (range: 2-40 degrees 2θ; source: Cu Kα1 and Kα2).

In a certain embodiment, the crystalline composition comprising Lysine and SAHA is characterized by a Differential Scanning Calorimetry (DSC) thermogram, wherein the endotherm of the crytalline composition exhibits an extrapolated onset temperature of approximately 182° C., as measured by a TA Instruments Q1000 differential scanning calorimeter at a heating rate of 10° C./min from room temperature to 300° C.

The crystalline composition comprising Lysine and SAHA can be synthesized according to the methods described in International Patent Application Publication No. WO2008/042146.

In certain embodiments, combination therapies described herein result in synergy or a synergistic effect. In a specific embodiment, a synergistic effect of a combination therapy permits the use of lower dosages (e.g., sub-optimal doses) of an anti-KIT antibody described herein and/or an additional therapy and/or less frequent administration of an anti-KIT antibody described herein or an additional therapy to a subject. In certain embodiments, the ability to utilize lower dosages of an anti-KIT antibody and/or of an additional therapy and/or to administer an anti-KIT antibody or said additional therapy less frequently reduces the toxicity associated with the administration of an anti-KIT antibody or of said additional therapy, respectively, to a subject without reducing the efficacy of an anti-KIT antibody or of said additional therapy, respectively, in the treatment of a KIT-mediated disorder or disease. In some embodiments, a synergistic effect results in improved efficacy of an anti-KIT antibody described herein and/or of said additional therapies in treating a KIT-mediated disorder or disease. In some embodiments, a synergistic effect of a combination of an anti-KIT antibody described herein and one or more additional therapies avoids or reduces adverse or unwanted side effects associated with the use of any single therapy.

5.7 Diagnostic Methods

Labeled or otherwise detectable antibodies, which immunospecifically bind to a KIT antigen (e.g., the D4/D5 region of KIT, for example, human KIT) can be used for diagnostic purposes to detect, diagnose, or monitor a KIT-mediated disease.

Provided herein are methods for detecting KIT expression in samples obtained from patients with a KIT-mediated disorder or disease. In a particular embodiment, a method for detecting KIT expression in a sample obtained from a patient comprises contacting the sample with an anti-KIT antibody described herein and detecting the expression level of KIT in the samples. Methods for detection are known to one of skill in the art.

In certain aspects, provided herein are methods for diagnosing a patient with a KIT-mediated disorder or disease. In a certain aspect, a method for diagnosing a subject with a KIT-mediated disorder or disease comprises contacting a sample obtained from the subject with an anti-KIT antibody described herein (or an antigen-binding fragment thereof) and detecting the expression level of KIT in the sample. In certain embodiments, a method for diagnosing a patient with a KIT-mediated disorder or disease is an in vitro method. In particular embodiments, a method for diagnosing a patient with a KIT-mediated disorder or disease is an ex vivo method.

In certain aspects, provided herein are methods for the detection of a KIT-mediated disease comprising: (a) assaying the expression of a KIT antigen in cells or a tissue sample of a subject using one or more antibodies described herein; and (b) comparing the level of the KIT antigen with a control level, e.g., levels in normal tissue samples (e.g., from a patient not having a KIT-mediated disease, or from the same patient before disease onset), whereby an increase in the assayed level of KIT antigen compared to the control level of the KIT antigen is indicative of a KIT-mediated disease.

Methods for detection are known to one of skill in the art. For example, the anti-KIT antibody can be conjugated to a detectable molecule (e.g., as described in section 5.1.1), and the detectable molecule can be visualized using standard techniques (e.g., microscopy). Antibodies described herein can be used to assay KIT antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as ELISA and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. In specific embodiments, diagnostic methods described herein involve using naked or unlabeled antibodies not conjugated to a detectable marker, and the naked or unlabeled antibodies are detected indirectly, e.g., by using a secondary antibody, which can be labeled.

In certain embodiments, high expression of KIT in a sample relative to a normal control sample (e.g., sample obtained from a healthy patient not suffering from a KIT-mediated disorder or disease) indicates that the patient is suffering from a KIT-mediated disorder or disease.

A method for diagnosing a patient with a KIT-mediated disorder or disease, such as cancer, in a sample obtained from a patient comprises contacting the sample with an anti-KIT antibody described herein and detecting the expression level of KIT in the sample. In certain embodiments, high expression of KIT in a sample relative to a normal control sample (e.g., sample obtained from a healthy patient not suffering from a KIT-mediated disorder or disease) indicates that the patient is suffering from a KIT-mediated disorder or disease.

In certain embodiments, a sample can be a tumor sample derived from, or comprising tumor cells from, a patient's tumor. Examples of tumor samples herein include, but are not limited to, tumor biopsies, circulating tumor cells, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples. In certain embodiments, a sample is a fixed tumor sample which has been histologically preserved using a fixative. In some embodiments, a sample is a formalin-fixed tumor sample which has been preserved using formaldehyde as the fixative. In certain embodiments, a sample is an embedded tumor sample which is surrounded by a firm and generally hard medium such as paraffin, wax, celloidin, or a resin. Embedding makes possible the cutting of thin sections for microscopic examination or for generation of tissue microarrays (TMAs). In particular embodiments, a sample is a paraffin-embedded tumor sample which is surrounded by a purified mixture of solid hydrocarbons derived from petroleum. In certain embodiments, a sample is a frozen tumor sample which is, or has been, frozen. In a specific embodiment, a sample, for example, a paraffin-embedded sample or frozen sample, is sectioned.

In certain aspects, a cancer or biological sample which displays KIT expression, amplification, or activation is one which, in a diagnostic test, expresses (including overexpresses) a KIT receptor, has amplified KIT gene, and/or otherwise demonstrates activation or phosphorylation of a KIT receptor.

Also provided herein is the detection and diagnosis of a KIT-mediated disease in a human. In one embodiment, diagnosis comprises: a) administering (for example, parenterally, subcutaneously, or intraperitoneally) to a subject an effective amount of a labeled antibody described herein; b) waiting for a time interval following the administering for permitting the labeled antibody to preferentially concentrate at sites in the subject where the KIT antigen is expressed (and for unbound labeled molecule to be cleared to background level); c) determining background level; and d) detecting the labeled antibody in the subject, such that detection of labeled antibody above the background level indicates that the subject has a KIT-mediated disease. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to preferentially concentrate at sites in the subject and for unbound labeled antibody to be cleared to background level is 6 to 48 hours or 6 to 24 hours or 6 to 12 hours. In another embodiment the time interval following administration is 5 to 20 days or 5 to 10 days.

In one embodiment, monitoring of a KIT-mediated disease is carried out by repeating the method for diagnosing the a KIT-mediated disease, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that can be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.8 Methods

Provided herein are methods for inhibiting KIT activity in a cell expressing KIT comprising contacting the cell with an effective amount of an antibody described herein (e.g., antibody 37M or 37C, or an antigen binding fragment thereof (e.g., KIT-binding fragment thereof), or a humanized version of antibody 37M or 37C, or a conjugate comprising, for example antibody 37M or 37C, a KIT-binding fragment thereof, or an antibody comprising CDRs of antibody 37M or 37C, linked, covalently or non-covalently, to a therapeutic agent). Also provided herein are methods for inducing or enhancing apoptosis in a cell expressing KIT comprising contacting the cell with an effective amount of an antibody described herein. Also provided herein are methods for inducing or enhancing cell differentiation in a cell expressing KIT comprising contacting the cell with an effective amount of an antibody described herein.

KIT activity and, for example, the effect of an antibody on KIT activity can routinely be assessed using, e.g., cell-based assays such as those described herein.

Non-limiting examples of KIT activity which can be inhibited by the methods provided herein can include any activity of KIT known or described in the art, e.g., KIT receptor dimerization, KIT receptor phosphorylation (tyrosine phosphorylation), signaling downstream of the KIT receptor (e.g., Stat, AKT, MAPK, or Ras signaling), KIT ligand (e.g., SCF) induced transcriptional regulation (e.g., SCF-induced transcriptional activation of c-Myc), induction or enhancement of cell proliferation, or cell survival.

In certain embodiments, a method for inhibiting (e.g., partially inhibiting) KIT activity in a cell expressing KIT comprises contacting the cell with an effective amount of an antibody described herein (e.g., antibody 37M or 37C, or an antigen binding fragment thereof (e.g., KIT-binding fragment thereof), or a humanized version of antibody 37M or 37C, or a conjugate comprising, for example antibody 37M or 37C, a KIT-binding fragment thereof, or an antibody comprising CDRs of antibody 37M or 37C, linked, covalently or non-covalently, to a therapeutic agent) sufficient to inhibit or antagonize KIT activity by at least about 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art (e.g., ELISA). In certain embodiments, a method for inhibiting (e.g., partially inhibiting) KIT activity in a cell expressing KIT comprises contacting the cell with an effective amount of an antibody described herein (e.g., antibody 37M or 37C, or an antigen binding fragment thereof (e.g., KIT-binding fragment thereof), or a humanized version of antibody 37M or 37C, or a conjugate comprising, for example antibody 37M or 37C, a KIT-binding fragment thereof, or an antibody comprising CDRs of antibody 37M or 37C, linked, covalently or non-covalently, to a therapeutic agent) sufficient to inhibit or antagonize KIT activity by at least about 25%, 35%, 45%, 55%, or 65%, as assessed by methods described herein and/or known to one of skill in the art (e.g., ELISA). Non-limiting examples of KIT activity can include KIT receptor phosphorylation, KIT receptor signaling, KIT ligand (e.g., SCF) mediated cell proliferation, KIT ligand (e.g., SCF) mediated cell survival, and transcriptional activation of a KIT target gene (e.g., c-Myc).

In a particular embodiment, a method for inhibiting KIT activity in a cell expressing KIT comprises contacting the cell with an effective amount of an antibody described herein (e.g., antibody 37M or 37C, or an antigen binding fragment thereof (e.g., KIT-binding fragment thereof), or a humanized version of antibody 37M or 37C, or a conjugate comprising, for example antibody 37M or 37C, a KIT-binding fragment thereof, or an antibody comprising CDRs of antibody 37M or 37C, linked, covalently or non-covalently, to a therapeutic agent) sufficient to inhibit (e.g., partially inhibit) or antagonize downstream KIT signaling, for example, signaling of a member of the Src family kinases, PI 3-kinases, or Ras-MAPK.

In another particular embodiment, a method for inhibiting (e.g., partially inhibiting) one or more KIT activities in a cell expressing KIT, comprises contacting the cell with an effective amount of an antibody described herein sufficient to inhibit or antagonize downstream KIT signaling such as phosphorylation of MAPK, phosphorylation of AKT, or phosphorylation of Stat1, Stat3, or Stat5. Thus, in certain embodiments, a method for an inhibiting (e.g., partially inhibiting) or antagonizing KIT activity in a cell expressing KIT comprises contacting the cell with an effective amount of an antibody described herein sufficient to inhibit or to reduce phosphorylation of MAPK (e.g., KIT ligand (e.g., SCF) induced phosphorylation of MAPK) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay. In certain embodiments, a method for an inhibiting (e.g., partially inhibiting) or antagonizing KIT activity in a cell expressing KIT comprises contacting the cell with an effective amount of an antibody described herein sufficient to inhibit or to reduce phosphorylation of MAPK (e.g., KIT ligand (e.g., SCF) induced phosphorylation of MAPK) by at least about 25%, 35%, 45%, 55%, or 65%, as assessed by methods described herein or known to one of skill in the art, e.g., Western blot or ELISA assay as described in section 6 or immunoblotting assay.

In certain embodiments, a method for inhibiting (e.g., partially inhibiting) KIT activity in a cell expressing KIT comprises contacting the cell with an effective amount of an antibody described herein sufficient to inhibit or to reduce phosphorylation of AKT (e.g., KIT ligand (e.g., SCF) induced phosphorylation of AKT) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay. In certain embodiments, a method for inhibiting e.g., partially inhibiting) KIT activity in a cell expressing KIT comprises contacting the cell with an effective amount of an antibody described herein sufficient to inhibit or to reduce phosphorylation of AKT (e.g., KIT ligand (e.g., SCF) induced phosphorylation of AKT) by at least about 25%, 35%, 45%, 55%, or 65%, as assessed by methods described herein or known to one of skill in the art, e.g., Western blot or ELISA assay as described in section 6 or immunoblotting assay.

In particular embodiments, a method for inhibiting (e.g., partially inhibiting) KIT activity in a cell expressing KIT comprises contacting the cell with an effective amount of an antibody described herein sufficient to inhibit or reduce phosphorylation of Stat3 (e.g., KIT ligand (e.g., SCF) induced phosphorylation of Stat3) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay. In particular embodiments, a method for inhibiting (e.g., partially inhibiting) KIT activity in a cell expressing KIT comprises contacting the cell with an effective amount of an antibody described herein sufficient to inhibit or reduce phosphorylation of Stat3 (e.g., KIT ligand (e.g., SCF) induced phosphorylation of Stat3) by at least about 25%, 35%, 45%, 55%, or 65%, as assessed by methods described herein or known to one of skill in the art, e.g., Western blot or ELISA assay as described in section 6 or immunoblotting assay.

In particular embodiments, a method for inhibiting (e.g., partially inhibiting) KIT activity in a cell expressing KIT comprises contacting the cell with an effective amount of an antibody described herein sufficient to inhibit or reduce phosphorylation of Stat1 or Stat5 (e.g., KIT ligand (e.g., SCF) induced phosphorylation) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay. In particular embodiments, a method for inhibiting (e.g., partially inhibiting) KIT activity in a cell expressing KIT comprises contacting the cell with an effective amount of an antibody described herein sufficient to inhibit or reduce phosphorylation of Stat1 or Stat5 (e.g., KIT ligand (e.g., SCF) induced phosphorylation) by at least about 25%, 35%, 45%, 55%, or 65%, as assessed by methods described herein or known to one of skill in the art, e.g., Western blot or ELISA assay as described in section 6 or immunoblotting assay.

In certain aspects, a method for inhibiting (e.g., partially inhibiting) KIT activity in a cell expressing KIT comprises contacting the cell with an effective amount of an antibody described herein sufficient to inhibit proliferation of the cell. Cell proliferation assays are described in the art and can be readily carried out by one of skill in the art. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H) thymidine incorporation (see, e.g., Blechman et al., Cell, 1995, 80:103-113; Chen, J., 1996, Oncogene 13:1395-403; Jeoung, J., 1995, J. Biol. Chem. 270:18367 73), by direct cell count at various time intervals (e.g., 12-hour or 24-hour intervals), or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription.

In specific embodiments, a method for inhibiting (e.g., partially inhibiting) KIT activity in cells expressing KIT comprises contacting the cells with an effective amount of an antibody described herein sufficient to inhibit cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., BrdU incorporation assay). In specific embodiments, a method for inhibiting (e.g., partially inhibiting) KIT activity in cells expressing KIT comprises contacting the cells with an effective amount of an antibody described herein sufficient to inhibit cell proliferation by at least about 25%, 35%, 45%, 55%, or 65%, as assessed by methods described herein or known to one of skill in the art (e.g., BrdU incorporation assay). In specific embodiments, a method for an inhibiting or antagonizing KIT activity in cells expressing KIT comprises contacting the cells with an effective amount of an antibody described herein sufficient to inhibit cell proliferation by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., BrdU incorporation assay).

In certain aspects, a method provided herein for inhibiting KIT activity in a cell expressing KIT comprises contacting the cell with an effective amount of an antibody described herein sufficient to reduce or to inhibit survival of the cell. Cell survival assays are described in the art and can be readily carried out by one of skill in the art. For example, cell viability can be assessed by using trypan-blue staining or other cell death or viability markers known in the art. In a specific embodiment, the level of cellular ATP is measured to determined cell viability. In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes can include enlargement, granularity, cells with ragged edges, a filmy appearance, rounding, detachment from the surface of the well, or other changes. These changes are given a designation of T (100% toxic), PVH (partially toxic-very heavy—80%), PH (partially toxic-heavy—60%), P (partially toxic—40%), Ps (partially toxic slight—20%), or 0 (no toxicity—0%), conforming to the degree of cytotoxicity seen. A 50% cell inhibitory (cytotoxic) concentration ($IC_{50}$) is determined by regression analysis of these data.

In specific embodiments, a method provided herein for inhibiting (e.g., partially inhibiting) KIT activity in cells expressing KIT comprises contacting the cells with an effective amount of an antibody described herein sufficient to reduce or to inhibit survival of the cells by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., trypan blue exclusion assay). In specific embodiments, a method provided herein for inhibiting (e.g., partially inhibiting) KIT activity in cells expressing KIT comprises contacting the cells with an effective amount of an antibody described herein sufficient to reduce or to inhibit survival of the cells by at least about 25%, 35%, 45%, 55%, or 65%, as assessed by methods described herein or known to one of skill in the art (e.g., trypan blue exclusion assay). In specific embodiments, a method provided herein for inhibiting KIT activity in cells expressing KIT comprises contacting the cells with an effective amount of an antibody described herein sufficient to reduce or to inhibit survival of the cells by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., trypan blue assay).

In a specific embodiment, a method provided herein for inhibiting (e.g., partially inhibiting) KIT activity in cells expressing KIT comprises contacting the cells with an effective amount of an antibody described herein sufficient to induce apoptosis (i.e., programmed cell death). Methods for detecting apoptosis are described in the art and can be readily carried out by one of skill in the art. For example, flow cytometry can be used to detect activated caspase 3, an apoptosis-mediating enzyme, in cells undergoing apoptosis, or Western blotting can be used to detect cleavage of poly(ADP-ribose) polymerase (PARP (see, e.g., Smolich et al., Blood, 2001, 97:1413-1421). Cleavage of PARP is an indicator of apoptosis. In specific embodiments, a method provided herein for an inhibiting or antagonizing KIT activity in cells expressing KIT comprises contacting the cells with an effective amount of an antibody described herein sufficient to induce or enhance apoptosis by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., flow cytometry to detect activated caspases 3). In specific embodiments, a method provided herein for an inhibiting or antagonizing KIT activity in cells expressing KIT comprises contacting the cells with an effective amount of an antibody described herein sufficient to induce or enhance apoptosis by at least about 25%, 35%, 45%, 55%, or 65%, as assessed by methods described herein or known to one of skill in the art (e.g., flow cytometry to detect activated caspases 3). In specific embodiments, antibodies a method provided herein for inhibiting KIT activity in cells expressing KIT comprises contacting the cells with an effective amount of an antibody described herein sufficient to induce or enhance apoptosis by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., flow cytometry to detect activated caspase 3).

In a specific embodiment, a method provided herein for inhibiting (e.g., partially inhibiting) KIT activity in a cell expressing KIT comprises contacting the cells with an effective amount of an antibody described herein sufficient to induce differentiation. Methods for detecting differentiation are described in the art and can be readily carried out by one of skill in the art. For example, flow cytometry can be used to detect expression of one or more differentiation markers, or the lack of expression of one or more undifferentiated markers, in a cell contacted with an antibody described herein. Similarly, Western blotting can also be used to detect differentiation markers. Suitable differentiation markers and undifferentiated markers have been described and are one of skill in the art.

In specific embodiments, a method provided herein for inhibiting (e.g., partially inhibiting) KIT activity in cells expressing KIT comprises contacting the cells with an effective amount of an antibody described herein sufficient to induce differentiation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., flow cytometry). In specific embodiments, a method provided herein for inhibiting (e.g., partially inhibiting) KIT activity in cells expressing KIT comprises contacting the cells with an effective amount of an antibody described herein sufficient to induce differentiation by at least about 25%, 35%, 45%, 55%, or 65%, as assessed by methods described herein or known to one of skill in the art (e.g., flow cytometry). In specific embodiments, a method provided herein for inhibiting KIT activity in cells expressing KIT comprises contacting the cells with an effective amount of an antibody described herein sufficient to induce differentiation by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., flow cytometry).

Non-limiting examples of cells which can be differentiated by the methods described herein include stem cells (e.g., embryonic stem cells, hematopoietic stem cells) and progenitor cells. Exemplary hematopoietic stem cell markers include CD38, CD34, CD59, CD133, Sca-1, and ABCG2. Non-limiting examples of neural stem cell markers include Nestin, PSA-NCAM, p75 Neurotrophin R, and Vimentin. Other non-limiting examples of stem cell markers include, Oct4, Sox2, Klf4, LIN28, Nanog, SSEA-3, SSEA-4, Notch, and Wnt.

6. EXAMPLES

The examples in this section (i.e., section 6) are offered by way of illustration, and not by way of limitation.

6.1 Example 1: Generating Murine Anti-KIT Monoclonal Antibodies

Murine monoclonal antibodies that immunospecifically bind to the D4/D5 region of human KIT were obtained from immunized mice using hybridoma technology. From this process, antibody 37M was isolated.

Briefly, two female HTP™ mice (Abpro, Inc., Cambridge, Mass.) were immunized with a KIT immunogen corresponding to the D4/D5 fragment of human KIT (see FIG. 2, in particular FIG. 2A depicting the recombinant antigen (containing the D4/D5 region of human KIT)). Prior to immunization, the KIT immunogen was emulsified in Freund's Complete Adjuvant. Booster immunizations also were emulsified in Freund's Incomplete Adjuvant.

Antibody serum titers were determined after the 8th immunization on Day 18 by ELISA, and fusion was performed on Day 21 to generate hybridoma cells. Lymphocytes were obtained from the lymph nodes of one selected immunized mouse. Hybridoma cells were generated by fusing the lymphocytes with NS0 myeloma fusion partner cells using the HTP™ protocol. The hybridoma cells were divided into eight 96-well plates for screening.

A primary screen was performed with IgG-specific secondary antibody to identify hybridoma clones secreting IgG antibodies. Up to 48 samples were selected for expansion in 24-well plates.

Thirty-two pre-subclones were screened a second time for binding to the KIT immunogen (i.e., the D4/D5 region of human KIT) by ELISA and for blocking KIT phosphorylation by cell based assays, which are described in more detail in the sections below. Clones that reached a 25% inhibition determined by cell based phosphorylation assays were ranked and the 10 best clones were selected for subcloning.

Twenty subclones were tested for binding to the KIT immunogen by ELISA, and for blocking KIT phosphorylation by cell based assays. The best two clones were also tested by fluorescence-activated cell sorting (FACS) for binding to full-length KIT expressed on CHO cells. From these screening procedures, antibody 37M was isolated.

The sequences of the light chain and heavy chain of antibody 37M were obtained by PCR methods. The sequences of the variable light chain region and the variable heavy chain region, as well as the sequences of the CDRs and framework regions (FRs) were also determined based on the Kabat numbering system.

The DNA fragments encoding the VL chain region and the VH chain region of antibody 37M were cloned into the cassette vectors containing human constant region of a heavy chain (IgG1) and a light chain (Kappa) resulting in the antibody 37C, which is a chimeric antibody consisting of murine variable regions and human constant regions FIG. 3A shows the amino acid sequence of the VL domain of antibodies 37M and 37C. FIG. 3B shows the amino acid sequence of the VH domain of antibodies 37M and 37C. The CDR and FR amino acid sequences are labeled accordingly. FIG. 4 shows the amino acid sequences of the VL and VH domains of antibody 37M as well as the nucleic acid sequences encoding them. FIG. 5A shows the amino acid sequence of the light chain and heavy chain of antibody 37C. Both the light chain (SEQ ID NO: 6) and heavy chain (SEQ ID NO: 7) include a signal peptide, variable region containing CDRs and FRs, and a constant region. The signal peptide is cleaved during post-translational processing, and is not present in the mature form of the light chain and heavy chain. FIG. 5B shows the nucleotide sequence (SEQ ID NO: 10) encoding the light chain of antibody 37C, and the corresponding amino acid sequence (SEQ ID NO: 6). FIG. 5C shows the nucleotide sequence (SEQ ID NO: 11) encoding the heavy chain of antibody 37C, and the corresponding amino acid sequence (SEQ ID NO: 7).

6.2 Example 2: Antibodies 37M and 37C have High Affinity for the D4/D5 Region of Human KIT The binding activity of antibodies 37M and 37C obtained from mice immunized with a KIT immunogen containing the D4/D5 region of the human KIT extracellular region was characterized by solid phase ELISA. Specifically, the binding affinity of antibody 37M for antigens containing the D4 region (see FIG. 2B), D5 region (see FIG. 2C), or the D4/D5 region (see FIG. 2A) of human KIT was tested by solid phase ELISA. The binding affinity of antibody 37C for an antigen containing the D4/D5 region (see FIG. 2A) of human KIT was also tested by solid phase ELISA. The general protocol used for the solid phase ELISA experiments are described below.

Materials:
Recombinant antigen: Recombinant IG domain four and five of the extracellular region of KIT
Assay plates: Nunc MaxiSorp micro-titer plates 456537
plate sealers Fisher 353073
polypropylene dilution plates
TBS-T: 50 mM Tris pH 7.4, 150 mM NaCl, 0.1% Tween 20
TBS: 50 mM Tris pH 7.4, 150 mM NaCl
Blocking solution: 1% bovine serum albumin (BSA) in TBS
Dilution buffer: 1% BSA in TBS-T
Detection antibody solution: Goat anti-mouse IgG HRP antibody and Pierce goat anti-human F(ab')$_2$ specific conjugated with horseradish peroxidase (Thermo scientific 31414)
Detection Substrate: TMB (3,3',5,5' tetramethylbenzidine) Substrate kit (Thermo scientific #34021)
Plate Washer: NUNC Immunowash 470176
ELISA plate reader: BioTek Synergy HT, Software Gen5 1.08

Coating Plates with Antigen:
Recombinant antigens corresponding to the D4 region (see FIG. 2B), D5 region (see FIG. 2C), or D4/D5 region of the KIT extracellular domain (see FIG. 2A) were absorbed onto 96-well microtiter plates. Recombinant antigen (10 µg) were diluted into 10 mL of borate buffer, and 100 µL of the antigen solution were added to each well of a 96 well plate. The 96 well plate was covered with a plate sealer, was incubated at 4° C. overnight, and then stored at −80° C. until the day of the assay.

Preparation of Antibody Sample with Serial Dilution:
Dilution buffer (100 µL) was added to columns 1 and 7 of a 96 well plate, and 50 µL of dilution buffer were added to all the remaining wells. The test antibody (100 µL) was added to the first well containing 100 µL dilution buffer, mixed by pipetting, and 50 µL from the first well were removed and added into the second well and mixed. This dilution step was repeated across the row until the dilution step was repeated for a total of six dilutions. This dilution process was repeated for each sample.

ELISA: The plate with the absorbed antigen was removed from the −80° C. freezer and was allowed to thaw at room temperature. The borate buffer was removed by flicking the plate into the sink and blotting the plate dry. Blocking buffer (200 µL) was added to each well and was allowed to incubate at room temperature for one hour. The blocking buffer was removed, again by flicking the plate into the sink. Then, the diluted solution of test antibodies and controls were added to the plate in a volume of 50 µL and incubated at room temperature for one hour. The antibody solutions were removed, and the plate was washed four times with 300 µL of wash buffer with five minute incubations. After the last wash, the plate was blotted dry. Secondary antibody solution was diluted 1:8000 and was added to each well in a volume of 100 µL and allowed to incubate for one hour at room temperature. The diluted secondary antibody solution was removed, and the plate was washed four times with 300 µL of wash buffer with five minute incubations. The plate was then blotted dry, and freshly mixed TMB substrate solution was added to each well in a volume of 100 µL and was allowed to incubate at room temperature for 30 minutes. Subsequently, 100 µL of 2N H$_2$SO$_4$ were added to each well and immediately read on the plate reader. An irrelevant antibody served as the negative control, and an anti-KIT antibody against the D4 and/or D5 domain of the extracellular region of KIT served as the positive control. OD values for each sample were obtained at a wavelength of 450 nm.

Data analysis using Graph Pad Prism and Excel: Concentrations in ng/mL units were converted to µM based on the molecular weight of a Fab molecule (50 kDa) and of an IgG molecule (150 kDa). The OD values from the plate reader for the samples were exported into Graph Pad and the sample concentrations were transformed into log(X) and subjected to nonlinear regression (curve fit), then sigmoidal dose-response (variable slope) to obtain the concentration of antibodies at 50% binding to antigen.

FIG. 6A depicts a graph plotting OD450 versus log concentration (nM) of antibody 37M. The effective concentration at 50% binding ($EC_{50}$) for the binding affinity of antibody 37M to the D4/D5 region of human KIT was calculated to be approximately 192 pM. The $EC_{50}$ for the binding affinity of antibody 37M to the D4 region and to the D5 region of human KIT was calculated to be approximately 572 pM and greater than 3 pM, respectively. The results indicate that antibody 37M has high affinity to domain D4 and the entire antigen (D4/D5 region of KIT), but not to domain D5 alone.

FIG. 6B depicts a graph plotting OD450 versus log concentration (nM) of antibody 37C. The $EC_{50}$ for the binding affinity of antibody 37C to the D4/D5 region of human KIT was calculated to be approximately 196 pM. The results indicate that antibody 37C has high affinity for the D4/D5 region of human KIT. The results presented in FIGS. 6A and 6B show that the binding affinities of mouse antibody 37M and chimeric antibody 37C are comparable.

To confirm that antibody 37M can bind to KIT expressed on the surface of cells, flow cytometry assays were carried out using CHO cells that do (CHO/KIT-WT) and do not (parental CHO cells) exogenously express the full-length, wild-type human KIT receptor. Briefly, parental CHO cells and CHO/KIT-WT cells were washed and incubated with 0.01 nM, 0.1 nM, 1 nM or 10 nM of antibody 37M, a negative control isotype IgG antibody, or a commercial anti-KIT antibody as a positive control. The samples were processed for flow cytometry analysis. More specifically, cells were removed from the culture flasks using EDTA, and washed with PBS. Then, the cells were resuspended in media and counted. Each sample containing approximately 200,000 to 250,000 cells was spun, the media was removed, and the cells were resuspended in FC buffer (1% BSA, 0.01% sodium azide in 1×PBS) for the blocking step. The cells were incubated in FC buffer for 1 hour on ice. Then, primary antibody (e.g., antibody 37M, positive control anti-KIT antibody, or negative control antibody) was added to the cells. The samples were mixed and incubated on ice for 1 hour, followed by washing the cells with 0.5-1 mL FC buffer. The FC buffer was removed by spinning the cells at 1000 rpm for 5 minutes at 4° C., decanting the liquid. The cell pellets were resuspended in 200 µL FC buffer, and secondary antibody (DyLight 488 AffiniPure Goat Anti-Mouse IgG Jackson Laboratories) was added to the cells at a 1:1000 to 1:2000 dilution. The samples were mixed and incubated on ice for 1 hour, and then washed as described above. The samples were run on a fluorescence activated cell sorter (FACS) machine (Accuri FlowCytometer). Samples were analyzed by following channel FLA-1 for DyLight-conjugated samples.

FIG. 7 depicts the results from the flow cytometry analysis. In particular, more intense fluorescent signals were detected in samples where the CHO/KIT-WT cells were incubated with increasing concentrations of antibody 37M, while no such increase in fluorescent signals were detected in samples where CHO parental cells were incubated with increasing concentrations of antibody 37M. These results indicate that antibody 37M is able to bind to KIT expressed on the surface of cells.

Similar flow cytometery experiments were carried out with antibody 37M and CHO/KIT-WT cells sorted for high KIT expression. The following cell sort protocol was performed. CHO cells were transfected with KIT DNA constructs encoding full-length wild-type human KIT and a G418 resistance cassette. For selection of the highest KIT-expressing population, transfected CHO cells were stained for FACS analysis and sorted based on KIT expression. Briefly, parental CHO and transfected CHO cells were collected with the use of 2 mM EDTA and washed one time with FACS buffer (PBS+1% NBFCS+0.01% sodium azide). Approximately $10 \times 10^6$ cells were blocked in 1 mL FACS buffer on ice for 1 hr. Cells were then spun down and re-suspended in 3 mL FACS buffer plus anti-KIT-PE antibody (Dako, 1:200), placed on ice for 1 hr., followed by 2×1 mL washes with FACS buffer. Finally, cells were washed once with 2 mL Sort buffer (PBS+0.1% sodium azide) and re-suspended in 1 mL Sort buffer. Using FACSAria™ (BD Biosciences) instrumentation for analysis, PE fluorescence on KIT-negative, parental CHO cells ranged from $10^2$ to $10^3$. Therefore, to select for a population of highly KIT-positive cells, gating was set at $\geq 10^4$ (FIG. 10A, see gate P5). The sorted cells (gate P5 in FIG. 10A) were collected in CHO media containing G418 (1 mg/mL) and placed in normal culture conditions for future use.

FIG. 10C depicts the results from a flow cytometry experiment which was carried out with sorted (high KIT expression) CHO/KIT-WT cells. In particular, more intense fluorescent signals were detected in samples where the CHO/KIT-WT cells (FIG. 10C) were incubated with increasing concentrations of antibody 37M, while no such increase in fluorescent signals was detected in samples where CHO parental cells (untransfected CHO cells) (FIG. 10B) were incubated with increasing concentrations of antibody 37M.

6.3 Example 3: Antibodies 37M and 37C can Block KIT Phosphorylation Induced by SCF in Cell-Based Phospho-KIT Assays To further characterize the effect of antibodies 37M and 37C on KIT activity, specifically, SCF-induced tyrosine phosphorylation of the cytoplasmic domain of KIT, cell-based phospho-KIT assays were carried out as follows.

Materials:
CHO cells stably transfected with a plasmid encoding full-length human KIT (see FIG. 1), which was cloned from a human ovary cDNA library (OriGene, Rockville, Md.)
Complete cell culture media (see Table 5)
Starving media: Cell culture media described in Table 5 without FBS
Trypsin-EDTA (Cellgro 25-050-CI)
PBS (GIBCO 10010-023)
24-well cell culture plates BD Falcon (353226)
ELISA plates (Nunc, #436110)
SCF solution: rhSCF (RD Systems 255-SC/CF); final concentration 30 ng/mL Lysis buffer: 50 mM Tris pH 7.4, 150 mM NaCl, 1 mM EDTA, 1% Triton X-100, protease inhibitor cocktail tables EDTA free (Roche Diagnostics 04693132001), 1 mM $NaVO_4$ TBS-T: 50 mM Tris pH 7.4, 150 mM NaCl, 0.1% Tween 20

Blocking solution: 5% bovine serum albumin (BSA) in TBS-T

Dilution buffer: 1% BSA in TBS-T containing 1 mM $NaVO_4$

Detection antibody solution: anti-phospho-tyrosine antibody conjugated with horse radish peroxidase (Millipore, 4G10); dilution factor 1:500

Capture antibody: anti-CD117 antibody Ab3 from Thermo Scientific (MS-289-PABX)

Cell incubator: Thermo Scientific, HeraCell 150i $CO_2$ incubator

Cell Counter: Invitrogen Countess™ C10227

ELISA plate reader: BioTek Synergy HT, Software Gen5 1.08

TABLE 5

Cell Culture Media

| | |
|---|---|
| Cell line | CHO (parental or KIT transfected) |
| Basic medium | Gibco F12 Nutrient Mixture (Ham) 1× 11765 |
| Penicillin/Streptomycin (Cellgro 30-001-CI) | 50 IU/mL penicillin 50 µg/mL streptomycin |
| 100× GlutaMAX ™-I (Gibco 35050) | 1× GlutaMAX ™ |
| Geneticin (Invitrogen 10131027) | 1 mg/mL Geneticin (for selection of transfected cells only) |

Passaging of CHO/KIT-WT Cells: Confluent cells were washed once with sterile PBS, incubated with 0.25% Trypsin-EDTA at room temperature until cells detached from the plastic tissue culture plates. Complete culture medium, which contains FBS, was added to the plate to end the tryptic digestion.

Counting Cells: Ten microliters of cell suspension were mixed with 10 µL of 0.4% trypan blue. Half of this mixture (10 µL) was transferred into a cell counting chamber (Invitrogen), and the cells were counted. Cells (200,000 per well) were transferred into a 24-well cell culture plate, and cultivated in complete medium (Table 5) for 24 hours under normal cell culture conditions (i.e., humidified 95% air and 5% $CO_2$ atmosphere at 37° C.).

Cell Treatment: After the cells were plated in the 24-well plates and cultured overnight, the medium was removed, and the cell monolayer was washed once with starvation medium. The cells were then cultured for 24 hours in starvation medium under normal cell culture conditions. Then the cells were treated with antibody 37M or 37C or control antibody solutions for 2 hours under normal cell culture conditions. The final concentration for the antibody solution was 100 nM (5 µg/mL) or less. Subsequently, SCF solution was added to the cells pretreated with antibody 37M or 37C or control antibody at a final concentration of 30 ng/mL for 10 minutes under normal cell culture conditions.

Controls:
Negative controls: starved, untreated and non-stimulated cells
Positive control: starved, untreated and SCF-stimulated cells
Drug control: starved cells, treated with 1 pM Gleevec and stimulated with SCF
Antibody control: cells starved, treated with 100 nM blocking antibody (purified mouse anti-human KIT antibody (BioLegend A3C6E2) that binds to the SCF binding site)

Preparation of Cell Lysates: After stimulation, cells in the 24-well plate were placed on ice immediately, the cells were washed once with cold PBS, and lysed with 100 µL of cold lysis buffer.

Preparation of 96-Well ELISA Plate with Capture Antibody: Capture antibody (5 µL) was diluted in 10 mL 50 mM Borate buffer, and the capture antibody solution (100 µL or 50 ng/well) was added to each well of the 96-well ELISA plate. The 96-well plate was incubated at room temperature for 5-6 hours or overnight at 4° C. The capture antibody solution was removed prior to the blocking step. Blocking was carried out by adding 100 µL of blocking solution to each well and allowed to incubate at room temperature for 1 hour. The blocking solution was removed, the wells were washed once with dilution buffer, and 50 µL of dilution buffer were added to each well.

Phospho-KIT Assay: 50 µL of the cell lysates of each sample from a well of the 24-well plate were transferred into 1 well of the prepared 96-well plate containing 50 µL dilution buffer, and the 96-well plate was incubated overnight at 4° C. Following the overnight incubation, the supernatant was removed, and the plate was washed 3 times (5 minute incubation each time) with TBS-T. Detection antibody dilution (100 µL) was added to each well and incubated for 1 hour at room temperature in the dark. The plate was washed 3 times with TBS-T, washed once with TBS, and the TBS was removed. The "SuperSignal West Dura Extended Duration Substrate" reagents (Thermo Scientific) were mixed (1:1), and 100 µL of the mix were added to each well.

Luminescence was detected in the ELISA plate reader using the Gen5 protocol "Luminescence Glow" and the data were analyzed using Microsoft Excel. Both antibodies 37M and 37C inhibited KIT phosphorylation in these phospho-KIT assays.

FIG. 8 depicts a graph plotting the data from these experiments. The graph is a plot of arbitrary luminescence units versus log concentration (M) of either antibody 37M or antibody 37C. The 50% inhibition concentrations ($IC_{50}$) of antibody 37M and antibody 37C were calculated to be approximately 109 pM and 167 pM, respectively. FIG. 11A depicts the results of a separate experiment carried out with antibody 37M and CHO/KIT-WT cells. The $IC_{50}$ value in this experiment was calculated to be approximately 96 pM. The results indicate that antibodies 37M and 37C are effective inhibitors of ligand (SCF)-induced tyrosine phosphorylation of the cytoplasmic domain of KIT.

Cell-based phospho-KIT assays also were carried out with a population of CHO cells expressing wild-type KIT (CHO/KIT-WT cells) and of CHO cells expressing the KIT V560D mutant (CHO-V560D-KIT), wherein the cell population was sorted for selection of the highest KIT expressing cells. The cell sort for high KIT expression was carried out essentially as described in Section 6.2.

FIG. 11B depicts a graph plotting the data from cell-based phospho-KIT assays with sorted (high KIT expression) CHO/KIT-WT cells. The graph is a plot of relative luminescence units versus log concentration (M) of either antibody 37M or antibody 37C. The $IC_{50}$ values of antibody 37M and antibody 37C were calculated to be approximately 315 pM and 334 pM, respectively, using sorted CHO/KIT-WT cells. The results indicate that antibodies 37M and 37C are effective inhibitors of ligand (SCF)-induced tyrosine phosphorylation of the cytoplasmic domain of KIT. Here, these calculated $IC_{50}$ values are higher than the $IC_{50}$ values described in FIGS. 8 and 11A for phosphorylation inhibition assays using CHO/KIT-WT cells that were not presorted for high expression of KIT. The variation in $IC_{50}$ values obtained in FIG. 8 and FIG. 11B can be due to differences resulting from using sorted (high KIT expression) and unsorted CHO/KIT-WT cells. These data suggest that the blocking ability of antibody 37M may be related to the cell surface expression level of KIT protein.

6.4 Example 4: Blocking Ligand-Induced AKT Phosphorylation

Antibody 37M was assayed for the ability to inhibit or block AKT phosphorylation, which is a downstream signaling event of KIT signaling. The assay was carried out as described in section 6.3 with the following modifications. First, a mouse anti-AKT antibody was immobilized on the ELISA plates as a capture antibody. Second, the detection of AKT phosphorylation (phospho-AKT) was performed using a two-step method. After incubation of the cell lysates with the coated ELISA plate, a biotinylated mouse monoclonal antibody recognizing phospho-AKT (Ser473) was added to each well for 1 hour at room temperature at a dilution of 1:500. Following this incubation and subsequent washes, the phospho-AKT antibody was detected with Protein Western C Streptavidin-HRP antibody (BioRad) at a dilution of 1:2500. The final detection step with TMB substrate solution was performed as described in Example 2 (Section 6.2).

FIG. 13 depicts a graph plotting the data from phospho-AKT assays with sorted (high KIT expression) CHO/KIT-WT cells. The graph is a plot of relative luminescence units (RLUs) versus log concentration (M) of antibody 37M. The $IC_{50}$ value of antibody 37M was calculated to be approximately 138 pM based on data obtained with CHO/KIT-WT cells. The results indicate that antibody 37M is an effective inhibitor of ligand (SCF)-induced tyrosine phosphorylation of AKT downstream of KIT signaling.

6.5 Example 5: Animal Model Study of Anti-KIT Antibodies in Treating Cancer

The anti-tumor effects of anti-KIT antibodies described herein are confirmed using mouse models, such as xenograft mouse models, of human tumors. Various mouse models for studying cancer have been described (see, e.g., Fernandez et al., J. Clin. Invest., 2007, 117(12): 4044-4054). Below, mouse models, e.g., xenograft mouse models, derived from a variety of patient-derived, human cell lines are described. Mouse models for assessing toxicity are also described below.

Gastrointestional Stromal Tumor (GIST)

Mouse models of GIST have been described, for example, see, Fernández et al, J. Clin. Invest., 2007, 117(12): 4044-4054. For example, GIST cells are harvested from subconfluent cultures by a brief exposure to 0.05% trypsin-EDTA (Invitrogen). Trypsinization is stopped with medium containing 10% FBS. The cells are then washed twice in serum-free medium and resuspended in serum-free HBSS (Invitrogen). Single-cell suspensions with greater than 95% viability, as determined by Trypan blue exclusion, are used for the injections. To produce tumors, $1\times10^5$ to $1\times10^7$ GIST cells, for example $6\times10^6$ GIST cells per 100 l are injected subcutaneously into the unilateral flank of each SCID mouse (e.g., female C.B-17/IcrHsd-Prkdc$^{SCID}$ mice purchased from Harlan Sprague Dawley Inc.; housed in facilities approved by and in accordance with the American Association for Assessment and Accreditation of Laboratory Animal Care, the United States Department of Agriculture, the United States Department of Health and Human Services, and the NIH; and used according to institutional guidelines). Five to ten mice per group in the vehicle and anti-KIT antibody groups are used. Once tumors are palpable (e.g., approximately 8-11 weeks from injection), mice are started on therapy with injections of normal saline (vehicle) or anti-KIT antibodies (e.g., 37M or 37C antibodies, including antibody drug conjugates, for example, 37M or 37C antibody drug conjugates), for example, daily, weekly, or bi-weekly intraperitoneal injections. Treatment is continued for a period of time, e.g., approximately 6 weeks, with weekly 2-dimensional measurements of tumor size. Imaging methods for detecting tumor size can also be used, e.g., MRI. All mice are sacrificed when the tumor size approach approximately 1.5 cm in the control group. Tumors are collected, are fixed in formalin, and are analyzed by H&E staining. Representative images are taken from each tumor using a light microscope at ×40 and ×100 magnification.

A graph of tumor size or volume of each mouse plotted against time (e.g., days or weeks) after tumor injection is generated to ascertain the effect of the anti-KIT antibodies on tumor growth in the mice relative to the vehicle negative control.

Non-limiting examples of GIST cells which may be used in these mouse models include, GIST 430 cells and GIST882 cells (immortal GIST cells that possess a homozygous exon 13 missense mutation (i.e., K642E) in KIT (see, e.g., Tuveson et al., Oncogene, 2001, 20: 5054 5058)).

Leukemia

To study the effects of anti-KIT antibodies on leukemia, a xenograft mouse model using human leukemia cells (e.g., K562, HEL, or HL60 cells) is established essentially as described above, except that leukemia cells (e.g., K562, HEL, or HL60 cells) are injected into the mice instead of GIST cells. In particular, the tumor cells are collected from subconfluent suspensions. To produce tumors, $1\times10^5$ to $1\times10^7$ tumor cells per 100 µl are injected into each SCID mouse. The mice are then randomized into the following groups (n=5-10 per group): (a) normal saline daily; and (b) anti-KIT antibodies (e.g., 37M or 37C antibodies, including antibody drug conjugates, for example, 37M or 37C antibody drug conjugates). The mice are started on therapy (e.g., at day 0, 7, or 14 or when tumors are detectable) with injections of normal saline (vehicle) or anti-KIT antibodies (e.g., daily, weekly, or bi-weekly intraperitoneal injections). Treatment is continued for a period of time, e.g., approximately 6 weeks, with weekly 2-dimensional measurements of tumor size. Imaging methods for detecting tumor size can also be used, e.g., MRI. Tumors are measured weekly during treatment and at necropsy.

A graph of tumor size or volume of each mouse plotted against time (e.g., days or weeks) after tumor injection is generated to ascertain the effect of the anti-KIT antibodies on tumor growth in the mice relative to the vehicle negative control.

Mouse models of human leukemia also can be generated by injecting human leukemia cells into nude mice or irradiated mice, via other routes, such as intravenous route, and monitoring animal death as an indication of progression of leukemia in the presence or absence of treatment with anti-KIT antibodies. A survival curve is generated for each mouse to ascertain the effect of anti-KIT antibodies on survival.

Lung Cancer (e.g., Small Cell Lung Cancer)

A xenograft mouse model using human lung cancer cells, e.g., human small cell lung carcinoma cells (e.g., H526 cells, WBA cells, or NCI-H209 cells) is established essentially as described above, except for a few modifications. For example, lung cancer cells (e.g., small cell lung cancer cells) are injected into mice instead of GIST cells. Lung cancer cells, e.g., H526 tumor cells, are collected, and $1 \times 10^5$ to $1 \times 10^7$ lung cancer cells per 100 µl are injected into each mouse (e.g., SCID mouse). The mice are then randomized into the following groups (e.g. n=5-10 per group): (a) normal saline daily; and (b) anti-KIT antibodies (e.g., 37M or 37C antibodies, including antibody drug conjugates, for example, 37M or 37C antibody drug conjugates). The mice are started on therapy (e.g., at day 0, 7, or 14 or when tumors are detectable) with injections (e.g., daily, weekly, or bi-weekly intraperitoneal injections) of normal saline (vehicle) or anti-KIT antibodies. Treatment is continued for a period of time (e.g., approximately 6 weeks or more), with weekly 2-dimensional measurements of tumor size. Imaging methods for detecting tumor size can also be used, e.g., MRI. Tumors are measured weekly during treatment and at necropsy.

A graph of tumor size or volume of each mouse plotted against time (e.g., days or weeks) after tumor injection is generated to ascertain the effect of the anti-KIT antibodies on tumor growth in the mice relative to the vehicle negative control. A survival curve is generated to ascertain the effect of the anti-KIT antibodies (e.g., antibody 37M, antibody comprising CDRs of antibody 37M, or a conjugate thereof) on animal survival.

Mouse models for lung cancer (e.g., small cell lung cancer) have been described (see, e.g., Garton et al., 2006, Cancer Res. 66(2):1015-24; and Wolff et al., 2004, Clin Cancer Res. 10:3528-3534), and may be adapted accordingly to study the effects of anti-KIT antibodies described herein.

Sarcoma

Xenograft models are established using cell lines derived from Ewing's family of tumors, such as RD-ES, SK-ES-1 or SK-N-MC, or rhabdomyosarcomas, such as A-673. Cell lines are available from the American Type Culture Collection (ATCC; Manassas, Va.). Generally, methods similar to those described above are utilized. For example, $2.5-5 \times 10^6$ cells are suspended with trypsin/EDTA or re-suspended in 100-200 µL growth medium and implanted subcutaneously into the flank of 6-8 week old immunodeficient mice (NuNu, SCID) (Charles River Laboratories, Wilmington, Mass.). Five to ten mice per group in both the vehicle and anti-KIT antibody groups are used. Once tumors are palpable or have reached 100-200 mm$^3$, mice are started on therapy with injections (e.g., daily, weekly, or bi-weekly intraperitoneal injections) of normal saline (vehicle) or anti-KIT antibodies (e.g., 37M or 37C antibodies, including anti-KIT antibody drug conjugates, for example, 37M or 37C antibody drug conjugates). Treatment is continued for a period of time, e.g., approximately 6 weeks or more, and tumor size is evaluated (e.g., twice weekly by way of 2-dimensional measurements). Imaging methods for detecting tumor size can be used, e.g., MRI. Mice are sacrificed when the tumor size approach a certain size (e.g., approximately 1.5 cm) in the control group. Tumors are collected, are fixed in formalin, and are analyzed by H&E staining. Representative images are taken from each tumor using a light microscope at, e.g., at ×40 and ×100 magnification.

A graph of tumor size or volume of each mouse plotted against time (e.g., days or weeks) after tumor injection is generated to ascertain the effect of the anti-KIT antibodies on tumor growth in the mice relative to the vehicle negative control.

Mouse models for sarcoma (e.g., Ewing's sarcoma) have been described, for example, see the following list of publications, and may be adapted accordingly to evaluate the effects of anti-KIT antibodies (e.g., antibody 37M or 37C):

González et al., 2004, Clin Cancer Res. 10(2):751-61;
Landuzzi et al., 2000, Am J Pathol. 157(6):2123-31 (6647 cells);
Merchant et al., 2002, JNCI 94(22):1673-1679 (TC71 cells);
Sturla et al., 2000, Cancer Res. 60(21):6160-70 (TC32 and RD-ES cells);
Powis et al., 2006, Mol Cancer Ther. 5(3):630-636 (A-673 cells);
Watanabe et al., 2008, Hum Gene Ther. 19(3):300-10 (A-673 cells);
Rouleau et al., 2008, Clin Cancer Res. 14(22):7223-7236 (A-673 cells);
Karmakar et al, 2011, World J Oncol. 2(2):53-63 (RD-ES and SK-N-MC cells);
Wang et al., 2009, In Vivo 23(6):903-9 (TC71 cells); and
Ikeda et al., 2010, Mol Cancer Ther. (3):653-60 (TC71 cells and A4573 cells).

Humanized Mouse Model

Studies with anti-KIT antibodies, including anti-KIT antibody drug conjugates, for example, 37M or 37C antibodies, including 37M or 37C antibody drug conjugates are carried out with mouse models generated by engraftment of immunodeficient mice with components of human immune system, e.g., humanized NSG mice (The Jackson Laboratory, Bar Harbor, Me.). Humanized NSG mice are NOD scid IL-2 receptor gamma chain knockout mice (NSG) engrafted with human hematopoietic stem cells (hCD34$^+$ cells) to reconstitute a human immune system.

These mice can serve as a platform for studying toxicity of anti-KIT antibodies. For example, groups of mice (e.g., 1-5 mice) are injected with various concentrations of anti-KIT antibodies over a period of time (e.g., 4-16 weeks). The mice are assessed for toxicity indicators, e.g., body weight, survival length.

6.6 Example 6: Competitive Binding Assays

Competitive binding assays were carried out with antibody 37M or 37C as described below and using solid phase ELISA as described in Example 2 (Section 6.2). In particular, serial dilutions of the reference antibody (either 37M or 37C) were combined with constant concentrations of a competing antibody (37M in the case of 37C, and 37C in the case of 37M) and incubated in wells of 96-well plates coated with a recombinant KIT polypeptide containing the D4/D5 region depicted in FIG. 2A. Reference antibody binding was then detected through the use of an HRP-conjugated, species-specific secondary antibody. Antibody 37M has a mouse constant region while antibody 37C has a human constant region. Therefore, when antibody 37M was used as a reference antibody and antibody 37C was used as a competing antibody, the reference antibody was detected using an anti-mouse IgG secondary antibody; and when antibody 37C was used as a reference antibody and antibody 37M was used as a competing antibody, the reference antibody was detected using an anti-human IgG secondary antibody. In certain variations of these competitive binding assays, the reference antibody can be conjugated to a detection molecule, e.g., biotin or a fluorescent molecule.

Coating plates with antigen: Recombinant antigen containing the D4/D5 region of the KIT extracellular Ig-like region (see FIG. 2A) was absorbed to 96-well microtiter plates. Recombinant antigen, i.e., D4/D5 region of human KIT (10 μg), was diluted into 10 mL of borate buffer, and 100 μL of the antigen solution were added to each well of a 96 well plate. The 96 well plate was covered with a plate sealer and incubated at 4° C. overnight.

Eight, 3-fold dilutions of the reference antibody samples were prepared beginning at 20 nM (2x), and combined 1:1 with a 20 nM solution of the competing antibody to yield final 1x values. The plate with the absorbed antigen, was incubated with 200 μL blocking buffer at room temperature for one hour, prior to incubation with the reference and competitor antibodies. The control wells were incubated with buffer and reference antibody alone at the concentrations tested. After 1 hour, the plates were washed, and HRP-conjugated secondary antibody (anti-mouse-HRP or anti-human-HRP) was added to each well. The plates were processed similarly as described above for data collection on a plate reader. Data analysis was carried out using Graph Pad Prism and Excel as described above.

An increase in the $EC_{50}$ value for the reference antibody in the presence of the competitor antibody relative to the reference antibody alone demonstrated that antibodies 37M and 37C compete for binding to the KIT D4/D5 antigen, as shown in FIGS. 14A-B. FIG. 14A depicts the results from competition assays where antibody 37M served as the reference antibody and antibody 37C served as the competitor antibody (10 nM). As shown in FIG. 14A, the $EC_{50}$ value for reference antibody 37M, which was calculated to be 115 pM, increased to 2.8 nM in the presence of the competitor antibody 37C (10 nM). FIG. 14B depicts the results from competition assays where antibody 37C served as the reference antibody and antibody 37M served as the competitor antibody (10 nM). As shown in FIG. 14B, the $EC_{50}$ value for reference antibody 37C, which was calculated to be 48 pM, increased to 1 nM in the presence of competitor antibody 37M (10 nM).

Variations of these competition assays include flow cytometry assays for detecting binding of a reference antibody at various concentrations, in the presence and absence of a competitor antibody, to cells expressing KIT on the cell surface.

6.7 Example 7: Inhibition of Colony Formation by KIT Expressing CHO Cells in Soft Agar Assays Antibody 37M was also tested for its ability to inhibit anchorage independent cell growth in soft agar assays of CHO/KIT-WT cells. Soft agar assay for colony formation is an anchorage independent growth assay, which is a useful assay for detecting malignant transformation of cells. In vitro transformation is associated with certain phenotypic changes such as loss of contact inhibition (cells can grow over one another) and anchorage independence (cells form colonies in soft agar). In general, nontransformed cells fail to grow when suspended in a viscous fluid or gel (e.g. agar or agarose), however when these cells are transformed, they are able to grow in a viscous fluid or gel and become anchorage-independent. The process by which these phenotypic changes occur, is assumed to be closely related to the process of in vivo carcinogenesis.

The soft agar assays were carried out as follows. Base agar layer (containing agar and cell culture medium) was added to each well of a 96 well plate. Cell agar layer (containing agar, cell culture medium and cell suspension) was added on top of the base agar layer. Anti-KIT antibody 37M was diluted in cell culture medium and pipetted on top of the layers. The control samples did not contain any antibodies. Plates were incubated at 37° C. and 5% $CO_2$ for 5-8 days in the presence or absence of 30 ng/mL SCF. The ligand SCF and the antibody 37M (100 nM) were added concurrently to the agar.

When treatment was completed, the agar was solubilized and the cells were lysed. The green fluorescent Cyquant® GR dye was mixed with the lysates. This dye exhibits fluorescence when bound to cellular nucleic acids. Fluorescence was measured at 480 nm excitation and 520 nm emission.

The results from the soft agar assays are depicted in FIG. 9. Antibody 37M was able to inhibit soft agar formation induced by SCF.

6.8 Example 8: Antibody 37M Binds to Mutant KIT Containing a Duplication of Ala502 and Tyr503

In certain cases, a somatic mutation associated with GIST in the extracellular domain of KIT (exon 9 of human KIT) has been observed, wherein the Ala and Tyr residues at positions 502 and 503, respectively, are duplicated (KIT A502-Y503 duplication mutant) (see, e.g., Marcia et al., (2000) Am. J. Pathol. 156(3):791-795; and Debiec-Rychter et al., (2004) European Journal of Cancer. 40:689-695a). Specifically, this mutation is in domain 5 (D5) of the extracellular domain of human KIT. Binding studies were carried out to characterize the specific binding of antibody 37M to the KIT A502-Y503 duplication mutant.

For example, a FACS-based study was performed. Briefly, sorted (high KIT expression) CHO cells expressing wild-type KIT (see, e.g., FIG. 10C) or KIT A502-Y503 duplication mutant (CHO-KIT-A502-Y503) were harvested with 2 mM EDTA and blocked in PBS buffer containing 1% FBS and 0.01% Sodium Azide (to prevent receptor internalization) (FACS buffer) for one hour on ice. Next, cells were incubated with antibody 37M or an IgG control antibody for one hour on ice in FACS buffer. Cells were washed two times with FACS buffer, and run through the ACCURI® cytometer (Ann Arbor, Mich.) for analysis with BD Cflow® software. CHO cells stably transfected with full-length, wild-type KIT were compared to CHO cells stably transfected with the KIT 502-503 duplication mutant. Antibody 37M bound to the wild-type-KIT-expressing cells evidenced by a clear shift in the fluorescence peak following staining with the anti-KIT antibody compared to the IgG control. In staining the CHO-KIT-A502-Y503, the 37M antibody also generated a shift in the fluorescence peak compared to IgG controls. These FACS data indicate that antibody 37M binds to the KIT 502-503 duplication mutant, as well as to wild-type KIT, expressed on cell surfaces. FIG. 12 depicts the results from the flow cytometry experiment which was carried out with sorted CHO-KIT-A502-Y503. In particular, more intense fluorescent signals were detected in samples where the sorted CHO-KIT-A502-Y503 cells were incubated with increasing concentrations of antibody 37M.

6.9 Example 9: Antibody Internalization by NIH3T3 Cells Expressing Exogenous Human, Wild-Type KIT Immunofluorescence staining assays were carried out to determine if antibody 37M or 37C is internalized by cells. The immunofluorescence staining assays were carried out essentially as described below with NIH3T3 cells engineered to express exogenous human, wild-type KIT (full-length) ("NIH3T3/KIT"). Materials and reagents for the immunofluorescence assays include the following:

Tissue culture slides: Poly-D-Lysine coated four or eight well chamber slide

Antibodies: Antibody 37M conjugated with the fluorescent dye Alexa-488 (antibody 37M-Alexa-488) and antibody 37C conjugated with the fluorescent dye Alexa-488 (antibody 37C-Alexa-488)

Fixative: 4% paraformaldehyde (PFA) (store 40% PFA microscopy grade in fridge and dilute 1:10 with PBS just before use)

Mounting media: Prolong Gold antifade reagent with DAPI (4',6-diamidino-2-phenylindole)

NIH3T3 cells were engineered to express exogenous human, wild-type KIT (full-length) ("NIH3T3/KIT")

NIH3T3/KIT cells (15,000 to 30,000 cells per well) were seeded onto tissue culture slides. The cells were cultivated for at least 24 hours before starvation in media containing no fetal bovine serum overnight. Antibody 37M-Alexa488 or antibody 37C-Alexa488 was diluted in starvation media containing 1% bovine serum albumin and pipetted onto the cell layer. Cell layers were washed once with PBS (room temperature) 5 to 60 minutes later. Cell layers were fixed for 18 minutes with fixative at room temperature, and were washed 3 times with PBS. The cells were mounted between slide and coverslip and were kept at room temperature overnight. Internalization of the antibody was analyzed by confocal microscopy.

The immunofluorescence staining assays demonstrated that antibodies 37M and 37C bound to the surface of NIH3T3/KIT cells, and were internalized by NIH3T3/KIT cells.

6.10 Example 10: Antibody Internalization by CHO Cells Expressing Wild-Type KIT or Mutant KIT Immunofluorescence staining assays were carried out to assess internalization of antibody 37M by CHO cells expressing mutant KIT (CHO/KIT-V560D/Y823D or CHO/KIT-502.503) relative to CHO cells expressing wild-type KIT ("CHO/KIT-WT"). Certain mutations in KIT have been associated with cancer, such as a mutant KIT containing a duplication of Ala502 and Tyr503 (KIT A502-Y503 duplication mutant). This mutation is in domain 5 (D5) of the extracellular domain of human KIT. For these experiments, CHO cells were engineered to express the KIT A502-Y503 duplication mutant ("CHO/KIT-502.503"). Another mutant KIT that has been associated with cancer is mutant KIT containing mutations V560D and Y823D. Also for these experiments, CHO cells were engineered to express KIT containing mutations V560D and Y823D ("CHO/KIT-V560D/Y823D").

The immunofluorescence staining assays were carried out essentially as described below. Materials and reagents for the immunofluorescence assays included the following:

24 well tissue culture plates 12 mm, optically clear, round glass coverslips

Primary antibodies: antibody 37M, β-Tubulin (9F3) rabbit monoclonal antibody (mAb) (Cell Signaling #2128)

Secondary antibodies: goat anti-mouse antibody conjugated to Oregon Green® 488 (Invitrogen #011038), goat anti-rabbit antibody conjugated to Texas Red (Invitrogen # T2767)

Fixative: 4% paraformaldehyde (PFA) (store 40% PFA microscopy grade in fridge and dilute 1:10 with PBS just before use)

Permeabilization solution: PBS with 0.1% Triton X-100 and 0.5% BSA, sterile filtered Blocking/dilution solution: 2% BSA in PBS, sterile filtered Mounting media: ProLong® Gold antifade reagent with DAPI (P36931 Invitrogen) (4',6-diamidino-2-phenylindole)

Microscope slides: FisherFinest Superfrost Microscope Slides (Fisher #22-038-103)

Microscope: Nikon Eclipse Ti and NIS-Elements Software

CHO cells engineered to express exogenous human, wild-type KIT (full-length) ("CHO/KIT-WT") or mutant KIT (CHO/KIT-V560D/Y823D, CHO/KIT-502.503)

CHO cells (75,000 cells per well) were seeded into a 24-well tissue culture plate containing one round glass coverslip per well. The cells were cultivated for at least 6 hours before overnight starvation in media containing no fetal bovine serum. Following starvation, the culture media was removed from the cells and antibody 37M, diluted to 33.3 nM in starvation media containing 1% bovine serum albumin, was transferred onto the cell layer at time 0 minute, 30 minutes, 45 minutes or 55 minutes to generate a time course. Cells were incubated for the indicated times under standard culture conditions (37° C. and 5% $CO_2$). Cell layers were washed once with PBS (room temperature) 5 to 60 minutes after addition of the antibody. Cell layers were fixed for 20 minutes with 4% PFA at room temperature, and were washed 3 times with PBS. Cell membranes were permeabilized by the addition of permeabilization solution for 3 minutes followed by 3 washes with PBS. Blocking solution was added to each well, and cells were blocked for 20 minutes at room temperature. The β-Tubulin (9F3) rabbit mAb was diluted 1:100 in dilution solution and incubated with the cell layers for 1 hour at room temperature followed by 2 washes with PBS and one with blocking solution. Both secondary antibodies were diluted together at 1:200 in dilution solution before being added to the cells. Cells were incubated in secondary antibody in the dark at room temperature for 1 hour followed by 3 PBS washes. The cells on the coverslips were mounted against the glass slides using one drop of ProLong® Gold antifade reagent with DAPI and were kept at room temperature overnight. Internalization of the antibody was analyzed by fluorescence microscopy at various time point, e.g., 5 minutes and 60 minutes of exposure to antibody 37M.

The immunofluorescence staining assays demonstrated that, in all three cell populations CHO/KIT-WT cells, CHO/KIT-V560D/Y823D cells, and CHO/KIT-502.503 cells, antibody 37M bound to the surface of these cells, and were internalized by these cells. In particular, images of cells exposed to antibody 37M show staining of membrane-associated structures at early time points, such as at 5 minutes after exposure to antibody 37M, and show staining of internal structures (e.g., vesicles) at later time points, such as at 60 minutes after exposure to antibody 37M. In contrast, images of cells exposed with anti-β-Tubulin antibody, as a control, showed staining of elongated structures throughout the cytoplasm of the cells. These results indicate that antibody 37M has specific affinity for wild-type KIT as well as these mutant forms of KIT associated with cancer, and can be internalized by cells expressing these forms of KIT. Effective internalization of antibody 37M is useful, e.g., for delivering toxins to cancer cells expressing KIT, utilizing both wild-type and mutant forms of KIT associated with cancer.

6.11 Example 11: Antibody Internalization by H526 Cells Expressing Wild-Type KIT Immunofluorescence staining assays were performed to assess internalization of antibody 37M by the small cell lung cancer cell line, H526 which expresses wild-type KIT. Anti-KIT 37M antibody conjugated with the fluorescent dye Alexa488 (37M-Alexa488) was used in these immunofluorescence staining assays and were shown to be internalized by H526 cells. The immunofluorescence staining assays were carried out essentially as follows.

Material and Methods:

In each well of a four chamber slide coated with poly-D-lysine, 60,000 H526 cells were grown for 24 hours and then starved in the absence of fetal bovine serum for another 16 hours or overnight. Cells were incubated under normal culture conditions (37 degrees Celsius and 5% C02) for 10 and 30 minutes in the presence of 10, 30 and 100 nM antibody 37M conjugated with Alexa488 using the Alexa Fluor® 488 Protein Labeling Kit *3 labelings* from Molecular Probes (A10235 Invitrogen). Following the antibody incubations, cells were washed with PBS, fixed for 18 minutes with 4% paraformaldehyde and mounted in Pro-Long® Gold antifade reagent with DAPI (P36931 Invitrogen) underneath a microscope glass cover. As a control, H526 cells were incubated for 10 or 30 minutes in starvation media containing 0.2% BSA that was used to dilute the antibody. Samples were analyzed using a confocal laser scanning microscope.

Results:

In contrast to the control images showing background, blurry autofluorescence, antibody 37M-488 staining was visible distinctively in close proximity to, or at the plasma membrane of H526 cells 10 minutes after treatment with antibody 37M-488 at all three concentrations, i.e., 10, 30 and 100 nM. After 30 minutes of incubation with antibody 37M-488, staining of vesicular structures localized in the cytoplasm could be visualized, indicating internalization of antibody 37M-488 by H526 cells. The staining of these vesicular structures was more abundant and more distinct in cells treated with 100 nM of antibody 37M-488 than in cells treated with the lower concentrations. Such staining was not observed in the control samples treated only with the dilution buffer without antibody 37M-488.

6.12 Example 12: Antibody 37M as an Antibody-Drug Conjugate Blocks Cell Proliferation Cell proliferation experiments were performed to assess the effectiveness of antibody 37M as an antibody-drug conjugate (ADC) for use as an anti-cancer therapeutic. The Mab-Zap (Advanced Targeting Systems, San Diego, Calif.) saporin-secondary antibody system was used to generate an ADC with antibody 37M. Mab-Zap is a goat anti-mouse IgG secondary antibody that is conjugated to saporin, a ribosome-inactivating protein from the seeds of the plant *Saponaria officinalis*. Upon coincubation with the 37M mouse antibody, the Mab-Zap secondary antibody binds to the 37M antibody forming, via non-covalent interactions, an ADC that targets KIT. Once antibody 37M is internalized, and thus Mab-ZAP also is internalized, saporin breaks away from the targeting agent and inactivates the ribosomes, which causes protein inhibition and, ultimately, cell death.

This 37M-ADC was tested on GIST cells. Specifically, results were obtained with the GIST cell line GIST 430 (FIGS. 15A-B). GIST 430 cells are derived from imatinib-resistant human GIST and have a heterozygous primary KIT exon 11 (juxtamembrane region) in-frame deletion, accompanied by a heterozygous secondary exon 13 (kinase ATP-binding region) missense mutation (V654A) (see, e.g., Bauer et al., Cancer Res. 2006, 66:9153-9161).

The cells were plated onto 96-well plates, and then were treated with various doses of antibody 37M (ranging from 100 fM to 100 nM) in 2% FBS medium, generating a dose curve, and the Mab-Zap secondary antibody (25 ng/100 µL or 50 ng/100 µL). Following 96 hours in culture, CellTiter-Glo® reagent (Promega Madison, Wis.) was used to determine ATP content in each well (an indirect measurement of cell proliferation).

Specifically, dose-dependent inhibition of cell proliferation was observed when GIST 430 cells were treated with 37M-ADC (FIG. 15A), but not with an ADC of an antibody that specifically binds to VEGFR-2 (anti-VEGFR2 mAb) (FIG. 15B). Moreover, inhibition of cell proliferation was not observed when a GIST cell line that does not express KIT protein, the GIST 48B cell line, was treated with 37M-ADC (FIGS. 15C-D). These results indicate that the 37M-ADC can specifically inhibit proliferation of GIST cells that express KIT.

This 37M-ADC also was tested with CHO cells engineered to express wild-type KIT, for example, CHO/WT-KIT cells, or a mutant form of KIT, for example, CHO/KIT-502.503 cells (CHO cells expressing the KIT 502-503 duplication mutant) or CHO/KIT-V560D/Y823D, as follows. The cells were plated onto 96-well plates, and then were treated with various doses of antibody 37M (ranging from 100 fM to 100 nM) in 2% FBS medium, generating a dose curve, and the Mab-Zap secondary antibody (25 ng/100 µL or 50 ng/100 µL). Following 72 hours in culture, Cell-Titer-Glo® reagent (Promega Madison, Wis.) was used to determine ATP content in each well (an indirect measurement of cell proliferation). In parallel experiments, CHO cells were treated with an ADC of anti-VEGFR-2 mAb.

The results from these experiments are depicted in FIGS. 16A-B (CHO/WT-KIT cells), FIGS. 16C-D (CHO/KIT-502.503 cells), and FIGS. 16E-F (CHO/KIT-V560D/Y823D cells). Specifically, the results show that inhibition of cell proliferation was observed when CHO cells expressing wild-type KIT or a mutant form of KIT (i.e., KIT-502.503 or KIT-V560D/Y823D) were treated with 37M-ADC, but not with an ADC of an anti-VEGFR2 mAb. These results indicate that 37M-ADC can specifically inhibit proliferation of cells that express wild-type KIT or at least certain mutant forms of KIT that have been associated with cancer.

6.13 Example 13: Antibody 37M Binds to Denatured KIT

Experiments described herein above demonstrate that antibody 37M binds native, cell surface expressed KIT. An immunoblot assay was performed to examine the ability of antibody 37M to bind denatured human KIT. The results of this experiment indicate that antibody 37M binds to denatured KIT protein. Briefly, CHO-WT KIT cells were lysed, and total cell lysate was denatured for 15 minutes at 75° C. and run on a 4-12% Bis-Tris SDS-PAGE gel in MOPS buffer. Protein was then transferred to nitrocellulose membranes. The membranes were blocked in 5% milk in TBS-T for 1 hour at room temperature and stained with either 1 µg/mL antibody 37M or g/mL antibody 37M and rabbit monoclonal anti-β-Tubulin antibody (Cell Signaling Technology®), which was used as a loading control, overnight in TBST+1% BSA at 4° C. Following washes in TBST, the membranes were stained with anti-rabbit-horseradish peroxidase (HRP) and anti-mouse-HRP secondary antibodies for 1 hour in TBST+1% BSA. Signals were detected with Pierce Supersignal® West Pico reagent. A band corresponding to the molecular weight of wild-type, full-length KIT was detected on the membrane immunoblotted with antibody 37M. For example, FIG. 17D is a Western blot, performed under denaturing conditions, showing that antibody 37M was able to detect KIT protein in denatured form.

6.14 Example 14: Affinity for Glycosylated Forms of KIT

To characterize the binding specificity of antibody 37M for glycosylated KIT and non-glycosylated KIT, solid phase ELISAs were performed. Briefly, KIT antigen containing either the entire extracellular domain (D1-D5) or domains 4 and 5 (D4/D5) was de-glycosylated using PNGase F (New England Biolabs # P0705). KIT antigen was combined with 1 μL of 10× glycoprotein denaturing buffer and water to a final volume of 10 μL, and denatured at 100° C. for 10 minutes. Next, 2 μL of 10 OX G7 reaction buffer, 2 μL of 10% NP40, 5 μL water and 1 μL PNGase F were added to the reaction before incubation at 37° C. for 1 hour. PNGase F-treated antigens were assessed for loss of glycosylation by SDS-PAGE. The shift of the protein to a lower molecular weight in the PNGaseF-treated samples compared to untreated proteins indicates loss of protein glycosylation (FIG. 17A). PNGase F-treated KIT ECD and KIT D4/D5 antigens, and corresponding non-treated antigens, were used for solid phase ELISA with the 37M antibody as described in Example 2 (Section 6.2). The results presented in FIGS. 17B-C demonstrate that the 37M antibody binds with similar affinity to both glycosylated and non-glycosylated KIT D4/D5 (FIG. 17B) or KIT ECD antigens (FIG. 17C).

To further confirm binding of the 37M antibody to both glycosylated and non-glycosylated KIT protein, immunoprecipitation assays were performed. CHO cells transfected and selected to stably express wildtype KIT protein as described above were collected and lysed in 50 mM Tris pH 7.4 with 150 mM NaCl, 1 mM EDTA, 1% Triton X-100, protease inhibitor cocktail tablets-EDTA free, and 1 mM NaVO$_4$. The protein concentration was determined by a standard Bradford Assay, and two pools of 2 mg total protein were incubated with rotation overnight at 4° C. with 10 μg antibody 37M in 1.7 mL microcentrifuge tubes. Antibody 37M-bound KIT protein was immunoprecipitated from each sample using protein G magnetic sepharose beads (GE Healthcare #28-9440-08) and the manufacturer's protocol. Following three washes of the beads with PBS, 2.5 μL of 10× denaturing buffer (New England Biolabs), 0.25 μL of 100× protease inhibitor mix (Roche Diagnostics) and 22.25 μL of water were added to each tube. Samples were boiled for 10 minutes. Following denaturation, 5 μL of 10× G7 reaction buffer, 5 μL of NP-40 and 9.75 μL of water were added to each tube. For the control (glycosylated) sample, 5 μL of water was then added, and for the de-glycosylated sample, 5 μL of PNGase F (NEB # P0705) was added. Samples were incubated for 1.5 hours at 37° C. The magnetic beads were then collected by centrifugation, and the supernatants (50 μL) were transferred to new tubes and combined with 17 μL 4× loading dye and 6 μL 10× sample reducing agent. For a second elution from the magnetic beads, 25 μL 1× loading dye/reducing agent was added to each tube and samples were incubated at 95° C. for 10 minutes. Control samples, PNGase F-treated samples and 50 μg input (cell lysate) were run on a NuPAGE 4-12% Bis-Tris gel (Invitrogen) in 1×MOPS buffer. Protein was then transferred to a nitrocellulose membrane and a Western blot for KIT protein and β-tubulin was performed as described above. The Western blot is shown in FIG. 17D. These data demonstrate that antibody 37M binds both glycosylated KIT protein (input and untreated samples, higher molecular weight KIT band) and non-glycosylated KIT protein (PNGase F samples, lower molecular weight KIT band).

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims. Furthermore, as used in this specification and claims, the singular forms "a," "an" and "the" include plural forms unless the content clearly dictates otherwise. Thus, for example, reference to "an antibody" includes a mixture of two or more such antibodies, and the like. Additionally, ordinarily skilled artisans will recognize that operational sequences must be set forth in some specific order for the purpose of explanation and claiming, but the present invention contemplates various changes beyond such specific order.

All references cited herein are incorporated herein by reference in their entirety and for all purposes to the same extent as if each individual publication or patent or patent application was specifically and individually indicated to be incorporated by reference in its entirety for all purposes.

Other embodiments are within the following claims.

---

What is claimed:

1. A method for treating or managing a KIT-mediated disorder, wherein the KIT-mediated disorder is associated with KIT expression and/or activity, the method comprising administering to a subject in need thereof a therapeutically effective amount of an antibody or an antigen-binding fragment thereof, which immunospecifically binds to human KIT and comprises:
   (i) a variable light ("VL") chain region comprising a VL CDR1, VL CDR2, and VL CDR3 comprising the amino acid sequences of SEQ ID NO: 20, SEQ ID NO: 21, and SEQ ID NO: 22, respectively; and
   (ii) a variable heavy ("VH") chain region comprising a VH CDR1, VH CDR2, and VH CDR3 comprising the amino acid sequences of SEQ ID NO: 23, SEQ ID NO: 24, and SEQ ID NO: 25, respectively.

2. A method for treating or managing a KIT-mediated disorder, wherein the KIT-mediated disorder is associated with KIT expression and/or activity, the method comprising administering to a subject in need thereof a therapeutically effective amount of a conjugate comprising an antibody or an antigen-binding fragment thereof, which immunospecifically binds to human KIT and comprises:
   (i) a VL chain region comprising a VL CDR1, VL CDR2, and VL CDR3 comprising the amino acid sequences of SEQ ID NO: 20, SEQ ID NO: 21, and SEQ ID NO: 22, respectively; and
   (ii) a VH chain region comprising a VH CDR1, VH CDR2, and VH CDR3 comprising the amino acid sequences of SEQ ID NO: 23, SEQ ID NO: 24, and SEQ ID NO: 25, respectively,
   which antibody or antigen-binding fragment thereof is linked to a therapeutic agent.

3. The method of claim 1, wherein the KIT-mediated disorder is cancer, an inflammatory condition, or fibrosis.

4. A method for inhibiting KIT activity in a cell expressing KIT comprising contacting the cell with an effective amount of an antibody or an antigen-binding fragment thereof, which immunospecifically binds to human KIT and comprises:
   (i) a VL chain region comprising a VL CDR1, VL CDR2, and VL CDR3 comprising the amino acid sequences of SEQ ID NO: 20, SEQ ID NO: 21, and SEQ ID NO: 22, respectively; and
   (ii) a VH chain region comprising a VH CDR1, VH CDR2, and VH CDR3 comprising the amino acid sequences of SEQ ID NO: 23, SEQ ID NO: 24, and SEQ ID NO: 25, respectively.

5. A method for inducing or enhancing apoptosis in a cell expressing KIT comprising contacting the cell with an effective amount of an antibody or an antigen-binding fragment thereof, which immunospecifically binds to human KIT and comprises:
   (i) a VL chain region comprising a VL CDR1, VL CDR2, and VL CDR3 comprising the amino acid sequences of SEQ ID NO: 20, SEQ ID NO: 21, and SEQ ID NO: 22, respectively; and
   (ii) a VH chain region comprising a VH CDR1, VH CDR2, and VH CDR3 comprising the amino acid sequences of SEQ ID NO: 23, SEQ ID NO: 24, and SEQ ID NO: 25, respectively.

6. A method for inducing cell differentiation comprising contacting a cell expressing KIT with an effective amount of an antibody or an antigen-binding fragment thereof, which immunospecifically binds to human KIT and comprises:

(i) a VL chain region comprising a VL CDR1, VL CDR2, and VL CDR3 comprising the amino acid sequences of SEQ ID NO: 20, SEQ ID NO: 21, and SEQ ID NO: 22, respectively; and (ii) a VH chain region comprising a VH CDR1, VH CDR2, and VH CDR3 comprising the amino acid sequences of SEQ ID NO: 23, SEQ ID NO: 24, and SEQ ID NO: 25, respectively.

7. The method of claim 2, wherein the KIT-mediated disorder is cancer, an inflammatory condition, or fibrosis.

8. The method of claim 3, wherein the cancer is leukemia, chronic myelogenous leukemia, lung cancer, small cell lung cancer, or gastrointestinal stromal tumors.

9. The method of claim 7, wherein the cancer is leukemia, chronic myelogenous leukemia, lung cancer, small cell lung cancer, or gastrointestinal stromal tumors.

10. The method of claim 3, wherein the cancer is refractory to treatment by a tyrosine kinase inhibitor.

11. The method of claim 7, wherein the cancer is refractory to treatment by a tyrosine kinase inhibitor.

12. The method of claim 10, wherein the tyrosine kinase inhibitor is imatinib mesylate or SU11248.

13. The method of claim 11, wherein the tyrosine kinase inhibitor is imatinib mesylate or SU11248.

14. The method of claim 1, wherein the method further comprises administering a second therapeutic agent.

15. The method of claim 2, wherein the method further comprises administering a second therapeutic agent.

16. The method of claim 14, wherein the second therapeutic agent is a chemotherapeutic agent, tyrosine kinase inhibitor, an antibody, or a cytokine.

17. The method of claim 15, wherein the second therapeutic agent is a chemotherapeutic agent, tyrosine kinase inhibitor, an antibody, or a cytokine.

18. The method of claim 16, wherein the tyrosine kinase inhibitor is imatinib mesylate or SU11248.

19. The method of claim 17, wherein the tyrosine kinase inhibitor is imatinib mesylate or SU11248.

20. The method of claim 6, wherein the cell is a stem cell.

21. The method of claim 1, wherein the KIT-mediated disorder is systemic mast cell disorder.

22. The method of claim 2, wherein the KIT-mediated disorder is systemic mast cell disorder.

\* \* \* \* \*

SEQUENCE LISTING

```
<160> NUMBER OF SEQ ID NOS: 49

<210> SEQ ID NO 1
<211> LENGTH: 972
<212> TYPE: PRT
<213> ORGANISM: Homo sapiens
<220> FEATURE:
<223> OTHER INFORMATION: full length human KIT
<300> PUBLICATION INFORMATION:
<308> DATABASE ACCESSION NUMBER: Genbank accession no. AAC50969

<400> SEQUENCE: 1

Met Arg Gly Ala Arg Gly Ala Trp Asp Phe Leu Cys Val Leu Leu Leu
1               5                   10                  15
```

```
Leu Leu Arg Val Gln Thr Gly Ser Ser Gln Pro Ser Val Ser Pro Gly
         20                  25                  30
Glu Pro Ser Pro Ser Ile His Pro Gly Lys Ser Asp Leu Ile Val
             35                  40                  45
Arg Val Gly Asp Glu Ile Arg Leu Leu Cys Thr Asp Pro Gly Phe Val
 50                  55                  60
Lys Trp Thr Phe Glu Ile Leu Asp Glu Thr Asn Glu Asn Lys Gln Asn
 65                  70                  75                  80
Glu Trp Ile Thr Glu Lys Ala Glu Ala Thr Asn Thr Gly Lys Tyr Thr
                 85                  90                  95
Cys Thr Asn Lys His Gly Leu Ser Asn Ser Ile Tyr Val Phe Val Arg
             100                 105                 110
Asp Pro Ala Lys Leu Phe Leu Val Asp Arg Ser Leu Tyr Gly Lys Glu
             115                 120                 125
Asp Asn Asp Thr Leu Val Arg Cys Pro Leu Thr Asp Pro Glu Val Thr
 130                 135                 140
Asn Tyr Ser Leu Lys Gly Cys Gln Gly Lys Pro Leu Pro Lys Asp Leu
 145                 150                 155                 160
Arg Phe Ile Pro Asp Pro Lys Ala Gly Ile Met Ile Lys Ser Val Lys
                 165                 170                 175
Arg Ala Tyr His Arg Leu Cys Leu His Cys Ser Val Asp Gln Glu Gly
             180                 185                 190
Lys Ser Val Leu Ser Glu Lys Phe Ile Leu Lys Val Arg Pro Ala Phe
             195                 200                 205
Lys Ala Val Pro Val Val Ser Val Ser Lys Ala Ser Tyr Leu Leu Arg
 210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                 245                 250                 255
Glu Lys Tyr Asn Ser Trp His His Gly Asp Phe Asn Tyr Glu Arg Gln
             260                 265                 270
Ala Thr Leu Thr Ile Ser Ser Ala Arg Val Asn Asp Ser Gly Val Phe
             275                 280                 285
Met Cys Tyr Ala Asn Asn Thr Phe Gly Ser Ala Asn Val Thr Thr Thr
 290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                 325                 330                 335
Tyr Glu Ala Phe Pro Lys Pro Glu His Gln Gln Trp Ile Tyr Met Asn
             340                 345                 350
Arg Thr Phe Thr Asp Lys Trp Glu Asp Tyr Pro Lys Ser Glu Asn Glu
             355                 360                 365
Ser Asn Ile Arg Tyr Val Ser Glu Leu His Leu Thr Arg Leu Lys Gly
 370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                 405                 410                 415
Thr Tyr Asp Arg Leu Val Asn Gly Met Leu Gln Cys Val Ala Ala Gly
             420                 425                 430
```

Phe Pro Glu Pro Thr Ile Asp Trp Tyr Phe Cys Pro Thr Glu Gln
                435                 440                 445

Arg Cys Ser Ala Ser Val Leu Pro Val Asp Val Gln Thr Leu Asn Ser
450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Glu Gln Ile
                500                 505                 510

His Pro His Thr Leu Phe Thr Pro Leu Leu Ile Gly Phe Val Ile Val
                515                 520                 525

Ala Gly Met Met Cys Ile Ile Val Met Ile Leu Thr Tyr Lys Tyr Leu
530                 535                 540

Gln Lys Pro Met Tyr Glu Val Gln Trp Lys Val Val Glu Glu Ile Asn
545                 550                 555                 560

Gly Asn Asn Tyr Val Tyr Ile Asp Pro Thr Gln Leu Pro Tyr Asp His
                565                 570                 575

Lys Trp Glu Phe Pro Arg Asn Arg Leu Ser Phe Gly Lys Thr Leu Gly
                580                 585                 590

Ala Gly Ala Phe Gly Lys Val Val Glu Ala Thr Ala Tyr Gly Leu Ile
                595                 600                 605

Lys Ser Asp Ala Ala Met Thr Val Ala Val Lys Met Leu Lys Pro Ser
                610                 615                 620

Ala His Leu Thr Glu Arg Glu Ala Leu Met Ser Glu Leu Lys Val Leu
625                 630                 635                 640

Ser Tyr Leu Gly Asn His Met Asn Ile Val Asn Leu Leu Gly Ala Cys
                645                 650                 655

Thr Ile Gly Gly Pro Thr Leu Val Ile Thr Glu Tyr Cys Cys Tyr Gly
                660                 665                 670

Asp Leu Leu Asn Phe Leu Arg Arg Lys Arg Asp Ser Phe Ile Cys Ser
                675                 680                 685

Lys Gln Glu Asp His Ala Glu Ala Ala Leu Tyr Lys Asn Leu Leu His
                690                 695                 700

Ser Lys Glu Ser Ser Cys Ser Asp Ser Thr Asn Glu Tyr Met Asp Met
705                 710                 715                 720

Lys Pro Gly Val Ser Tyr Val Val Pro Thr Lys Ala Asp Lys Arg Arg
                725                 730                 735

Ser Val Arg Ile Gly Ser Tyr Ile Glu Arg Asp Val Thr Pro Ala Ile
                740                 745                 750

Met Glu Asp Asp Glu Leu Ala Leu Asp Leu Glu Asp Leu Leu Ser Phe
                755                 760                 765

Ser Tyr Gln Val Ala Lys Gly Met Ala Phe Leu Ala Ser Lys Asn Cys
770                 775                 780

Ile His Arg Asp Leu Ala Ala Arg Asn Ile Leu Leu Thr His Gly Arg
785                 790                 795                 800

Ile Thr Lys Ile Cys Asp Phe Gly Leu Ala Arg Asp Ile Lys Asn Asp
                805                 810                 815

Ser Asn Tyr Val Val Lys Gly Asn Ala Arg Leu Pro Val Lys Trp Met
                820                 825                 830

Ala Pro Glu Ser Ile Phe Asn Cys Val Tyr Thr Phe Glu Ser Asp Val
                835                 840                 845

Trp Ser Tyr Gly Ile Phe Leu Trp Glu Leu Phe Ser Leu Gly Ser Ser

```
                    850                 855                 860
Pro Tyr Pro Gly Met Pro Val Asp Ser Lys Phe Tyr Lys Met Ile Lys
865                 870                 875                 880

Glu Gly Phe Arg Met Leu Ser Pro Glu His Ala Pro Ala Glu Met Tyr
                    885                 890                 895

Asp Ile Met Lys Thr Cys Trp Asp Ala Asp Pro Leu Lys Arg Pro Thr
            900                 905                 910

Phe Lys Gln Ile Val Gln Leu Ile Glu Lys Gln Ile Ser Glu Ser Thr
            915                 920                 925

Asn His Ile Tyr Ser Asn Leu Ala Asn Cys Ser Pro Asn Arg Gln Lys
            930                 935                 940

Pro Val Val Asp His Ser Val Arg Ile Asn Ser Val Gly Ser Thr Ala
945                 950                 955                 960

Ser Ser Ser Gln Pro Leu Leu Val His Asp Val
            965                 970
```

<210> SEQ ID NO 2
<211> LENGTH: 108
<212> TYPE: PRT
<213> ORGANISM: mouse
<220> FEATURE:
<223> OTHER INFORMATION: variable light chain region of anti-KIT
      antibodies 37M and 37C

<400> SEQUENCE: 2

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Arg Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Arg
                85                  90                  95

Thr Phe Gly Gly Gly Thr Lys Leu Glu Ile Lys Arg
            100                 105
```

<210> SEQ ID NO 3
<211> LENGTH: 116
<212> TYPE: PRT
<213> ORGANISM: mouse
<220> FEATURE:
<223> OTHER INFORMATION: variable heavy chain region of anti-KIT
      antibody 37M

<400> SEQUENCE: 3

```
Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
            35                  40                  45

Ala Arg Ile Tyr Pro Gly Ser Gly Asn Thr Tyr Tyr Asn Glu Lys Phe
        50                  55                  60

Lys Gly Lys Ala Thr Leu Thr Ala Glu Lys Ser Ser Ser Thr Ala Tyr
```

```
65              70              75              80
Met Gln Leu Ser Ser Leu Thr Ser Glu Asp Ser Ala Val Tyr Phe Cys
                85              90              95

Ala Arg Gly Val Tyr Tyr Phe Asp Tyr Trp Gly Gln Gly Thr Thr Leu
            100             105             110

Thr Val Ser Ser
        115

<210> SEQ ID NO 4

<400> SEQUENCE: 4

000

<210> SEQ ID NO 5
<211> LENGTH: 116
<212> TYPE: PRT
<213> ORGANISM: Artificial Sequence
<220> FEATURE:
<223> OTHER INFORMATION: variable heavy chain region of anti-KIT
      antibody 37C

<400> SEQUENCE: 5

Gln Val Gln Leu Lys Gln Ser Gly Ala Glu Leu Val Arg Pro Gly Ala
1               5               10              15

Ser Val Lys Leu Ser Cys Lys Ala Ser Gly Tyr Thr Phe Thr Asp Tyr
                20              25              30

Tyr Ile Asn Trp Val Lys Gln Arg Pro Gly Gln Gly Leu Glu Trp Ile
            35              40              45

Ala Arg Ile Tyr Pro Gly Ser Gly Asn Thr Tyr Tyr Asn Glu Lys Phe
    50              55              60

Lys Gly Lys Ala Thr Leu Thr Ala Glu Lys Ser Ser Ser Thr Ala Tyr
65              70              75              80

Met Gln Leu Ser Ser Leu Thr Ser Glu Asp Ser Ala Val Tyr Phe Cys
                85              90              95

Ala Arg Gly Val Tyr Tyr Phe Asp Tyr Trp Gly Gln Gly Thr Thr Leu
            100             105             110

Thr Val Ser Ala
        115

<210> SEQ ID NO 6
<211> LENGTH: 233
<212> TYPE: PRT
<213> ORGANISM: Artificial Sequence
<220> FEATURE:
<223> OTHER INFORMATION: light chain of antibody 37C

<400> SEQUENCE: 6

Met Gly Trp Ser Cys Ile Ile Leu Phe Leu Val Ala Thr Ala Thr Gly
1               5               10              15

Val His Ser Asp Ile Val Met Thr Gln Ser Lys Phe Met Ser Thr
                20              25              30

Ser Val Gly Asp Arg Val Ser Val Thr Cys Lys Ala Ser Gln Asn Val
            35              40              45

Arg Thr Asn Val Ala Trp Tyr Gln Gln Lys Pro Gly Gln Ser Pro Lys
    50              55              60

Ala Leu Ile Tyr Ser Ala Ser Tyr Arg Tyr Ser Gly Val Pro Asp Arg
65              70              75              80

Phe Thr Gly Ser Gly Ser Gly Thr Asp Phe Thr Leu Thr Ile Ser Asn
```

```
                       85                  90                  95
Val Gln Ser Glu Asp Leu Ala Asp Tyr Phe Cys Gln Gln Tyr Asn Ser
                100                 105                 110

Tyr Pro Arg Thr Phe Gly Gly Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 7
<211> LENGTH: 465
<212> TYPE: PRT
<213> ORGANISM: Artificial Sequence
<220> FEATURE:
<223> OTHER INFORMATION: heavy chain of antibody 37C

<400> SEQUENCE: 7

Met Gly Trp Ser Cys Ile Ile Leu Phe Leu Val Ala Thr Ala Thr Gly
1               5                   10                  15

Val His Ser Gln Val Gln Leu Lys Gln Ser Gly Ala Glu Leu Val Arg
                20                  25                  30

Pro Gly Ala Ser Val Lys Leu Ser Cys Lys Ala Ser Gly Tyr Thr Phe
            35                  40                  45

Thr Asp Tyr Tyr Ile Asn Trp Val Lys Gln Arg Pro Gly Gln Gly Leu
        50                  55                  60

Glu Trp Ile Ala Arg Ile Tyr Pro Gly Ser Gly Asn Thr Tyr Tyr Asn
65                  70                  75                  80

Glu Lys Phe Lys Gly Lys Ala Thr Leu Thr Ala Glu Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Gly Val Tyr Tyr Phe Asp Tyr Trp Gly Gln Gly
        115                 120                 125

Thr Thr Leu Thr Val Ser Ala Ala Ser Thr Lys Gly Pro Ser Val Phe
        130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
```

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
            245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
450                 455                 460

Lys
465

<210> SEQ ID NO 8
<211> LENGTH: 324
<212> TYPE: DNA
<213> ORGANISM: Artificial Sequence
<220> FEATURE:
<223> OTHER INFORMATION: sequence encoding VL domain of anti-KIT
      antibody 37M

<400> SEQUENCE: 8
gacattgtga tgacccagtc tcaaaaattc atgtccacat cagtaggaga cagggtcagc      60
gtcacctgca aggccagtca gaatgtgcgt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagactattt ctgtcagcaa tataacagct atcctcggac gttcggtgga     300
ggcaccaagc tggaaatcaa acgt                                            324

<210> SEQ ID NO 9
<211> LENGTH: 348
<212> TYPE: DNA
<213> ORGANISM: Artificial Sequence
<220> FEATURE:

<223> OTHER INFORMATION: sequence encoding VH domain of anti-KIT
      antibody 37M

<400> SEQUENCE: 9

| caggtccagc | tgaagcagtc | tggggctgag | ctggtgaggc | ctggggcctc | agtgaagctg | 60 |
| tcctgcaagg | cttctggcta | cactttcact | gactactata | taaactgggt | gaagcagagg | 120 |
| cctggacagg | gacttgagtg | gattgcaagg | atttaccctg | aagtggtaa | tacttactac | 180 |
| aatgagaagt | tcaagggcaa | ggccacactg | actgcagaaa | aatcctccag | cactgcctac | 240 |
| atgcagctca | gcagcctgac | atctgaggac | tctgctgtct | atttctgtgc | aaggggggtg | 300 |
| tactactttg | actactgggg | ccaaggcacc | actctcacag | tctcctca | | 348 |

<210> SEQ ID NO 10
<211> LENGTH: 702
<212> TYPE: DNA
<213> ORGANISM: Artificial Sequence
<220> FEATURE:
<223> OTHER INFORMATION: sequence encoding the light chain of antibody
      37C

<400> SEQUENCE: 10

| atgggctgga | gctgcatcat | cctgttcctg | gtggccaccg | ccaccggtgt | gcacagcgac | 60 |
| attgtgatga | cccagtctca | aaaattcatg | tccacatcag | taggagacag | ggtcagcgtc | 120 |
| acctgcaagg | ccagtcagaa | tgtgcgtact | aatgtagcct | ggtatcaaca | gaaaccaggg | 180 |
| caatctccta | aagcactgat | ttactcggca | tcctaccggt | acagtggagt | ccctgatcgc | 240 |
| ttcacaggca | gtggatctgg | gacagatttc | actctcacca | tcagcaatgt | gcagtctgaa | 300 |
| gacttggcag | actatttctg | tcagcaatat | aacagctatc | ctcggacgtt | cggtggaggc | 360 |
| accaagctcg | agatcaagag | aaccgtggcc | gcccccagcg | tgttcatctt | ccccccagc | 420 |
| gacgagcagc | tgaagagcgg | caccgccagc | gtggtgtgcc | tgctgaacaa | cttctacccc | 480 |
| agagaggcca | aggtgcagtg | gaaggtggac | aacgccctgc | agagcggcaa | cagccaggag | 540 |
| agcgtgaccg | agcaggacag | caaggacagc | acctacagcc | tgagcagcac | cctgaccctg | 600 |
| agcaaggccg | actacgagaa | gcacaaggtg | tacgcctgcg | aggtgaccca | ccagggcctg | 660 |
| agcagccccg | tgaccaagag | cttcaacaga | ggcgagtgct | ga | | 702 |

<210> SEQ ID NO 11
<211> LENGTH: 1398
<212> TYPE: DNA
<213> ORGANISM: Artificial Sequence
<220> FEATURE:
<223> OTHER INFORMATION: sequence encoding the heavy chain of antibody
      37C

<400> SEQUENCE: 11

| atgggctgga | gctgcatcat | cctgttcctg | gtggccaccg | ccaccggcgt | gcacagccag | 60 |
| gtgcaattga | agcagtctgg | ggctgagctg | gtgaggcctg | ggcctcagt | gaagctgtcc | 120 |
| tgcaaggctt | ctggctacac | tttcactgac | tactatataa | actgggtgaa | gcagaggcct | 180 |
| ggacagggac | ttgagtggat | tgcaaggatt | taccctggaa | gtggtaatac | ttactacaat | 240 |
| gagaagttca | aggcaaggc | cacactgact | gcagaaaaat | cctccagcac | tgcctacatg | 300 |
| cagctcagca | gcctgacatc | tgaggactct | gctgtctatt | tctgtgcaag | ggggggtgtac | 360 |
| tactttgact | actggggcca | aggcaccact | ctcacagtct | ccgcggccag | cactaagggc | 420 |
| ccagcgtgt | tcccgctagc | ccccagcagc | aagagcacca | gcggcggcac | cgccgccctg | 480 |

```
ggctgcctgg tgaaggacta cttccccgag cccgtgaccg tgagctggaa cagcggcgcc      540
ctgaccagcg gcgtgcacac cttccccgcc gtgctgcaga gcagcggcct gtacagcctg      600
agcagcgtgg tgaccgtgcc cagcagcagc ctgggcaccc agacctacat ctgcaacgtg      660
aaccacaagc ccagcaacac caaggtggac aagaaggtgg agcccaagag ctgcgacaag      720
acccacacct gccccccctg cccgccccc  gagctgctgg gcggcccag cgtgttcctg        780 ttcccccca  agcccaagga caccctgatg atcagcagaa ccccgaggt gacctgcgtg       840 gtggtggacg tgagccacga ggaccccgag gtgaagttca actggtacgt ggacggcgtg      900
gaggtgcaca cgccaagac caagcccaga gaggagcagt acaacagcac ctacagagtg       960
gtgagcgtgc tgaccgtgct gcaccaggac tggctgaacg gcaaggagta caagtgcaag     1020
gtgagcaaca aggccctgcc cgcccccatc gagaagacca tcagcaaggc caagggccag     1080
cccagagagc cccaggtgta caccctgccc ccagcagag acgagctgac caagaaccag      1140
gtgagcctga cctgcctggt gaagggcttc taccccagcg acatcgccgt ggagtgggag     1200
agcaacggcc agcccgagaa caactacaag accaccccc  ccgtgctgga cagcgacggc     1260
agcttcttcc tgtacagcaa gctgaccgtg gacaagagca gatggcagca gggcaacgtg     1320
ttcagctgca gcgtgatgca cgaggccctg cacaaccact acacccagaa gagcctgagc     1380
ctgagccccg gcaagtag                                                     1398

<210> SEQ ID NO 12
<211> LENGTH: 106
<212> TYPE: PRT
<213> ORGANISM: Artificial Sequence
<220> FEATURE:
<223> OTHER INFORMATION: light chain constant domain of antibody 37C

<400> SEQUENCE: 12

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 13
<211> LENGTH: 330
<212> TYPE: PRT
<213> ORGANISM: Artificial Sequence
<220> FEATURE:
<223> OTHER INFORMATION: heavy chain constant domain of antibody 37C

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                 165                 170                 175

Glu Gln Tyr Asn Ser Thr Tyr Arg Val Val Ser Val Leu Thr Val Leu
             180                 185                 190

His Gln Asp Trp Leu Asn Gly Lys Glu Tyr Lys Cys Lys Val Ser Asn
         195                 200                 205

Lys Ala Leu Pro Ala Pro Ile Glu Lys Thr Ile Ser Lys Ala Lys Gly
     210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                 245                 250                 255

Pro Ser Asp Ile Ala Val Glu Trp Glu Ser Asn Gly Gln Pro Glu Asn
             260                 265                 270

Asn Tyr Lys Thr Thr Pro Pro Val Leu Asp Ser Asp Gly Ser Phe Phe
         275                 280                 285

Leu Tyr Ser Lys Leu Thr Val Asp Lys Ser Arg Trp Gln Gln Gly Asn
     290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                 325                 330

<210> SEQ ID NO 14
<211> LENGTH: 246
<212> TYPE: PRT
<213> ORGANISM: Artificial Sequence
<220> FEATURE:
<223> OTHER INFORMATION: recombinant KIT D4/D5 polypeptide

<400> SEQUENCE: 14

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
             20                  25                  30

Glu Val Asp Lys Gly Phe Ile Asn Ile Phe Pro Met Ile Asn Thr Thr
             35                  40                  45

Val Phe Val Asn Asp Gly Glu Asn Val Asp Leu Ile Val Glu Tyr Glu
         50                  55                  60
```

```
Ala Phe Pro Lys Pro Glu His Gln Gln Trp Ile Tyr Met Asn Arg Thr
 65                  70                  75                  80

Phe Thr Asp Lys Trp Glu Asp Tyr Pro Lys Ser Glu Asn Glu Ser Asn
                 85                  90                  95

Ile Arg Tyr Val Ser Glu Leu His Leu Thr Arg Leu Lys Gly Thr Glu
                100                 105                 110

Gly Gly Thr Tyr Thr Phe Leu Val Ser Asn Ser Asp Val Asn Ala Ala
                115                 120                 125

Ile Ala Phe Asn Val Tyr Val Asn Thr Lys Pro Glu Ile Leu Thr Tyr
130                 135                 140

Asp Arg Leu Val Asn Gly Met Leu Gln Cys Val Ala Ala Gly Phe Pro
145                 150                 155                 160

Glu Pro Thr Ile Asp Trp Tyr Phe Cys Pro Gly Thr Glu Gln Arg Cys
                165                 170                 175

Ser Ala Ser Val Leu Pro Val Asp Val Gln Thr Leu Asn Ser Ser Gly
                180                 185                 190

Pro Pro Phe Gly Lys Leu Val Val Gln Ser Ser Ile Asp Ser Ser Ala
                195                 200                 205

Phe Lys His Asn Gly Thr Val Glu Cys Lys Ala Tyr Asn Asp Val Gly
210                 215                 220

Lys Thr Ser Ala Tyr Phe Asn Phe Ala Phe Lys Glu Gln Ile His Pro
225                 230                 235                 240

His His His His His His
                245

<210> SEQ ID NO 15
<211> LENGTH: 208
<212> TYPE: PRT
<213> ORGANISM: Homo sapiens
<220> FEATURE:
<223> OTHER INFORMATION: V308 to H515 of Human KIT amino acids sequence
      (KIT D4/D5 region)

<400> SEQUENCE: 15

Val Asp Lys Gly Phe Ile Asn Ile Phe Pro Met Ile Asn Thr Thr Val
  1               5                  10                  15

Phe Val Asn Asp Gly Glu Asn Val Asp Leu Ile Val Glu Tyr Glu Ala
                 20                  25                  30

Phe Pro Lys Pro Glu His Gln Gln Trp Ile Tyr Met Asn Arg Thr Phe
                 35                  40                  45

Thr Asp Lys Trp Glu Asp Tyr Pro Lys Ser Glu Asn Glu Ser Asn Ile
         50                  55                  60

Arg Tyr Val Ser Glu Leu His Leu Thr Arg Leu Lys Gly Thr Glu Gly
 65                  70                  75                  80

Gly Thr Tyr Thr Phe Leu Val Ser Asn Ser Asp Val Asn Ala Ala Ile
                 85                  90                  95

Ala Phe Asn Val Tyr Val Asn Thr Lys Pro Glu Ile Leu Thr Tyr Asp
                100                 105                 110

Arg Leu Val Asn Gly Met Leu Gln Cys Val Ala Ala Gly Phe Pro Glu
                115                 120                 125

Pro Thr Ile Asp Trp Tyr Phe Cys Pro Gly Thr Glu Gln Arg Cys Ser
        130                 135                 140

Ala Ser Val Leu Pro Val Asp Val Gln Thr Leu Asn Ser Ser Gly Pro
145                 150                 155                 160

Pro Phe Gly Lys Leu Val Val Gln Ser Ser Ile Asp Ser Ser Ala Phe
                165                 170                 175
```

```
Lys His Asn Gly Thr Val Glu Cys Lys Ala Tyr Asn Asp Val Gly Lys
            180                 185                 190

Thr Ser Ala Tyr Phe Asn Phe Ala Phe Lys Glu Gln Ile His Pro His
            195                 200                 205

<210> SEQ ID NO 16
<211> LENGTH: 144
<212> TYPE: PRT
<213> ORGANISM: Artificial Sequence
<220> FEATURE:
<223> OTHER INFORMATION: recombinant D4 domain polypeptide

<400> SEQUENCE: 16

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Val Asp Lys Gly Phe Ile Asn Ile Phe Pro Met Ile Asn Thr Thr
        35                  40                  45

Val Phe Val Asn Asp Gly Glu Asn Val Asp Leu Ile Val Glu Tyr Glu
50                  55                  60

Ala Phe Pro Lys Pro Glu His Gln Gln Trp Ile Tyr Met Asn Arg Thr
65                  70                  75                  80

Phe Thr Asp Lys Trp Glu Asp Tyr Pro Lys Ser Glu Asn Glu Ser Asn
                85                  90                  95

Ile Arg Tyr Val Ser Glu Leu His Leu Thr Arg Leu Lys Gly Thr Glu
            100                 105                 110

Gly Gly Thr Tyr Thr Phe Leu Val Ser Asn Ser Asp Val Asn Ala Ala
        115                 120                 125

Ile Ala Phe Asn Val Tyr Val Asn Thr Lys His His His His His His
    130                 135                 140

<210> SEQ ID NO 17
<211> LENGTH: 105
<212> TYPE: PRT
<213> ORGANISM: Homo sapiens
<220> FEATURE:
<223> OTHER INFORMATION: V308 to K412 of Human KIT amino acids sequence

<400> SEQUENCE: 17

Val Asp Lys Gly Phe Ile Asn Ile Phe Pro Met Ile Asn Thr Thr Val
1               5                   10                  15

Phe Val Asn Asp Gly Glu Asn Val Asp Leu Ile Val Glu Tyr Glu Ala
            20                  25                  30

Phe Pro Lys Pro Glu His Gln Gln Trp Ile Tyr Met Asn Arg Thr Phe
        35                  40                  45

Thr Asp Lys Trp Glu Asp Tyr Pro Lys Ser Glu Asn Glu Ser Asn Ile
50                  55                  60

Arg Tyr Val Ser Glu Leu His Leu Thr Arg Leu Lys Gly Thr Glu Gly
65                  70                  75                  80

Gly Thr Tyr Thr Phe Leu Val Ser Asn Ser Asp Val Asn Ala Ala Ile
                85                  90                  95

Ala Phe Asn Val Tyr Val Asn Thr Lys
            100                 105

<210> SEQ ID NO 18
<211> LENGTH: 148
<212> TYPE: PRT
```

```
<213> ORGANISM: Artificial Sequence
<220> FEATURE:
<223> OTHER INFORMATION: recombinant D5 domain polypeptide

<400> SEQUENCE: 18

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Asn Thr Lys Pro Glu Ile Leu Thr Tyr Asp Arg Leu Val Asn Gly
        35                  40                  45

Met Leu Gln Cys Val Ala Ala Gly Phe Pro Glu Pro Thr Ile Asp Trp
50                  55                  60

Tyr Phe Cys Pro Gly Thr Glu Gln Arg Cys Ser Ala Ser Val Leu Pro
65                  70                  75                  80

Val Asp Val Gln Thr Leu Asn Ser Ser Gly Pro Pro Phe Gly Lys Leu
                85                  90                  95

Val Val Gln Ser Ser Ile Asp Ser Ser Ala Phe Lys His Asn Gly Thr
            100                 105                 110

Val Glu Cys Lys Ala Tyr Asn Asp Val Gly Lys Thr Ser Ala Tyr Phe
        115                 120                 125

Asn Phe Ala Phe Lys Gly Asn Asn Lys Glu Gln Ile His Pro His His
    130                 135                 140

His His His His
145

<210> SEQ ID NO 19
<211> LENGTH: 110
<212> TYPE: PRT
<213> ORGANISM: Homo sapiens
<220> FEATURE:
<223> OTHER INFORMATION: N410 to H515 of Human KIT amino acids sequence

<400> SEQUENCE: 19

Asn Thr Lys Pro Glu Ile Leu Thr Tyr Asp Arg Leu Val Asn Gly Met
1               5                   10                  15

Leu Gln Cys Val Ala Ala Gly Phe Pro Glu Pro Thr Ile Asp Trp Tyr
            20                  25                  30

Phe Cys Pro Gly Thr Glu Gln Arg Cys Ser Ala Ser Val Leu Pro Val
        35                  40                  45

Asp Val Gln Thr Leu Asn Ser Ser Gly Pro Pro Phe Gly Lys Leu Val
    50                  55                  60

Val Gln Ser Ser Ile Asp Ser Ser Ala Phe Lys His Asn Gly Thr Val
65                  70                  75                  80

Glu Cys Lys Ala Tyr Asn Asp Val Gly Lys Thr Ser Ala Tyr Phe Asn
                85                  90                  95

Phe Ala Phe Lys Gly Asn Asn Lys Glu Gln Ile His Pro His
            100                 105                 110

<210> SEQ ID NO 20
<211> LENGTH: 11
<212> TYPE: PRT
<213> ORGANISM: Artificial Sequence
<220> FEATURE:
<223> OTHER INFORMATION: VL CDR1 of antibody 37M and 37C

<400> SEQUENCE: 20

Lys Ala Ser Gln Asn Val Arg Thr Asn Val Ala
1               5                   10
```

<210> SEQ ID NO 21
<211> LENGTH: 7
<212> TYPE: PRT
<213> ORGANISM: Artificial Sequence
<220> FEATURE:
<223> OTHER INFORMATION: VL CDR2 of antibody 37M and 37C

<400> SEQUENCE: 21

Ser Ala Ser Tyr Arg Tyr Ser
1               5

<210> SEQ ID NO 22
<211> LENGTH: 9
<212> TYPE: PRT
<213> ORGANISM: Artificial Sequence
<220> FEATURE:
<223> OTHER INFORMATION: VL CDR3 of antibody 37M and 37C

<400> SEQUENCE: 22

Gln Gln Tyr Asn Ser Tyr Pro Arg Thr
1               5

<210> SEQ ID NO 23
<211> LENGTH: 5
<212> TYPE: PRT
<213> ORGANISM: Artificial Sequence
<220> FEATURE:
<223> OTHER INFORMATION: VH CDR1 of antibody 37M and 37C

<400> SEQUENCE: 23

Asp Tyr Tyr Ile Asn
1               5

<210> SEQ ID NO 24
<211> LENGTH: 17
<212> TYPE: PRT
<213> ORGANISM: Artificial Sequence
<220> FEATURE:
<223> OTHER INFORMATION: VH CDR2 of antibody 37M and 37C

<400> SEQUENCE: 24

Arg Ile Tyr Pro Gly Ser Gly Asn Thr Tyr Tyr Asn Glu Lys Phe Lys
1               5                   10                  15

Gly

<210> SEQ ID NO 25
<211> LENGTH: 7
<212> TYPE: PRT
<213> ORGANISM: Artificial Sequence
<220> FEATURE:
<223> OTHER INFORMATION: VH CDR3 of antibody 37M and 37C

<400> SEQUENCE: 25

Gly Val Tyr Tyr Phe Asp Tyr
1               5

<210> SEQ ID NO 26
<211> LENGTH: 23
<212> TYPE: PRT
<213> ORGANISM: Artificial Sequence
<220> FEATURE:
<223> OTHER INFORMATION: VL FR1 of antibody 37M and 37C

<400> SEQUENCE: 26

Asp Ile Val Met Thr Gln Ser Gln Lys Phe Met Ser Thr Ser Val Gly

```
1               5                   10                  15
Asp Arg Val Ser Val Thr Cys
            20
```

<210> SEQ ID NO 27
<211> LENGTH: 15
<212> TYPE: PRT
<213> ORGANISM: Artificial Sequence
<220> FEATURE:
<223> OTHER INFORMATION: VL FR2 of antibody 37M and 37C

<400> SEQUENCE: 27

```
Trp Tyr Gln Gln Lys Pro Gly Gln Ser Pro Lys Ala Leu Ile Tyr
1               5                   10                  15
```

<210> SEQ ID NO 28
<211> LENGTH: 32
<212> TYPE: PRT
<213> ORGANISM: Artificial Sequence
<220> FEATURE:
<223> OTHER INFORMATION: VL FR3 of antibody 37M and 37C

<400> SEQUENCE: 28

```
Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Asp Tyr Phe Cys
            20                  25                  30
```

<210> SEQ ID NO 29
<211> LENGTH: 11
<212> TYPE: PRT
<213> ORGANISM: Artificial Sequence
<220> FEATURE:
<223> OTHER INFORMATION: VL FR4 of antibody 37M and 37C

<400> SEQUENCE: 29

```
Phe Gly Gly Gly Thr Lys Leu Glu Ile Lys Arg
1               5                   10
```

<210> SEQ ID NO 30
<211> LENGTH: 30
<212> TYPE: PRT
<213> ORGANISM: Artificial Sequence
<220> FEATURE:
<223> OTHER INFORMATION: VH FR1 of antibody 37M

<400> SEQUENCE: 30

```
Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr
            20                  25                  30
```

<210> SEQ ID NO 31
<211> LENGTH: 14
<212> TYPE: PRT
<213> ORGANISM: Artificial Sequence
<220> FEATURE:
<223> OTHER INFORMATION: VH FR2 of antibody 37M

<400> SEQUENCE: 31

```
Trp Val Lys Gln Arg Pro Gly Gln Gly Leu Glu Trp Ile Ala
1               5                   10
```

<210> SEQ ID NO 32
<211> LENGTH: 32

<212> TYPE: PRT
<213> ORGANISM: Artificial Sequence
<220> FEATURE:
<223> OTHER INFORMATION: VH FR3 of antibody 37M

<400> SEQUENCE: 32

Lys Ala Thr Leu Thr Ala Glu Lys Ser Ser Thr Ala Tyr Met Gln
1               5                  10                  15

Leu Ser Ser Leu Thr Ser Glu Asp Ser Ala Val Tyr Phe Cys Ala Arg
            20                  25                  30

<210> SEQ ID NO 33
<211> LENGTH: 11
<212> TYPE: PRT
<213> ORGANISM: Artificial Sequence
<220> FEATURE:
<223> OTHER INFORMATION: VH FR4 of antibody 37M

<400> SEQUENCE: 33

Trp Gly Gln Gly Thr Thr Leu Thr Val Ser Ser
1               5                  10

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38
<211> LENGTH: 30
<212> TYPE: PRT
<213> ORGANISM: Artificial Sequence
<220> FEATURE:
<223> OTHER INFORMATION: VH FR1 of antibody 37C

<400> SEQUENCE: 38

Gln Val Gln Leu Lys Gln Ser Gly Ala Glu Leu Val Arg Pro Gly Ala
1               5                  10                  15

Ser Val Lys Leu Ser Cys Lys Ala Ser Gly Tyr Thr Phe Thr
            20                  25                  30

<210> SEQ ID NO 39
<211> LENGTH: 14
<212> TYPE: PRT
<213> ORGANISM: Artificial Sequence
<220> FEATURE:
<223> OTHER INFORMATION: VH FR2 of antibody 37C

<400> SEQUENCE: 39

-continued

Trp Val Lys Gln Arg Pro Gly Gln Gly Leu Glu Trp Ile Ala
1               5                   10

<210> SEQ ID NO 40
<211> LENGTH: 32
<212> TYPE: PRT
<213> ORGANISM: Artificial Sequence
<220> FEATURE:
<223> OTHER INFORMATION: VH FR3 of antibody 37C

<400> SEQUENCE: 40

Lys Ala Thr Leu Thr Ala Glu Lys Ser Ser Thr Ala Tyr Met Gln
1               5                   10                  15

Leu Ser Ser Leu Thr Ser Glu Asp Ser Ala Val Tyr Phe Cys Ala Arg
            20                  25                  30

<210> SEQ ID NO 41
<211> LENGTH: 11
<212> TYPE: PRT
<213> ORGANISM: Artificial Sequence
<220> FEATURE:
<223> OTHER INFORMATION: VH FR4 of antibody 37C

<400> SEQUENCE: 41

Trp Gly Gln Gly Thr Thr Leu Thr Val Ser Ala
1               5                   10

<210> SEQ ID NO 42

<400> SEQUENCE: 42

000

<210> SEQ ID NO 43
<211> LENGTH: 19
<212> TYPE: PRT
<213> ORGANISM: Artificial Sequence
<220> FEATURE:
<223> OTHER INFORMATION: signal peptide of antibody 37C or 37M light
      chain

<400> SEQUENCE: 43

Met Gly Trp Ser Cys Ile Ile Leu Phe Leu Val Ala Thr Ala Thr Gly
1               5                   10                  15

Val His Ser

<210> SEQ ID NO 44
<211> LENGTH: 19
<212> TYPE: PRT
<213> ORGANISM: Artificial Sequence
<220> FEATURE:
<223> OTHER INFORMATION: signal peptide of antibody 37C or 37M heavy
      chain

<400> SEQUENCE: 44

Met Gly Trp Ser Cys Ile Ile Leu Phe Leu Val Ala Thr Ala Thr Gly
1               5                   10                  15

Val His Ser

<210> SEQ ID NO 45
<211> LENGTH: 107
<212> TYPE: PRT
<213> ORGANISM: Artificial Sequence
<220> FEATURE:
<223> OTHER INFORMATION: VL chain region of Ab1

<400> SEQUENCE: 45

Asp Ile Gln Met Thr Gln Ser Pro Thr Ser Leu Ser Ala Phe Val Gly
1               5                   10                  15

Asp Arg Val Thr Ile Thr Cys Gln Ala Ser Gln Asp Ile Gly Asn Tyr
            20                  25                  30

Leu Asn Trp Tyr Gln Gln Lys Ser Gly Glu Pro Pro Lys Leu Leu Val
        35                  40                  45

Tyr Asp Ala Ser Phe Leu Lys Lys Gly Val Pro Ser Arg Phe Ser Gly
50                  55                  60

Ser Gly Ser Gly Thr Gln Tyr Phe Leu Thr Ile Tyr Ser Leu Gln Pro
65                  70                  75                  80

Glu Asp Phe Ala Thr Tyr Phe Cys Gln His Ser Asp Asn Leu Ser Val
                85                  90                  95

Thr Phe Gly Gly Gly Thr Lys Val Glu Val Lys
            100                 105

<210> SEQ ID NO 46
<211> LENGTH: 122
<212> TYPE: PRT
<213> ORGANISM: Artificial Sequence
<220> FEATURE:
<223> OTHER INFORMATION: VH chain region of Ab1 or Ab21

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Ser Trp Val Arg Gln Ala Pro Gly Lys Gly Leu Glu Trp Val
        35                  40                  45

Ser Ser Ile Val Pro Ser Gly Gly Phe Thr His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gln Thr Gly Ser Trp Arg Val His Ala Phe Asp Ile Trp
            100                 105                 110

Gly Gln Gly Thr Met Val Thr Val Ser Ser
        115                 120

<210> SEQ ID NO 47
<211> LENGTH: 107
<212> TYPE: PRT
<213> ORGANISM: Artificial Sequence
<220> FEATURE:
<223> OTHER INFORMATION: VL chain region of Ab21

<400> SEQUENCE: 47

Asp Ile Gln Met Thr Gln Ser Pro Thr Ser Leu Ser Ala Phe Val Gly
1               5                   10                  15

Asp Arg Val Thr Ile Thr Cys Gln Ala Ser Gln Asp Ile Gly Asn Tyr
            20                  25                  30

Leu Asn Trp Tyr Gln Gln Lys Ser Gly Glu Pro Pro Lys Leu Leu Val
        35                  40                  45

Tyr Asp Ala Ser Phe Leu Lys Lys Gly Val Pro Ser Arg Phe Ser Gly
50                  55                  60

```
Ser Gly Ser Gly Thr Gln Tyr Phe Leu Thr Ile Tyr Ser Leu Gln Pro
65                  70                  75                  80

Glu Asp Phe Ala Thr Tyr Phe Cys Gln His Ser Asp Ser Leu Ser Val
                85                  90                  95

Thr Phe Gly Gly Gly Thr Lys Val Glu Val Lys
            100                 105

<210> SEQ ID NO 48
<211> LENGTH: 17
<212> TYPE: PRT
<213> ORGANISM: Artificial Sequence
<220> FEATURE:
<223> OTHER INFORMATION: a KIT epitope

<400> SEQUENCE: 48

Ser Glu Leu His Leu Thr Arg Leu Lys Gly Thr Glu Gly Gly Thr Tyr
1               5                   10                  15

Thr

<210> SEQ ID NO 49
<211> LENGTH: 10
<212> TYPE: PRT
<213> ORGANISM: Artificial Sequence
<220> FEATURE:
<223> OTHER INFORMATION: a KIT epitope

<400> SEQUENCE: 49

Leu Thr Arg Leu Lys Gly Thr Glu Gly Gly
1               5                   10
```